US011767302B2

(12) United States Patent
Fox et al.

(10) Patent No.: US 11,767,302 B2
(45) Date of Patent: Sep. 26, 2023

(54) REAGENTS AND METHODS FOR TETRAZINE SYNTHESIS

(71) Applicant: University of Delaware, Newark, DE (US)

(72) Inventors: Joseph M. Fox, Landenberg, PA (US); William Lambert, Gurnee, IL (US); Yinzhi Fang, Newark, DE (US); Christopher William am Ende, Mystic, CT (US); Subham Mahapatra, Groton, CT (US); Yixin Xie, Newark, DE (US); Chuanqi Wang, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 17/492,016

(22) Filed: Oct. 1, 2021

(65) Prior Publication Data
US 2022/0106278 A1 Apr. 7, 2022

Related U.S. Application Data

(60) Provisional application No. 63/086,132, filed on Oct. 1, 2020.

(51) Int. Cl.
| | |
|---|---|
| *C07D 257/08* | (2006.01) |
| *C07D 401/04* | (2006.01) |
| *C07D 403/08* | (2006.01) |
| *C07D 405/04* | (2006.01) |
| *C07D 409/04* | (2006.01) |
| *C07F 5/02* | (2006.01) |
| *C07D 401/14* | (2006.01) |
| *B01J 31/24* | (2006.01) |
| *B01J 31/02* | (2006.01) |
| *B01J 31/22* | (2006.01) |
| *C07J 43/00* | (2006.01) |

(52) U.S. Cl.
CPC ........ *C07D 257/08* (2013.01); *B01J 31/0298* (2013.01); *B01J 31/2265* (2013.01); *B01J 31/2409* (2013.01); *C07D 401/04* (2013.01); *C07D 401/14* (2013.01); *C07D 403/08* (2013.01); *C07D 405/04* (2013.01); *C07D 409/04* (2013.01); *C07F 5/022* (2013.01); *C07J 43/003* (2013.01); *B01J 2531/824* (2013.01)

(58) Field of Classification Search
CPC .................................................. C07D 257/08
See application file for complete search history.

(56) References Cited

PUBLICATIONS

Tolshchina et al. (Russian Chemical Bulletin (2011), 60(5), 985-991. Abstract.*
Pasteris et al. (WO 2018080859) Abstract. 2018.*
Wu et al., "Development and Evaluation of 18F-TTCO-Cys40-Exendin-4: A PET Probe for Imaging Transplanted Islets", The Journal of Nuclear Medicine, vol. 54, No. 2, Feb. 2013, 244-251.
Wu et al., "Inverse Electron-Demand Diels-Alder Bioorthogonal Reactions", Top Curr. Chem (Z) (2016) 374:3, 109-130.
Xie et al., "Divergent Synthesis of Monosubstituted and Unsymmetrical 3,6-Disubstituted Tetrazines from Carboxylic Ester Precursors", Angew. Chem Int. Ed., 2020, 59, 16967-16973.
Zeng et al., "The Growing Impact of Bioorthogonal Click Chemistry on the Development of Radiopharmaceuticals", J, Nucl. Med., Jun. 2013; 54(6): 829-832.
Bach, R., "Ring Strain Energy in the Cyclooctyl System. The Effect of Strain Energy on [3+2] Cycloaddition Reactions with Azides", J. Am. Chem. Soc. 2009, 131, 5233-5233.
Boger et al., "Total Synthesis of Ningalin D", J. Am. Chem. Soc. 2005, 127. 10767-10770.
Butler et al., "Azetidine and Piperidine Carbamates as Efficient, Covalent Inhibitors of Monoacylglycerol Lipase", J. Med. Chem. 2017, 60, 9860-9873.
Cope et al., "Cyclic Polyolefins. XXVII, cis- and trans-Cyclooctene from N,N-Dimethylcyclooctylamine1" contribution from the Department of Chemistry, Massachusetts Institute of Technology, vol. 75, 1953, 3212-3215, downloaded via University of Delaware, Dec. 7, 2021.
Cope et al., "Molecular Asymmetry of Olefins. I. Resolution of trans-Cyclooctene1-3", contribution from the Department of Chemistry, Massachusetts Institute of Technology, 1963, 3276-3279, downloaded via University of Delaware, Dec. 7, 2021.
Corey et al., "The Direct Synthesis of Optically Active trans-Cyclooctene", Tetrahedron Letters, No. 33, 1968, 3655-3658.
Egawa et al., "Development of a fluorescein analogue, TokyoMagenta, as a novel scaffold for fluorescence probes in red region", Chem. Commun. 2011, 47, 4162-4164.
Feng et al., "improving Tumor-to-Background Contrast through Hydrophilic Tetrazines: The Construction of 18F-Labeled PET Agents Targeting Nonsmall Cell Lung Carcinoma", Chem. Eur. J., 2020, 26, 4690-4694.
Fields et al., "A Simple Route to Unsymmetrically Substituted 1,2,4,5-Tetrazines", J. Org. Chem. 1994, 59, 8284-8287.
Inoue et al., "Asymmetric cis-trans Photoisomerization of Cyclooctene Sensitized by Chiral Aromatic Esters", J.C.S. Chem. Commun. 1978, 1024-1025.
Kotschy et al., "First Cross-Coupling Reactions on Tetrazines", Org. Lett., 2003, 5, 19, 3495-3497.
Lang et al., "Bioorthogonal Reactions for Labeling Proteins", ACS Chem. Biol. 2014, 9, 1, 16-20.
Mboyi et al., "Building Diversity in ortho-Substituted s-Aryltetrazines by Tuning N-Directed Palladium C—H Halogenation: Unsymmetrical Polyhalogenated and Biphenyl s-Aryltetrazines", ACS Catal. 2017, 7, 8493-8501.
Pagel, M., "Inverse electron demand Diels-Alder (IEDDA) reactions in peptide chemistry", J. Pept. Sci. 2019, 25, e3141, 10 pages.
Patterson et al., "Finding the Right (Bioorthogonal) Chemistry", ACS Chem. Biol. 2014, 9, 592-605.

(Continued)

*Primary Examiner* — Bruck Kifle
(74) *Attorney, Agent, or Firm* — RATNERPRESTIA

(57) ABSTRACT

Disclosed herein are mono- and di-substituted tetrazines and methods of their preparation and converting an oxetanyl ester to a thio-substituted tetrazine, which is then converted to a mono-substituted tetrazine, a di-substituted tetrazine, or a vinylether disubstituted tetrazine.

21 Claims, 17 Drawing Sheets

(56) References Cited

PUBLICATIONS

Pouplana et al., "Synthesis and Application of 3-Bromo-1 2,4,5-Tetrazine for Protein Labeling to Trigger Click-to-Release Biorthogonal Reactions", Bioconj. Chem. 2020, 31, 933-938.
Qu et al., "Metal-Free Synthetic Approach to 3-Monosubstituted Unsymmetrical 1,2,4,5-Tetrazines Useful for Bio-orthogonal Reactions", Angew. Chem. Int. Ed. 2018, 57, 12057-12061.
Riera et al., "Synthesis of 3-alkyl-6-methyl-1,2,4,5-tetrazines via a Sonogashira-type cross-coupling reaction", Chem. Commun. 2020, 56, 11086-11089.
Roger et al., "Ortho-Functionalized Aryltetrazines by Direct Palladium-Catalyzed C—H Halogenation: Application to Fast Electrophilic Fluorination Reactions", Angew. Chem. Int. Ed. 2016, 55, 5555-5559.
Rossin et al., "Triggered Drug Release from an Antibody-Drug Conjugate Using Fast 'Click-to-Release' Chemistry in Mice", Bioconjug. Chem., 2016, 27, 1697-1706.
Royzen et al., "A Photochemical Synthesis of Functionalized trans-Cyclooctenes Driven by Metal Complexation", J. Am. Chem. Soc. 2008, 130, 12, 3760-3761.
Sauer et al., Tetrahedron Lett. 1990, 31, 6851-6854. (English abstract only).
Seo et al., "Facile synthesis and biological evaluation of a cell-permeable probe to detect redox-regulated proteins", Bioorganic & Med. Chem. Lett. 2009, 19, 356-359.
Suzenet et al., "Efficient Palladium-Catalyzed Synthesis of Unsymmetrical (Het)aryl-tetrazines", Synlett 2007, No. 2, 204-210.
Swenton, J., "Photoisomerization of cis-Cyclooctene to trans-Cyclooctene1", J. Org. Chem., 1969, 34, 10, 3217-3218.
Taylor, M., Ph.D. Dissertation, "Applications of Highly Reactive Carbonoids and Chiral Olefins in Stereoselective Synthesis and Bioorthogonal Labeling Chemistry", 2012, 234 pages.
Van Onzen et al., "Bioorthogonal Tetrazine Carbamate Cleavage by Highly Reactive trans-Cyclooctene", J. Am. Chem. Soc. 2020, 142, 10955-10963.
Vedejs et al., "Olefin Inversion by the Phosphorus Betaine Method", Journal of the American Chemical Society, 93:16, Aug. 11, 1971, 4070-4072.
Wang et al., "Recent synthesis of functionalized s-tetrazines and their application in ligation reactions under physiological conditions: a concise overview" Catal. Rev. 2020, vol. 62, No. 4, 524-565.
Weissleder et al., "BODIPY-Tetrazine Derivatives as Superbright Bioorthogonal Turn-on Probes", Angew. Chem. Int. Ed. 2013, 52, 1-5.
Whitham et al., "trans-Cycloalkenes. Part V. 1-Methyl-trans-cyclooctene", J.C.S. Perkin I, 1975, 2264-2267, downloaded via University of Delaware, Dec. 7, 2021.
Whitham et al., "trans-Cycloalkenes. Part VI. Addition of Iodine(i) Azide to trans-Cyclo-Octene", J.C.S. Perkin I, 1975, 2267-2270, downloaded via University of Delaware, Dec. 7, 2021.
Wiseman et al., "Ionization Potentials of Deformed π-Bonds(1)", Angew. Chem., Int. Ed, Engl., 1973, 12, 4, 312-314.
Wu et al., "Organocatalytic and Scalable Syntheses of Unsymmetrical 1,2,4,5-Tetrazines by Thiol-containing Promotors", Angew. Chem. Int. Ed. 2019, 58, 1106-1169.
Xu et al., "Iridium-cataiyzed C—H amidation of s-tetrazines", Chem. Commun. 2020, 56, 4692-4695.
Hofmann et al., "The effect of hydrazine on dicyandiamide", Ber. Dtsch. Chem. Ges. 1912, 45, 2731-2740, with partial translation.
Coates et al., "A Readily Synthesized and Highly Active Epoxide Carbonylation Catalyst Based on a Chromium Porphyrin Framework: Expanding the Range of Available β-Lactones", Orig. Lett., vol. 6, No. 3, (2004), 373-376.
Alcock et al., "Norbomene Probes for the Detection of Cysteine Sulfenic Acid in Cells", ACS Chem. Biol. 2019, 14, 594-598.
Bello et al., "Cell Chemical Biology", 8th Chemical Protein Synthesis Meeting Report, Jun. 16-19, 2019, Berlin, Germany, 12 pages.

Benitez et al., "The Inactivation of the Acyl Phosphatase Activity Catalyzed by the Sulfenic Acid Form of Glyceraldehyde 3-Phosphate Dehydrogenase by Dimedone and Olefins*", The Journal of Biological Chemistry, vol. 249, No. 19, Iss. 1, Oct. 10, 1974, pp. 6234-6243.
Blackman et al., "The Tetrazine Ligation: Fast Bioconjugation Based on Inverse-electron-demand Diels-Alder Reactivity", J. Am. Chem. Soc., 130(41) Oct. 15, 2008, pp. 13518-13519.
Darko et al., "Conformationally Strained trans-Cyclooctene with Improved Stability and Excellent Reactivity in Tetrazine Ligation", Chem Sci., 5(10), Oct. 1, 2014, pp. 3770-3776.
Darko et al., "Large-Scale Flow Photochemical Synthesis of Functionalized trans-Cyclooctenes Using Sulfonated Silica Gel", Synthesis (Stuttg).; 50(24), Dec. 2018, pp. 4875-4882.
Denmark et al., "Observation of Direct Sulfenium and Selenenium Group Transfer from Thiiranium and Seleniranium Ions to Alkenes", J. Chem Soc., 2009, 131, pp. 3490-3492.
Devaraj et al., "A Convenient In-Situ Synthesis of Alkenyl Tetrazines for Highly Fluorogenic Bioorthogonal Live-Cell Imaging Probes", Angew Chem Int Ed Engl., 53(23), Jun. 2, 2014, pp. 5805-5809.
Devaraj et al., "Biomedical Applications of Tetrazine Cycloadditions", Ace Chem Res., Sep. 20, 2011; 44(9): 816-827.
Devaraj et al., "Metal Catalyzed One-Pot Synthesis of Tetrazines Directly from Aliphatic Nitriles and Hydrazine", Angew Chem Int Ed Engl., May 21, 2012; 51(21): 5222-5225.
Devaraj et al., "Tetrazine-Based Cycloadditions: Applications to Pretargeted Live Cell Imaging", Bioconjug. Chem, Dec. 2008, 19(12): 2297-2299.
Fang et al. "Photochemical Syntheses, Transformations, and Bioorthogonal Chemistry of trans-cycloheptene and sila Trans-cycloheptene Ag(1) Complexes", Chem Sci., 2018, 9, pp. 1953-1963.
Fu et al., "A Design Concept of Long-wavelength Fluorescent Analogs of Rhodamine Dyes: Replacement of Oxygen with Silicon Atom", Chem. Common., 2008, 1780-1782.
Grimm et al., "General Synthetic Method for Si-Fluoresceins and Si-Rhodamines", ACS Cent. Sci., 2017, 3, 975-985.
Gupta et al., "Diverse Redoxome Reactivity Profiles of Carbon Nucleophiles", J. Am. Chem Soc., Apr. 19, 2017; 139(15): 5588-5595.
Gupta et al., "Profiling the Reactivity of Cyclic C-nucleophiles Towards Electrophilic Sulfur in Cysteine Sulfenic Acid", Chem. Sci., 2016, 7, 400-415.
Gupta et al., "Sulfenic Acid Chemistry, Detection and Cellular Lifetime*", Biochimica et Biophysica Acta 1840, (2014), 847-875.
Jang et al., "Access to Faster Eukaryotic Cell Labeling With Encoded Tetrazine Amino Acids", J. Am. Chem Soc., Apr. 22, 2020; 142(16): 7245-7249.
Kang et al., "Tetrazine Ligation for Chemical Proteomics", Proteame Science (2017) 15:15, 13 pages.
Knall et al., "Inverse Electron Demand Diels-Alder (iEDDA)-initiated Conjugation: A (High) Potential Click Chemistry Scheme", Chem. Soc. Rev., 2013, 42, 5131-5142.
Kozma et al., "Bio-orthogonal Fluorescent Labelling of Biopolymers through Inverse-Electron-Demand Diels-Alder Reactions", ChemBioChem 2017, 18, 486-501.
Lambert et al., "Computationally Guided Discovery of a Reactive, Hydrophilic Trans-5-oxocene Dienophile for Bioorthogonal Labeling", Org. Biomol. Chem., 2017, 15, 6640-6644.
Lambert et al., "Installation of Minimal Tetrazines through Silver-Mediated Liebeskind-Srogl Coupling with Arylboronic Acids", J. Am. Chem. Soc., 2019, 141, 17068-17074.
Li et al., "Tetrazine-trans-Cyclooctene Ligation for the Rapid Construction of 18F Labeled Probes", Chem Commun. (Camb), Nov. 14, 2010; 46(42): 8043-8045.
Liang et al., "A Real-time, Click Chemistry Imaging Approach Reveals Stimulus-specific Subcellular Locations of Phospholipase D Activity", PNAS, Jul. 30, 2019, vol. 116, No. 31, 15453-15462.
Lindsley et al., "Preparation of Unsymmetrical 1,2,3,4,5-Tetrazines via a Mild Suzuki Cross Coupling Reaction", Org. Lett., 2017, 19, 5693-5696.

(56) References Cited

PUBLICATIONS

Liu et al., "Efficient 18F Labeling of Cysteine-Containing Peptides and Proteins Using Tetrazine-Trans-Cyclooctene Ligation", Molecular Imaging, vol. 12, No. 2, (Mar.-Apr. 2013): 121-128.

Meyer et al., "Click Chemistry and Radiochemistry: The First 10 Years", Bioconjug. Chem, Dec. 21, 2016; 27(12): 2791-2807.

Nikos et al., "Organelle Markers", Mater Methods, 2013;3:181, 19 pages.

Oliveira et al., "Inverse Electron Demand Diels-Alder Reactions in Chemical Biology", Chem. Soc. Rev., 2017, 46, 4895-4950.

Pigga et al., "Flow Photochemical Syntheses of trans-Cyclooctenes and trans-Cycloheptenes Driven by Metal Complexation", Isr. J. Chem, Mar. 2020; 60(3-4): 207-218.

Poole et al., "Fluorescent and Affinity-based Tools to Detect Cysteine Sulfenic Acid Formation in Proteins", Bioconjug. Chem, 2007; 18(6): 2004-2017.

Poole et al. "Strained Cycloalkynes as New Protein Sulfenic Acid Traps", J. Am. Chem. Soc., 2014, 136, 6167-6170.

Poole et al., "Synthesis of Chemical Probes to Map Sulfenic Acid Modifications on Proteins", Bioconjugate Chem. 2005, 16, 1624-1628.

Reddie et al., "A Chemical Approach for Detecting Sulfenic Acid-modified Proteins in Living Cells", Mol. Biosyst., Jun. 2008; 4(6): 521-531.

Royzen et al., "Total Synthesis of Hyacinthacine A2: Stereocontrolled 5-aza-cyclooctene Photoisomerization and Transannular Hydroamination with Planar-to-point Chirality Transfer", Chem Sci., 2011, 2, 2162-2165.

Ruvio et al., "Preclinical Evaluation of a Novel 18F-Labeled dTCO-Amide Derivative for Bioorthogonal Pretargeted Positron Emission Tomography Imaging", ACS Omega, 2020, 5, 4449-4456.

Schnell et al., "3-Bromotetrazine: Labeling of Macromolecules via Monosubstituted Bifunctional s-tetrazines", Chem Sci., 2020, 11, 3042-3047.

Scinto et al., "Dual-Reactivity trans-Cyclooctenol Probes for Sulfenylation in Live Cells Enable Temporal Control via Bioorthogonal Quenching", J. Am. Chem Soc., Jul. 17, 2019; 141(28): 10932-10937.

Se kut et al., "Expanding Room for Tetrazine Ligations in the In Vivo Chemistry Toolbox", Curr. Opin. Chem Biol., Oct. 2013; 17(5): 761-767.

Selvaraj et al., "Improved Metabolic Stability for 18F PET Probes Rapidly Constructed via Tetrazine trans-Cyclooctene Ligation", Bioconjug. Chem, Mar. 18, 2015; 26(3): 435-442.

Selvaraj et al., "trans-Cyclooctene—A Stable, Voracious Dienophile for Bioorthogonal Labeling", Curr. Opin. Chem Biol., Oct. 2013; 17(5): 753-760.

Sletton et al., "Bioorthogonal Chemistry: Fishing for Selectivity in a Sea of Functionality", Angew Chemie Int. Ed. Engl., 2009, 48(38): 6974-6998.

Taylor et al., "Design and Synthesis of Highly Reactive Dienophiles for the Tetrazine-trans-Cyclooctene Ligation", J. Am. Chem Soc., Jun. 29, 2011; 133(25): 9646-9649.

Trout et al., "Rapid Bioorthogonal Chemistry Turn-on through Enzymatic or Long Wavelength Photocatalytic Activation of Tetrazine Ligation", J. Am. Chem Soc., May 11, 2016; 138(18): 5978-5983.

Wang et al., "Conformationally Strained trans-Cyclooctene (sTCO) Enables the Rapid Construction of 18F-PET Probes via Tetrazine Ligation", Theranostics, 2016, vol. 6, Issue 6, 887-895.

Wang et al., "Hydrophilic 18 F-labeled trans-5-oxocene (oxoTCO) for Efficient Construction of PET Agents with Improved Tumor-to-background Ratios in Neurotensin Receptor (NTR) imaging", Chem Commun., 2019, 55, 2485.

Weissleder et al., "BODIPY-Tetrazine Derivatives as Superb right Bioorthogonal Turn-on Probes", Angew Chem Int. Ed. Engl., Jul. 1, 2013; 52, 1-5.

Wombacher et al., "Green—to far-red-emitting Fluorogenic Tetrazine Probes—Synthetic Access and No-wash Protein Imaging Inside Living Cells", Chem Sci., 2017, 8, 1506-1510.

Wu et al., "Advances in Tetrazine Bioorthogonal Chemistry Driven by the Synthesis of Novel Tetrazines and Dienophiles", Acc. Chem Res., May 15, 2018; 51(5): 1249-1259.

\* cited by examiner

A *Common Approach*

B *Cross-Coupling Approach*

C *Installation of tetrazines from carboxylic esters*

REAGENTS AND METHODS FOR TETRAZINE SYNTHESIS

CROSS REFERENCE TO RELATED APPLICATION

This application claims priority from U.S. Provisional Application No. 63/086,132, filed Oct. 1, 2020, the disclosure of which is incorporated herein by reference in its entirety for all purposes.

STATEMENT REGARDING FEDERALLY SPONSORED RESEARCH

This invention was made with government support under Grant Nos. GM132460, P20GM104316, P30GM110758, S10RR026962, and S10OD016267 awarded by National Institute of Health and Grant Nos. CHE-0840401, CHE-1229234, and CHE-1048367 awarded by the National Science Foundation. The government has certain rights in the invention.

BACKGROUND OF THE INVENTION

Bioorthogonal reactions have become increasingly important to chemistry and biology since the term was initially coined early in this century. The bioorthogonal reactions of tetrazines have become widely used in various fields, including natural product synthesis, cargo delivery, genetic code expansion, fluorogenic labeling, radiochemistry, coordination chemistry, and material science. In particular, the bioorthogonal reactions of tetrazines have emerged as important tools for chemical biology over the last decade. Cycloadditions involving a range of dienophiles including trans-cyclooctenes, cyclopropenes and norbornenes have been developed as tools for a variety of applications including cellular labeling, in vivo imaging, unnatural amino acid mutagenesis, targeted drug delivery, proteomics, as well as in the fabrication and patterning of biomaterials. Additionally, tetrazines have found applications in explosives technology, in metal-organic frameworks and in natural product synthesis.

Coupled to the growing utility of tetrazine-based bioorthogonal chemistry is the need for mild, safe and general methods of introducing tetrazine groups to complex molecules. Carboxylic esters are ubiquitous functional groups that have been used as handles for the introduction of preformed tetrazine groups via amide bond forming reactions, as represented in FIG. 1A. For this approach, linkers are required which can add bulk and hydrophilicity to the conjugate. A major limitation of this approach is that large and hydrophobic linkers can negatively impact the physiochemical properties of an attached ligand.

Hence, complementary new methods for the introduction of tetrazines to small molecules are needed, which may further advance their potential as bioorthogonal probes and chemical reporters. However, there are currently few methods for the direct attachment of tetrazine fragments to target molecules. Additionally, many approaches to tetrazine synthesis undesirably produce high-nitrogen byproducts and involve harsh reaction conditions that can limit scalability and scope.

Classical tetrazine synthesis involves the condensation of Pinner salts or nitriles with excess hydrazine followed by oxidation. Catalytic nitrile condensation with neat anhydrous hydrazine, most notably with $Zn(OTf)_2$ and $Ni(OTf)_2$, has expanded access to unsymmetrical tetrazines. Further, thiol catalysis has been shown to promote tetrazine synthesis from nitriles using hydrazine hydrate. The most practiced procedures utilize excess acetonitrile or formamidine acetate and produce volatile tetrazine byproducts with high-nitrogen content (FIG. 2B). Recently, a sulfur-catalyzed reaction of nitriles with hydrazine hydrate and dichloromethane has been described for 3-aryltetrazine synthesis. A safety consideration for all of these procedures is the direct addition of an oxidant to a reaction mixture containing hydrazine. While these methods for preparing tetrazines have been transformative to the field of bioorthogonal chemistry, there is a continuing need for safer alternatives with complementary functional group compatibility.

Tetrazines have been used in a limited number of metal catalyzed CH activations, cross-couplings, and in Heck reactions with in situ generated 3-vinyl-6-methyltetrazine. Recently, 3-amino-6-chlorotetrazines have been cross-coupled under Suzuki conditions (FIG. 2C). Liebeskind-Srogl cross-couplings have also been reported with 3-amino-6-thiomethyltetrazines at 200° C. (FIG. 2C). The 3-aminotetrazine products of these methods are valuable in medicinal chemistry, but their utility in bioorthogonal chemistry is attenuated by the deactivating amino substituent. The tetrazines most useful to bioorthogonal chemistry are also sensitive to basic conditions, making them incompatible with many conditions commonly associated with cross-coupling chemistry. Previously, there was a single method of cross-coupling to introduce a 3-methyltetrazine fragment via Stille coupling with 3-bromo-6-methyltetrazine, which is prepared from 3-hydrazino-6-methyltetrazine (FIG. 2C).

While these methods for tetrazine synthesis have been enabling, there is a continuing need to broaden the types of precursors that allow for the direct installation of tetrazines with improved functional group tolerance.

SUMMARY OF THE INVENTION

Disclosed herein is the installation of tetrazines through cross coupling of arylboronic acids with a new class of thio-substituted tetrazine reagents that have been tested for safety (FIG. 1B).

Also disclosed herein is a method to directly introduce the 6-methyltetrazin-3-yl group to arylboronic acids through the first example of an Ag-mediated Liebeskind-Srogl reaction (FIG. 1B). Cross-coupling with arylboronic acids and a thio-substituted tetrazine proceeds under mild conditions to introduce a linker-free tetrazine functionality.

Also disclosed herein is a new strategy for an one-pot synthesis of 3-thiomethyltetrazines from carboxylic esters of commercially available 3-methyl-3-oxetanemethanol. The compounds serve as versatile intermediates for the divergent synthesis of a broad range of functionalized tetrazines via Pd-catalyzed cross-coupling and in the first example of catalytic reduction of thio-substituted tetrazines to form monosubstituted tetrazines (FIG. 1C). This 'carboxylate-to-tetrazine' strategy complements known approaches of tetrazine construction, tolerates a range of heterocycles and functional groups, and generates classes of tetrazines that are most useful to bioorthogonal chemistry.

According to an aspect of the present invention, the thio-substituted tetrazine compound 30 is prepared by the described method:

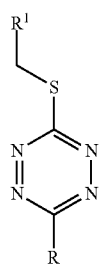
(30)

wherein R is hydrogen, an alkyl group, a substituted alkyl group, an aryl group, a substituted aryl group, a heteroaryl group or a substituted heteroaryl group, and wherein $R^1$ is an aryl group, a substituted aryl group, a heteroaryl group, or a substituted heteroaryl group.

In an embodiment, R and $R^1$ are the same and in another embodiment, R and $R^1$ are different from each other.

In embodiments of the compound 30, $R^1$ is selected from the following structures:

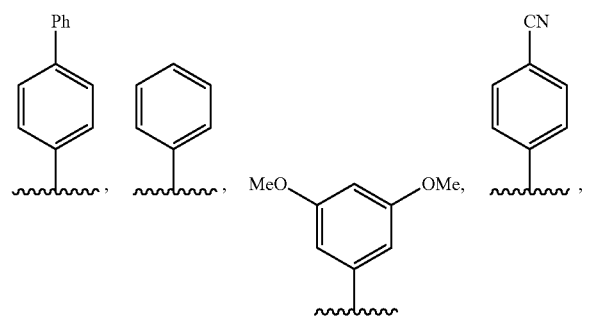

In an aspect, the compound 30 has one of the following structures:

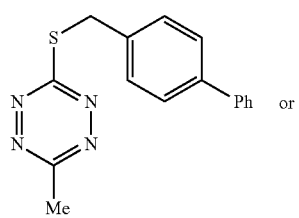
(32)

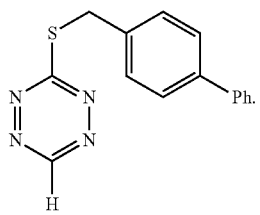
(34)

In another aspect, the tetrazine compound 60 is prepared by the described method:

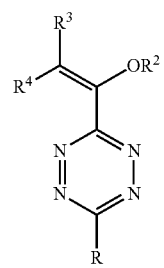
(60)

wherein R is hydrogen, an alkyl group, a substituted alkyl group, an aryl group, a substituted aryl group, a heteroaryl group or a substituted heteroaryl group, wherein $R^2$ is hydrogen, an alkyl group, a substituted alkyl group, an aryl group, a substituted aryl group, a cycloalkyl group, a substituted cycloalkyl group, a heterocyclic group, or a substituted heterocyclic group, and wherein $R^3$ and $R^4$ are independently H, an alkyl group, a cycloalkyl group, or a heterocyclic group.

In an embodiment of the tetrazine compound 60, $R^3$ and $R^4$ are independently H or C1-C4 alkyl group.

In yet another aspect, the tetrazine compound 70 is prepared by the described method:

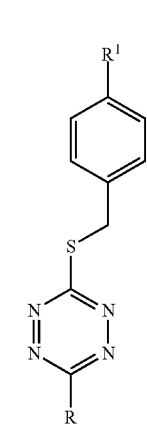
(70)

wherein $R^1$ is an aryl group, a substituted aryl group, a heteroaryl group, or a substituted heteroaryl group.

In an aspect, there is a compound having one of the following structures:

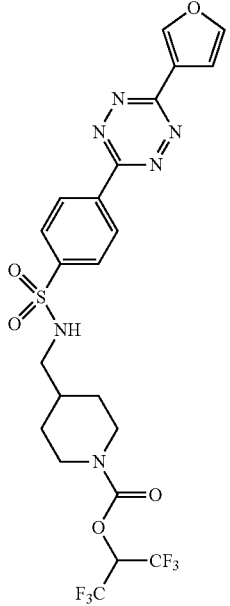

100a

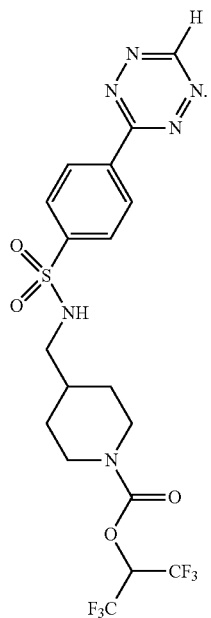

100c

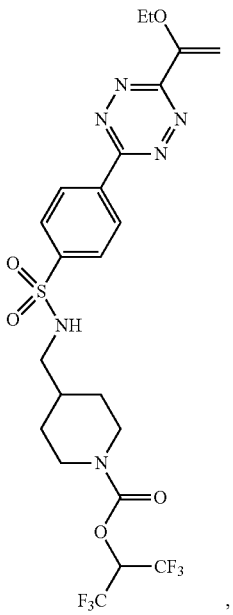

100b

, or

In an embodiment, at least one of the compounds 100a, 100b, and 100c is used as a probe in the study of monoacylglycerol lipase (MAGL), a serine hydrolase involved in endocannaboid signaling.

In an aspect, there is a method for converting an oxetanyl ester 15 to a thio-substituted tetrazine 30, the method comprising contacting the oxetanyl ester 15 with a Lewis base and a S-isothiocarbonohydrazidium salt 20 to form a thio-substituted tetrazine 30, as shown below in reaction scheme (1):

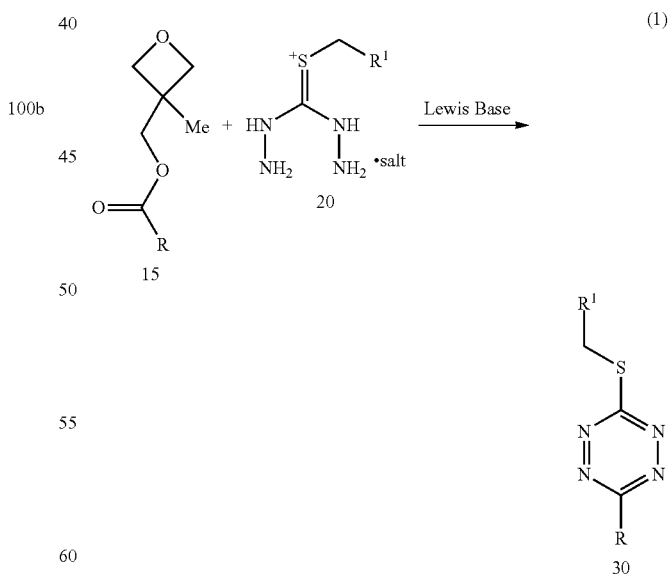

(1)

wherein R is hydrogen, an alkyl group, a substituted alkyl group, an aryl group, a substituted aryl group, a heteroaryl group or a substituted heteroaryl group; and wherein $R^1$ is an aryl group, a substituted aryl group, a heteroaryl group, or a substituted heteroaryl group.

Any suitable Lewis base can be used in the above scheme (1), including, but not limited to, pyridine, triethylamine, potassium carbonate, cesium carbonate, or potassium tert-butoxide.

In an embodiment, S-isothiocarbonohydrazidium salt is a halide, such as for example S-isothiocarbonohydrazidium iodide. However, any suitable salt may be used, such as, for example, S-isothiocarbonohydrazidium chloride, S-isothiocarbonohydrazidium bromide, S-isothiocarbonohydrazidium hexafluorophosphate, S-isothiocarbonohydrazidium tetrafluoroborate, S-isothiocarbonohydrazidium tetraphenylborate.

In various non-limiting embodiments, the R group is substituted with a functional group selected from an aryl ether, a protected amino acid such as tert-butyloxycarbonyl (Boc) amino, nitro, alkoxy, halo, nitrile, ester, heterocycle, optionally substituted pyridine or phenyl, biotin, or fluoroborondipyrromethene (BODIPY-FL).

In various non-limiting embodiments, the R group of the thio-substituted tetrazine 30 is selected from any one of the formulae 3a to 3w, as shown in FIG. 9.

In an aspect, there is a method for converting the thio-substituted tetrazine 30 to a mono-substituted tetrazine 4, the method comprising reducing the thio-substituted tetrazine 30 in the presence of a catalyst and a reductant, followed by treatment with an oxidant to form the mono-substituted tetrazine 4, as shown below in reaction scheme (2):

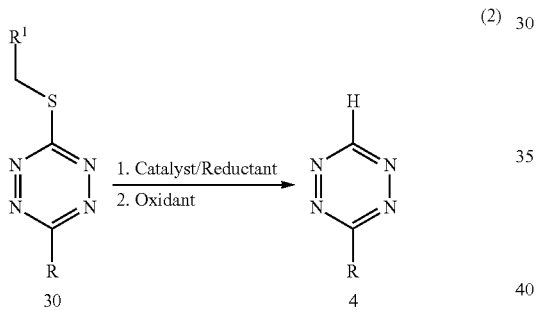

(2)

In various embodiments, the catalyst is a Pd-containing catalyst, a Pt-containing catalyst, or a Ni-containing catalyst.

Suitable Pd-containing catalysts, Pt-containing catalysts or Ni-containing catalysts for use in the above scheme (2) include, but are not limited to, $PdCl_2$, $Pd/CPd(OAc)_2$, $Pd_2(dba)_3$, $PtCl_2$, Pt/C, or Ra—Ni.

Suitable reductants for use in the above scheme (2) include, but are not limited to, silanes, formic acid, formate salts, or hydrogen gas. Suitable examples of silanes include, but are not limited to, triethylsilane, triphenylsilane, diphenylsilane, and the like.

Suitable examples of an oxidant for use in the above scheme (2) include, but are not limited to, phenyliodonium diacetate (PIDA), $NaNO_2$, isoamyl nitrite, quinones, $FeCl_3$, or a $Cu(OAc)_2$ in air, or air alone.

In an embodiment of the method for converting the thio-substituted tetrazine 30 to a mono-substituted tetrazine 4, the conversion reaction in scheme (2) is carried out as a one pot synthesis, whereby the intermediate dihydrotetrazine is not isolated, but is directly converted in the same flask to the tetrazine product.

In a specific embodiment of the conversion reaction, the catalyst is a palladium-containing catalyst, the reductant is triethylsilane, and the oxidant is phenyliodonium diacetate (PIDA).

In an aspect, the method depicted in scheme (2) comprises converting the thio-substituted tetrazine 30 to a mono-substituted tetrazine compound 4 having one of the structures from 4a to 4m, as shown in FIG. 10.

In an aspect, a method is described for catalytically converting the thio-substituted tetrazine 30 to a di-substituted tetrazine 50, the method comprising reacting thio-substituted tetrazine 30 as an electrophile in a silver-mediated, catalyzed coupling with a substituted boronic acid to form the di-substituted tetrazine 50, as shown below in reaction scheme (3):

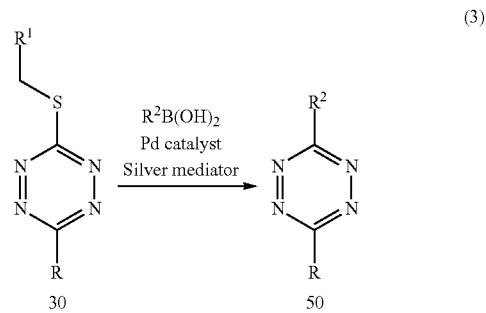

(3)

wherein R is selected from hydrogen, an alkyl group, a substituted alkyl group, an aryl group, a substituted aryl group, a heteroaryl group or a substituted heteroaryl group, wherein $R^1$ is selected from an aryl group, a substituted aryl group, a heteroaryl group, or a substituted heteroaryl group, wherein $R^2$ is selected from hydrogen, an alkyl group, a substituted alkyl group, an aryl group, a substituted aryl group, a cycloalkyl group, a substituted cycloalkyl group, a heterocyclic group, or a substituted heterocyclic group, and wherein the catalyst is a Pd-containing catalyst.

Any suitable silver compound may be used in the reaction (3), including, but not limited to, $Ag_2O$, $Ag_2CO_3$, $Ag_3PO_4$, Ag(salicylate), $AgBF_4$, Ag(acetate), $AgPF_6$, or Ag(trifluoromethanesulfonate).

In an embodiment, the Pd-containing catalyst is at least one of:

(i) Pd ligand combination of 1,1'-bis(diphenylphosphino)ferrocene]dichloropalladium(II) ($Pd(dppf)Cl_2$), $Pd(dppf)Cl_2$ and $PdI_2$ with 1,1'-Bis(diisopropylphosphino)ferrocene (DiPPF);

(ii) $Pd(OAc)_2$, $Pd_2(DBA)_3$, $Pd(COD)(CH_2TMS)_2$, CyJohnPhos/$Pd_2(DBA)_3$, $PdCl_2$(XantPhos), $PdCl_2$(N-XantPhos), $Pd(XantPhos)_2$, $Pd(N-XantPhos)_2$, $PdCl_2(PPh_3)$, $Pd(PPh_3)_4$, Pd-PEPPSI-IPr, Pd—PEPPSI-SiPr, CyJohnphos Pd G4;

(iii) $Pd_2DBA_3$ in combination with $PPh_3$, $AsPh_3$, trifurylphosphine, diphenyl-(2-pyridyl)phosphine, tri-(p-methoxyphenyl)phosphine, tri-otolylphosphine, Cy-JohnPhos, SPhos, DavePhos, JohnPhos, XPhos, BrettPhoss, MetBuXPhos, RuPhos, APhos, MePhos, TrixiePhos, or Ph-DavePhos, and (iv) PdI$_2$, PdCl$_2$ or PdBr$_2$ in combination with the following ligands:
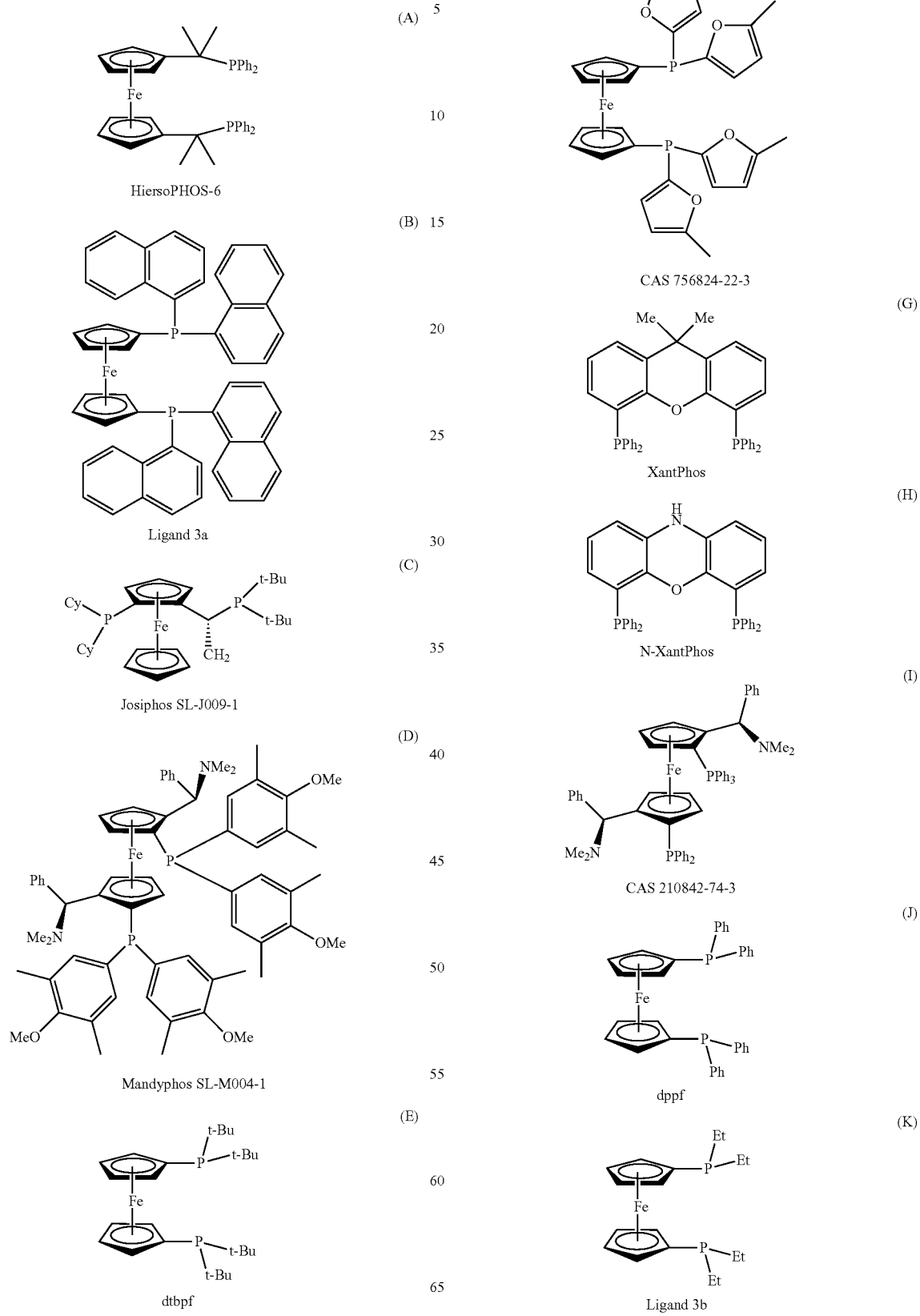

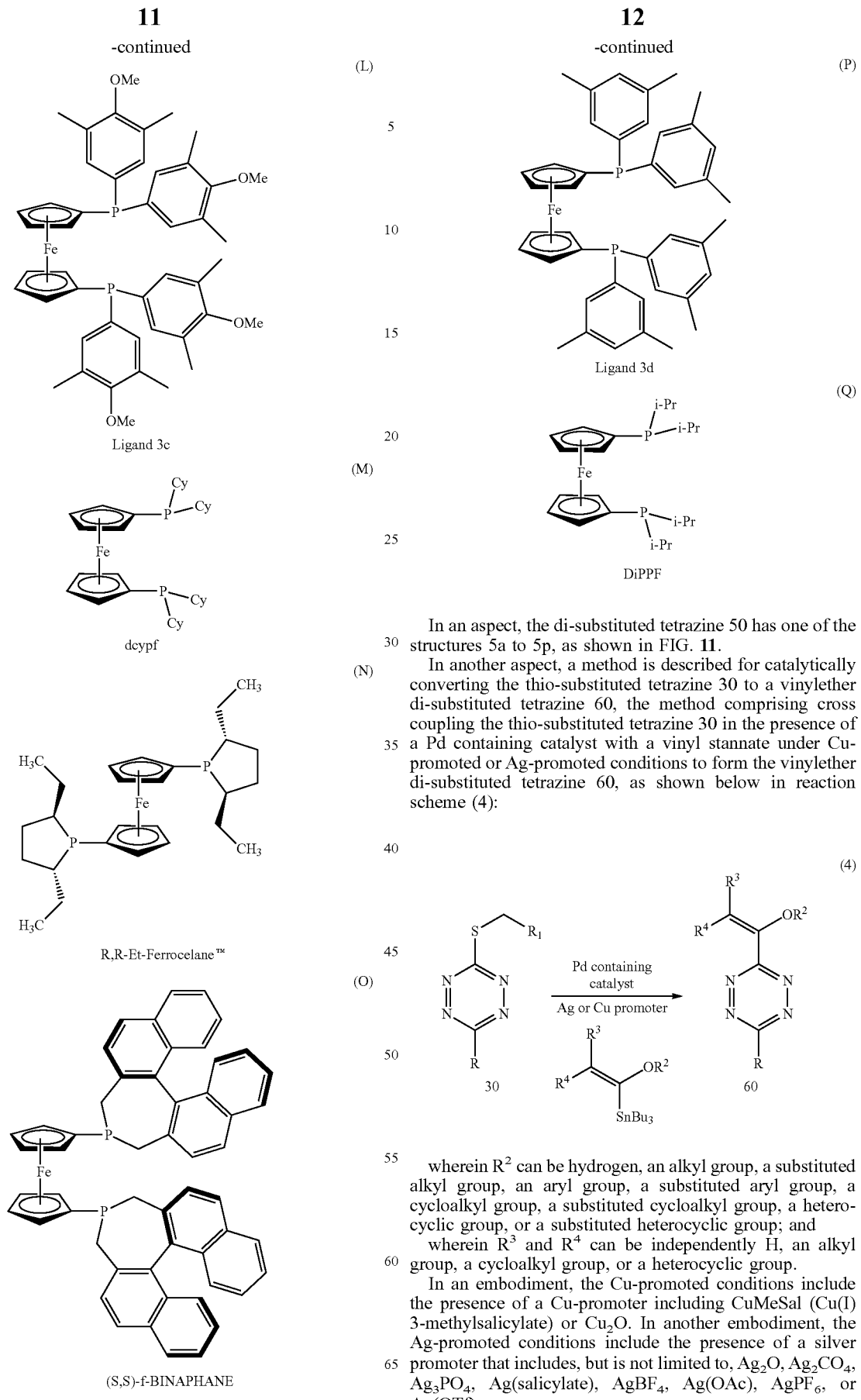

In an aspect, the di-substituted tetrazine 50 has one of the structures 5a to 5p, as shown in FIG. 11.

In another aspect, a method is described for catalytically converting the thio-substituted tetrazine 30 to a vinylether di-substituted tetrazine 60, the method comprising cross coupling the thio-substituted tetrazine 30 in the presence of a Pd containing catalyst with a vinyl stannate under Cu-promoted or Ag-promoted conditions to form the vinylether di-substituted tetrazine 60, as shown below in reaction scheme (4):

wherein $R^2$ can be hydrogen, an alkyl group, a substituted alkyl group, an aryl group, a substituted aryl group, a cycloalkyl group, a substituted cycloalkyl group, a heterocyclic group, or a substituted heterocyclic group; and wherein $R^3$ and $R^4$ can be independently H, an alkyl group, a cycloalkyl group, or a heterocyclic group.

In an embodiment, the Cu-promoted conditions include the presence of a Cu-promoter including CuMeSal (Cu(I) 3-methylsalicylate) or $Cu_2O$. In another embodiment, the Ag-promoted conditions include the presence of a silver promoter that includes, but is not limited to, $Ag_2O$, $Ag_2CO_4$, $Ag_3PO_4$, Ag(salicylate), $AgBF_4$, Ag(OAc), $AgPF_6$, or Ag(OTf).

In yet another embodiment, any suitable Pd-containing catalyst, as disclosed hereinabove may be used.

In an aspect, the vinylether di-substituted tetrazine 60 has one of the structures 6a to 6e, as shown in FIG. 12.

In an embodiment, a method is described for installing a 6-methyltetrazinyl-3-yl group through a Ag-mediated Liebeskind-Srogl cross-coupling, as shown above in Scheme (3). A combination of a Pd-containing catalyst and Ag mediator was found to be uniquely effective for coupling 3-thioalkyl-6-methyltetrazines with arylboronic acids. Safety-testing guided the design of the reactive substrate b-Tz 1a, which can be synthesized from commercially available materials on decagram scale in 47% overall yield, as shown in FIG. 3. Cross-coupling of b-Tz with boronic acids proceeds under mild conditions with broad functional group tolerance. Alternatively, 3-(methylthio)-6-phenyl-tetrazine 3 undergoes cross-coupling with arylboronic acids to give 3,6-diaryltetrazines 4a, as shown in FIG. 5B.

In an aspect, application of the methods described herein to the synthesis of chemical biology tools has been demonstrated. As an example, a BODIPY-tetrazine conjugate was synthesized in a 78% yield, which is substantially higher than what is possible using traditional hydrazine-based synthesis.

In another embodiment, a one-pot method as shown in Scheme (1) is described for the conversion of (3-methyl-oxetan-3-yl)methyl carboxylic esters into 3-thiomethyltetrazines that can subsequently serve as a platform for divergent tetrazine synthesis via Pd-catalyzed cross-coupling and the first example of monosubstituted tetrazine synthesis via catalytic thioether reduction. The utility of the method has been demonstrated through the synthesis of aliphatic, aromatic, and heterocyclic substituted tetrazines and to the development and biological evaluation of a new series of tetrazine-coupled probes for monoacylglycerol lipase (MAGL).

In an embodiment, a tetrazine-functionalized probe for MAGL was synthesized in high yield and was shown to covalently label endogenous MAGL with good selectivity in live cells. It is anticipated that methods for introducing tetrazines to chemical probes will serve as an important tool for studying protein targets at endogenous levels in their native environments.

DETAILED DESCRIPTION OF THE INVENTION

Figure 1A:
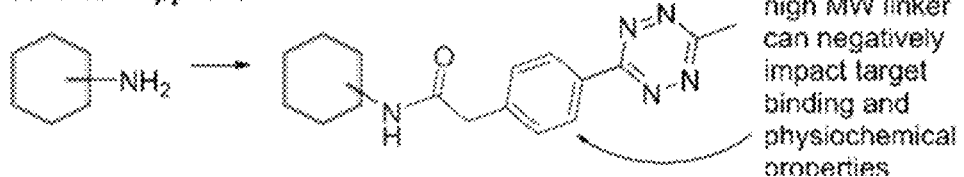
FIG. 1A (Prior Art): The most common approach to tetrazine conjugation uses bulky linkers to attach molecules of interest.
Figure 1B:
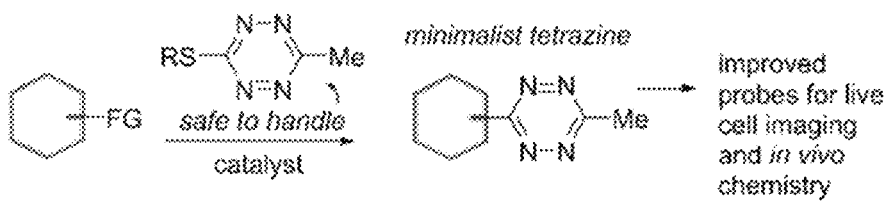
FIG. 1B: Cross-coupling approach according to embodiments of the present invention.
Figure 1C:
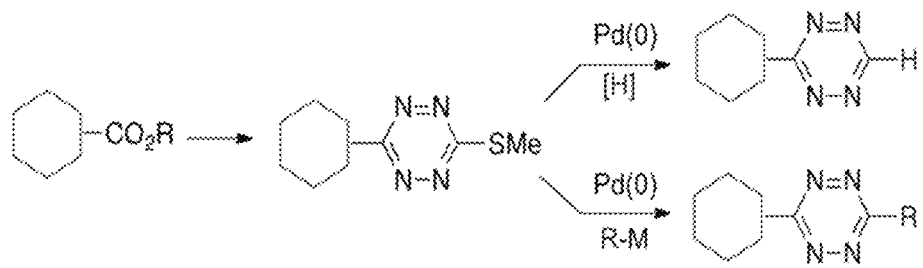
FIG. 1C: Direct approach for the introduction of a tetrazine functionality from carboxylic ester precursors according to embodiments of the present invention.
Figure 2A:
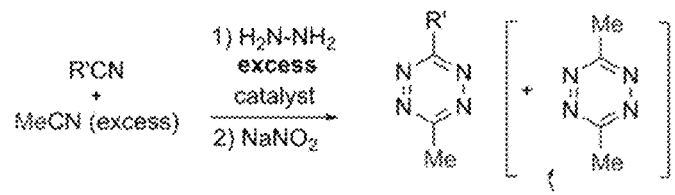
FIG. 2A (Prior Art): Unsymmetrical tetrazine synthesis based on condensation of nitriles with hydrazine.
Figure 2B:
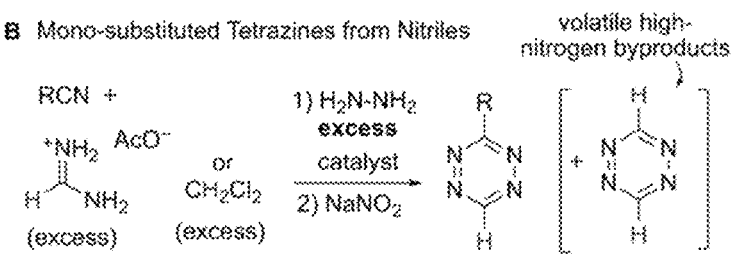
FIG. 2B (Prior Art): Mono-substituted tetrazine synthesis based on condensation of nitriles or Pinner reagents with hydrazine.
Figure 2C:
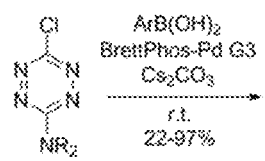
FIG. 2C (Prior Art): Cross-couplings of tetrazine electrophiles with arylboronic acids have been limited to N-substituted tetrazines, which are deactivated for bioorthogonal chemistry applications. Stille coupling has been used to couple 3-bromo-6-methyltetrazine to fluorophores (Lindsley et al., Org. Lett. 2017, 19, 5693-5696; Suzenet et al., Synlett 2007, 2007, 204-210; Wombacher et al., Chem. Sci. 2017, 8, 1506-1510).
Figure 2C:
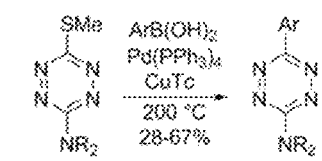
Figure 2C:
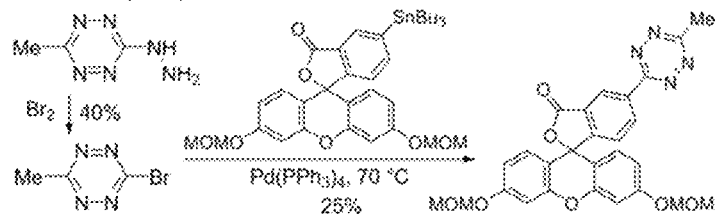

As used herein, the term "alkyl group" refers to a saturated aliphatic hydrocarbon group such as a methyl group, an ethyl group, an n-propyl group, an isopropyl group, an n-butyl group, a sec-butyl group, or a tert-butyl group, and the alkyl group may have a substituent or no substituent. The term "substituted alkyl group" refers to an alkyl group bonded to a substituent, the additional substituent is not particularly limited. Examples of the additional substituent include an alkyl group, a halogen, a cycloalkyl group, a heterocyclic group, an aryl group, and a heteroaryl group, and the same holds true in the description below. An alkyl group substituted with a halogen is also referred to as a haloalkyl group. The number of carbon atoms in the alkyl group is not particularly limited, and is preferably in the range of 1-20, or such as 1-15, or such as 1-10.

As used herein, the term "cycloalkyl group" refers to a saturated alicyclic hydrocarbon group such as a cyclopropyl group, a cyclobutyl group, a cyclopentyl group, a cyclohexyl group, a cycloheptyl group, a norbornyl group, or an adamantyl group, and the cycloalkyl group may have a substituent or no substituent. The number of carbon atoms in the alkyl group moiety is not particularly limited, and is preferably in the range of 3-20, or such as 3-15, or such as 3-10.

As used herein, the term "heterocyclic group" refers to an aliphatic ring having an atom other than carbon in the ring, such as a piperazine ring, a pyrrolidine ring, a pyrrolidone ring, an azetidine ring, a morpholine ring, a dioxane ring, a tetrahydrofuran ring, an oxirane ring, a pyran ring, a piperidine ring, or a cyclic amide, and the heterocyclic group may have a substituent or no substituent. The number of carbon atoms in the heterocyclic group is not particularly limited, and is preferably in the range of 3-20, or such as 3-15, or such as 3-10.

As used herein, the term "aryl group" refers to an aromatic hydrocarbon group such as a phenyl group, a biphenyl group, a naphthalene group, or a terphenyl group. The aryl group may have a substituent or no substituent. The term "substituted aryl group" refers to an aryl group bonded to a substituent, the additional substituent is not particularly limited. An aryl group substituted with a halogen is also referred to as a haloaryl group. The number of carbon atoms in the aryl group is not particularly limited, and is preferably in the range of 6-40, or such as 6-30, or such as 6-20.

In a substituted phenyl group having two adjacent carbon atoms each having a substituent, the substituents may form a ring structure. The resulting group may correspond to any one or more of a "substituted phenyl group", an "aryl group having a structure in which two or more rings are condensed", and a "heteroaryl group having a structure in which two or more rings are condensed" depending on the structure.

As used herein, the term "heteroaryl group" refers to a cyclic aromatic group having one or a plurality of atoms other than carbon in the ring, such as a pyridyl group, a furanyl group, a thiophenyl group, a quinolinyl group, an isoquinolinyl group, a pyrazinyl group, a pyrimidyl group, a pyridazinyl group, a pyrrolyl group, an imidazolyl group, an oxazolyl group, an isoxazolyl group, a thiazolyl group, an isothiazolyl group, an indazolyl group, a benzofuranyl group, a benzothiophenyl or a triazinyl group. The heteroaryl group may have a substituent or no substituent. The number of carbon atoms in the heteroaryl group is not particularly limited, and is preferably in the range of 2-30, or such as 2-20, or such as 4-10.

As used herein, the term "thio-substituted" refers to a group in which an oxygen atom is substituted with a sulfur atom and the term "alkylthio group" refers to a group where an ether bond in an alkoxy group substituted with a sulfur atom. The hydrocarbon group in the alkylthio group may have a substituent or no substituent.

The number of carbon atoms in the alkylthio group is not particularly limited, and is preferably in the range of 1-20, or such as 1-15, or such as 1-10.

As used herein, the term "halide" refers to an ion selected from fluoride, chloride, bromide, and iodide.

As used herein, the term "acyl group" refers to a functional group having an alkyl group, a cycloalkyl group, an alkenyl group, an alkynyl group, an aryl group, or a heteroaryl group bonded via a carbonyl group, such as an acetyl group, a propionyl group, a benzoyl group, or an acrylyl group, and these substituents may be further substituted. The number of carbon atoms in the acyl group is not particularly limited, and is 1-20, or such as 1-15, or such as 1-10.

Any suitable substituent may be used in a substituted alkyl group, a substituted aryl group, or a substituted heteroaryl group, including, but not limited to, an alkyl group, a halogen, an aryl group, and a heteroaryl group, as defined hereinabove, Boc-amino group, protected amino acids, nitro group, methoxy group, nitrile group, ester group, heterocycles, biotin, and BODIPY-FL.

Figure 3:
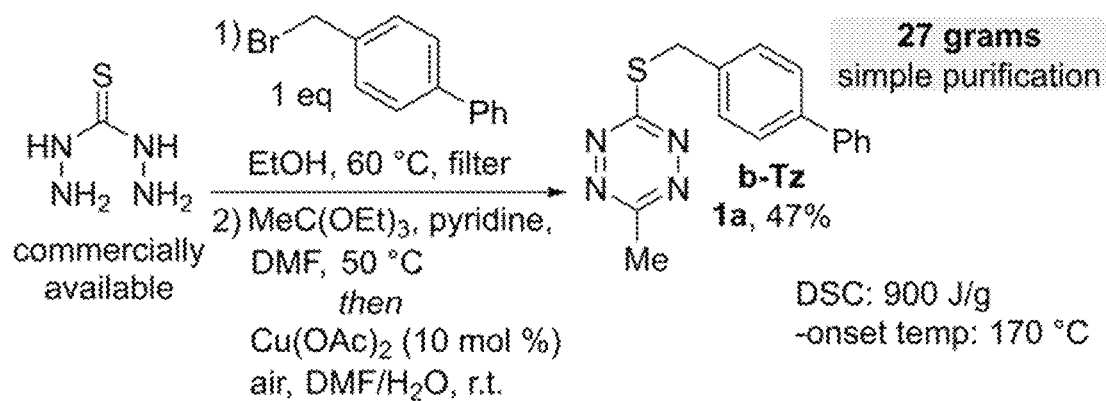
FIG. 3: Decagram synthesis and thermal stability of b-Tz 1a, according to embodiments of the present invention.

Tetrazines through silver-mediated Liebeskind-Sroql couplinq with arylboronic acids The inventors found that 3-thioalkyl-6-methyltetrazines were useful in the preparation of 3-aryl-6-methyltetrazines, which are attractive bioorthogonal reagents due to their balance of rapid kinetics toward dienophiles and high stability in the cellular environment. By modifying a method for the synthesis of 3-thiomethyl-6-methyltetrazine, compounds 1a-g were prepared with the rationale that a sacrificial S-benzylic substituent could serve to tune cross-coupling efficiency and improve the safety profile of the tetrazine. As shown in FIG. 3, the 4-phenylbenzyl derivative b-Tz 1a was prepared on large scale via alkylation of commercially available thiocarbohydrazide with 4-bromomethylbiphenyl followed by one-pot condensation with triethylorthoacetate and a novel $Cu(OAc)_2$-catalyzed air-oxidation of the dihydrotetrazine intermediate. The b-Tz product was isolated on a 27-gram scale with a 47% overall yield after simple silica plug filtration and is a bench-stable crystalline solid (m.p. 141° C.). The differential scanning calorimetry (DSC) profile of b-Tz had an onset temperature of 170° C. and a transition enthalpy of 900 J/g and was not flagged as potentially shock sensitive or explosive by a modified Yoshida correlation.

Figure 4:
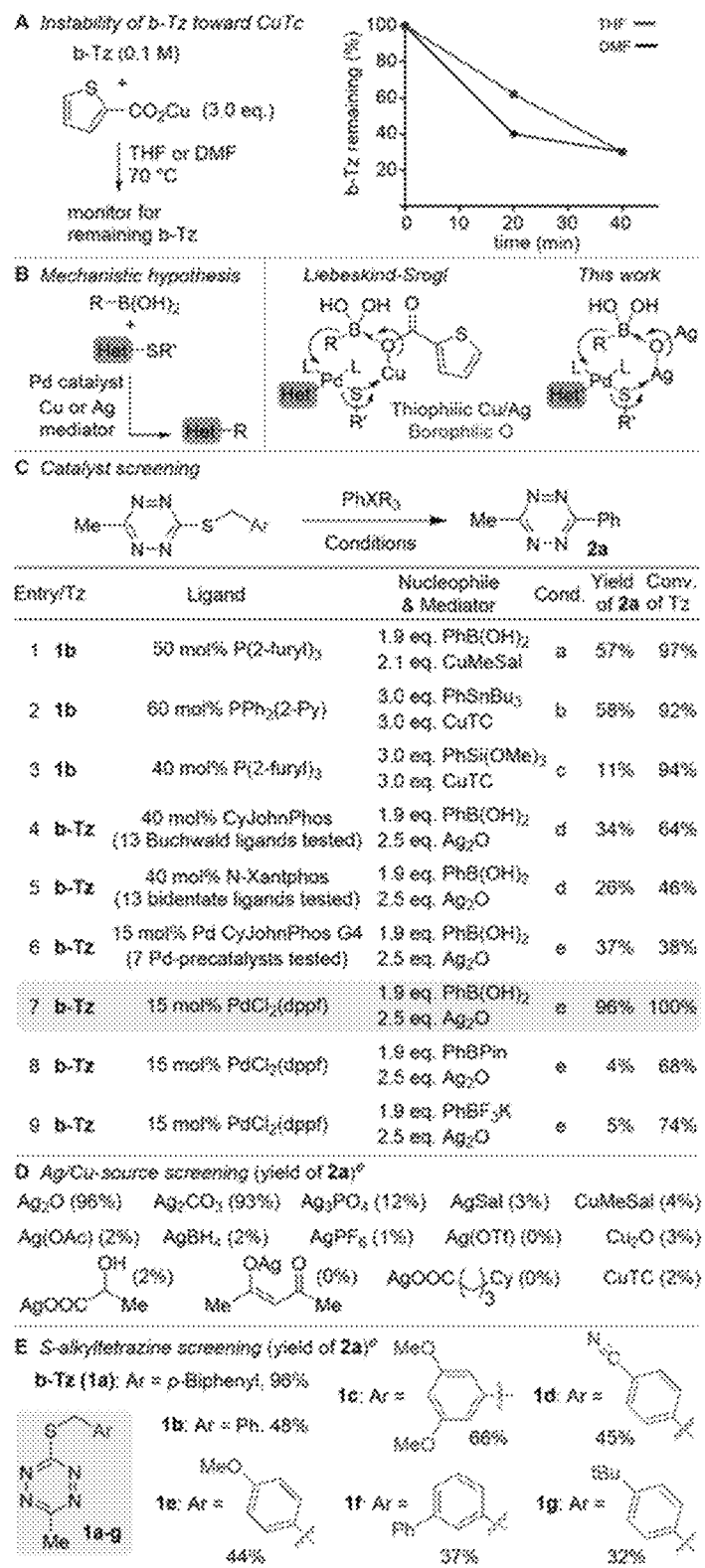
FIG. 4: (A) Rapid decomposition of b-Tz in CuTC. (B) Proposed Liebeskind-Srogl transmetallation mechanism. (C) Optimized Pd-catalyzed cross-coupling of tetrazines b-Tz and 1b with various nucleophiles (yields determined by GC w/dodecane as a standard). Conditions: (a) $Pd_2dba_3$ (12.5 mol %), $Cs_2CO_3$ (3.0 eq.), dioxane, 70° C., 90 min. (b) [Pd(allyl)Cl]2 (10 mol %), THF, 70° C., 2 h. (c) $Pd(OAc)_2$ (10 mol %), TBAF (1.0 eq.), dioxane, 70° C., 2.5 h. (d) $Pd_2dba_3$ (15 mol %), DMF, 60° C., 20 h. (e) DMF, 60° C., 20 h. (D) Screening of silver(I) and copper(I) additives for condition e. (E) Screening of tetrazines 1a-g under condition e.

After extensive screening, it was found that copper(I)-mediated Liebeskind-Srogl conditions promoted cross-coupling of benzylic thioether tetrazines with $PhB(OH)_2$, $PhSnBu_3$, and $PhSi(OMe)_3$ (FIG. 4C entries 1-3). Under Cu-mediated conditions, tetrazine 1b was a preferred substrate; however, the generality under these conditions was modest. The rapid consumption of tetrazine starting materials during the reaction led the inventors to test if Cu(I) was causing decomposition of the reagent. It was found that heating b-Tz with Cu(I)-thiophene carboxylate (CuTC) at 70° C. resulted in rapid decomposition of the b-Tz and produced 4-phenylbenzaldehyde as the only identifiable side product (FIG. 4A).

Copper has been proposed to promote the Liebeskind-Srogl reaction by facilitating transmetallation as shown in FIG. 4B. It was hypothesized that silver(I) salts might be similarly capable as promotors, whereby transmetallation would be promoted in a dual role by the thiophilic capture of benzylic thiolate by silver and the borophilic capture by oxygen. Ag(I) additives have been shown to promote Rh-catalyzed coupling of arylboronic acids with arylmethylsulfides bearing ortho-directing groups, and the Cu-catalyzed coupling of arylboronic acids with aromatic thioesters. It is believed that a Ag-mediated variation of the Liebeskind-Srogl reaction has not heretofore been reported. After extensive optimization (FIG. 4C entries 4-7), PdCl$_2$(dppf) (15 mol %) was found to be especially effective for cross-coupling of 3-thioalkyl-6-methyltetrazines with arylboronic acids in polar, aprotic solvents (such as DMF, DMSO) at 60° C. A screening of silver(I) additives revealed Ag$_2$O as the most general promotor, although Ag$_2$CO$_3$ was also effective (FIG. 4D). Substitution of Ag$_2$O by Cu$_2$O gave only trace product formation. Arylboronic acids are particularly effective nucleophiles, whereas PhBF$_3$K and PhBPin were both less effective under identical reaction conditions (FIG. 4C entries 8-9). Further, a series of 3-arylmethyl-6-methyltetrazines 1a-g were evaluated as coupling partners (FIG. 4E). Of these, the 4-phenylbenzyl derivative b-Tz 1a was identified as the substrate with both the best cross-coupling yield as well as the most favorable thermal stability. The cost of Ag$_2$O (currently <$3/g) is similar to the common promotor CuTC, and is minor in the context of bioorthogonal chemistry reagents which are typically required only in small amounts.

Figure 5:
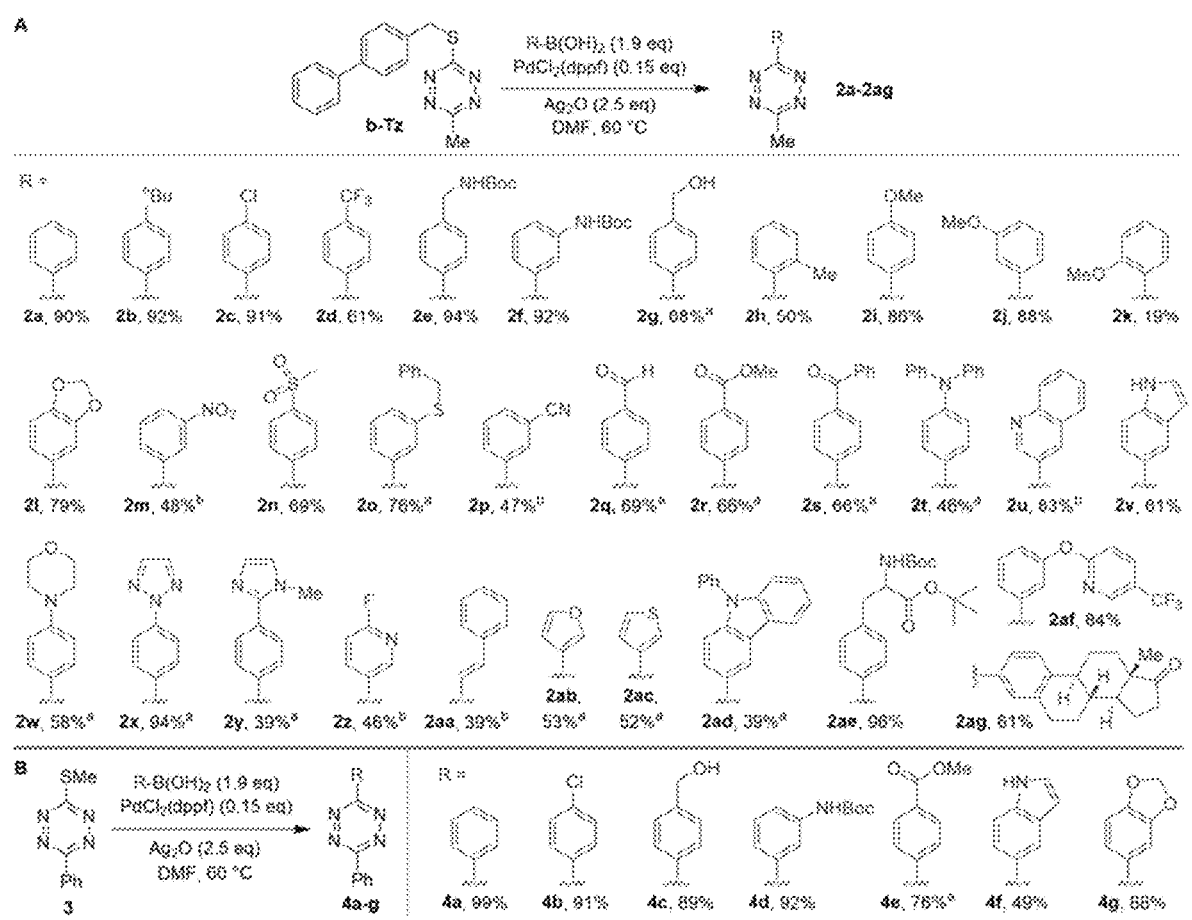
FIG. 5: Reaction scope of b-Tz (5A) and 3 (5B) according to embodiments of the present invention. Typical conditions: thioalkyl tetrazine b-Tz or 3 (1.0 equiv.), $RB(OH)_2$ (1.9 equiv.), $PdCl_2$(dppf) (15 mol %), $Ag_2O$ (2.5 equiv.), DMF (0.1M), 60° C., 19-21 h, average isolated yields of duplicate synthesis (+5%). For the compounds 2g, 2o, 2q, 2r, 2s, 2t, 2w, 2x, 2y, 2aa, 2ab, 2ac, 2ad: 3.0 equiv. of $RB(OH)_2$. For the compounds 2m, 2p, 2u, 2z, 2aa: 3.0 equiv. of $RB(OH)_2$ did not significantly improve yield (<5%), 1.9 equiv. of $RB(OH)_2$ was used.

The scope of the Ag-mediated, Pd-catalyzed coupling of b-Tz with arylboronic acids is summarized in FIG. 5A. Successful reactions were observed for arylboronic acids containing chloro, fluoro, secondary and tertiary amino, alcohol, ether, nitro, sulfonyl, thioether, nitrile, aldehyde, ester, ketone, carbamate, and styryl groups. Heterocyclic functionality tolerated on the boronic acid component included quinoline, indole, pyridine, triazole, N-methylimidazole, furan and thiophene groups. The protected amino acid 2ae coupled with b-Tz in 96% yield. Estrone-tetrazine 2ag was also synthesized in 61%. In general, couplings were carried out using 1.9 equiv. of boronic acid, but 3.0 equiv. were utilized in reactions where homocoupling of the boronic acid was pronounced. ortho-Substituted heteroatoms were observed to have a deleterious impact, with a relatively low yield observed for ortho-methoxy tetrazine 2k and only trace product with N-Boc-2-aminophenylboronic acid and 2-hydroxyphenylboronic acid. While protected thiol and amine functionalities were well tolerated (FIG. 5), additives with free thiol or primary alkyl amine groups were not (Example 4). Also unsuccessful were 2-pyridyl- and 4-pyridylboronic acids which are regarded as problematic across other cross-coupling reactions.

This cross-coupling method is not limited to S-benzylic thioethers or methyl-substituted tetrazines. 3-(Methylthio)-6-phenyl-tetrazine 3 was prepared from triethyl orthobenzoate and evaluated as a reagent in the synthesis of diaryltetrazines (FIG. 5B). Successful reactions were observed for arylboronic acids bearing chloro, alcohol, carbamate, ester, indole and ether groups with yields comparable to b-Tz. The improved syntheses of the present invention, such as the synthesis of 3-(4-hydroxymethylphenyl)-6-phenyltetrazine 4c, is useful to create cell-contact guiding microfibrous materials for tissue-culture applications.

Figure 6:
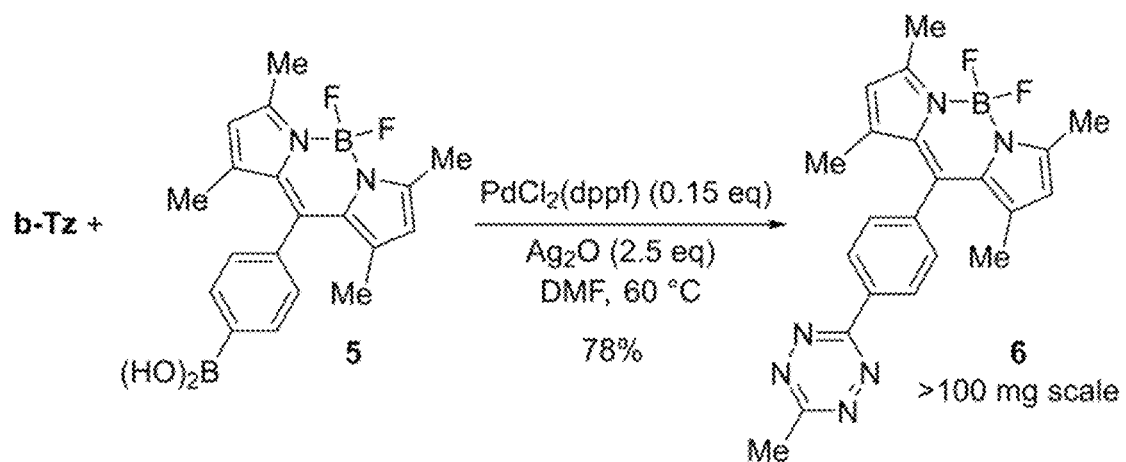
FIG. 6: Synthesis of 3-BODIPY-6-methyltetrazine 6 according to embodiments of the present invention.

In an aspect, the present invention allows for application of b-Tz for the construction of fluorophore-tetrazine conjugate-compounds that have utility in live cell imaging. As an example, BODIPY-dye 6 with a directly attached tetrazine has been developed as a 'superbright' bioorthogonal probe for fluorogenic labeling in live cells. The condensation of nitriles with hydrazine produces 6 in 8% yield. As shown in FIG. 6, compound 6 can be accessed in 78% yield through the Ag-mediated cross-coupling of boronic acid 5 with b-Tz.

Figure 7:
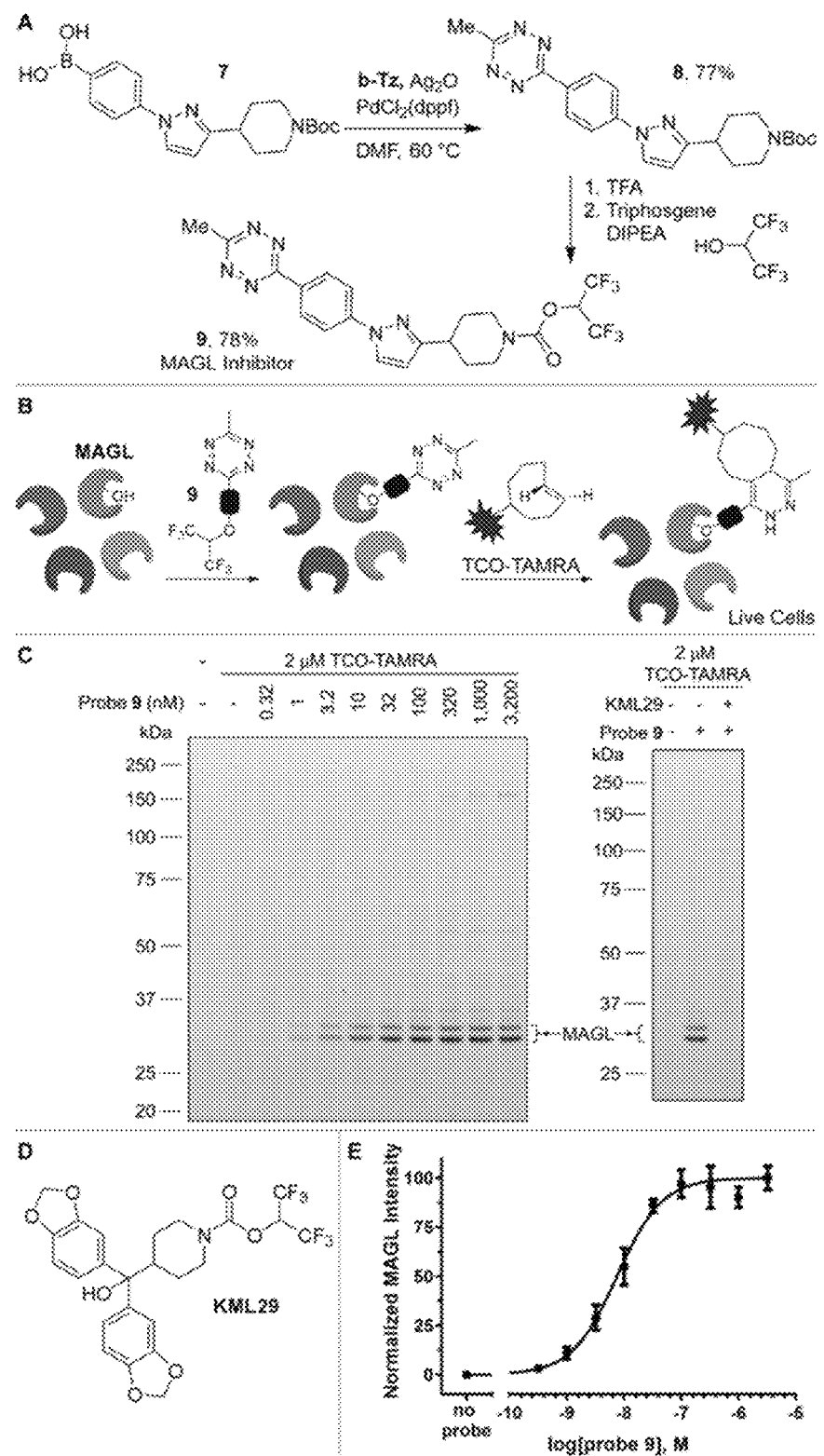
FIG. 7: (A) Synthesis of MAGL reactive probe 9 according to embodiments of the present invention. (B) Live cells were treated with probe 9 for 1 h, followed by 2 µM TCO-TAMRA for 30 min, cell lysis, and analysis by in-gel fluorescence (C) In-gel fluorescence signals for a dose response of probe 9. Probe 9 (32 nM, 1 h) was competed by pre-treatment with MAGL inhibitor KML29 (300 nM, 1 h). (D) KML29 also incorporates a HFIP carbamate warhead. (E) Dose response fitting of the fluorescence signals of MAGL normalized by the total protein amount indicated by Coomassie staining. Data are reported as mean±SEM (n=2).

To further demonstrate the utility of b-Tz in synthesizing chemical probes for studying endogenous levels of a protein in a native biological system, a tetrazine probe was constructed for monoacylglycerol lipase (MAGL). MAGL is a serine hydrolase in the endocannabinoid signaling pathway, and has attracted increasing interest as a target for neurological and metabolic disorders. A MAGL probe 9 was designed by appending a 6-methyltetrazine moiety to a pyrazolylpiperidine scaffold with an electrophilic hexafluoroisopropyl (HFIP) carbamate warhead for covalently labeling the active site serine (FIG. 7A). Synthesis was accomplished by cross-coupling of b-Tz with boronic acid 7 resulting in a 77% yield of 8. The reactive HFIP carbamate was installed by Boc deprotection followed by in situ addition to a triphosgene and hexafluoroisopropanol mixture, giving the MAGL reactive probe 9 in 78% yield. The reaction rate of 9 toward trans-cyclooctene is similar to that of 3-methyl-6-(4-aminomethyl)tetrazine ($k_{rel}$ 1.1). Probe 9 inhibited MAGL activity with 31 nM IC$_{50}$ in an in vitro assay. To test the labeling of endogenous MAGL in live cells, human brain vascular pericytes were treated with probe 9 for 1 h, followed by labeling with 2 μM of TCO-TAMRA for 30 min in live cells (FIG. 7B). After cell lysis, MAGL labeling was assessed with a gel-based activity-based protein profiling (ABPP) analysis (FIG. 7C-E).

Strong fluorescence signals were observed for MAGL with non-specific labeling from TCO-TAMRA. The labeling by probe 9 was dose responsive with a cellular IC$_{50}$ of 8 nM, and was competed by a MAGL inhibitor, KML29. The HFIP warhead also labeled an additional protein at ~35 kDa, which is consistent with its reactivity with α/β-hydrolase domain 6 (ABHD6), and other off-targets at higher concentrations.

Figure 8:
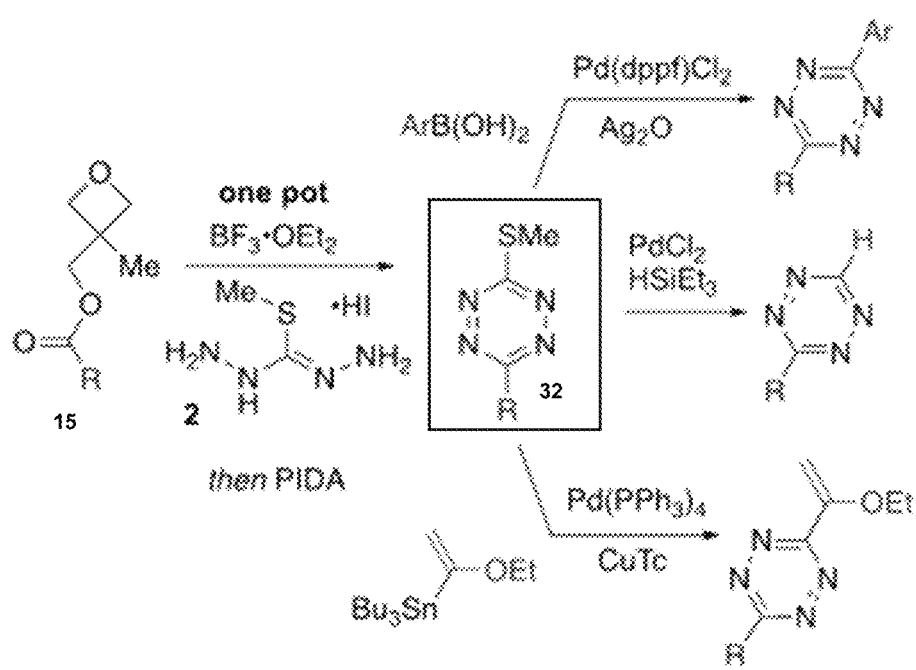
FIG. 8: Synthesis of tetrazines 32 from ester precursors 15 according to embodiments of the present invention.

Divergent Synthesis of Monosubstituted and Unsymmetrical 3,6-Disubstituted Tetrazines from Carboxylic Ester Precursors The inventors discovered a one-pot and a step-wise procedure for the conversion of (3-methyloxetan-3-yl)methyl carboxylic esters 15 to unsymmetrical 3-thiomethyltetrazines 32 via condensation of oxabicyclo[2.2.2]octyl (OBO) orthoester intermediates with 2 and subsequent oxidation (FIG. 8). The activated esters 32 were prepared simply and in high yield from the corresponding carboxylic acids and inexpensive 3-methyl-3-oxetanemethanol. These compounds provide a divergent platform for 3,6-disubstituted tetrazine synthesis and a new approach to monosubstituted tetrazines (FIG. 8).

Compound 2 is available commercially or can be prepared in one step from iodomethane and thiocarbohydrazide. The differential scanning calorimetry (DSC) profile of 2 has an onset temperature of 135° C. and a transition enthalpy of 875

J/g. The OBO orthoester 1a' was prepared by treating its (3-methyloxetan-3-yl) methyl ester with $BF_3 \cdot OEt_2$. Table 1 shows exemplary conditions for optimizing the condensation of 1a' with 2, with subsequent oxidation by phenyliodosodiacetate (PIDA) to provide thiomethyltetrazine 3a. DMF was the only effective solvent likely due to the limited solubility of salt 2 in other solvents. Simple combination of 1a' and 2 at r.t. gave 3a in only 18% yield (Table 1, entry 1). Given the acid-lability of orthoesters, a number of basic additives were explored (entries 2-6). Pyridine was found to be uniquely effective, and further optimization showed that the temperature could be raised to 80° C. and reaction time shortened without sacrificing yield (entry 7). Using 3 equiv. of pyridine and increasing the concentration to 1 M had a significant impact and raised the yield to 54% (entry 8). Using 1.4 equiv. of 1a' further raised the yield to 87% (entry 10).

TABLE 1

Optimization of condensation between 1a' and 2.

| entry | additive | equiv of 1a' | temp. | time | conc. | yield of 3a |
|---|---|---|---|---|---|---|
| 1 | none | 1.0 | r.t. | 6 h | 0.2M | 18% |
| 2 | $NEt_3$ (1 equiv) | 1.0 | r.t. | 6 h | 0.2M | 0 |
| 3 | DMAP (1 equiv) | 1.0 | r.t. | 6 h | 0.2M | 0 |
| 4 | $Cs_2CO_3$ (1 equiv) | 1.0 | r.t. | 7 h | 0.2M | 0 |
| 5 | KOtBu (1 equiv) | 1.0 | r.t. | 6 h | 0.2M | 0 |
| 6 | pyridine (1 equiv) | 1.0 | r.t. | 7 h | 0.2M | 24% |
| 7 | pyridine (3 equiv) | 1.0 | 80° C. | 1 h | 0.2M | 23% |
| 8 | pyridine (3 equiv) | 1.0 | 80° C. | 20 min | 1.0M | 54% |
| 9 | pyridine (3 equiv) | 1.25 | 80° C. | 20 min | 1.0M | 75% |
| 10 | pyridine (3 equiv) | 1.4 | 80° C. | 20 min | 1.0M | 87% |

Figure 9:
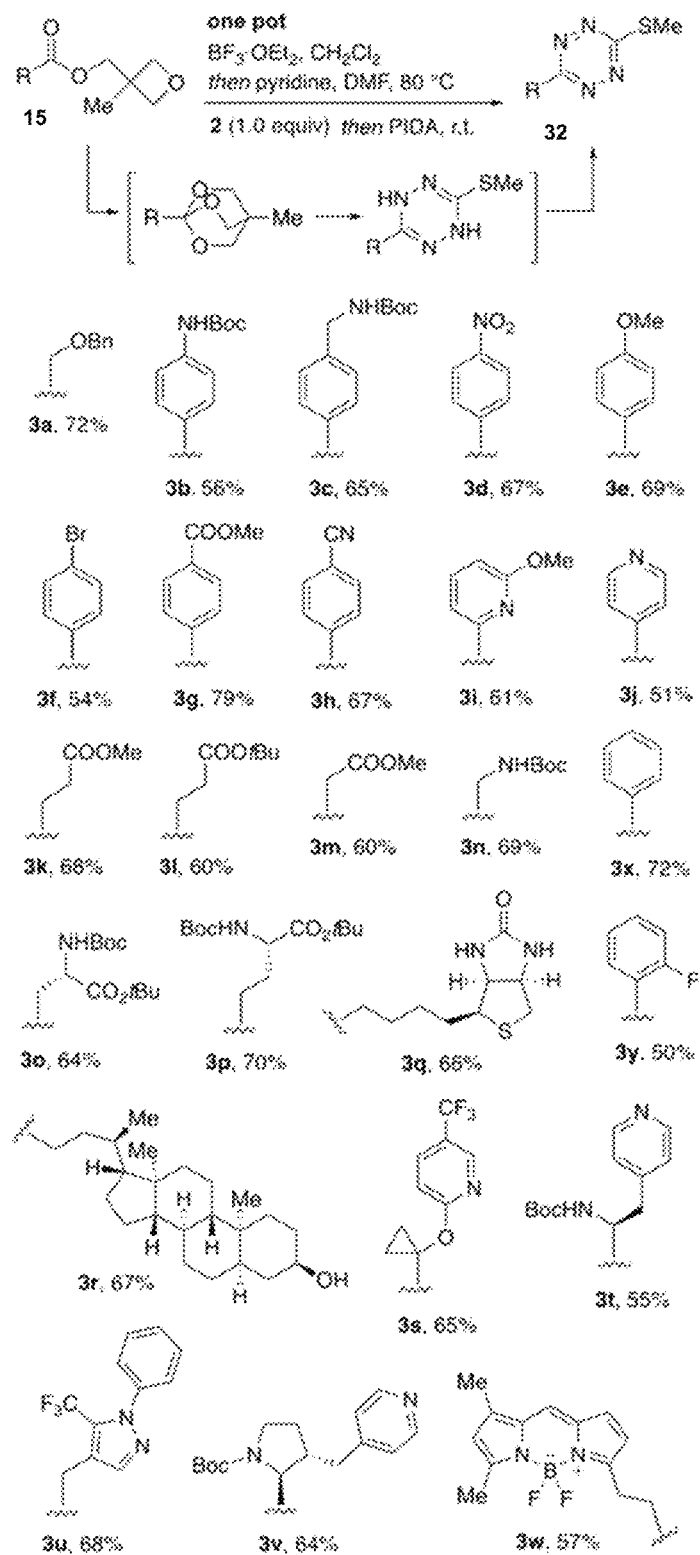
FIG. 9: One-pot synthesis of thiomethyltetrazines 32 from oxetane esters 15 according to embodiments of the present invention.

In another aspect, a one-pot or step-wise method for the synthesis of 3-thiomethyltetrazines 32 from esters 15 was discovered, where the esters 15 were easily prepared in high yield (>90%) and inexpensive 3-methyl-3-oxetanemethanol from the corresponding acids by Steglich esterification. After initial treatment of 15 in $CH_2Cl_2$ with $BF_3 \cdot OEt_2$ to form the OBO orthoester, pyridine and 2 were added. The solvent was exchanged with DMF, and after heating at 80° C., the dihydrotetrazine solution was cooled and directly treated with PIDA to provide tetrazines 32 in 50-79% yield (FIG. 9). Aromatic and alkyl substituents with a variety of functional groups were tolerated including Boc-amino (3b-c, 3n), nitro (3d) and methoxy (3e) groups. The method also tolerates nitrile (3h) and ester (3g, 3k-m) groups which are generally not compatible with tetrazine synthesis. Protected amino acids (3o-p), biotin (3q), BODIPY-FL (3w) and a number of heterocycles (3i-j, 3s-v) were also successful and highlighted the ability to directly conjugate biologically relevant compounds. While the ester of 2-fluoro benzoic acid provided 3y in 50% yield, esters with bulkier ortho-substituents (2-nitro or N-Boc-2-amino) were unsuccessful.

Figure 10:
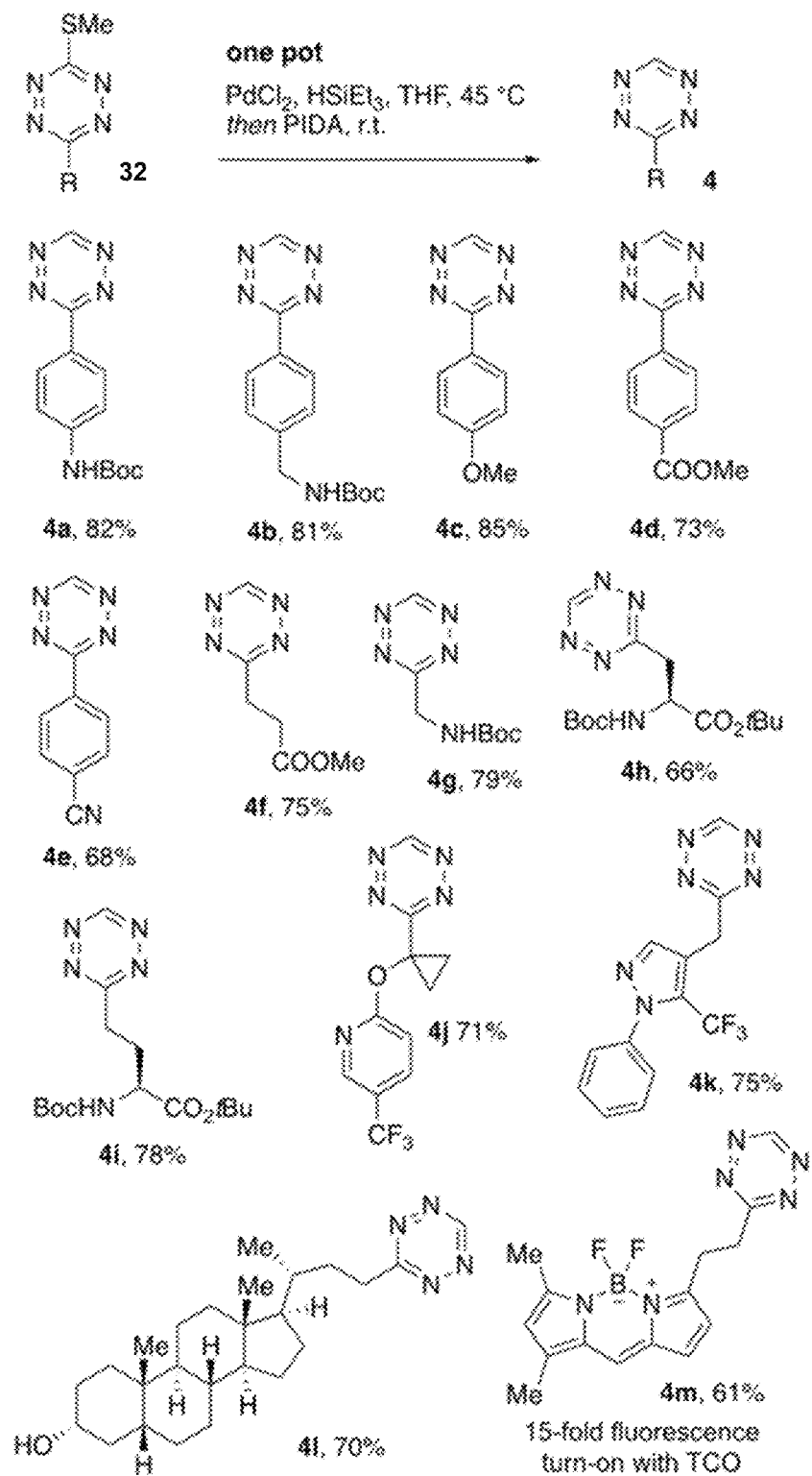
FIG. 10: Synthesis of 3-monosubstituted tetrazines 4 according to embodiments of the present invention. Conditions: 32 (1 equiv), $PdCl_2$ (10 mol %), $HSiEt_3$ (3 equiv.), THF, 45° C., 24 h; PIDA (1.2 equiv.), r.t., 1 h.

Monosubstituted tetrazines are valued in bioorthogonal chemistry for their rapid kinetics and minimal size. In another aspect, a method of preparing monosubstituted tetrazines 4 through thiomethyltetrazine 32 reduction is described (FIG. 10). After optimization (see Table 2 in Example 18), it was found that efficient reduction could be realized with catalytic $PdCl_2$ (10 mol %) and triethylsilane (3 equiv) in THF at 45° C. followed by treatment with PIDA to oxidize the initially formed dihydrotetrazine. The method provides monosubstituted tetrazines derived from aliphatic and aromatic esters with a variety of functional groups, including Boc-amino (4a-b, 4g), methoxy (4c), ester (4d, 4f) nitrile (4e), protected amino acids (4h-i), and heterocycles (4j-k). Reduction of 3w gave BODIPY-FL derivative (4m), which showed a 15-fold turn-on of fluorescence upon reaction with eq-5-hydroxy-trans-cyclooctene (5-hydroxyTCO). Pyridine derivatives (3i-j, 3t, 3v) gave low conversions and attempted reduction of 3q was unsuccessful, possibly due to overreduction of the biotin core.

Figure 11:
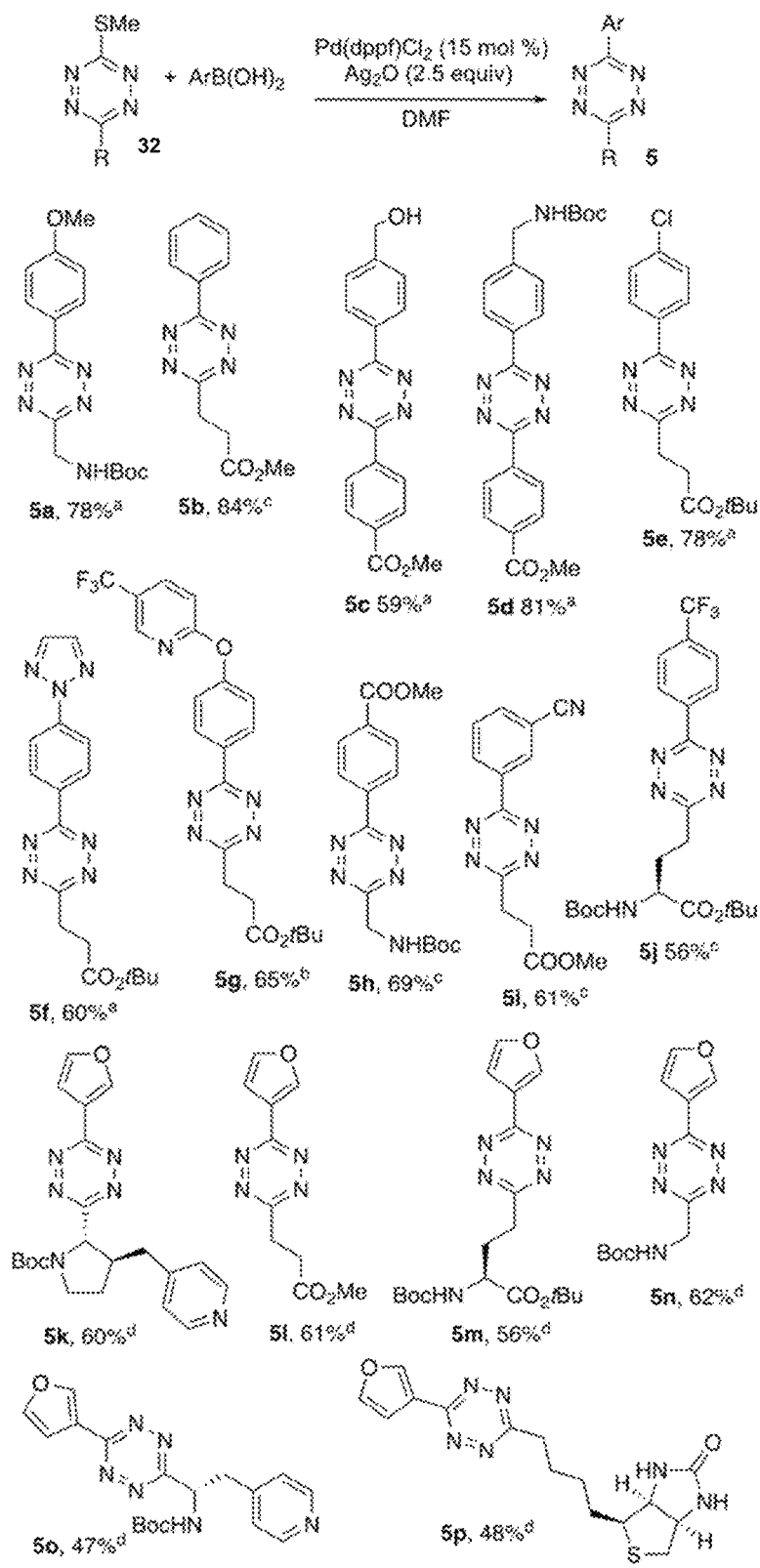
FIG. 11: Synthesis of unsymmetrical tetrazines 5 via Ag-mediated Pd-catalyzed Liebeskind-Srogl coupling according to embodiments of the present invention. [a]ArB$(OH)_2$ (1.9 equiv.), 60° C., 20 h. [b] $ArB(OH)_2$ (3 equiv.), 60° C., 20 h. [c] $ArB(OH)_2$ (3 equiv.), microwave 100° C., 3 h. [d] Pd(dppf)$Cl_2$ (30 mol %), $Ag_2O$ (5 equiv.), $ArB(OH)_2$ (6 equiv.), microwave 100° C., 3 h.

Thiomethyltetrazines 32 also served as electrophiles for Ag-mediated Liebeskind-Srogl coupling reactions with thioethers bearing either aliphatic or aromatic groups (FIG. 11). Tolerated functional groups include ether, chloride, ester, nitrile, trifluoromethyl, alcohol, Boc-amino, and protected amino acids as well as pyridyl and triazole groups. Additionally, the 3-furyl group was readily introduced to a range of thiomethyltetrazines via Ag-mediated Liebeskind-Srogl coupling. In line with previous observation, electron rich arylboronic acids were the most efficient nucleophiles.

Figure 12:
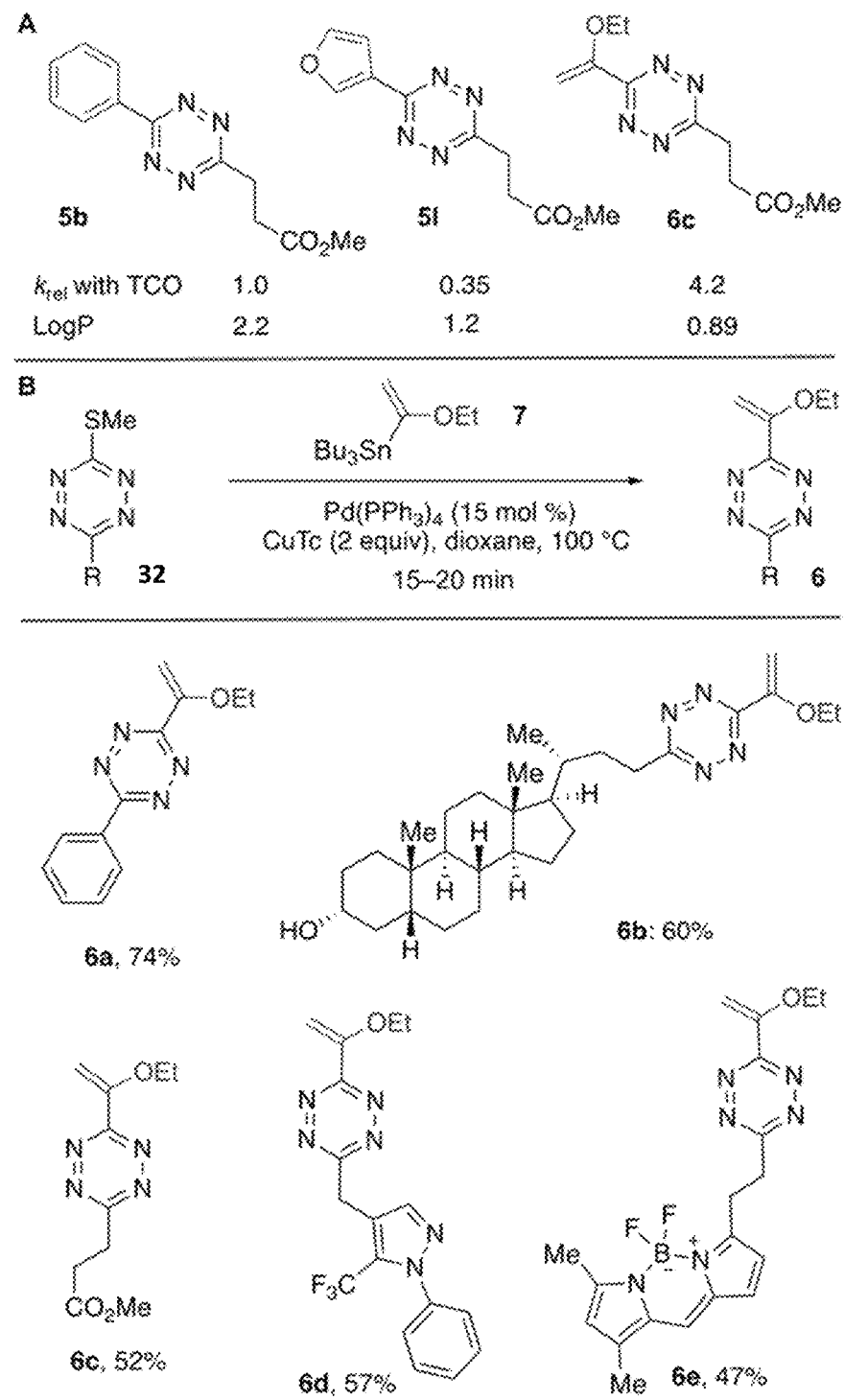
FIG. 12: Furyl-5i and vinylether-6c substituted tetrazines with favorable kinetics, small size and hydrophilicity according to embodiments of the present invention. (A) Relative reactivity and log P value. (B) Synthesis via CuTc-mediated Liebeskind-Srogl coupling.
Figure 13:
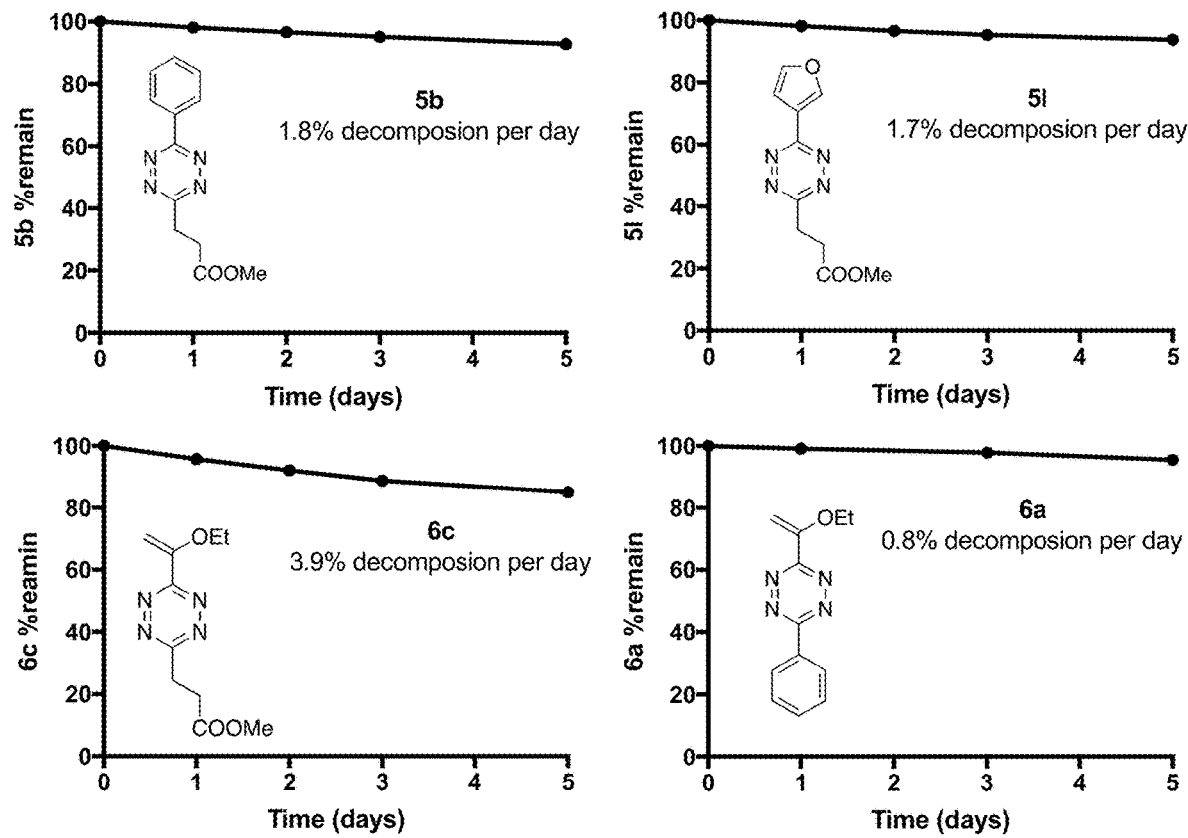
FIG. 13: Stability of tetrazines 5b, 5l, 6c, and 6a in PBS buffer in ambient light at 25° C.
Figure 14:
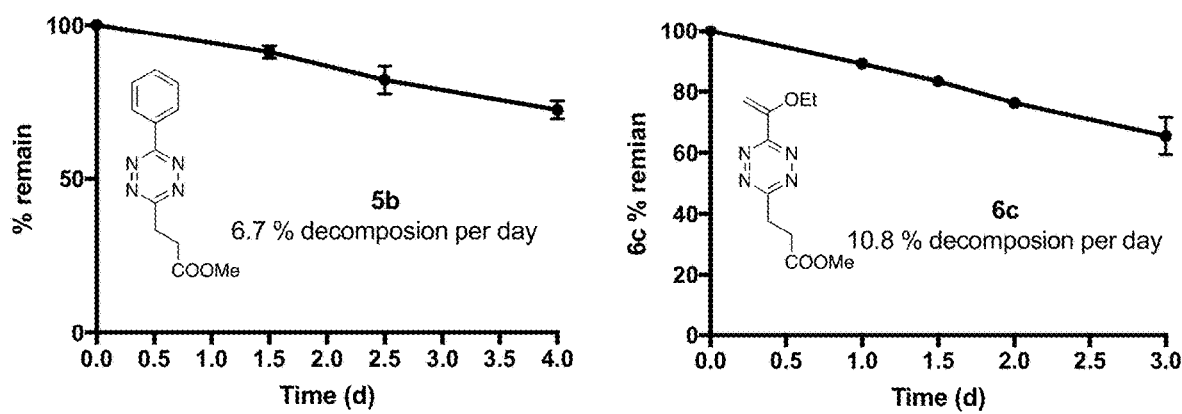
FIG. 14: Stability of tetrazine 5b and 6c in Opti-MEM media in ambient light at 25° C.

3,6-Disubstituted aromatic tetrazines 5 have been used broadly for bioorthogonal chemistry due to their combination of stability and rapid kinetics but can be limited by their hydrophobicity. It is anticipated that furyl or vinylether groups introduced through cross-coupling could serve as small and solubilizing alternatives to phenyl groups. Shown in FIG. 12A are the experimental log P values for three tetrazine analogs and their rate constants in reactions with 5-hydroxyTCO (Example 19). Furyl analog 5l (log P 1.2) is found to be considerably more hydrophilic albeit 2.9 times less reactive than phenyl derivative 5b (log P 2.2). Vinylether 6c is the most reactive and hydrophilic member of the series with log P 0.89 and a reactivity that is 4.2 times faster than 5b. Vinylether-substituted tetrazines represent a new class of dienophiles with a favorable combination of kinetics, small size and hydrophilicity. Tetrazines 5b, 5l and 6c all display >96% stability after 24 h incubation in PBS at 25° C. (FIG. 13). Tetrazines 5b and 6c displayed 6.7% and 10.8% decomposition per day, respectively, in Opti-MEM media (FIG. 14). To introduce the 2-ethoxyvinyl group, commercially available stannane was employed. Here, coupling reactions were most efficient under conventional CuTc-promoted conditions with a brief reaction time. As shown in FIG. 12B, these cross-coupling procedures can tolerate a broad range of functional groups and heterocycles of biological interest.

Figure 15:
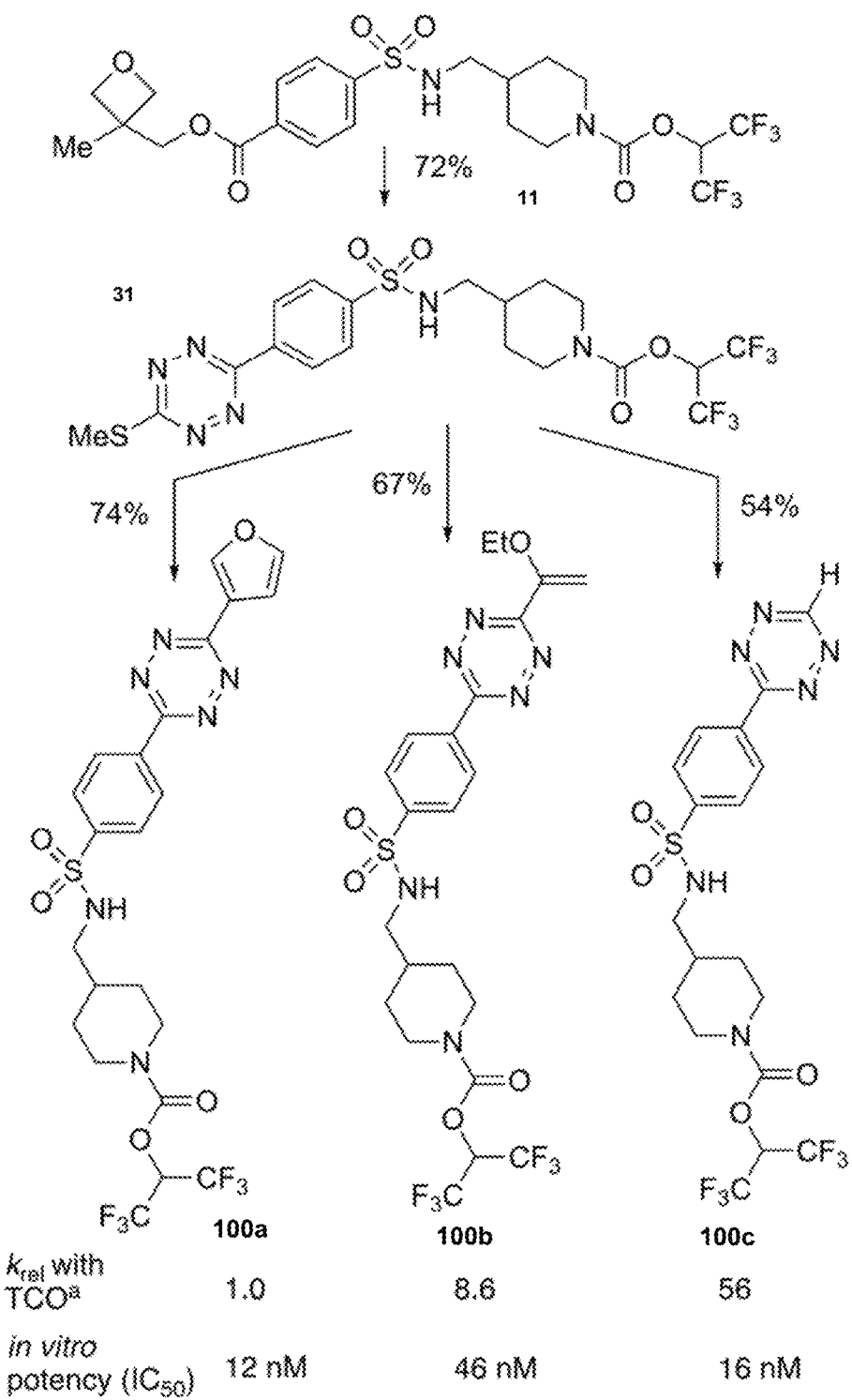
FIG. 15: Divergent synthesis of tetrazine-coupled MAGL-probes 100a-100c from common ester starting material and thiomethyltetrazine intermediate according to embodiments of the present invention.

This divergent approach to synthesizing tetrazine-coupled probes was applied to the study of MAGL, a serine hydrolase involved in endocannabinoid signaling. The inventors' previous approach to studying this drug target was limited by the need for a scaffold with a relatively uncommon boronic acid group, thus restricting the types of drug candidates that could be studied. It was hypothesized that a divergent approach could be used to tune reaction kinetics and/or inhibitory affinity of a new class of MAGL-tetrazine probes. As shown in FIG. 15, probes 100a-100c were designed based on a 4-(arylsulfonamidomethyl)piperidine scaffold bearing an electrophilic hexafluoroisopropyl (HFIP) carbamate warhead. Thus, reaction of 2 with the (3-methyloxetane-3-yl) methyl ester 11 gave a 72% yield of thiomethyltetrazine 31, which served as common intermediate for the synthesis of furyl-substituted 100a, vinylether-substituted 100b, and monosubstituted tetrazine 100c. Stopped flow kinetics with 5-hydroxyTCO showed 100c was 6.5-times more reactive than 100b, which in turn was 8.6-fold more reactive than 100a. All of these probes were 3 to 162 times more reactive than a previously described MAGL probe based on a different drug scaffold (12 Table 3 in Example 31).

Figure 16:
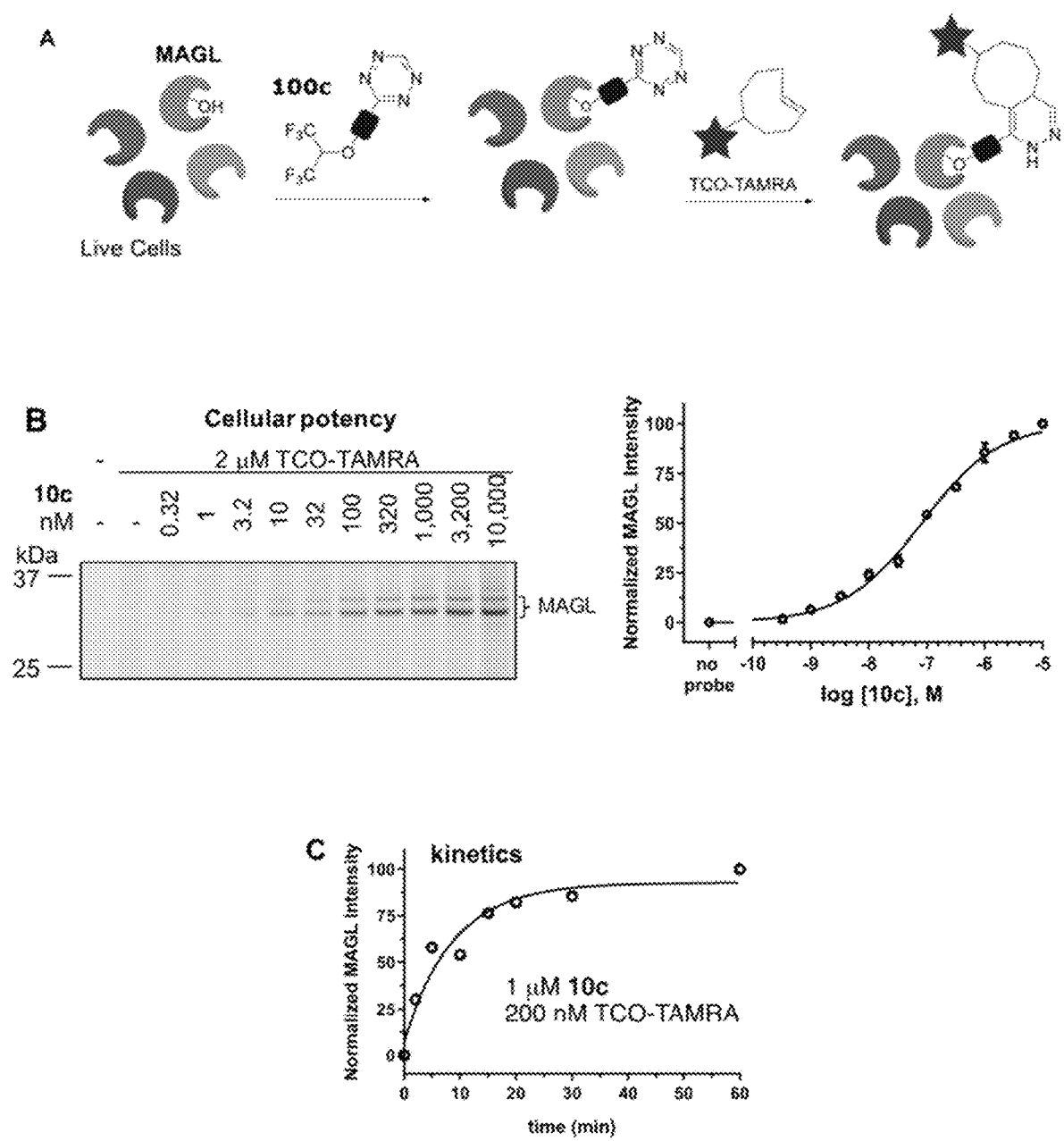
FIG. 16: (A) Live cells were treated with probe 100c for 1 h, followed by TCO-TAMRA treatment for 30 min, cell lysis, and analysis by gel-based ABPP. (B) In-gel fluorescence and dose response fitting of probe 100c. (C) Cellular labeling kinetics of 100c.
Figure 17:
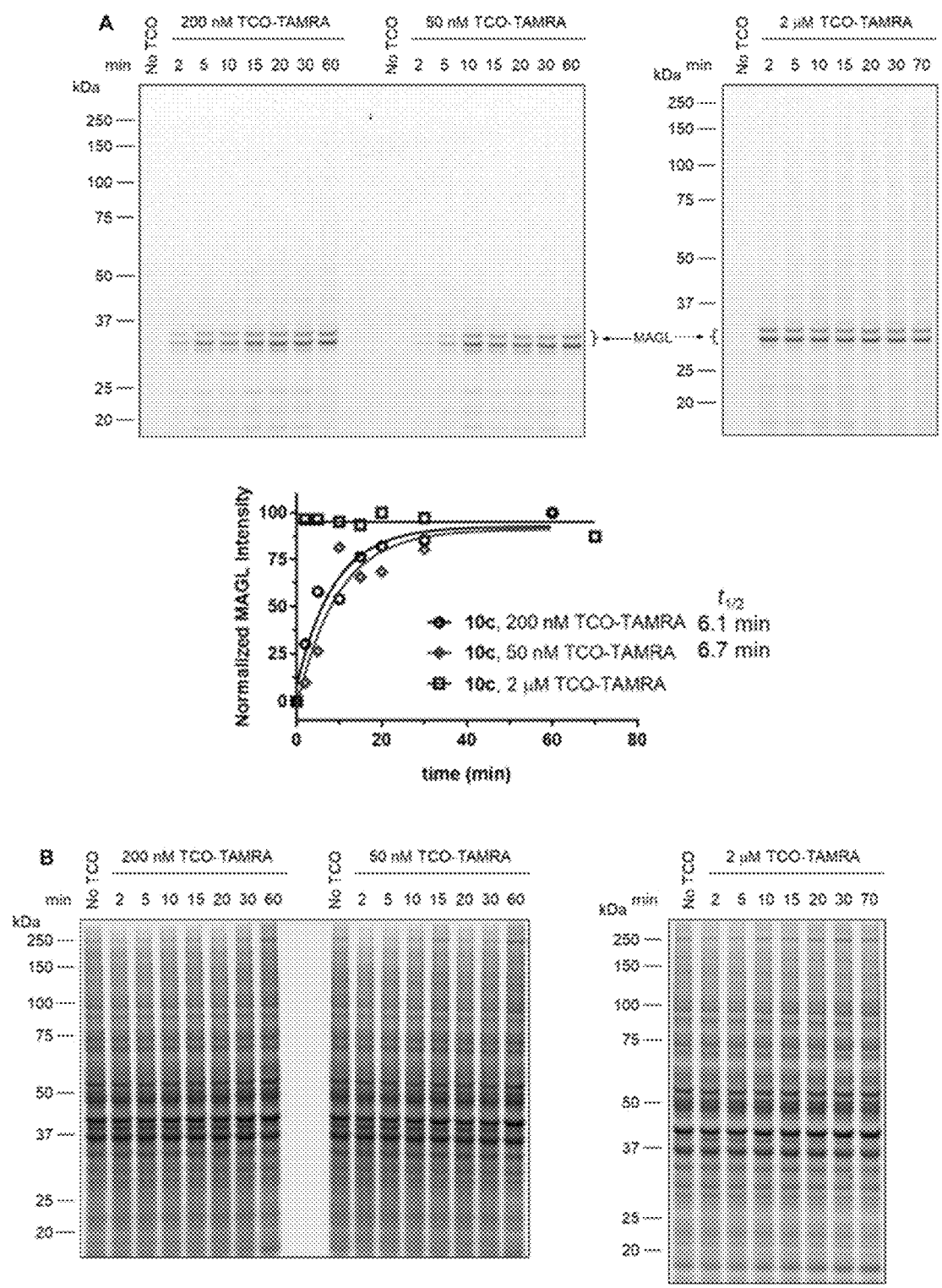
FIG. 17: Cellular labeling kinetics of TCO-TAMRA with 100c (1 μM, 1 h) in live human brain vascular pericytes. (A) Full gel of in-gel fluorescence data (200 nM TCO-TAMRA in FIG. 3D). (B) Coomassie staining of total proteins.
Figure 18:
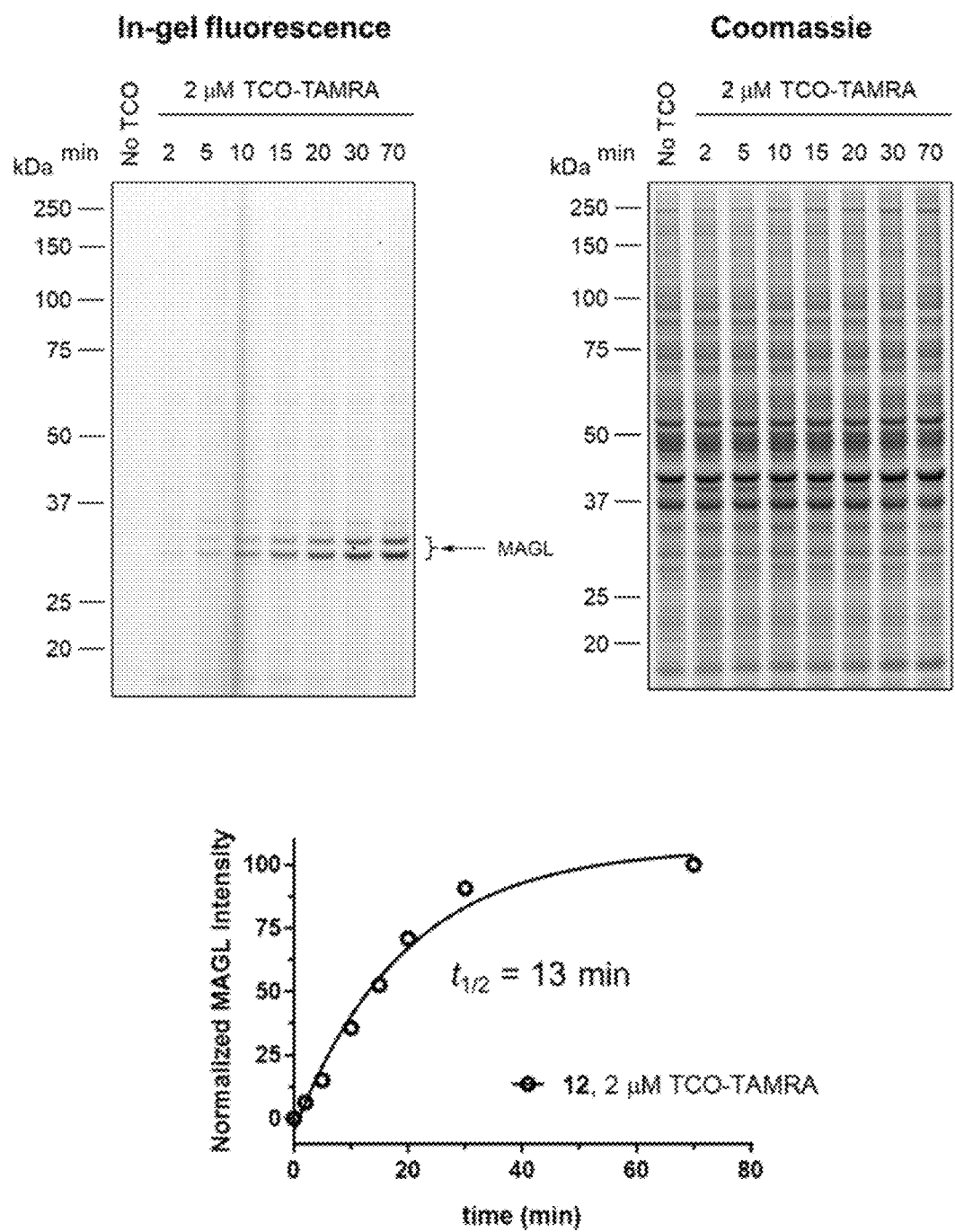
FIG. 18: Cellular labeling kinetics of TCO-TAMRA with 12 (32 nM, 1 h) in live human brain vascular pericyte

In an in vitro assay, probes 100a-100c inhibited MAGL activity with $IC_{50}$ values of 12 nM (100a), 46 nM (100b) and 16 nM (100c). The most reactive probe 100c was further investigated for labeling of endogenous MAGL in live cells. Human brain vascular pericytes were treated with probe 100c for 1 h, followed by labeling with 2 µM TCO-TAMRA for 30 min. After cell lysis, gel-based activity-based protein profiling (ABPP, FIG. 16A) showed strong labeling of MAGL. The labeling was dose responsive (FIG. 16B), and treating cells with 100c (1 µM, 1 h) followed by incubation with 200 nM TCO-TAMRA gave complete labeling with ti/2 of 6.1 min (FIG. 16C). Similar kinetics were observed when the concentration of TCO-TAMRA was dropped to 50 nM (FIG. 17), and with a higher concentration of TCO-TAMRA (2 µM), labeling was complete when the first data point was collected after 2 min. By contrast, the previous 6-methyltetrazin-3-yl probe for MAGL displayed slower labeling kinetics (ti/2 of 13 min) with 2 uM TCO-TAMRA (FIG. 18). Together, these experiments illustrate how modifying the structure of tetrazine-coupled probes can be used to tune the $IC_{50}$ and labeling kinetics.

EXAMPLES

Although the invention is illustrated and described herein below with reference to specific embodiments, the invention is not intended to be limited to the details shown. Rather, various modifications may be made in the details within the scope and range of equivalents of the claims and without departing from the invention.

General Considerations

All cross-coupling reactions were conducted in flame dried schlenk flasks or 4 mL sealed vials. All other reactions were conducted in flame dried round-bottom flasks. Additionally, all reactions were run under $N_2$ unless otherwise noted. Silica gel chromatography was performed on Silicycle Siliaflash P60 silica gel (40-63 µm, 60 Å) or on Yamazen reverse-phase prepacked Universal Column C18-silica gel (40-60 µm, 120 Å). Automated column chromatography was performed on a Teledyne Isco Combiflash Rf. Commercially available chemicals were purchased from Sigma-Aldrich, Combi-Blocks, Acros Organics, Alfa Aesar, Oakwood Chemical, TCI Chemicals, and Frontier Scientific. Solvents were purchased from Thermo Fisher Chemical, Acros Organics, Decon Laboratories Inc., Mediatech, Inc., and Sigma-Aldrich. Human brain vascular pericytes and pericyte growth supplement were purchased from ScienCell Research Laboratories. Anhydrous dichloromethane was freshly prepared by an alumina column solvent purification system. Anhydrous tetrahydrofuran was freshly distilled from sodium/benzophenone. Deuterated solvents were purchased from Cambridge Isotope. A Bruker AV400 was used to record NMR spectra ($^1$H: 400 MHz, $^{13}$C: 101 MHz, $^{19}$F: 376 MHz). Chemical shifts are reported in ppm and all spectra are referenced to their residual non-deuterated solvent peaks as follows: $CDCl_3$ ($^1$H: 7.26 ppm, $^{13}$C: 77.16 ppm), Methanol-d4 ($^1$H: 3.31 ppm, $^{13}$C: 49.00 ppm), DMSO-d6 ($^1$H: 2.50 ppm, $^{13}$C: 39.52 ppm). Coupling constants (J) are reported to the nearest 0.1 Hz. Multiplicities are reported as follow: singlet (s), doublet (d), triplet (t), quartet (q), pentet (pent), sextet (sext), heptet (hept), multiplet (m), 'broad' (br), and 'apparent' (app). $^{13}$C NMR resonances are proton decoupled and an APT pulse sequence was used to determine type of carbon as follows: quaternary and methylene (C or $CH_2$) carbons appear 'up' and methine and methyl (CH or $CH_3$) carbons appear 'down'. Gas chromatography was carried out on a Shimadzu GC-2010 Plus with a Shimadzu AOC-20i auto-injector. Low resolution mass spectra were taken on a Water SQ detector 2 which was attached to a Waters Acquity H-Class UPLC. High resolution mass spectra were obtained using a Waters GCT Premier. Infrared spectra were taken on a Nicolet *Magna* IR 560 spectrometer. Stopped-flow kinetics were obtained using an Applied Photophysics Ltd. SX 18MV-R stopped-flow spectrophotometer. Differential Scanning Calorimetry was assayed with a Mettler-Toledo Differential Scanning Calorimeter 3+. Optical rotations were measures on a Jasco P-2000 polarimeter equipped with a tungsten-halogen lamp and a 589 nm filter. For fluorescence imagining, gels were scanned with a Typhoon FLA 9500 Biomolecular Imager (GE Healthcare) with the TAMRA channel with 532 nm excitation and a 575 nm long pass emission filter. To measure total protein loading, the gels were scanned with an Odyssey Imager (Li-COR) at the 700 nm channel.

Differential Scanning Calorimetry (DSC)

DSC data was obtained on a Mettler-Toledo Differential Scanning Calorimeter 3+. Samples were loaded into a gold-plated high-pressure pan, held at 30° C. for 10 minutes, then a gradient of 30° C. to 400/500° C. at 5° C./min.

Example 1: ([1,1'-biphenyl]-4-ylmethyl)thiocarbohydrazide bromide

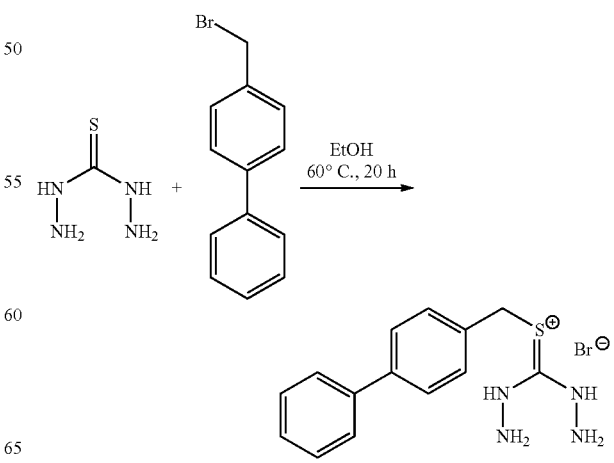

Thiocarbohydrazide (21.20 g, 200 mmol, 1.0 eq) and 4-bromomethyl biphenyl (49.40 g, 200 mmol, 1.0 eq) were suspended in ethanol (300 mL, 0.66 M) in a round bottom flask. The flask was flushed with nitrogen and heated to 60° C. for 20 h. A thick white slurry forms during the reaction. The reaction was brought to room temperature and the slurry was broken up with 300 mL diethyl ether. The white solids were isolated by vacuum filtration, washed 5×250 mL diethyl ether, and then dried under rotary evaporation to give ([1,1'-biphenyl]-4-ylmethyl)-thiocarbohydrazide bromide as a white powder (65.55 g, 93%). $^1$H NMR (400 MHz, Methanol-d4) δ 7.66-7.60 (m, 4H), 7.49 (app d, J=8.4 Hz, 2H), 7.46-7.43 (app t, J=7.9 Hz, 2H), 7.35 (app tt, J=7.6, 2.0 Hz, 1H), 4.28 (s, 2H). FTIR (KBr, thin film) 3440, 2067, 1637, 533 cm$^{-1}$. HRMS (ESI+) [M-Br]$^+$ Calculated for C14H17N$_4$S$^+$ 273.1168; found 273.1173.

Example 2: 3-([1,1'-biphenyl]-4-ylmethylthio)-6-methyl-1,2,4,5-tetrazine (b-Tz, 1a)

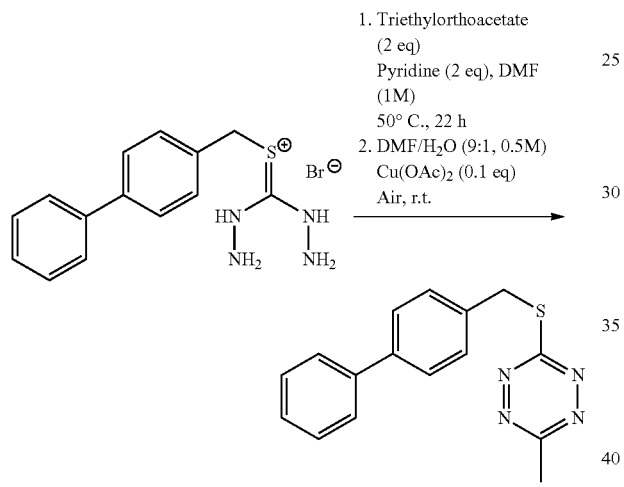

([1,1'-biphenyl]-4-ylmethyl)-thiocarbohydrazide bromide (65.55 g, 186 mmol, 1.0 eq), Pyridine (33 mL, 371 mmol, 2.0 eq), and DMF (186 mL, 1.0M) were stirred under nitrogen at 50° C. Triethylorthoacetate (70 mL, 371 mmol, 2.0 eq) was added dropwise over 1 h and the reaction was stirred an additional 22 h. The reaction was then cooled to r.t. and opened to air. DMF (149 mL) and H$_2$O (37 mL) (9:1 org/aq, 0.5M) were added followed by Cu(II)(OAc)$_2$ (3.38 g, 18.6 mmol, 0.1 eq). Air was then bubbled into the reaction and the solution was stirred vigorously for 24 h, after which complete oxidation of tetrazine was observed (monitored by TLC, iodine on silica visualization). Bubbling of air was stopped and 250 mL additional H$_2$O was added to precipitate tetrazine. The heterogeneous mixture was then filtered and the solids were washed 5×100 mL H$_2$O. Any remaining solvent was removed by rotary evaporation.

The solids were then dissolved in a minimal amount of hot DCM and loaded on to a plug of silica gel (2 in. diameter, 4 in. deep). Tetrazine was eluted with 3:2 DCM/hexanes and then concentrated by rotary evaporation resulting in 3-([1,1'-biphenyl]-4-ylmethylthio)-6-methyl-1,2,4,5-tetrazine (b-Tz) as a bright coral red crystalline solid (27.45 g, 93 mmol, 50%). $^1$H NMR (400 MHz, CDCl$_3$) δ 7.58-7.53 (m, 6H), 7.45-7.41 (app t, J=7.4 Hz, 2H), 7.35 (app tt, J=7.2, 2.0 Hz, 1H), 4.57 (s, 2H), 2.98 (s, 3H). $^{13}$C NMR (101 MHz, CDCl$_3$) δ 174.7 (C), 165.5 (C), 140.9 (C), 140.6 (C), 134.8 (C), 129.8 (CH), 128.9 (CH), 127.6 (CH), 127.6 (CH), 127.2 (CH), 34.5 (CH$_2$), 20.9 (CH$_3$). FTIR (KBr, thin film) 3452, 1635, 1370, 740, 694 cm$^{-1}$. HRMS (ESI+) [M+H]$^+$ Calculated for C16H15N$_4$S$^+$ 295.1017; found 295.1015.

Example 3: General Procedure for the Synthesis of Tetrazines 1b-1g

Note: the following procedures 1b-1g are unoptimized. For an optimized procedure please refer to tetrazine 1a.

Thiocarbohydrazide (see below, 1.0 eq.) and a benzylic bromide reactant (see below, 1.0 eq.) were suspended in ethanol (0.2 M) in a round bottom flask. The flask was flushed with nitrogen and heated to 70° C. for 2 h. The reaction was then brought to room temperature and the solids were isolated by vacuum filtration, washed with diethyl ether, and then dried under rotary evaporation.

The resulting solids (1.0 eq) were dissolved in DMF (0.2 M) under nitrogen and triethylorthoacetate (1.3 eq.) was added. The reaction was stirred at 70° C. for 2 h and then cooled to 0° C. (Diacetoxyiodo)benzene (1.0 eq.) was added portionwise over 5 min and then the reaction was brought to r.t. and stirred 1 h. The reaction was diluted in DCM and washed 4× H$_2$O, 1× brine, and then dried on MgSO$_4$. The tetrazine products were purified by silica gel chromatography as described below.

Example 3A: 3-(benzylthio)-6-methyl-1,2,4,5-tetrazine (1b)

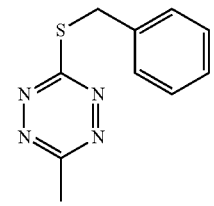

Prepared using Thiocarbohydrazide (4.06 g, 38.3 mmol) and benzyl bromide (4.6 mL, 38.3 mmol). Benzylthiocarbohydrazide bromide was precipitated from the reaction solution with 150 mL hexanes. Silica gel chromatography (25% DCM/hexanes) yielded 3-(benzylthio)-6-methyl-1,2,4,5-tetrazine as a red oil (789 mg, 3.6 mmol, 9%). $^1$H NMR (400 MHz, CDCl$_3$) δ 7.49-7.46 (m, 2H), 7.36-7.27 (m, 3H), 4.54 (s, 2H), 2.97 (s, 3H). $^{13}$C NMR (101 MHz, CDCl$_3$) δ 174.7 (C), 165.4 (C), 135.8 (C), 129.4 (CH), 128.8 (CH), 128.0 (CH), 34.8 (CH$_2$), 20.8 (CH$_3$). FTIR (KBr, thin film) 3446, 3086, 3063, 3030, 2932, 2296, 1495, 1453, 1383, 1316, 1162, 1069, 883, 702 cm$^{-1}$. HRMS (ESI+) [M+H]$^+$ Calculated for C$_{10}$H$_{11}$N$_4$S$^+$ 219.0704; found 219.0709.

Example 3B: 3-((3,5-dimethoxybenzyl)thio)-6-methyl-1,2,4,5-tetrazine (1c)

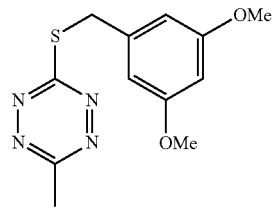 [SMILES: COc1cc(CSc2nnc(C)nn2)cc(OC)c1]

Prepared using Thiocarbohydrazide (1.15 g, 10.8 mmol) and 3,5-Dimethoxybenzyl bromide (2.49 g, 10.8 mmol). Silica gel chromatography (0-20% ethyl acetate/petroleum ether) yielded 3-((3,5-dimethoxybenzyl)thio)-6-methyl-1,2,4,5-tetrazine as a pink crystalline solid (305 mg, 1.1 mmol, 10%). $^1$H NMR (400 MHz, CDCl$_3$) δ 6.61 (d, J=2.0 Hz, 2H), 6.34 (t, J=2.0 Hz, 1H), 4.48 (s, 2H), 3.78 (s, 6H), 2.97 (s, 3H). $^{13}$C NMR (101 MHz, CDCl$_3$) δ 174.8 (C), 165.4 (C), 161.1 (C), 137.9 (C), 107.3 (CH), 100.0 (CH), 55.5 (CH$_3$), 35.0 (CH$_2$), 20.9 (CH$_3$). FTIR (KBr, thin film) 3459, 3003, 2962, 2838, 2105, 1610, 1316, 1206, 1158, 1066 cm$^{-1}$. HRMS (ESI+) [M+H]$^+$ Calculated for C$_{12}$H$_{15}$O$_2$N$_4$S$^+$ 279.0916; found 279.0922.

Example 3C: 4-(((6-methyl-1,2,4,5-tetrazin-3-yl)thio)methyl)benzonitrile (1d)

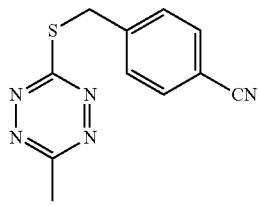 [SMILES: Cc1nnc(SCc2ccc(C#N)cc2)nn1]

Prepared using Thiocarbohydrazide (530 mg, 5.0 mmol) and 4-(Bromomethyl)benzonitrile (980 mg, 5.0 mmol). Silica gel chromatography (25% ethyl acetate/petroleum ether) yielded 4-(((6-methyl-1,2,4,5-tetrazin-3-yl)thio)methyl)benzonitrile as a pink crystalline solid (350 mg, 1.4 mmol, 29%). $^1$H NMR (400 MHz, CDCl$_3$) δ 7.64-7.59 (m, 4H), 4.55 (s, 2H), 2.97 (s, 3H). $^{13}$C NMR (101 MHz, CDCl$_3$) δ 173.9 (C), 165.8 (C), 141.7 (C), 132.6 (CH), 130.1 (CH), 118.6 (C), 111.8 (C), 34.1 (CH$_2$), 20.9 (CH$_3$). FTIR (KBr, thin film) 3428, 3086, 3051, 2996, 2229, 1636, 1606, 1384, 1316, 1160, 883 cm$^{-1}$. HRMS (ESI+) [M+H]$^+$ Calculated for C$_{11}$H$_{10}$N$_5$S$^+$ 244.0657; found 244.0661.

Example 3D: 3-((4-methoxybenzyl)thio)-6-methyl-1,2,4,5-tetrazine (1e)

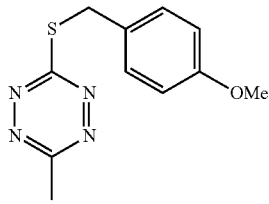 [SMILES: COc1ccc(CSc2nnc(C)nn2)cc1]

Prepared using Thiocarbohydrazide (1.95 g, 18.4 mmol) and 4-Methoxybenzyl bromide (3.70 g, 18.4 mmol). Silica gel chromatography (0-20% ethyl acetate/petroleum ether) yielded 3-((4-methoxybenzyl)thio)-6-methyl-1,2,4,5-tetrazine as a pink crystalline solid (144 mg, 0.6 mmol, 3%). $^1$H NMR (400 MHz, CDCl$_3$) δ 7.41-7.37 (app d, J=8.9 Hz, 2H), 6.88-6.84 (app d, J=8.9 Hz, 2H), 4.50 (s, 2H), 3.79 (s, 3H), 2.97 (s, 3H). $^{13}$C NMR (101 MHz, CDCl$_3$) δ 174.8 (C), 165.3 (C), 159.3 (C), 130.6 (CH), 127.6 (C), 114.2 (CH), 55.4 (CH$_3$), 34.4 (CH$_2$), 20.8 (CH$_3$). FTIR (KBr, thin film) 3427, 3034, 3001, 2956, 2934, 2908, 2835, 1610, 1512, 1383, 1316, 1244, 1164, 1032, 884, 833 cm$^{-1}$. HRMS (ESI+) [M+H]$^+$ Calculated for C$_{11}$H$_{13}$ON$_4$S$^+$ 249.0810; found 249.0814.

Example 3E: 3-((([1,1'-biphenyl]-3-ylmethyl)thio)-6-methyl-1,2,4,5-tetrazine (1f)

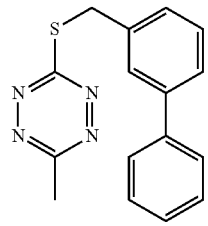 [SMILES: Cc1nnc(SCc2cccc(-c3ccccc3)c2)nn1]

Prepared using Thiocarbohydrazide (1.07 g, 10.1 mmol) and 3-Phenylbenzyl bromide (2.49 g, 10.1 mmol). Silica gel chromatography (25-50% DCM/hexanes) yielded 3-((([1,1'-biphenyl]-3-ylmethyl)thio)-6-methyl-1,2,4,5-tetrazine as a pink crystalline solid (708 mg, 2.4 mmol, 24%). $^1$H NMR (400 MHz, CDCl$_3$) δ 7.70-7.69 (app t, J=1.9 Hz, 1H), 7.60-7.57 (m, 2H), 7.52 (app dt, 7.6, 1.6 Hz, 1H), 7.48-7.39 (m, 4H), 7.38-7.34 (m, 1H), 4.61 (s, 2H), 2.97 (s, 3H). $^{13}$C NMR (101 MHz, CDCl$_3$) δ 174.7 (C), 165.5 (C), 141.9 (C), 140.7 (C), 136.3 (C), 129.3 (CH), 129.0 (CH), 128.3 (CH), 128.2 (CH), 127.7 (CH), 127.3 (CH), 126.8 (CH), 34.9 (CH$_2$), 20.9 (CH$_3$). FTIR (KBr, thin film) 3456, 3060, 3033, 2932, 1636, 1599, 1479, 1383, 1316, 1160, 1068, 884, 761, 699 cm$^{-1}$. HRMS (ESI+) [M+H]$^+$ Calculated for C$_{16}$H15N$_4$S$^+$ 295.1017; found 295.1024.

Example 3F: 3-((4-(tert-butyl)benzyl)thio)-6-methyl-1,2,4,5-tetrazine (1g)

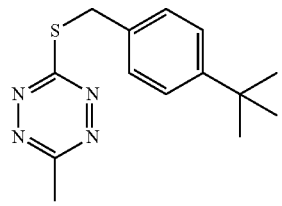 [SMILES: Cc1nnc(SCc2ccc(C(C)(C)C)cc2)nn1]

Prepared using Thiocarbohydrazide (1.01 g, 9.5 mmol) and 4-tert-Butylbenzyl bromide (1.7 mL, 9.5 mmol). ([1-tert-butyl-4-ylmethyl)thiocarbohydrazide bromide was precipitated from the reaction solution with 50 mL hexanes. Silica gel chromatography (40% DCM/hexanes) yielded 3-((4-(tert-butyl)benzyl)thio)-6-methyl-1,2,4,5-tetrazine as a red oil (727 mg, 2.7 mmol, 28%). $^1$H NMR (400 MHz, CDCl$_3$) δ 7.39 (app d, J=8.5 Hz, 1H), 7.36 (app d, J=8.5 Hz, 1H), 4.52 (s, 2H), 2.97 (s, 3H), 1.30 (s, 9H). $^{13}$C NMR (101 MHz, CDCl$_3$) δ 174.9 (C), 165.4 (C), 151.0 (C), 132.6 (C), 129.1 (CH), 125.8 (CH), 34.5 (CH$_2$), 31.4 (CH$_3$), 20.9 (CH$_3$). FTIR (KBr, thin film) 3428, 3055, 3027, 2963, 2906, 2868, 1383, 1316, 1162, 1068, 885 cm$^{-1}$. HRMS (ESI+) [M+H]$^+$ Calculated for C$_{14}$H$_{19}$N$_4$S$^+$ 275.1330; found 275.1336.

Example 4: Effect of Unprotected Heteroatoms (ethylene glycol, ethanolamine, or mercaptoethanol) on Cross-coupling Yields

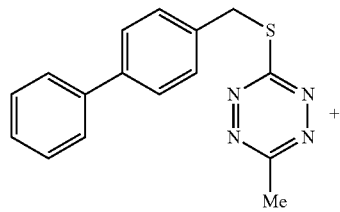

b-Tz

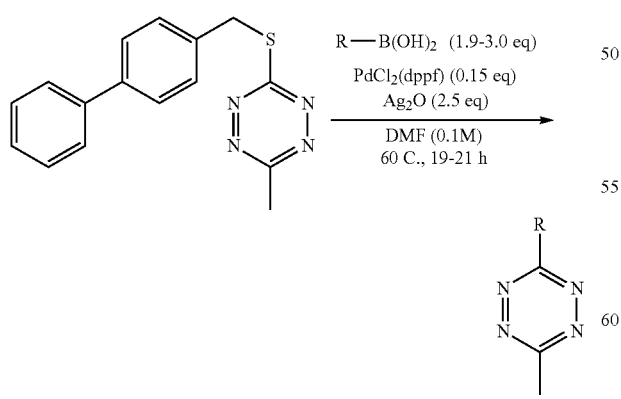

Yield of 2i
R = OH 76%
NH₂ 0%
SH 0%

Using standard cross-coupling conditions for the synthesis of 2i, the following additives were included to test the effect of unprotected heteroatoms on overall yield: ethylene glycol (63 µL, 3.0 eq.), ethanolamine (68 µL, 3.0 eq.), or mercaptoethanol (79 µL, 3.0 eq.). Alcohol has little effect on overall yield. Decomposition of b-Tz was observed with ethanolamine. Conversely, mercaptoethanol does not decompose b-Tz, but likely poisons the Pd-catalyst and/or Ag-mediator.

Example 5: General Procedure for Methyl Tetrazine Cross-Coupling

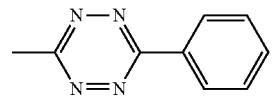

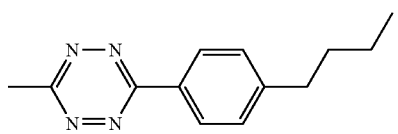 [SMILES: CCCCc1ccc(-c2nnc(C)nn2)cc1]

b-Tz 1a (110 mg, 375 µmol, 1 eq.) boronic acid (713 µmol, 1.9 eq. or 1125 µmol, 3.0 eq., see below), [1,1'-Bis(diphenylphosphino)ferrocene]dichloropalladium(II) (41 mg, 56 µmol, 0.15 eq.) and silver(I) oxide (218 mg, 938 µmol, 2.5 eq.) were added to a vacuum dried schlenk flask equipped with a stir bar. The solids were dissolved/suspended as a heterogeneous slurry with N,N-Dimethylformamide (3.75 mL, 0.1M) and the flask was flushed with nitrogen and sealed. The reaction was stirred at 60° C. for 19-21 h, then brought to room temperature and the solvent was removed by rotary evaporation.

The crude solids were chromatographed directly on silica gel. Elution systems are described below. Each reaction was run in duplicate to obtain an average yield.

Example 5A: 3-methyl-6-phenyl-1,2,4,5-tetrazine (2a)

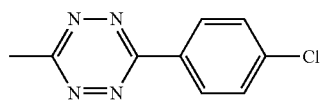

Prepared using phenylboronic acid (87 mg, 713 µmol, 1.9 eq). Silica gel chromatography (75% DCM/hexanes) yielded an average of 90% as a purple crystalline solid (run 1: 58 mg, 91%; run 2: 57 mg, 88%). $^1$H NMR (400 MHz, CDCl$_3$) b 8.61-8.58 (m, 2H), 7.65-7.57 (m, 3H), 3.10 (s, 3H). $^{13}$C NMR (101 MHz, CDCl$_3$) b 167.4 (C), 164.2 (C), 132.7 (CH), 131.9 (C), 129.4 (CH), 128.0 (CH), 21.3 (CH$_3$). FTIR (KBr, thin film) 3446, 3072, 2918, 2849, 1660, 1402, 1362, 890, 759, 692, 564 cm$^{-1}$. HRMS (ESI+) [M+H]$^+$ Calculated for C$_9$H$_9$N$_4^+$ 172.0827; found 173.0827.

Example 5B: 3-(4-butylphenyl)-6-methyl-1,2,4,5-tetrazine (2b)

Prepared using 4-Butylphenylboronic acid (127 mg, 713 µmol, 1.9 eq). Silica gel chromatography (60% DCM/hexanes) yielded an average of 92% as a purple crystalline solid (run 1: 79 mg, 93%; run 2: 78 mg, 91%). $^1$H NMR (400 MHz, CDCl$_3$) δ 8.49 (app d, J=8.3 Hz 2H), 7.40 (app d, J=8.3 Hz, 2H), 3.08 (s, 3H), 2.72 (app t, J=8.0 Hz, 2H), 1.67 (app pent, J=7.6 Hz, 2H), 1.39 (app sext, J=7.2 Hz, 2H), 0.95 (t, J=7.2 Hz, 3H). $^{13}$C NMR (101 MHz, CDCl$_3$) δ 167.1 (C), 164.3 (C), 148.3 (C), 129.5 (CH), 129.3 (C), 128.0 (CH), 35.9 (CH$_2$), 33.5 (CH$_2$), 22.5 (CH$_2$), 21.3 (CH$_3$), 14.1 (CH$_3$). FTIR (KBr, thin film) 3455, 2950, 2927, 2862, 1962, 1606, 1403, 1361, 1088, 889, 570 cm$^{-1}$. HRMS (ESI+) [M+H]$^+$ Calculated for C$_{13}$H$_{17}$N$_4^+$ 229.1453; found 229.1456.

Example 5C: 3-(4-chlorophenyl)-6-methyl-1,2,4,5-tetrazine (2c)

Prepared using 4-Chlorophenylboronic acid (111 mg, 713 µmol, 1.9 eq). Silica gel chromatography (60% DCM/hexanes) yielded an average of 91% as a magenta crystalline solid (run 1: 70 mg, 91%; run 2: 70 mg, 91%). $^1$H NMR (400 MHz, CDCl$_3$) δ 8.55 (app d, J=8.7 Hz, 2H), 7.57 (app d, J=8.7 Hz, 2H), 3.11 (s, 3H). $^{13}$C NMR (101 MHz, CDCl$_3$) δ 167.6 (C), 163.6 (C), 139.3 (C), 130.4 (C), 129.8 (CH), 129.3 (CH), 21.4 (CH$_3$). FTIR (KBr, thin film) 3460, 3090, 2075, 1949, 1636, 1396, 1108, 1098, 889, 854, 800, 563 cm$^{-1}$. HRMS (ESI+) [M+H]$^+$ Calculated for C$_9$H$_8$ClN$_4$$^+$ 207.0437; found 207.0439.

Example 5D: 3-methyl-6-(4-(trifluoromethyl)phenyl)-1,2,4,5-tetrazine (2d)

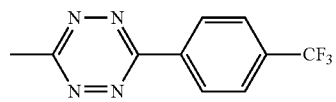

Prepared using 4-(Trifluoromethyl)phenylboronic acid (136 mg, 713 µmol, 1.9 eq). Silica gel plug (50% DCM/hexanes) then reverse phase C$_{18}$ silica gel chromatography (50-80% MeOH/H$_2$O) yielded an average of 61% as a magenta crystalline solid (run 1: 56 mg, 62%; run 2: 54 mg, 60%). $^1$H NMR (400 MHz, CDCl$_3$) δ 8.73 (app d, J=8.4 Hz, 2H), 7.86 (app d, J=8.4 Hz, 2H), 3.14 (s, 3H). $^{13}$C NMR (101 MHz, CDCl$_3$) δ 168.0 (C), 163.4 (C), 135.2 (C, q, J$_{C-F}$=1.0 Hz), 134.2 (C, q, J$_{C-F}$=32.9 Hz), 128.4 (CH), 126.3 (CH, q, J$_{C-F}$=3.7 Hz), 123.8 (CF$_3$, q, J$_{C-F}$=273.6 Hz), 21.4 (CH$_3$). FTIR (KBr, thin film) 3444, 2066, 1636, 1404, 1331, 1162, 1122, 550 cm-1. HRMS (ESI+) [M+H]$^+$ Calculated for C$_{10}$H$_8$F$_3$N$_4$$^+$ 241.0701; found 241.0698.

Example 5E: tert-butyl 4-(6-methyl-1,2,4,5-tetrazin-3-yl)benzylcarbamate (2e)

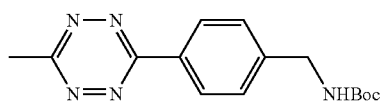 [SMILES: Cc1nnc(-c2ccc(CNC(=O)OC(C)(C)C)cc2)nn1]

Prepared using 4-(N-Boc-aminomethyl)phenylboronic acid (179 mg, 713 µmol, 1.9 eq). Silica gel plug (0.75% acetone/DCM) then reverse phase C$_{18}$ silica gel chromatography (50-80% MeOH/H$_2$O) yielded an average of 94% as a pink powdery solid (run 1: 110 mg, 97%; run 2: 103 mg, 91%). $^1$H NMR (400 MHz, CDCl$_3$) δ 8.55 (app d, J=8.0 Hz, 2H), 7.50 (app d, J=8.0 Hz, 2H), 5.00 (NH, br s, 1H), 4.44 (d, J=6.0 Hz, 2H), 3.09 (s, 3H), 1.48 (s, 9H). $^{13}$C NMR (101 MHz, CDCl$_3$) δ 167.3 (C), 164.0 (C), 156.1 (C), 144.1 (C), 130.9 (C), 128.3 (CH), 128.2 (C), 80.0 (C), 44.5 (CH$_2$), 28.5 (CH$_3$), 21.3 (CH$_3$). FTIR (KBr, thin film) 3349, 3004, 2977, 2931, 2248, 1696, 1612, 1521, 1405, 1365, 1272, 1250, 1167, 1089, 891, 796, 732, 562 cm$^{-1}$. HRMS (ESI+) [M+H]$^+$ Calculated for C$_{15}$H$_{20}$O$_2$N$_5$$^+$ 302.1617; found 302.1616.

Example 5F: tert-butyl (3-(6-methyl-1,2,4,5-tetrazin-3-yl)phenyl)carbamate (2f)

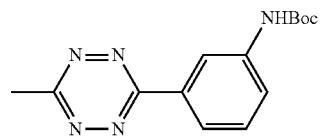 [SMILES: Cc1nnc(-c2cccc(NC(=O)OC(C)(C)C)c2)nn1]

Prepared using 3-(N-Boc-amino)phenylboronic acid (169 mg, 713 µmol, 1.9 eq). Silica gel chromatography (0.5% acetone, 0.75% ethanol, 98.75% chloroform) yielded an average of 92% as a pink powdery solid (run 1: 98 mg, 91%; run 2: 100 mg, 93%). $^1$H NMR (400 MHz, DMSO-d$_6$) δ 9.71 (NH, s, 1H), 8.71 (app s, 1H), 8.07 (app d, J=7.6 Hz, 1H), 7.69 (app d, J=7.2 Hz, 1H), 7.53 (app t, J=8.0 Hz, 1H), 3.99 (s, 3H), 1.50 (s, 9H). $^{13}$C NMR (101 MHz, DMSO-d$_6$) δ 167.2 (C), 163.3 (C), 153.8 (C), 140.6 (C), 132.4 (C), 129.8 (CH), 121.8 (CH), 121.1 (CH), 116.6 (CH), 79.5 (C), 28.1 (CH$_3$), 20.9 (CH$_3$). FTIR (KBr, thin film) 3299, 3066, 2979, 2931, 1718, 1541, 1392, 1367, 1235, 1156, 688 cm$^{-1}$. HRMS (ESI+) [M+H]$^+$ Calculated for C$_{14}$H$_{18}$O$_2$N$_5$$^+$ 288.1460; found 288.1459.

Example 5G: (4-(6-methyl-1,2,4,5-tetrazin-3-yl)phenyl)methanol (2g)

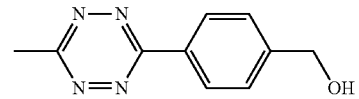

Prepared using 4-(Hydroxymethyl)phenylboronic acid (171 mg, 1125 µmol, 3.0 eq). Silica gel chromatography (3% acetone/DCM) yielded an average of 68% as a magenta crystalline solid (run 1: 49 mg, 65%; run 2: 53 mg, 70%). $^1$H NMR (400 MHz, CDCl$_3$) δ 8.59 (app d, J=8.5 Hz, 2H), 7.59 (app d, J=8.5 Hz, 2H), 4.84 (s, 2H), 3.10 (s, 3H), 1.85 (br s, 1H). $^{13}$C NMR (101 MHz, CDCl$_3$) δ 167.4 (C), 164.1 (C), 145.7 (C), 131.1 (C), 128.3 (CH), 127.5 (CH), 64.9 (CH$_2$), 21.3 (CH$_3$). FTIR (KBr, thin film) 3446, 2069, 1636, 1403, 1362, 1038, 562 cm$^{-1}$. HRMS (ESI+) [M+H]$^+$ Calculated for C$_{10}$H$_{11}$ON$_4$$^+$ 203.0933; found 203.0934.

Example 5H: 3-methyl-6-(o-tolyl)-1,2,4,5-tetrazine (2h)

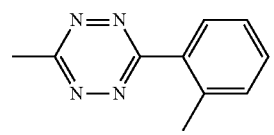

Prepared using o-Tolylboronic acid (97 mg, 713 µmol, 1.9 eq). Silica gel chromatography (90% DCM/hexanes) yielded an average of 50% as a magenta crystalline solid (run 1: 36 mg, 51%; run 2: 35 mg, 49%). $^1$H NMR (400 MHz, CDCl$_3$) δ 8.05 (app d, J=7.6 Hz, 1H), 7.49 (app td, J=7.6, 1.6 Hz, 1H), 7.44-7.39 (m, 2H), 3.12 (s, 3H), 2.63 (s, 3H). $^{13}$C NMR (101 MHz, CDCl$_3$) δ 167.3, 166.4, 138.6, 132.0, 131.8, 131.5, 131.0, 126.6, 21.5, 21.4. FTIR (KBr, thin film) 3436, 3079, 2966, 2929, 1602, 1450, 1436, 1398, 1364, 1086, 1041, 1020, 886, 757, 722, 573, 466 cm$^{-1}$. HRMS (ESI+) [M+H]$^+$ Calculated for $C_{10}H_{11}N_4^+$ 187.0984; found 187.0986.

Example 5I: 3-(4-methoxyphenyl)-6-methyl-1,2,4,5-tetrazine (2i)

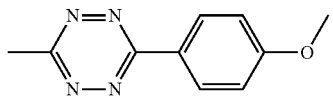

Prepared using 4-Methoxyphenylboronic acid (108 mg, 713 μmol, 1.9 eq). Silica gel chromatography (90% DCM/hexanes) yielded an average of 86% as a dark pink crystalline solid (run 1: 62 mg, 81%; run 2: 68 mg, 90%). $^1$H NMR (400 MHz, CDCl$_3$) δ 8.50 (app d, J=9.0 Hz, 2H), 7.08 (app d, J=9.0 Hz, 2H), 3.92 (s, 3H), 3.06 (s, 3H). $^{13}$C NMR (101 MHz, CDCl$_3$) δ 166.7 (C), 163.9 (C), 163.4 (C), 129.9 (CH), 124.3 (C), 114.8 (CH), 55.7 (CH$_3$), 21.2 (CH$_3$). FTIR (KBr, thin film) 3446, 2042, 1636, 1609, 1405, 1248, 1022, 890, 843, 801, 683, 562 cm$^{-1}$. HRMS (ESI+) [M+H]$^+$ Calculated for $C_{10}H_{11}ON_4^+$ 203.0933; found 203.0934.

Example 5J: 3-(3-methoxyphenyl)-6-methyl-1,2,4,5-tetrazine (2j)

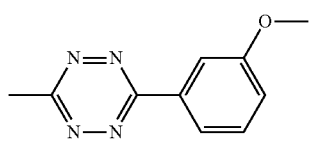

Prepared using 3-Methoxyphenylboronic acid (108 mg, 713 μmol, 1.9 eq). Silica gel chromatography (90% DCM/hexanes) yielded an average of 88% as a dark pink crystalline solid (run 1: 69 mg, 91%; run 2: 65 mg, 85%). $^1$H NMR (400 MHz, CDCl$_3$) δ 8.20 (app dt, J=8.0, 1.3 Hz, 1H), 8.12 (dd, J=2.8, 1.6 Hz, 1H), 7.50 (app t, J=8.0 Hz, 1H), 7.17 (ddd, J=8.4, 2.8, 1.2 Hz, 1H), 3.93 (s, 3H), 3.10 (s, 3H). 13C NMR (101 MHz, CDCl$_3$) δ 167.5 (C), 164.1 (C), 160.4 (C), 133.1 (C), 130.5 (CH), 120.6 (CH), 119.4 (CH), 112.2 (CH), 55.7 (CH$_3$), 21.3 (CH$_3$). FTIR (KBr, thin film) 3446, 2958, 2041, 1636, 1597, 1220, 1022, 900, 871, 793, 691, 626, 492 cm$^{-1}$.

HRMS (ESI+) [M+H]$^+$ Calculated for $C_{10}H_{11}ON_4^+$ 203.0933; found 203.0934.

Example 5K: 3-(2-methoxyphenyl)-6-methyl-1,2,4,5-tetrazine (2k)

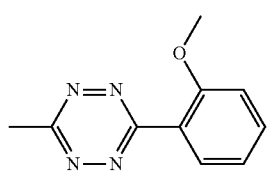

Prepared using 2-Methoxyphenylboronic acid (108 mg, 713 μmol, 1.9 eq). Silica gel chromatography (1% acetone/DCM) yielded an average of 19% as a dark pink oil (run 1: 13 mg, 18%; run 2: 14 mg, 19%). $^1$H NMR (400 MHz, CDCl$_3$) δ 7.91 (dd, J=7.6, 2.0 Hz, 1H), 7.56 (ddd, J=8.8, 7.2, 1.6 Hz, 1H), 7.16 (app td, J=7.6, 1.2 Hz, 1H), 7.11 (app d, J=8.4 Hz, 1H), 3.90 (s, 3H), 3.11 (s, 3H). $^{13}$C NMR (101 MHz, CDCl$_3$) δ 166.3 (C), 166.0 (C), 158.3 (C), 133.2 (CH), 131.9 (CH), 122.2 (C), 121.2 (CH), 112.2 (CH), 56.2 (CH$_3$), 21.4 (CH$_3$). FTIR (KBr, thin film) 3488, 3078, 3007, 2932, 2838, 1602, 1498, 1467, 1436, 1399, 1363, 1289, 1264, 1239, 1021, 885, 756 cm$^{-1}$. HRMS (ESI+) [M+H]$^+$ Calculated for $C_{10}H_{11}ON_4^+$ 203.0933; found 203.0932

Example 5L: 3-(benzo[d][1,3]dioxol-5-y)-6-methyl-1,2,4,5-tetrazine (2l)

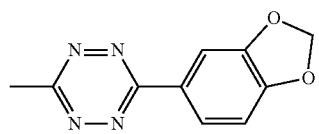

Prepared using 3,4-(Methylenedioxy)phenylboronic acid (118 mg, 713 μmol, 1.9 eq). Silica gel chromatography (90% DCM/hexanes) yielded an average of 79% as a salmon colored crystalline solid (run 1: 66 mg, 81%; run 2: 63 mg, 77%). $^1$H NMR (400 MHz, CDCl$_3$) δ 8.22 (dd, J=8.4, 1.6 Hz, 1H), 8.03 (d, J=1.6 Hz, 1H), 7.00 (d, J=8.4 Hz, 1H), 6.10 (s, 2H), 3.06 (s, 3H). $^{13}$C NMR (101 MHz, CDCl$_3$) δ 166.9 (C), 163.8 (C), 151.7 (C), 148.8 (C), 125.9 (C), 123.6 (CH), 109.2 (CH), 107.8 (CH), 102.0 (CH$_2$), 21.2 (CH$_3$). FTIR (KBr, thin film) 3456, 2361, 2337, 1659, 1395, 1247, 901, 798, 668, 629, 502 cm$^{-1}$. HRMS (ESI+) [M+H]$^+$ Calculated for $C_{10}H_9O_2N_4^+$ 217.0726; found 217.0728.

Example 5M: 3-methyl-6-(3-nitrophenyl)-1,2,4,5-tetrazine (2m)

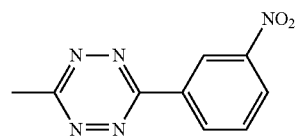 [SMILES: Cc1nnc(-c2cccc([N+](=O)[O-])c2)nn1]

Prepared using 3-Nitrophenylboronic acid (119 mg, 713 μmol, 1.9 eq). Silica gel chromatography (0.5% acetone/DCM) yielded an average of 48% as a pink crystalline solid (run 1: 39 mg, 48%; run 2: 39 mg, 48%). $^1$H NMR (400 MHz, CDCl$_3$) δ 9.74 (app t, J=2.0 Hz, 1H), 8.96-8.93 (m, 1H), 8.49 (ddd, J=8.0, 2.4, 1.2 Hz, 1H), 7.82 (app t, J=8.0 Hz, 1H), 3.16 (s, 3H). $^{13}$C NMR (101 MHz, CDCl$_3$) δ 168.3 (C), 162.8 (C), 149.2 (C), 133.8 (C), 133.5 (CH), 130.6 (CH), 127.1 (CH), 123.0 (CH), 21.5 (CH$_3$). FTIR (KBr, thin film) 3090, 1621, 1588, 1525, 1482, 1402, 1349, 1107, 1082, 870, 826, 805, 757, 738, 683, 574 cm$^{-1}$. HRMS (LIFDI) m/z Calculated for $C_9H_7O_2N_5$ 217.0600; found 217.0593.

Example 5N: 3-methyl-6-(4-(methylsulfonyl)phenyl)-1,2,4,5-tetrazine (2n)

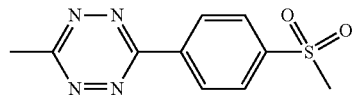

Prepared using 4-(Methanesulfonyl)phenylboronic acid (143 mg, 713 µmol, 1.9 eq). Silica gel chromatography (1% Acetone/DCM) yielded an average of 69% as a magenta crystalline solid (run 1: 60 mg, 64%; run 2: 69 mg, 73%). $^1$H NMR (400 MHz, CDCl$_3$) δ 8.83-8.80 (m, 2H), 8.19-8.16 (m, 2H). 3.16 (s, 3H), 3.14 (s, 3H). 13C NMR (101 MHz, CDCl$_3$) δ 168.2 (C), 163.1 (C), 144.0 (C), 136.9 (C), 128.9 (CH), 128.4 (CH), 44.5 (CH$_3$), 21.5 (CH$_3$). FTIR (KBr, thin film) 3098, 3008, 2918, 1402, 1365, 1303, 1149, 1085, 968, 891, 778, 572, 545 cm$^{-1}$. HRMS (LIFDI) m/z Calculated for C$_{10}$H$_{10}$O$_2$N$_4$S 250.0524; found 250.0529.

Example 5O: 3-(3-(benzylthio)phenyl)-6-methyl-1,2,4,5-tetrazine (2o)

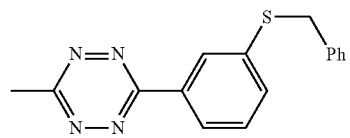 [SMILES: Cc1nnc(-c2cccc(SCc3ccccc3)c2)nn1]

Prepared using (3-(Benzylthio)phenyl)boronic acid (275 mg, 1125 µmol, 3.0 eq). Due to difficult separation of the resulting product 20 and unreacted b-Tz, additional reactants were added as follows to consume the remaining b-Tz: 4-Methoxyphenylboronic acid (57 mg, 375 µmol, 1.0 eq), [1,1'-Bis(diphenylphosphino)ferrocene]dichloropalladium (II) (27 mg, 38 µmol, 0.1 eq.) and silver(I) oxide (87 mg, 375 µmol, 1.0 eq.) stirred at 60° C. for 6 h. Silica gel chromatography (75% DCM/hexanes) yielded an average of 76% as a dark red crystalline solid (run 1: 84 mg, 77%; run 2: 83 mg, 75%). $^1$H NMR (400 MHz, Acetone-d6) δ 8.49-8.48 (m, 1H), 8.34-8.32 (m, 1H), 7.63 (ddd, J=8.0, 2.0, 1.2 Hz, 1H), 7.56 (app td, J=8.0, 0.8 Hz, 1H), 7.45-7.42 (m, 2H), 7.33-7.28 (m, 2H) 7.25-7.21 (m, 1H), 4.36 (s, 2H), 3.04 (s, 3H). $^{13}$C NMR (101 MHz, Acetone-d6) δ 168.53 (C), 164.30 (C), 139.29 (C), 138.17 (C), 133.97 (C), 133.10 (CH), 130.65 (CH), 129.81 (CH). 129.29 (CH), 128.06 (CH), 128.05 (CH), 125.83 (CH), 38.21 (CH$_2$), 21.21 (CH$_3$). FTIR (KBr, thin film) 3446, 3077, 3028, 2919, 2850, 2361, 2337, 1455, 1394, 1359, 1302, 1076, 1067, 1031, 898, 875, 780, 714, 698, 687, 599, 470 cm$^{-1}$. HRMS (ESI+) [M+H]$^+$ Calculated for C$_{16}$H$_{15}$N$_4$S$^+$ 295.1017; found 295.1008.

Example 5P: 3-(6-methyl-1,2,4,5-tetrazin-3-yl)benzonitrile (2p)

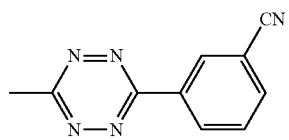

Prepared using 3-Cyanophenylboronic acid (105 mg, 713 µmol, 1.9 eq). Silica gel chromatography (100% DCM) yielded an average of 47% as a bright pink powdery solid (run 1: 34 mg, 46%; run 2: 35 mg, 47%). $^1$H NMR (400 MHz, CDCl$_3$) δ 8.93 (app t, J=2.0 Hz, 1H), 8.85 (app dt, J=8.0, 1.6 Hz, 1H), 7.92 (app dt, J=7.6, 1.4 Hz, 1H), 7.74 (app t, J=8.0 Hz, 1H), 3.15 (s, 3H). $^{13}$C NMR (101 MHz, CDCl$_3$) δ 168.2 (C), 162.8 (C), 135.7 (CH), 133.3 (C), 131.9 (CH), 131.5 (CH), 130.3 (CH), 118.1 (C), 113.9 (C), 21.4 (CH$_3$). FTIR (KBr, thin film) 3445, 2228, 2066, 1636, 1400, 887, 797, 687, 521 cm$^{-1}$. HRMS (ESI+) [M+H]$^+$ Calculated for C$_{10}$H$_8$N$_5$$^+$ 198.0780; found 198.0781.

Example 5Q: 4-(6-methyl-1,2,4,5-tetrazin-3-yl)benzaldehyde (2q)

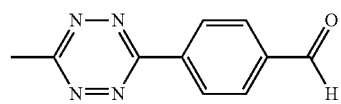

Prepared using 4-formylphenylboronic acid (169 mg, 1125 µmol, 3.0 eq). Silica gel chromatography (0.5% acetone, 0.75% ethanol, 98.75% chloroform) yielded an average of 69% as a magenta crystalline solid (run 1: 51 mg, 68%; run 2: 52 mg, 69%). $^1$H NMR (400 MHz, CDCl$_3$) δ 10.16 (s, 1H), 8.79 (app d, J=8.4 Hz, 2H), 8.11 (app d, J=8.4 Hz, 2H), 3.15 (s, 3H). Minor peaks attributable to an impurity were detected at 10.09, 8.00 and 7.81 ppm. $^{13}$C NMR (101 MHz, CDCl$_3$) δ 191.8 (CH), 167.9 (C), 163.6 (C), 139.0 (C), 137.1 (C), 130.5 (CH), 128.6 (CH), 21.5 (CH$_3$). FTIR (KBr, thin film) 3446, 2855, 2073, 1684, 1636, 1396, 887, 853, 801, 566 cm$^{-1}$. HRMS (ESI+) [M+H]$^+$ Calculated for C$_{10}$H$_9$ON$_4$$^+$ 201.0776; found 201.0778.

Example 5R: methyl 4-(6-methyl-1,2,4,5-tetrazin-3-yl)benzoate (2r)

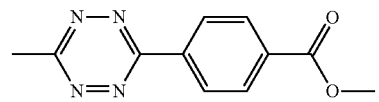

Prepared using 4-Methoxycarbonylphenylboronic acid (203 mg, 1125 µmol, 3.0 eq). Silica gel chromatography (15% EtOAc/hexanes) yielded an average of 66% as a bright pink crystalline solid (run 1: 61 mg, 70%; run 2: 53 mg, 62%). $^1$H NMR (400 MHz, CDCl$_3$) δ 8.68 (app d, J=8.7 Hz, 2H), 8.25 (app d, J=8.7 Hz, 2H), 3.98 (s, 3H), 3.13 (s, 3H). $^{13}$C NMR (101 MHz, CDCl$_3$) δ 167.8 (C), 166.5 (C), 163.7 (C), 135.8 (C), 133.7 (C), 130.5 (CH), 128.0 (CH), 52.7 (CH$_3$), 21.4 (CH$_3$). FTIR (KBr, thin film) 3457, 2996, 2951, 2917, 2849, 1722, 1653, 1406, 1276, 1258, 1109, 768, 696, 563 cm$^{-1}$. HRMS (ESI+) [M+H]$^+$ Calculated for C$_{11}$H$_{11}$O$_2$N$_4$$^+$ 231.0882; found 231.0884.

Example 5S: (4-(6-methyl-1,2,4,5-tetrazin-3-yl)phenyl)(phenyl)methanone (2s)

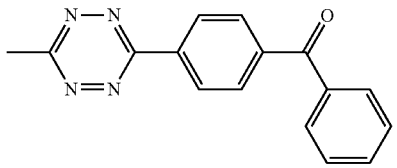 [SMILES: Cc1nnc(-c2ccc(C(=O)c3ccccc3)cc2)nn1]

Prepared using (4-benzoylphenyl)boronic acid (254 mg, 1125 μmol, 3.0 eq). Silica gel chromatography (1% EtOAc/DCM) yielded an average of 66% as a bright pink crystalline solid (run 1: 68 mg, 66%; run 2: 68 mg, 66%). $^1$H NMR (400 MHz, CDCl$_3$) δ 8.73 (app d, J=8.5 Hz, 2H), 8.00 (app d, J=8.5 Hz, 2H), 7.88-7.85 (m, 2H), 7.64 (app tt, J=7.6, 1.2 Hz, 1H), 7.55-7.51 (m, 2H), 3.15 (s, 3H). $^{13}$C NMR (101 MHz, CDCl$_3$) δ 196.2 (C), 167.8 (C), 163.7 (C), 141.0 (C), 137.1 (C), 135.2 (C), 133.1 (CH), 130.8 (CH), 130.3 (CH), 128.6 (CH), 127.9 (CH), 21.4 (CH$_3$). FTIR (KBr, thin film) 3447, 2070, 1654, 1403, 894, 867, 789, 742, 700, 585, 551 cm$^{-1}$. HRMS (ESI+) [M+H]$^+$ Calculated for C$_{16}$H$_{13}$ON$_4{}^+$ 277.1089; found 277.1093.

Example 5T: 4-(6-methyl-1,2,4,5-tetrazin-3-yl)-N,N-diphenylaniline (2t)

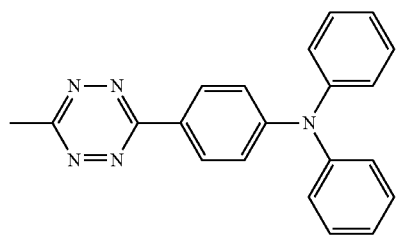 [SMILES: Cc1nnc(-c2ccc(N(c3ccccc3)c3ccccc3)cc2)nn1]

Prepared using 4-(diphenylamino)phenyl boronic acid (325 mg, 1125 μmol, 3.0 eq). Silica gel chromatography (70% DCM/hexanes) yielded an average of 46% as a reddish orange powdery solid (run 1: 61 mg, 48%; run 2: 56 mg, 44%). $^1$H NMR (400 MHz, CDCl$_3$) δ 8.40 (app d, J=9.0 Hz, 2H), 7.36-7.31 (m, 4H), 7.22-7.18 (m, 4H), 7.16-7.12 (m, 4H), 3.04 (s, 3H). $^{13}$C NMR (101 MHz, CDCl$_3$) δ 166.4 (C), 163.9 (C), 152.0 (C), 146.7 (C), 129.8 (CH), 129.1 (CH), 126.0 (CH), 124.7 (CH), 123.8 (C), 121.1 (CH), 21.2 (CH$_3$). FTIR (KBr, thin film) 3462, 2065, 1636, 1591, 1488, 1403, 1364, 1331, 1283, 1177, 1086, 891, 801, 756, 697, 622, 563, 515 cm$^{-1}$. HRMS (ESI+) [M+H]$^+$ Calculated for C$_{21}$H$_{18}$N$_5{}^+$ 340.1562; found 340.1566.

Example 5U: 3-(6-methyl-1,2,4,5-tetrazin-3-yl)quinoline (2u)

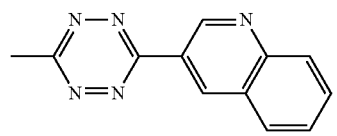 [SMILES: Cc1nnc(-c2cnc3ccccc3c2)nn1]

Prepared using 3-Quinolineboronic acid (123 mg, 713 μmol, 1.9 eq). Silica gel chromatography (2% acetone/DCM) yielded an average of 63% as a magenta hairy solid (run 1: 54 mg, 64%; run 2: 51 mg, 61%). $^1$H NMR (400 MHz, CDCl$_3$) δ 10.04 (d, J=2.0 Hz, 1H), 9.42 (d, J=2.4, 1H), 8.23 (d, J=8.4 Hz, 1H), 8.04 (d, J=8.4, 1H), 7.88 (app t, J=7.8 Hz, 1H), 7.68 (app t, J=7.6 Hz, 1H), 3.17 (s, 3H). $^{13}$C NMR (101 MHz, CDCl$_3$) δ 167.9 (C), 163.4 (C), 149.9 (C), 148.7 (CH), 136.4 (CH), 132.0 (CH), 129.7 (CH), 129.3 (CH), 127.9 (CH), 127.5 (C), 124.8 (C), 21.5 (CH$_3$). FTIR (KBr, thin film) 3454, 3058, 2922, 2362, 2337, 1615, 1598, 1497, 1401, 1320, 808, 787, 758, 650, 562, 475 cm$^{-1}$. HRMS (ESI+) [M+H]$^+$ Calculated for C$_{12}$H$_{10}$N$_5{}^+$ 224.0936; found 224.0938.

Example 5V: 5-(6-methyl-1,2,4,5-tetrazin-3-yl)-1H-indole (2v)

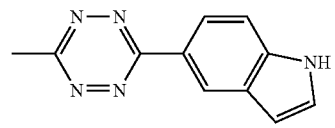 [SMILES: Cc1nnc(-c2ccc3[nH]ccc3c2)nn1]

Prepared using 5-Indoleboronic acid (115 mg, 713 μmol, 1.9 eq). Silica gel chromatography (2% acetone/DCM) yielded an average of 61% as an orange hairy solid (run 1: 45 mg, 57%; run 2: 51 mg, 65%). $^1$H NMR (400 MHz, DMSO-d$_6$) δ 11.57 (NH, br s, 1H), 8.59-8.58 (m, 1H), 8.13 (dd, J=8.4, 1.6 Hz, 1H), 7.78 (d, J=8.4 Hz, 1H), 7.61 (app t, J=2.8 Hz, 1H), 6.58-6.56 (m, 1H), 2.96 (s, 3H). $^{13}$C NMR (101 MHz, DMSO-d$_6$) δ 166.4 (C), 164.3 (C), 136.1 (C), 131.0 (C), 129.2 (CH), 124.2 (C), 121.0 (CH), 117.9 (CH), 111.3 (CH), 101.8 (CH), 20.7 (CH$_3$). FTIR (KBr, thin film) 3448, 2071, 1636, 1401, 1360, 512 cm$^{-1}$. HRMS (ESI+) [M+H]$^+$ Calculated for C$_{11}$H$_{10}$N$_5{}^+$ 212.0936; found 212.0938.

Example 5W: 4-(4-(6-methyl-1,2,4,5-tetrazin-3-yl)phenyl)morpholine (2w)

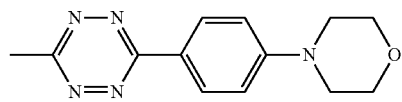 [SMILES: Cc1nnc(-c2ccc(N3CCOCC3)cc2)nn1]

Prepared using 4-Morpholinophenylboronic Acid (233 mg, 1125 μmol, 3.0 eq). Silica gel chromatography (3% acetone/DCM) yielded an average of 58% as a dark red crystalline solid (run 1: 58 mg, 60%; run 2: 53 mg, 55%). $^1$H NMR (400 MHz, CDCl$_3$) δ 8.49 (d, J=9.1 Hz, 2H), 7.04 (d, J=9.1 Hz, 2H), 3.90 (app t, J=5.0 Hz, 4H) 3.35 (app t, J=5.0 Hz, 4H), 3.04 (s, 3H). $^{13}$C NMR (101 MHz, CDCl$_3$) δ 166.3 (C), 163.9 (C), 154.1 (C), 129.5 (CH), 122.1 (C), 114.7 (CH), 66.7 (CH$_2$), 47.9 (CH$_2$), 21.2 (CH$_3$). FTIR (KBr, thin film) 3428, 2988, 2953, 2926, 2868, 2853, 2361, 1923, 1611, 1415, 1267, 1118, 890, 799, 562 cm$^{-1}$. HRMS (ESI+) [M+H]$^+$ Calculated for C$_{13}$H$_{16}$ON$_5{}^+$ 258.1355; found 258.1359.

Example 5X: 3-(4-(2H-1,2,3-triazol-2-yl)phenyl)-6-methyl-1,2,4,5-tetrazine (2x)

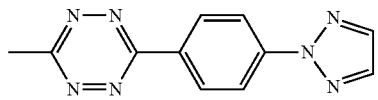 [SMILES: Cc1nnc(-c2ccc(-n3nccn3)cc2)nn1]

Prepared using 4-(triazol-2-yl)phenylboronic acid (213 mg, 1125 µmol, 3.0 eq). Silica gel chromatography (1% EtOAc/DCM) yielded an average of 94% as a dark pink powdery solid (run 1: 84 mg, 94%; run 2: 83 mg, 93%). $^1$H NMR (400 MHz, CDCl$_3$) δ 8.74 (app d, J=8.9 Hz, 2H), 8.33 (app d, J=8.9 Hz, 2H), 7.89 (s, 2H), 3.12 (s, 3H). $^{13}$C NMR (101 MHz, CDCl$_3$) δ 167.5 (C), 163.6 (C), 142.8 (C), 136.5 (CH), 130.8 (C), 129.3 (CH), 119.5 (CH), 21.4 (CH$_3$). FTIR (KBr, thin film) 3435, 2921, 2361, 2356, 2044, 1653, 1635, 1604, 1405, 890, 856, 824, 802, 668, 566 cm-1. HRMS (ESI+) [M+H]$^+$ Calculated for C$_{11}$H$_{10}$N$_7^+$ 240.0998; found 240.0999.

Example 5Y: 3-methyl-6-(4-(1-methyl-1H-imidazol-2-yl)phenyl)-1,2,4,5-tetrazine (2y)

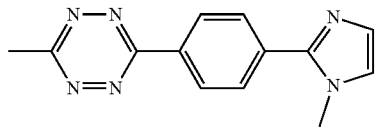 [SMILES: Cc1nnc(-c2ccc(-c3nccn3C)cc2)nn1]

Prepared using 4-(1-methyl-1H-imidazol-2-yl)phenylboronic acid (see page S37 for synthesis, 227 mg, 1125 µmol, 3.0 eq). Silica gel plug (2% EtOH/DCM) then reverse phase C$_{18}$ silica gel chromatography (20-60% MeOH/H$_2$O) yielded an average of 39% as a bright pink crystalline solid (run 1: 36 mg, 38%; run 2: 42 mg, 40%). $^1$H NMR (400 MHz, CDCl$_3$) δ 8.70 (app d, J=8.6 Hz, 2H), 7.91 (app d, J=8.6 Hz, 2H), 7.20 (d, J=1.2 Hz, 1H), 7.05 (d, J=1.2 Hz, 1H), 3.86 (s, 3H), 3.12 (s, 3H). $^{13}$C NMR (101 MHz, CDCl$_3$) δ 167.5 (C), 163.9 (C), 146.7 (C), 134.4 (C), 131.8 (C), 129.3 (CH), 129.0 (CH), 128.2 (CH), 123.5 (CH), 35.0 (CH$_3$), 21.4 (CH$_3$). FTIR (KBr, thin film) 3445, 2989, 2949, 2066, 1636, 1477, 1407, 1277, 897, 860, 801, 710, 576 cm-1. HRMS (ESI+) [M+H]$^+$ Calculated for C$_{13}$H$_{13}$N$_6^+$ 253.1202; found 253.1201.

Example 5Z: 3-(6-fluoropyridin-3-yl)-6-methyl-1,2,4,5-tetrazine (2z)

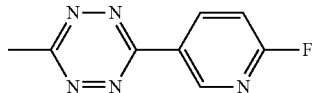

Prepared using 6-Fluoro-3-pyridinylboronic acid (101 mg, 713 µmol, 1.9 eq). Silica gel chromatography (1% acetone/DCM) yielded an average of 46% as a bright pink crystalline solid (run 1: 35 mg, 49%; run 2: 31 mg, 43%). $^1$H NMR (400 MHz, CDCl$_3$) δ 9.46 (d, J=2.4 Hz, 1H), 8.97 (ddd, J=8.8, 7.6, 2.4 Hz, 1H), 7.21 (dd, J=8.8, 2.4 Hz, 1H), 3.14 (s, 3H). $^{13}$C NMR (101 MHz, CDCl$_3$) δ 168.2 (C), 166.1 (CF, d, J$_{C-F}$=246.6 Hz), 162.4 (C), 148.5 (CH, d, J$_{C-F}$=16.4 Hz), 140.6 (CH, d, J$_{C-F}$=8.9 Hz), 126.3 (C, d, J$_{C-F}$=4.6 Hz), 110.5 (CH, d, J$_{C-F}$=37.8 Hz), 21.5 (CH$_3$). FTIR (KBr, thin film) 3438, 2073, 1635, 1589, 1493, 1412, 1368, 1259, 1126, 1016, 887, 848, 506, 750, 692, 635, 575 cm$^{-1}$. HRMS (ESI+) [M+H]$^+$ Calculated for C$_8$H$_7$FN$_5^+$ 192.0685; found 192.0686.

Example 5AA: (E)-3-methyl-6-styryl-1,2,4,5-tetrazine (2aa)

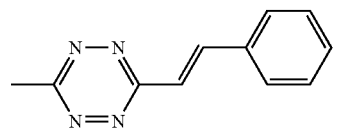

Prepared using trans-2-Phenylvinylboronic acid (106 mg, 713 µmol, 1.9 eq). Silica gel chromatography (90% DCM/hexanes) yielded an average of 39% as a salmon colored crystalline solid (run 1: 27 mg, 37%; run 2: 30 mg, 41%). $^1$H NMR (400 MHz, CDCl$_3$) δ 8.32 (d, J=16.4 Hz, 1H), 7.70-7.67 (m, 2H), 7.49-7.40 (m, 4H), 3.06 (s, 3H). $^{13}$C NMR (101 MHz, CDCl$_3$) δ 166.5 (C), 164.9 (C), 141.1 (CH), 135.2 (C), 130.4 (CH), 129.2 (CH), 128.2 (CH), 120.7 (CH), 21.4 (CH$_3$). FTIR (KBr, thin film) 3447, 3052, 3027, 2918, 1631, 1449, 1402, 1362, 1004, 748, 687, 470 cm-1. HRMS (ESI+) [M+H]$^+$ Calculated for C$_{11}$H$_{11}$N$_4^+$ 199.0984; found 199.0985.

Example 5AB: 3-(furan-3-yl)-6-methyl-1,2,4,5-tetrazine (2ab)

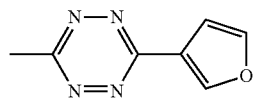

Prepared using 3-Furanylboronic acid (140 mg, 1125 µmol, 3.0 eq). Silica gel chromatography (70% DCM/hexanes) yielded an average of 53% as a hot pink crystalline solid (run 1: 33 mg, 55%; run 2: 31 mg, 51%). $^1$H NMR (400 MHz, CDCl$_3$) δ 8.50 (s, 1H), 7.61 (app t, J=1.6 Hz, 1H), 7.22 (d, J=1.6 Hz 1H), 3.05 (s, 3H). $^{13}$C NMR (101 MHz, CDCl$_3$) δ 167.1 (C), 161.8 (C), 145.8 (CH), 145.0 (CH), 121.1 (C), 108.8 (CH), 21.4 (CH$_3$). FTIR (KBr, thin film) 3176, 3153, 3127, 2920, 2850, 1589, 1517, 1423, 1381, 1360, 1157, 1085, 1000, 870, 801, 753, 648, 601, 515 cm$^{-1}$. HRMS (ESI+) [M+H]$^+$ Calculated for C$_7$H$_7$ON$_4^+$163.0620; found 163.0620.

Example 5AC: 3-methyl-6-(thiophen-3-yl)-1,2,4,5-tetrazine (2ac)

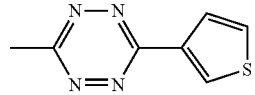

Prepared using 3-Thienylboronic acid (144 mg, 1125 µmol, 1.9 eq). Silica gel chromatography (60% DCM/ hexanes) yielded an average of 52% as a bright pink crystalline solid (run 1: 36 mg, 55%; run 2: 32 mg, 49%). $^1$H NMR (400 MHz, CDCl$_3$) δ 8.58 (d, J=3.6 Hz, 1H), 8.04 (d, J=4.8 Hz, 1H), 7.51 (dd, J=5.2, 3.2 Hz, 1H), 3.06 (s, 3H). $^{13}$C NMR (101 MHz, CDCl$_3$) δ 166.9 (C), 161.9 (C), 134.9 (C), 130.0 (CH), 127.6 (CH), 126.6 (CH), 21.4 (CH$_3$). FTIR (KBr, thin film) 3118, 3093, 2921, 2851, 1535, 1433, 1339, 892, 789, 662, 507 cm$^{-1}$. HRMS (ESI+) [M+H]$^+$ Calculated for C$_7$H$_7$SN$_4$$^+$ 179.0391; found 179.0391.

Example 5AD: 3-(6-methyl-1,2,4,5-tetrazin-3-yl)-9-phenyl-9H-carbazole (2ad)

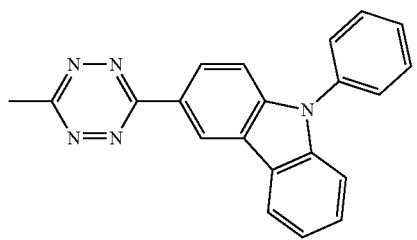 [SMILES: Cc1nnc(-c2ccc3c(c2)c2ccccc2n3-c2ccccc2)nn1]

Prepared using N-phenyl-9H-carbazol-3-boronic acid (323 mg, 1125 µmol, 3.0 eq). Silica gel chromatography (80% DCM/hexanes) yielded an average of 39% as a salmon colored powdery solid (run 1: 51 mg, 40%; run 2: 47 mg, 37%). $^1$H NMR (400 MHz, CDCl$_3$) δ 9.43 (d, J=1.6 Hz, 1H), 8.65 (dd, J=8.8, 2.0 Hz, 1H), 8.26 (app d, J=7.6 Hz, 1H), 7.68-7.35 (m, 9H), 3.09 (s, 3H). $^{13}$C NMR (101 MHz, CDCl$_3$) δ 166.7 (C), 164.8 (C), 143.6 (C), 141.8 (C), 137.1 (C), 130.2 (CH), 128.2 (CH), 127.3 (CH), 126.9 (CH), 125.9 (CH), 124.2 (C), 123.5 (C), 123.5 (C), 121.1 (CH), 120.0 (CH), 120.9 (CH), 110.6 (CH), 110.4 (CH), 21.3 (CH$_3$). FTIR (KBr, thin film) 3448, 2072, 1626, 1597, 1502, 1397, 1365, 745, 698, 625 cm$^{-1}$. HRMS (ESI+) [M+H]$^+$ Calculated for C$_{21}$H$_{16}$N$_5$$^+$ 338.1406; found 338.1409.

Example 5AE: tert-butyl 2-((tert-butoxycarbonyl)amino)-3-(4-(6-methyl-1,2,4,5-tetrazin-3-yl)phenyl)propanoate (2ae)

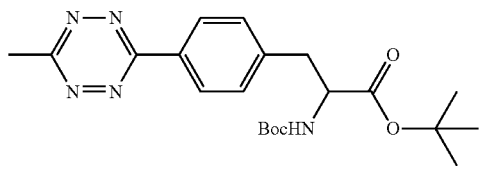

b-Tz 1a (44 mg, 150 µmol, 1.0 eq.), (4-(3-(tert-butoxy)-2-((tert-butoxycarbonyl)amino)-3-oxopropyl)phenyl)boronic acid[1] (104 mg, 285 µmol, 1.9 eq), [1,1'-bis(diphenylphosphino)ferrocene]dichloropalladium(II) (17 mg, 23 µmol, 0.15 eq.) and silver(I) oxide (87 mg, 375 µmol, 2.5 eq.) were added to a vacuum dried 4 mL glass vial equipped with a stir bar. The solids were dissolved/suspended as a heterogeneous slurry with N,N-Dimethylformamide (1.5 mL, 0.1M) and the vial was flushed with nitrogen and sealed. The reaction was stirred at 60° C. for 20 h, then brought to room temperature and the solvent was removed by rotary evaporation. The crude solids were chromatographed directly on silica gel (90-100% DCM/hexanes, then 0-2% acetone/DCM) yielding an average of 96% as a magenta wax (run 1: 61 mg, 98%; run 2: 58 mg, 94%). $^1$H NMR (400 MHz, Acetone-d6) δ 8.48 (d, J=8.0 Hz, 2H), 7.56 (d, J=8.0 Hz, 2H), 6.18 (d, J=8.4 Hz, NH), 4.37 (app td, J=8.4, 5.6 Hz, 1H), 3.25 (dd, J=13.6, 5.6 Hz, 1H), 3.12 (dd, J=13.6, 8.4 Hz, 1H), 3.03 (s, 3H), 1.43 (s, 9H), 1.37 (s, 9H). $^{13}$C NMR (101 MHz, Acetone-d6) δ 171.65 (C), 168.25 (C), 164.66 (C), 156.15 (C), 143.50 (C), 131.60 (C), 131.21 (CH), 128.29 (CH), 81.79 (C), 79.26 (C), 56.39 (CH), 38.34 (CH$_2$), 28.49 (CH$_3$), 28.10 (CH$_3$), 21.17 (CH$_3$) [α]$^{24}$$_D$=+49.0° (c=0.11, CH$_2$Cl$_2$). FTIR (KBr, thin film) 3368, 2978, 2932, 1715, 1611, 1498, 1456, 1405, 1366, 1250, 1154, 1089, 1056, 1018, 890, 846, 799, 568 cm$^{-1}$. HRMS (ESI+) [M+H]$^+$ Calculated for C$_{21}$H$_{30}$O$_4$N$_5$$^+$ 416.2298; found 416.2287.

Example 5AF: 3-methyl-6-(3-((5-(trifluoromethyl)pyridin-2-yl)oxy)phenyl)-1,2,4,5-tetrazine (2af)

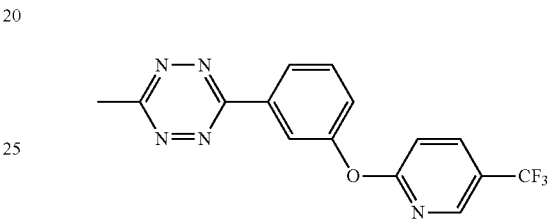

Prepared using 3-([5-(trifluoromethyl)pyridin-2-yl]oxy)phenylboronic acid (202 mg, 713 µmol, 1.9 eq). Silica gel chromatography (95% DCM/hexanes) yielded an average of 84% as a magenta oil (run 1: 105 mg, 84%; run 2: 103 mg, 83%). $^1$H NMR (400 MHz, CDCl$_3$) δ 8.52 (app dt, J=8.0, 1.6 Hz, 1H), 8.44-8.43 (m, 1H), 8.40 (app t, J=2.0 Hz, 1H), 7.96 (dd, J=8.4, 2.4 Hz, 1H), 7.67 (app t, J=8.0 Hz, 1H), 7.43 (ddd, J=8.4, 2.4, 1.2 Hz, 1H), 7.12 (d, J=8.4 Hz, 1H), 3.11 (s, 3H). $^{13}$C NMR (101 MHz, CDCl$_3$) δ 167.7 (C), 165.5 (C, q, J$_{C-F}$=1.1 Hz), 163.6 (C), 154.1 (C), 145.5 (CH, q, J$_{C-F}$=4.3 Hz), 137.1 (CH, q, J$_{C-F}$=3.2 Hz), 133.7 (C), 130.8 (CH), 125.9 (CH), 125.0 (CH), 123.7 (CF$_3$, q, J$_{C-F}$=272.6 Hz), 122.1 (C, q, J$_{C-F}$=33.4 Hz), 121.1 (CH), 111.9 (CH), 21.4 (CH$_3$). FTIR (KBr, thin film) 3449, 3078, 2925, 2853, 2088, 1613, 1588, 1488, 1398, 1363, 1327, 1284, 1282, 1161, 1125, 1077, 1012, 919, 891, 838, 794, 689, 679 cm$^{-1}$. HRMS (ESI+) [M+H]$^+$ Calculated for C$_{15}$H$_{11}$OF$_3$N$_5$$^+$ 334.0916; found 334.0918.

Example 5AG: (8R,9S,13S,14S)-13-methyl-3-(6-methyl-1,2,4,5-tetrazin-3-yl)-7,8,9,11,12,13,15,16-octahydro-6H-cyclopenta[a]phenanthren-17(14H)-one (2ag)

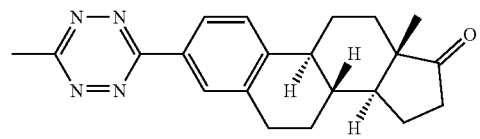

b-Tz 1a (59 mg, 200 µmol, 1.0 eq.), estrone-boronic acid[2] (113 mg, 380 µmol, 1.9 eq), [1,1'-bis(diphenylphosphino)ferrocene]dichloropalladium(II) (22 mg, 30 µmol, 0.15 eq.) and silver(I) oxide (116 mg, 500 µmol, 2.5 eq.) were added to a vacuum dried 4 mL glass vial equipped with a stir bar. The solids were dissolved/suspended as a heterogeneous slurry with N,N-Dimethylformamide (2.0 mL, 0.1M) and the vial was flushed with nitrogen and sealed. The reaction was stirred at 60° C. for 20 h, then brought to room temperature and the solvent was removed by rotary evaporation. The crude solids were chromatographed directly on silica gel (0.5% acetone, 0.75% EtOH, 98.75% chloroform) and then on reverse phase Cis silica (50-90% MeOH/H$_2$O) yielding 2ag as a magenta crystalline solid (42 mg, 61%). $^1$H NMR (400 MHz, CDCl$_3$) δ 8.36-8.33 (m, 2H), 7.52 (d, J=8.0 Hz, 1H), 3.11-3.03 (m, 5H), 2.57-2.48 (m, 2H), 2.44-2.37 (m, 1H), 2.22-1.99 (m, 4H), 1.73-1.47 (m, 6H), 0.94 (s, 3H). $^{13}$C NMR (101 MHz, CDCl$_3$) δ 220.8 (C), 167.2 (C), 164.2 (C), 145.0 (C), 137.8 (C), 129.3 (C), 128.5 (CH), 126.5 (CH), 125.4 (CH), 50.6 (CH), 48.0 (C), 44.8 (CH), 38.0 (CH), 36.0 (CH$_2$), 31.7 (CH$_2$), 29.5 (CH$_2$), 26.4 (CH$_2$), 25.7 (CH$_2$), 21.7 (CH$_2$), 21.3 (CH$_3$), 14.0 (CH$_3$). FTIR (KBr, thin film) 3442, 2935, 2877, 2857, 2077, 1733, 1635, 1397, 1356, 890, 805, 735, 712, 632, 590 cm$^{-1}$. HRMS (ESI+) [M+H]$^+$ Calculated for C$_{21}$H$_{25}$ON$_4$$^+$ 349.2028; found 349.2027.

Example 6:
(4-(1-methyl-1H-imidazol-2-yl)phenyl)boronic acid

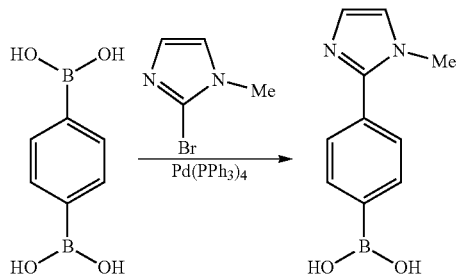

To a stirred mixture of 1,4-phenylenediboronic acid (69.5 g, 0.42 mol, 1.1 eq.), 2-bromo-1-methyl-1H-imidazole (61.4 g, 0.39 mol, 1.0 eq.) and Pd(PPh$_3$)$_4$ (4.64 g, 4.1 mmol, 1.1 mol %) in 800 mL of toluene and 700 mL of methanol was added aq. Na$_2$CO$_3$ (10% solution in water, 48.6 g, 0.46 mol, 1.2 eq.) at rt in one portion under nitrogen atmosphere. After the addition, the mixture was heated to reflux for 8 h. TLC (DCM/MeOH=5:1) indicated the complete consumption of the starting material. The mixture was evaporated under reduced pressure; the residue was taken up with 1 L of MeOH, the mixture was filtered to remove inorganic salt, and the filtrate was concentrated. The crude product was re-crystallized from methanol, and then further purification by prep-HPLC in basic condition to afford (4-(1-methyl-1H-imidazol-2-yl)phenyl)boronic acid (2.6 g) as an off-purple solid and by prep-HPLC in acid condition to afford (4-(1-methyl-1H-imidazol-2-yl)phenyl)boronic acid (20.6 g) as a white solid, the total yield was 29%. $^1$H NMR (400 MHz, DMSO-d$_6$) δ 8.40 (br s, 2H), 8.03 (app d, J=8.4 Hz, 2H), 7.87 (d, J=2.0 Hz, 1H, 7.81-7.79 (m, 3H), 3.89 (s, 3H). $^{13}$C NMR (101 MHz, DMSO-d$_6$) δ 143.9, 138.2 134.6, 128.4, 124.9, 123.8, 119.2, 35.7. FTIR (KBr, thin film) 3218, 1618, 1597, 1503, 1399, 1332, 1267, 1122, 1010, 709, 683, 641 cm$^{-1}$. HRMS (ESI+) [M+H]$^+$ Calculated for C$_{10}$H$_{12}$BO$_2$N$_2$$^+$ 203.0986; found 203.0980.

Example 7:
3-(methylthio)-6-phenyl-1,2,4,5-tetrazine (3)

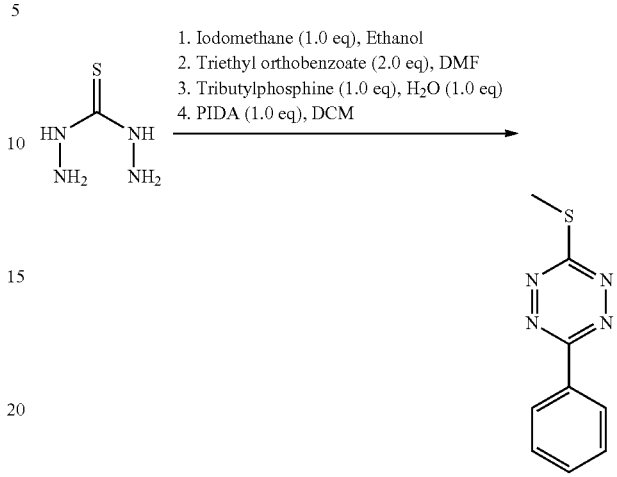

Step 1: Thiocarbohydrazide (5.30 g, 50.0 mmol, 1.00 eq.) was dissolved in ethanol (75 mL, 0.66 M) in a round bottom flask. The flask was flushed with nitrogen and heated to 60° C. Iodomethane (3.11 mL, 50.0 mmol, 1.0 eq.) was added and the reaction was stirred for 22 h. The flask was then cooled to r.t. and 100 mL hexanes was slowly added to precipitate a white solid. The heterogeneous solution was then filtered, and the solids were washed 3×75 mL hexanes and subsequently dried under vacuum to afford methylthiocarbohydrazide iodide as a white solid (9.89 g, 80%) Step 2: The methylthiocarbohydrazide iodide powder (9.89 g, 39.9 mmol, 1.00 eq.) and pyridine (7.1 mL, 79.8 mmol, 2.0 eq.) were dissolved in DMF (40 mL, 1.0M) and stirred under nitrogen at 50° C. Triethyl orthobenzoate (18.0 mL, 79.8 mmol, 2.0 eq.) was added dropwise over 1 h. The reaction was stirred for 24 h at 50° C. to give a mixture of 1,4-dihydrotetrazine and tetrazine products.

Step 3: The tetrazine was reduced in situ with tributylphosphine (10.0 mL, 39.9 mmol, 1.00 eq.) and deionized water (717 µL, 1.0 eq.) stirred for 30 minutes. The reaction was then diluted in in 500 mL DCM and washed 1×100 mL aq. sat. NaHCO$_3$, 5×100 mL water and 1×100 mL brine. The crude 1,4-dihydrotetrazine was then preabsorbed on to silica gel, dried by rotary evaporation, and chromatographed (80% DCM/hexanes to elute triethyl orthobenzoate, then 3% MeOH/DCM to elute 1,4-dihydrotetrazine).

Step 4: The 1,4-dihydrotetrazine was dissolved in DCM (200 mL) and cooled to 0° C. (Diacetoxyiodo)benzene (12.84 g, 39.9 mmol, 1.0 eq.) was added slowly and then the reaction was stirred at room temperature for 2 h. The solvent was removed by rotary evaporation and the crude mixture was chromatographed directly (35% DCM/hexanes) yielding 3-(methylthio)-6-phenyl-1,2,4,5-tetrazine as a red crystalline solid (4.65 g, 57% steps 2-4—46% over 4 steps). $^1$H NMR (400 MHz, CDCl$_3$) δ 8.55-8.52 (m, 2H), 7.64-7.56 (m, 3H), 2.80 (s, 3H). $^{13}$C NMR (101 MHz, CDCl$_3$) b 175.4 (C), 162.4 (C), 132.5 (CH), 131.7 (C), 129.4 (CH), 127.6 (CH), 13.6 (CH$_3$). FTIR (KBr, thin film) 3449, 2937, 2067, 1636, 1355, 1196, 897, 760, 694, 561 cm$^{-1}$. HRMS (ESI+) [M+H]$^+$ Calculated for C$_9$H$_9$N$_4$S$^+$ 205.0548; found 205.0552.

Example 8: General Procedure for Phenyl Tetrazine Cross-Coupling

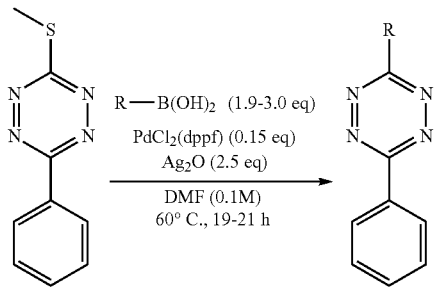

Tetrazine thioether 3 (77 mg, 375 μmol, 1 eq.), boronic acid (713 μmol, 1.9 eq. or 1125 μmol, 3.0 eq., see below), [1,1'-Bis(diphenylphosphino)ferrocene]dichloropalladium (II) (41 mg, 56 μmol, 0.15 eq.) and silver(I) oxide (218 mg, 938 μmol, 2.5 eq.) were added to a vacuum dried schlenk flask equipped with a stir bar. The solids were dissolved/suspended as a heterogeneous slurry with N,N-Dimethylformamide (3.75 mL, 0.1M) and the flask was flushed with nitrogen and sealed. The reaction was stirred at 60° C. for 19-21 h, then brought to room temperature and the solvent was removed by rotary evaporation. The crude solids were chromatographed directly on silica gel. Elution systems are described below. Each reaction was run in duplicate to obtain an average yield.

Example 8A: 3,6-diphenyl-1,2,4,5-tetrazine (4a)

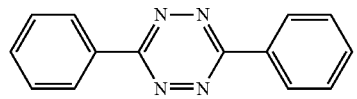

Prepared using phenylboronic acid (87 mg, 713 μmol, 1.9 eq). Silica gel chromatography (40% DCM/hexanes) yielded an average of 99% as a magenta crystalline solid (run 1: 87 mg, 99%; run 2: 86 mg, 98%). $^1$H NMR (400 MHz, CDCl$_3$) b 8.68-8.65 (m, 4H), 7.68-7.60 (m, 6H). $^{13}$C NMR (101 MHz, CDCl$_3$) b 164.1 (C), 132.9 (CH), 131.9 (C), 129.5 (CH), 128.1 (CH). FTIR (KBr, thin film) 3440, 1635, 1456, 1393, 919, 774, 767, 689, 589 cm$^{-1}$. HRMS (ESI+) [M+H]$^+$ Calculated for $C_{14}H_{11}N_4^+$ 235.0984; found 235.0984.

Example 8B: 3-(4-chlorophenyl)-6-phenyl-1,2,4,5-tetrazine (4b)

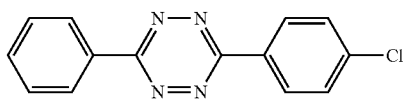 [SMILES: Clc1ccc(-c2nnc(-c3ccccc3)nn2)cc1]

Prepared using 4-Chlorophenylboronic acid (111 mg, 713 μmol, 1.9 eq). Silica gel chromatography (40% DCM/hexanes) yielded an average of 91% as a magenta hairy solid (run 1: 90 mg, 89%; run 2: 93 mg, 92%). $^1$H NMR (400 MHz, CDCl$_3$) δ 8.68-8.64 (m, 2H), 8.63-8.60 (m, 2H), 7.69-7.59 (m, 5H). $^{13}$C NMR (101 MHz, CDCl$_3$) δ 164.5 (C), 163.5 (C), 139.4 (C), 133.0 (CH), 131.7 (C), 130.4 (C), 129.8 (CH), 129.5 (CH), 129.3 (CH), 128.2 (CH). FTIR (KBr, thin film) 3444, 2087, 1635, 1395, 915, 813, 756, 687, 586 cm$^{-1}$. HRMS (ESI+) [M+H]$^+$ Calculated for $C_{14}H_{10}ClN_4^+$ 269.0594; found 269.0598.

Example 8C: (4-(6-phenyl-1,2,4,5-tetrazin-3-yl)phenyl)methanol (4c)

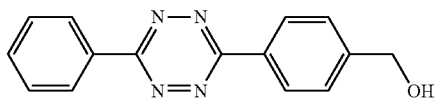

Prepared using 4-(Hydroxymethyl)phenylboronic acid (108 mg, 713 μmol, 1.9 eq). Silica gel chromatography (2% acetone, 0.75% EtOH, 97.25% chloroform) yielded an average of 89% as a magenta hairy solid (run 1: 84 mg, 85%; run 2: 91 mg, 92%). $^1$H NMR (400 MHz, DMSO-d$_6$) δ 8.56-8.50 (m, 4H), 7.75-7.67 (m, 3H), 7.63 (app d, J=8.4 Hz, 2H), 5.45 (OH, t, J=5.6 Hz, 1H), 4.67 (d, J=5.6 Hz, 2H). $^{13}$C NMR (101 MHz, DMSO-d$_6$) δ 163.3 (C), 163.3 (C), 147.7 (C), 132.6 (CH), 132.0 (C), 130.2 (C), 129.5 (CH), 127.5 (CH), 127.5 (CH), 127.2 (CH), 62.5 (CH$_2$). FTIR (KBr, thin film) 3439, 2072, 1636, 1394, 588 cm$^{-1}$. HRMS (ESI+) [M+H]$^+$ Calculated for $C_{15}H_{13}ON_4^+$ 265.1089; found 265.1091.

Example 8D: tert-butyl (3-(6-phenyl-1,2,4,5-tetrazin-3-yl)phenyl)carbamate (4d)

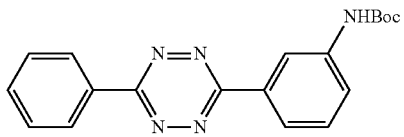 [SMILES: CC(C)(C)OC(=O)Nc1cccc(-c2nnc(-c3ccccc3)nn2)c1]

Prepared using 3-(N-Boc-amino)phenylboronic acid (169 mg, 713 μmol, 1.9 eq). Silica gel chromatography (0.5% EtOAc, 0.75% EtOH, 98.75% chloroform) yielded an average of 92% as a pink powdery solid (run 1: 121 mg, 92%; run 2: 119 mg, 91%). $^1$H NMR (400 MHz, DMSO-d$_6$) δ 9.76 (NH, s, 1H), 8.80 (app s, 1H), 8.56-8.53 (m, 2H), 8.15 (app dt, J=8.0, 1.6 Hz, 1H), 7.75-7.68 (m, 4H), 7.57 (app t, J=8.0 Hz, 1H), 1.52 (s, 9H). $^{13}$C NMR (101 MHz, DMSO-d$_6$) δ 163.4 (C), 163.3 (C), 152.8 (C), 140.7 (C), 132.7 (CH), 132.3 (C), 131.9 (C), 129.9 (CH), 129.5 (CH), 127.6 (CH), 122.0 (CH), 121.2 (CH), 116.8 (CH), 79.5 (C), 28.2 (CH$_3$). FTIR (KBr, thin film) 3445, 3343, 2987, 1697, 1639, 1593, 1532, 1388, 763, 686, 619, 551 cm$^{-1}$. HRMS (ESI+) [M+H]$^+$ Calculated for $C_{19}H_{20}O_2N_5^+$ 350.1617; found 350.1610.

Example 8E: methyl 4-(6-phenyl-1,2,4,5-tetrazin-3-yl)benzoate (4e)

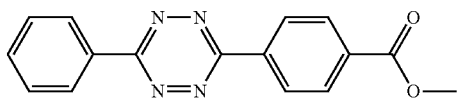 [SMILES: COC(=O)c1ccc(-c2nnc(-c3ccccc3)nn2)cc1]

Prepared using 4-Methoxycarbonylphenylboronic acid (203 mg, 1125 µmol, 3.0 eq). Silica gel chromatography (85% DCM/hexanes) yielded an average of 76% as a purple crystalline solid (run 1: 86 mg, 78%; run 2: 81 mg, 74%). $^1$H NMR (400 MHz, CDCl$_3$) δ 8.76-8.73 (m, 2H), 8.69-8.66 (m, 2H), 8.30-8.27 (m, 2H), 7.70-7.61 (m, 3H), 3.99 (s, 3H). $^{13}$C NMR (101 MHz, CDCl$_3$) δ 166.5 (C), 164.2 (C), 163.6 (C), 135.8 (C), 133.7 (C), 133.2 (CH), 131.6 (C), 130.6 (CH), 129.5 (CH), 128.3 (CH), 128.0 (CH), 52.7 (CH$_3$). FTIR (KBr, thin film) 3444, 2077, 1704, 1636, 1396, 1280, 774, 688, 686, 591 cm$^{-1}$. HRMS (ESI+) [M+H]$^+$ Calculated for C$_{16}$H$_{13}$O$_2$N$_4^+$ 293.1039; found 293.1038.

Example 8F: 5-(6-phenyl-1,2,4,5-tetrazin-3-yl)-1H-indole (4f)

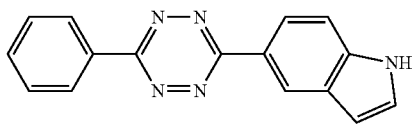 [SMILES: c1ccc(-c2nnc(-c3ccc4[nH]ccc4c3)nn2)cc1]

Prepared using 5-Indoleboronic acid (123 mg, 713 µmol, 1.9 eq). Silica gel chromatography (1% acetone/DCM) yielded an average of 49% as an orange powdery solid (run 1: 46 mg, 45%; run 2: 54 mg, 52%). $^1$H NMR (400 MHz, DMSO-d$_6$) δ 11.65 (NH, br s, 1H), 8.66 (s, 1H), 8.54-8.52 (m, 2H), 8.22 (dd, J=8.4, 1.6 Hz, 1H), 7.81 (d, J=8.4 Hz, 1H), 7.71-7.68 (m, 3H), 7.64 (t, J=2.8 Hz, 1H), 6.60-6.59 (m, 1H). $^{13}$C NMR (101 MHz, DMSO-d$_6$) δ 164.4 (C), 162.9 (C), 136.1 (C), 132.3 (CH), 132.1 (C), 131.3 (C), 129.5 (CH), 127.3 (2×CH), 124.1 (C), 121.1 (CH), 118.1 (CH), 111.6 (CH), 101.9 (CH). FTIR (KBr, thin film) 3439, 2072, 1636, 1393, 568 cm-1. HRMS (ESI+) [M+H]$^+$ Calculated for C$_{16}$H$_{12}$N$_5^+$ 274.1093; found 274.1093.

Example 8G: 3-(benzo[d][1,3]dioxol-5-yl)-6-phenyl-1,2,4,5-tetrazine (4g)

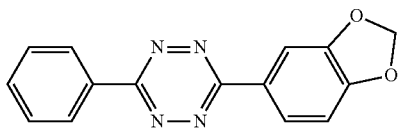 [SMILES: c1ccc(-c2nnc(-c3ccc4c(c3)OCO4)nn2)cc1]

Prepared using 3,4-(Methylenedioxy)phenylboronic acid (118 mg, 713 µmol, 1.9 eq). Silica gel chromatography (50% DCM/hexanes) yielded an average of 88% as a dark salmon colored hairy solid (run 1: 90 mg, 86%; run 2: 94 mg, 90%). $^1$H NMR (400 MHz, CDCl$_3$) δ 8.65-8.61 (m, 2H), 8.29 (dd, J=8.4, 1.6 Hz, 1H), 8.10 (d, J=1.6 Hz, 1H), 7.66-7.59 (m, 3H), 7.03 (d, J=8.0 Hz, 1H), 6.12 (s, 2H). $^{13}$C NMR (101 MHz, CDCl$_3$) δ 163.7 (C), 163.6 (C), 151.8 (C), 148.9 (C), 132.6 (CH), 132.0 (C), 129.4 (CH), 127.9 (CH), 125.9 (C), 123.8 (CH), 109.3 (CH), 107.8 (CH), 102.1 (CH$_2$). FTIR (KBr, thin film) 3446, 2074, 1636, 1388, 1110, 922, 877, 818, 688, 633, 561 cm$^{-1}$. HRMS (ESI+) [M+H]$^+$ Calculated for C$_{15}$H$_{11}$O$_2$N$_4^+$ 279.0882; found 279.0885.

Example 9: 3-BODIPY-6-methyltetrazine (6) synthesis (2 steps)

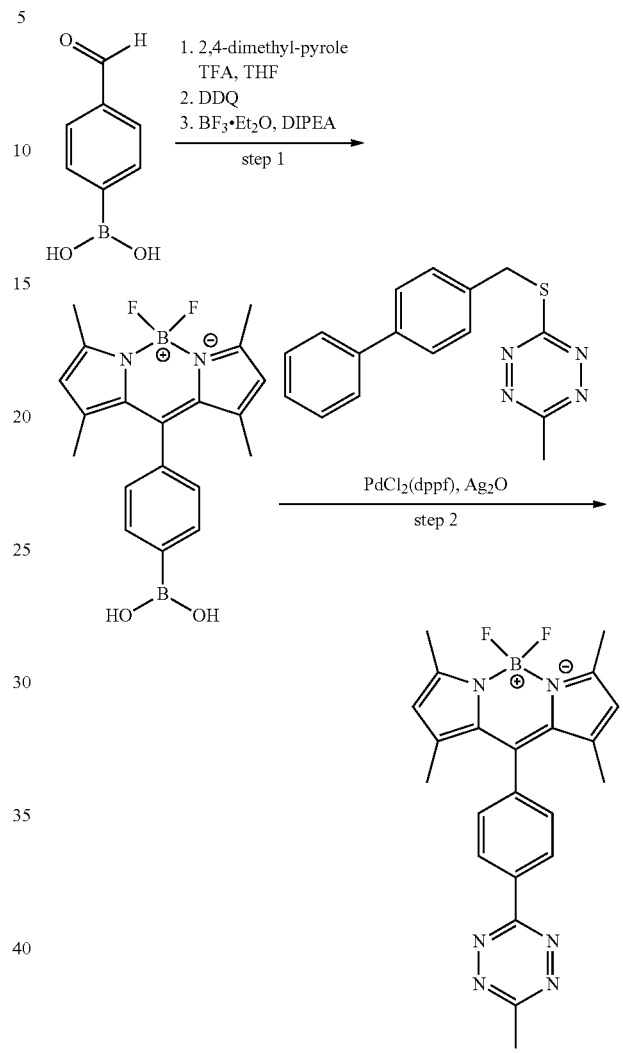

Example 10: (4-boronophenyl)-5,5-difluoro-1,3,7,9-tetramethyl-5H-dipyrrolo[1,2-c:2',1'-f][1,3,2]diazaborinin-4-ium-5-uide (5)

4-Formylphenylboronic acid (1.95 g, 13.0 mmol, 1.00 eq.) and 2,4-dimethyl-pyrrole (2.81 mL, 27.3 mmol, 2.10 eq.) were dissolved in THF (120 mL) and stirred under nitrogen at room temperature. Trifluoroacetic acid (0.40 mL, 5.20 mmol, 0.40 eq.) was added dropwise and the reaction was stirred until the aldehyde was fully consumed by TLC (1 h). 2,3-Dichloro-5,6-dicyano-1,4-benzoquinone (2.95 g, 13.0 mmol, 1.00 eq.) was added to the reaction and stirred for 16 h. Boron trifluoride diethyl etherate (16.0 mL, 130 mmol, 10.0 eq.) and N,N-Diisopropylethylamine (15.8 mL, 91.0 mmol, 7 eq.) were then added and the reaction was stirred a further 6 h. The organics were washed with 3×250 mL water and 2×25 mL brine. The organic phase was then dried on MgSO$_4$, filtered, and concentrated by rotary evaporation. The crude material was then dissolved in a minimal amount of hot 10% MeOH/DCM (~30 mL) after which hexanes (~500 mL) were slowly added to precipitate red/ black impurities. The mixture was filtered, and the filtrate was concentrated by rotary evaporation. Silica gel chromatography (80% DCM, 19% EtOAc, 1% MeOH) yielded 5 as a dark orange crystalline solid (574 mg, 12%). $^1$H NMR (400 MHz, CDCl$_3$) δ 8.41 (app d, J=7.6 Hz, 2H), 7.49 (app d, J=8.0 Hz, 2H), 6.01 (s, 2H), 2.58 (s, 6H), 1.40 (s, 6H). $^{13}$C NMR (101 MHz, CDCl$_3$) δ 155.9 (C), 143.1 (C), 141.2 (C), 139.9 (C), 136.5 (CH), 131.2 (C), 130.6 (C), 128.0 (CH), 121.5 (CH), 14.8 (CH$_3$), 14.6 (CH$_3$). FTIR (KBr, thin film) 3738, 3564, 2957, 2925, 1543, 1508, 1469, 1398, 1306, 1194, 1157, 979, 836, 719, 478 cm$^{-1}$. HRMS (ESI+) [M+H]$^+$ Calculated for C$_{19}$H$_{21}$B2F$_2$O$_2$N$_2$$^+$369.1757; found 369.1754.

Example 11: 5,5-difluoro-1,3,7,9-tetramethyl-10-(4-(6-methyl-1,2,4,5-tetrazin-3-yl)phenyl)-5H-dipyrrolo[1,2-c:2',1'-f][1,3,2]diazaborinin-4-ium-5-uide (6)

b-Tz 1a (run 1: 110.3 mg, 375 μmol, 1.0 eq.; run 2: 75.7 mg, 257 μmol, 1.0 eq.), 5 (run 1: 262 mg, 713 μmol, 1.9 eq.; run 2: 180 mg, 489 μmol, 1.9 eq.), [1,1'-bis(diphenylphosphino)ferrocene]dichloropalladium(II) (run 1: 41 mg, 56 μmol, 0.15 eq.; run 2: 28 mg, 39 μmol, 0.15 eq.) and silver(I) oxide (run 1: 218 mg, 938 μmol, 2.5 eq.; run 2: 149 mg, 643 μmol, 2.5 eq.) were added to a vacuum dried 4 mL glass vial equipped with a stir bar. The solids were dissolved/suspended as a heterogeneous slurry with N,N-Dimethylformamide (0.1M) and the vial was flushed with nitrogen and sealed. The reaction was stirred at 60° C. for 20 h, then brought to room temperature and the solvent was removed by rotary evaporation. The crude solids were chromatographed directly on silica gel (90% DCM/hexanes) yielding an average of 78% as a red/orange iridescent solid (run 1: 123 mg, 79%; run 2: 81 mg, 76%). $^1$H NMR (400 MHz, CDCl$_3$) δ 8.75 (app d, J=8.0 Hz, 2H), 7.56 (app d, J=8.0 Hz, 2H), 6.01 (s, 2H), 3.14 (s, 3H), 2.58 (s, 6H), 1.45 (s, 6H). $^{13}$C NMR (101 MHz, CDCl$_3$) δ 167.7 (C), 163.8 (C), 156.2 (C), 143.0 (C), 140.3 (C), 139.6 (C), 132.7 (C), 131.1 (C), 129.4 (CH), 128.7 (CH), 121.7 (CH), 21.4 (CH$_3$), 14.8 (4×CH$_3$). FTIR (KBr, thin film) 3431, 2963, 2926, 2855, 1546, 1512, 1403, 1308, 1194, 1157, 1084, 982, 711, 477 cm$^{-1}$. HRMS (ESI+) [M+H]$^+$ Calculated for C$_{22}$H$_{22}$BF$_2$N$_6$$^+$ 419.1967; found 419.1962

Example 12: tert-butyl 4-(1-(4-(4,4,5,5-tetramethyl-1,3,2-dioxaborolan-2-yl)phenyl)-1H-pyrazol-3-yl)piperidine-1-carboxylate

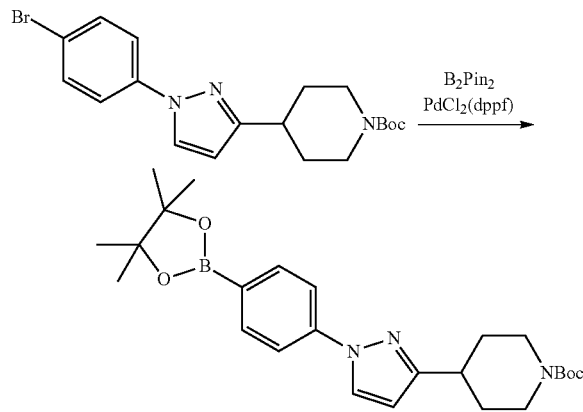

To a sealed tube was added Pd(dppf)Cl$_2$ (486 mg, 0.665 mmol, 0.3 eq.), Bis(pinacolato)diboron (1120 mg, 4.43 mmol, 2.0 eq.), potassium acetate (652 mg, 6.65 mmol, 3.0 eq.)), and tert-butyl 4-(1-(4-bromophenyl)-1H-pyrazol-3-yl)piperidine-1-carboxylate[3] (900 mg, 2.22 mmol, 1.0 eq.)) and degassed 1,4-dioxane (10 mL) under N$_2$ atmosphere at 25° C. The reaction mixture was then stirred at 100° C. for 18 h. The mixture was cooled to r.t. and diluted with EtOAc (150 mL). Then the mixture was washed with 1×100 mL water and 1×100 mL brine. The organic layer was concentrated under reduced pressure and the residue was purified by flash column chromatograph (40 g silica gel column, petroleum ether/EtOAc with EtOAc from 0-30%) to afford the crude product which was triturated with n-hexane (0° C., 30 mL) to afford the tert-butyl 4-(1-(4-(4,4,5,5-tetramethyl-1,3,2-dioxaborolan-2-yl)phenyl)-1H-pyrazol-3-yl)piperidine-1-carboxylate as pale yellow solid (530 mg, 53%). $^1$H NMR (400 MHz, CDCl$_3$) δ 7.88-7.85 (m, 3H), 7.66 (app d, J=8.0 Hz, 2H), 6.28 (d, J=2.0 Hz, 1H), 4.18 (app d, J=12.8 Hz, 2H), 2.96-2.85 (m, 3H), 1.99 (app d, J=13.2 Hz, 2H), 1.73-1.63 (m, 2H), 1.48 (s, 9H), 1.36 (s, 12H). $^{13}$C NMR (101 MHz, CDCl$_3$) δ 158.5, 155.0, 142.3, 136.2, 127.5, 117.8, 105.2, 84.1, 79.5, 44.0, 36.0, 32.1, 28.6, 25.0—Carbon directly attached to boron not observed. FTIR (KBr, thin film) 2976, 2932, 1685, 1607, 1356, 1232, 1165, 1143, 1092, 946, 858, 733, 653 cm$^{-1}$. HRMS (ESI+) [M+H]$^+$ Calculated for C$_{25}$H$_{37}$BO$_4$N$_3$$^+$ 454.2872; found 454.2857

Example 13: (4-(3-(1-(tert-butoxycarbonyl)piperidin-4-yl)-1H-pyrazol-1-yl)phenyl)boronic acid (7)

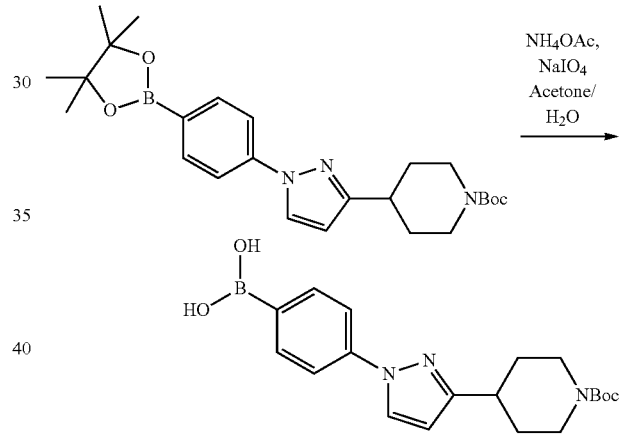

tert-butyl 4-(1-(4-(4,4,5,5-tetramethyl-1,3,2-dioxaborolan-2-yl)phenyl)-1H-pyrazol-3-yl)piperidine-1-carboxylate (297 mg, 0.66 mmol, 1.00 eq.), ammonium acetate (303 mg, 3.93 mmol, 6.00 eq.) and sodium periodate (842 mg, 3.93 mmol, 6.00 eq.) was stirred in a mixture of 5:2 acetone/H$_2$O (33 mL) at room temperature for 66 h. The acetone was removed by rotary evaporation and the aqueous phase was extracted with 3×25 mL DCM and washed with 1×25 mL aq. sat. NaHCO$_3$ and 1×25 mL brine. The organics were dried on MgSO$_4$ and concentrated. Silica gel chromatography (3% MeOH/DCM) yielded (4-(3-(1-(tert-butoxycarbonyl)piperidin-4-yl)-1H-pyrazol-1-yl)phenyl)boronic acid as a flakey white solid (214 mg, 88%). $^1$H NMR (400 MHz, Methanol-d$_4$) δ 8.09 (d, J=2.8 Hz, 1H), 7.82-7.61 (m, 4H), 6.34 (d, J=2.8 Hz, 1H), 4.14-4.09 (m, 2H), 3.28-3.26 (m, 2H), 2.89 (tt, J=11.6, 4.0 Hz, 1H), 1.94 (app dd, J=14.0, 3.6 Hz, 2H), 1.67-1.56 (m, 2H), 1.44 (s, 9H)—B(OH)$_2$ not observed due to solvent exchange. $^{13}$C NMR (101 MHz, DMSO-d$_6$+D20) δ 157.9 (C), 154.3 (C), 141.2 (C), 135.7 (CH), 131.3 (weak, CB), 128.5 (CH), 117.0 (CH), 105.8 (CH), 79.0 (C), 44.2 (br, CH$_2$), 43.2 (br, CH$_2$), 35.2 (CH), 31.7 (br, 2×CH$_2$), 28.4 (CH$_3$). FTIR (KBr, thin film) 3426, 2979, 2940, 2858, 2079, 1658, 1606, 1367, 1165, 737, 645, 544 cm$^{-1}$. HRMS (ESI+) [M+H]$^+$ Calculated for C$_{19}$H$_{27}$BO$_4$N$_3$$^+$ 372.2095; found 372.2088.

Example 14: tert-butyl 4-(1-(4-(6-methyl-1,2,4,5-tetrazin-3-yl)phenyl)-1H-pyrazol-3-yl)piperidine-1-carboxylate (8)

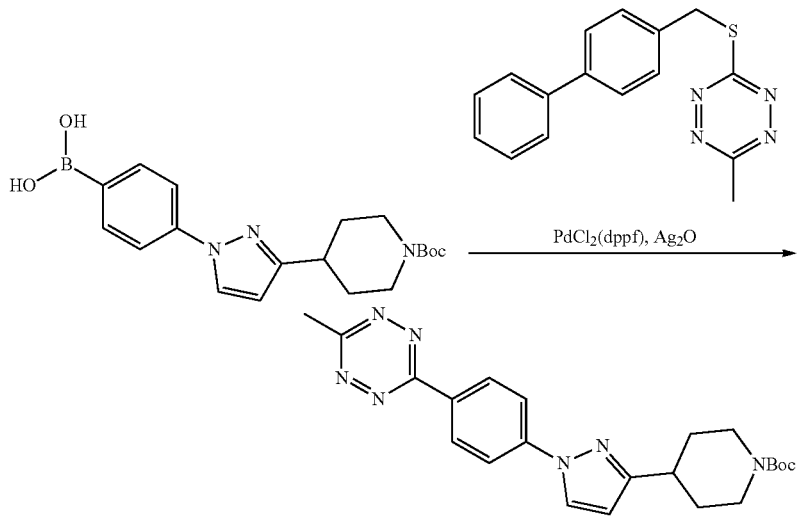

b-Tz 1a (29 mg, 100 µmol, 1.0 eq.) (4-(3-(1-(tert-butoxycarbonyl)piperidin-4-yl)-1H-pyrazol-1-yl)phenyl)boronic acid 7 (71 mg, 190 µmol, 1.9 eq), [1,1′-bis(diphenylphosphino)ferrocene]dichloropalladium(II) (11 mg, 15.0 µmol, 0.15 eq.) and silver(I) oxide (58 mg, 250 µmol, 2.5 eq.) were added to a vacuum dried 4 mL glass vial equipped with a stir bar. The solids were dissolved/suspended as a heterogeneous slurry with N,N-Dimethylformamide (1.0 mL, 0.1M) and the vial was flushed with nitrogen and sealed. The reaction was stirred at 60° C. for 20 h, then brought to room temperature and the solvent was removed by rotary evaporation. The crude solids were chromatographed directly on silica gel (5% acetone/DCM) yielding tert-butyl 4-(1-(4-(6-methyl-1,2,4,5-tetrazin-3-yl)phenyl)-1H-pyrazol-3-yl)piperidine-1-carboxylate as a bright pink powder (32 mg, 77%). $^1$H NMR (400 MHz, CDCl$_3$) δ 8.70-8.67 (app d, J=9.0 Hz, 2H), 7.79 (d, J=2.4 Hz, 1H), 7.92-7.89 (app d, J=9.0 Hz, 2H), 6.35 (d, J=2.8 Hz, 1H), 4.24-4.16 (m, 2H), 3.10 (s, 3H), 2.99-2.87 (m, 3H), 2.05-1.97 (m, 2H), 1.76-1.64 (m, 2H), 1.48 (s, 9H). $^{13}$C NMR (101 MHz, CDCl$_3$) δ 167.3 (C), 163.6 (C), 159.2 (C), 155.0 (C), 143.3 (C), 129.4 (CH), 129.1 (C), 127.5 (CH), 119.0 (CH), 106.1 (CH), 79.6 (C), 44.0 (CH$_2$), 36.0 (CH), 31.9 (CH$_2$), 28.6 (CH$_3$), 21.3 (CH$_3$). FTIR (KBr, thin film) 3470, 1326, 3109, 3005, 2977, 2937, 2850, 2246, 1676, 1605, 1533, 1408, 1366, 1181, 768, 722, 568 cm$^{-1}$. HRMS (ESI+) [M+H]$^+$ Calculated for C$_{22}$H$_{28}$O$_2$N$_7$$^+$ 422.2304; found 422.2305.

Example 15: 1,1,1,3,3,3-hexafluoropropan-2-yl 4-(1-(4-(6-methyl-1,2,4,5-tetrazin-3-yl)phenyl)-1H-pyrazol-3-yl)piperidine-1-carboxylate (9)

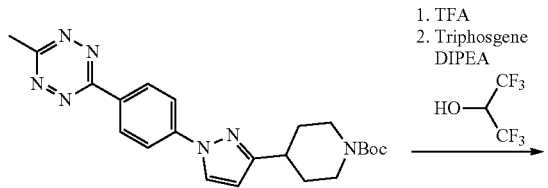

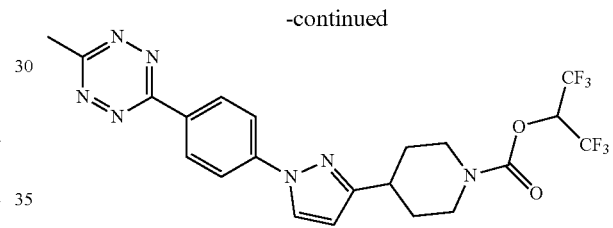

Step 1: tert-butyl 4-(1-(4-(6-methyl-1,2,4,5-tetrazin-3-yl)phenyl)-1H-pyrazol-3-yl)piperidine-1-carboxylate 8 (30 mg, 71.6 µmol, 1.0 eq.) and trifluoroacetic acid (82 µL, 1.07 mmol, 15.0 eq.) were stirred in dichloromethane (1.4 mL) for 2 h at room temperature. The solvent and tert-butanol biproduct was then removed by rotary evaporation leaving the Boc-deprotected reagent.

Step 2: Separately, triphosgene (21 mg, 71.6 µmol, 1.0 eq.) and dichloromethane (630 µL) were stirred at 0° C. under a nitrogen line equipped with an in-line column filled with powdered potassium hydroxide. A solution of 1,1,1,3′,3′,3′-hexafluoro-propanol (23 µL, 215 µmol, 3.0 eq.) and N,N-Diisopropylethylamine (149 µL, 859 µmol, 12.0 eq.) in dichloromethane (315 µL) was then dropwise added to the triphosgene solution. The reaction was stirred for 30 min at 0° C., then 2 h at room temperature. The solution turns a golden yellow color. The Boc-deprotected reagent was redissolved in dichloromethane (490 µL) and added to the triphosgene reaction which was then stirred for 16 h. The reaction was diluted in 30 mL dichloromethane and washed with 2×10 mL H$_2$O and 1×10 mL brine. The remaining solution was dried on MgSO$_4$, filtered, and the solvent was removed by rotary evaporation. The crude solids were chromatographed on silica gel (2% acetone/DCM) yielding 1,1,1,3,3,3-hexafluoropropan-2-yl 4-(1-(4-(6-methyl-1,2,4,5-tetrazin-3-yl)phenyl)-1H-pyrazol-3-yl)piperidine-1-carboxylate as a light pink powder. (29 mg, 78%). $^1$H NMR (400 MHz, CDCl$_3$) δ 8.70 (app d, J=8.8 Hz, 2H), 8.01 (d, J=2.4 Hz, 1H), 7.92 (app d, J=8.8 Hz, 2H), 6.38 (d, J=2.4 Hz, 1H), 5.82 (hept, J=6.2 Hz, 1H), 4.30-4.22 (m, 2H), 3.22-3.01 (m, 6H), 2.16-2.11 (m, 2H), 1.89-1.75 (m, 2H). $^{19}$F NMR (376 MHz, CDCl$_3$) δ −73.62 (d, $J_{F-H}$=6.0 Hz). $^{13}$C NMR (101 MHz, CDCl$_3$) δ 167.3 (C), 163.6 (C), 158.1 (C), 151.6 (C), 143.2 (C), 129.4 (CH), 129.3 (C), 120.9 (CF$_3$, q, $J_{C-F}$=283.7 Hz), 119.0 (CH), 106.0 (CH), 68.2 (CH, hept, $J_{C-F}$=34.5 Hz), 45.1 (CH$_2$), 44.5 (CH$_2$), 35.5 (CH), 31.7 (CH$_2$), 31.4 (CH$_2$), 21.3 (CH$_3$). FTIR (KBr, thin film) 3435, 2968, 2926, 2854, 1726, 1657, 1606, 1534, 1438, 1409, 1388, 1280, 1250, 1190, 1106, 892, 801, 755, 688, 564 cm$^{-1}$. HRMS (ESI+) [M+H]$^+$ Calculated for $C_{21}H_{20}F_6O_2N_7^+$ 516.1583; found 516.1601.

Example 16: Stopped-Flow Kinetics of Compound 9 Versus 10

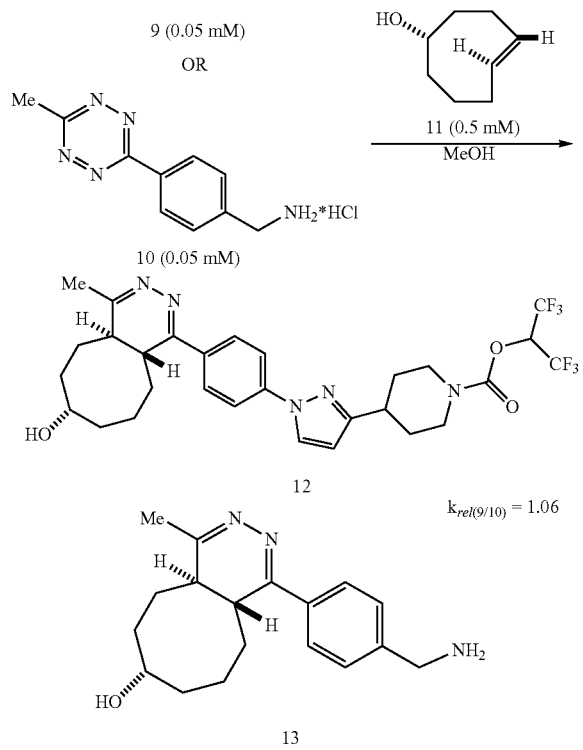

0.1 mM solutions (10 mL) in methanol were prepared from stock solutions of 9 (16.3 mg in 632 μL DMF, 50 mM) and 10 (10.0 mg in 422 μL MeOH, 100 mM). A 1.0 mM solution (25 mL) in methanol of axial 5-hydroxy-trans-cyclooctene 11 was also prepared from a stock solution (29.0 mg in 460 μL MeOH, 500 mM). The reaction between tetrazine and a trans-cyclooctene was measured under pseudo-first order conditions using a SX 18MV-R stopped-flow spectrophotometer (Applied Photophysics Ltd.). The 0.1 mM solution of tetrazines 9 or 10 and the 1.0 mM solution of trans-cyclooctene 11 were injected as equal volumes via syringe into the stopped-flow instrument which was held at 25° C., resulting in a final concentration of the tetrazine of 0.05 mM and a final concentration of the trans-cyclooctene of 0.5 mM. The reaction was monitored by the absorbance decay of tetrazine measured at 290 nm. Data points were collected every 0.1 second for 400 seconds and reaction was repeated in triplicate. Prism software was used to obtain the observed rate of each reaction, $k_{obs}$, which was determined by nonlinear regression analysis resulting in average rate constants of 0.01033 s$^{-1}$ for 9 and 0.00975 s$^{-1}$ for 10. The relative rate, $k_{rel}$, of 9 versus 10 was thus determined to be 1.06.

Example 17: Inhibition Assay by MAGL Probe 9

Materials. Tetrazine amine was purchased from Click Chemistry Tools. TCO-TAMRA were synthesized according to literature protocol. Human brain vascular pericytes and pericyte growth supplement were purchased from ScienCell Research Laboratories. Phosphate-based saline (PBS) was purchased from Mediatech, Inc. Media and other supplements for cell culture were purchased from Thermo Fisher Scientific unless otherwise noted. For cell treatments, all reagents were prepared as 1000× stock solutions in DMSO and stored at −80° C.

Cell culture and probe treatment. Human brain vascular pericytes were cultured in Dulbecco's Modified Eagle Medium/Nutrient Mixture F-12 (DMEM/F-12) GlutaMAX media supplemented with 5% heat-inactivated fetal bovine serum (HI FBS), 1× pericyte growth supplement (PGS), and 1× penicillin-streptomycin at 37° C. with 5% CO$_2$ in a humidified environment. Probe treatment was performed in duplicates. Cells were plated in 6-well plates and cultured overnight in growth media. Live cells were then treated with 300 nM KML29 as a competitor compound (or DMSO as a control) at 37° C. for 1 h. Cells were subsequently treated with probe 9 (0.3 nM-3.2 μM) at 37° C. for 1 h (cells pre-treated with KML29 were treated with 32 nM of probe 9), after which the cells were washed with fresh growth media. The media were then placed with fresh media containing 2 μM of TCO-TAMRA, and the cells were incubated at 37° C. for 30 min. To quench the reaction, the media were replaced with PBS containing 100 μM tetrazine amine, and the cells were washed with cold PBS and harvested with a scrapper. The suspensions were centrifuged at 10,000×g for 1 min at 37° C., and the cell pellets were lysed in PBS containing 0.25% sodium dodecyl sulfate (SDS) with sonication. The protein concentration was measured with a bicinchoninic acid (BCA) assay kit (Thermo Scientific) and normalized.

In-gel fluorescence and data analysis. The proteomes were analyzed with 1.0 mm thick 4-12% bis-tris 15-well protein gels in 2-(N-morpholino)ethanesulfonic acid (MES) buffer. The gels were scanned with a Typhoon FLA 9500 Biomolecular Imager (GE Healthcare) with the TAMRA channel with 532 nm excitation and a 575 nm long pass emission filter. To measure the total protein loading, the gels were treated with ClearPage Instant Blue (CBS Scientific) overnight, and after brief destaining with water, scanned with an Odyssey Imager (Li-COR) at the 700 nm channel. The in-gel fluorescence images were processed with ImageJ software (v1.47, NIH), and the intensities were quantified with Image Studio (v5.2, Li-COR) with background subtraction. The coomassie images were processed and quantified with the Image Studio software with background subtraction. For analysis of the cellular potency, the in-gel fluorescence intensities of the two MAGL bands were averaged, normalized with the total coomassie intensity of the corresponding sample, and fitted with a dose-response equation with Prism v7.02 (GraphPad).

Example 18: Optimization of Synthesizing 3-Monosubstituted Tetrazines

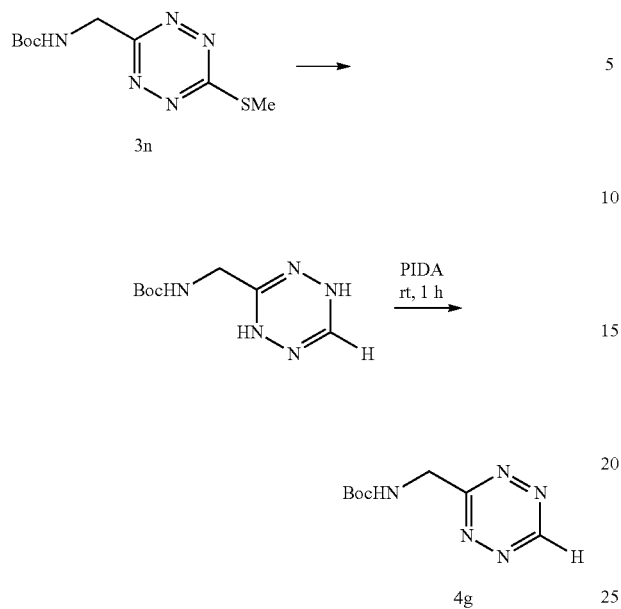

All reactions were conducted with 0.04 mmol scale of 3n at concentration of 0.1 M THF (entry 9 is in 0.1 M toluene). Oxidation of dihydrotetrazine was accomplished by adding PIDA (1 equiv.) and stirring at room temperature for 1 h. Yield was calculated by NMR with benzyl benzoate as internal standard. Results are summarized in Table 2 below.

TABLE 2

| Entry | Catalyst | Reductant | Temperature | Time | Conversion (%) | NMR Yield (%) |
|---|---|---|---|---|---|---|
| 1 | 5% wt Pd/C (10 mol %) | HSiEt$_3$ (4 equiv.) | r.t. | 24 h | 3 | Trace |
| 2 | 5% wt Pd/C (10 mol %) | hydrogen | r.t. | 24 h | 3 | Trace |
| 3 | 5% wt Pd/C (10 mol %) | HSiEt$_3$ (4 equiv.) | 70° C. | 3 h | 94 | 52 |
| 4 | PdCl$_2$ (10 mol %) | HSiEt$_3$ (4 equiv.) | 70° C. | 3 h | 97 | 69 |
| 5 | Pd(OAc)$_2$ (10 mol %) | HSiEt$_3$ (4 equiv.) | 70° C. | 3 h | 96 | 59 |
| 6 | PdCl$_2$(ACN)$_2$ (10 mol %) | HSiEt$_3$ (4 equiv.) | 70° C. | 3 h | 95 | 61 |
| 7 | [PdCl$_2$(allyl)]$_2$ (10 mol %) | HSiEt$_3$ (4 equiv.) | 70° C. | 3 h | 90 | 58 |
| 8 | Pd(acac)$_2$ (10 mol %) | HSiEt$_3$ (4 equiv.) | 70° C. | 3 h | 86 | 49 |
| 9 | Ni(cod)$_2$ (10 mol %) | HSiEt$_3$ (4 equiv.) | 70° C. | 2 h | 2 | 0 |
| 10 | NiCl$_2$ (10 mol %) | HSiEt$_3$ (4 equiv.) | 70° C. | 2 h | 1 | 0 |
| 11 | PdCl$_2$ (10 mol %) | HSiEt$_3$ (6 equiv.) | 70° C. | 3 h | 100 | 51 |
| 12 | PdCl$_2$ (10 mol %) | HSiEt$_3$ (3 equiv.) | 70° C. | 3 h | 88 | 80 |
| 13 | PdCl$_2$ (10 mol %) | HSiEt$_3$ (3 equiv.) | 45° C. | 20 h | 90 | 83 |
| 14 | PdCl$_2$ (10 mol %) | HSiEt$_3$ (3 equiv.) | 45° C. | 30 h | 73 | 66 |
| 15 | PdCl$_2$ (10 mol %) | HSiEt$_3$ (3 equiv.) | r.t. | 30 h | 61 | 57 |

Example 19: Optimization of Synthesizing 3-Monosubstituted Tetrazines

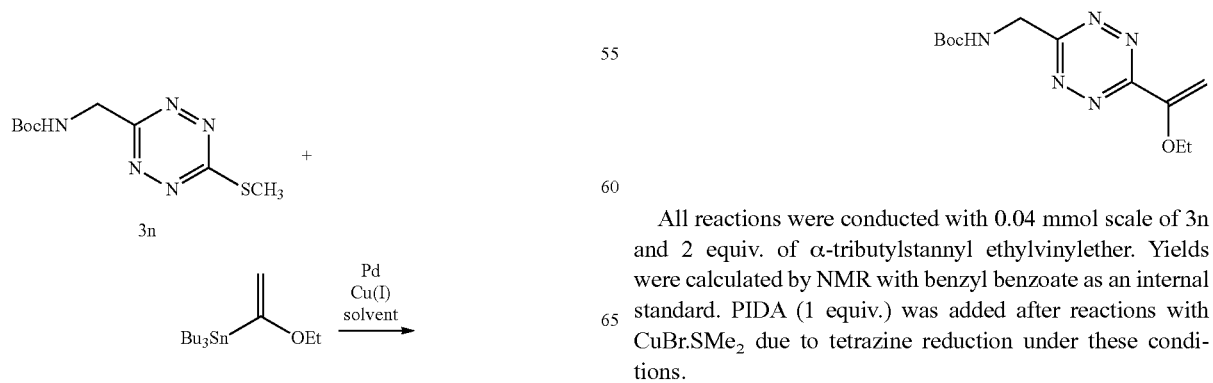

All reactions were conducted with 0.04 mmol scale of 3n and 2 equiv. of α-tributylstannyl ethylvinylether. Yields were calculated by NMR with benzyl benzoate as an internal standard. PIDA (1 equiv.) was added after reactions with CuBr.SMe$_2$ due to tetrazine reduction under these conditions.

TABLE 3

| Entry | Catalyst | Cu | Solvent (conc. of 3 n) | Temperature | Time | NMR yield (%) |
|---|---|---|---|---|---|---|
| 1 | Pd$_2$(dba)$_3$ (10 mol %) PPh$_3$ (40 mol %) | CuTc (2 equiv.) | THF (0.1 M) | 70° C. | 30 min | 10 |
| 2 | Pd(PPh$_3$)$_4$ (20 mol %) | CuTc (2 equiv.) | THF (0.1 M) | 70° C. | 30 min | 16 |
| 3 | Pd(PPh$_3$)$_4$Cl$_2$ (20 mol %) | CuTc (2 equiv.) | THF (0.1 M) | 70° C. | 30 min | 14 |
| 4 | Pd(dppf)Cl$_2$ (20 mol %) | CuTc (2 equiv.) | THF (0.1 M) | 70° C. | 30 min | 11 |
| 5 | Pd(OAc)$_2$ (20 mol %) PPh$_3$ (40 mol %) | CuTc (2 equiv.) | THF (0.1 M) | 70° C. | 30 min | 0 |
| 6 | Pd(PPh$_3$)$_4$ (20 mol %) | CuBr•SMe$_2$ (2.2 equiv.) | dioxane (0.1 M) | 50° C. | 14 h | 25 |
| 7 | Pd(PPh$_3$)$_4$Cl$_2$ (20 mol %) | CuBr•SMe$_2$ (2.2 equiv.) | dioxane (0.1 M) | 50° C. | 14 h | 24 |
| 8 | Pd(PPh$_3$)$_4$ (20 mol %) | CuBr•SMe$_2$ (3 equiv.) | THF (0.1 M) | 50° C. | 14 h | 24 |
| 9 | Pd(PPh$_3$)$_4$ (20 mol %) | CuBr•SMe$_2$ (2.2 equiv.) | THF (0.1 M) | 50° C. | 14 h | 24 |
| 10 | Pd(PPh$_3$)$_4$ (20 mol %) | CuTc (2 equiv.) | THF (0.1 M) | 70° C. | 3 min | 30 |
| 11 | Pd(PPh$_3$)$_4$ (20 mol %) | CuTc (2 equiv.) | THF (0.1 M) | r.t. | 1 h | 17 |
| 12 | Pd(PPh$_3$)$_4$ (20 mol %) | CuTc (2 equiv.) | dioxane (0.1 M) | 70° C. | 6 min | 35 |
| 13 | Pd(PPh$_3$)$_4$ (20 mol %) | CuTc (1.5 equiv.) | dioxane (0.1 M) | 70° C. | 10 min | 27 |
| 14 | Pd(PPh$_3$)$_4$ (20 mol %) | CuTc (2 equiv.) | dioxane/hexane 1/1 (0.1 M) | 70° C. | 30 min | 15 |
| 15 | Pd(PPh$_3$)$_4$ (20 mol %) | CuMeSal (2 equiv.) | dioxane (25 mM) | 70° C. | 5 min | 34 |
| 16 | Pd(PPh$_3$)$_4$ (20 mol %) | CuTc (2 equiv.) | dioxane (25 mM) | 70° C. | 3 min | 48 |
| 17 | Pd(PPh$_3$)$_4$ (20 mol %) | CuTc (2 equiv.) | dioxane (10 mM) | 70° C. | 8 min | 50 |
| 18 | Pd(PPh$_3$)$_4$ (20 mol %) | CuTc (2 equiv.) | dioxane (5 mM) | 70° C. | 15 min | 55 |
| 19 | Pd(PPh$_3$)$_4$ (20 mol %) | CuTc (2 equiv.) | dioxane (2 mM) | 70° C. | 30 min | 35 |
| 20 | Pd(PPh$_3$)$_4$ (15 mol %) | CuTc (2 equiv.) | dioxane (5 mM) | 70° C. | 15 min | 58 |
| 21 | Pd(PPh$_3$)$_4$ (15 mol %) | CuTc (2 equiv.) | dioxane (5 mM) | 100° C. | 16 min | 61 |
| 22 | Pd(PPh$_3$)$_4$ (15 mol %) | CuTc (2 equiv.) | dioxane (5 mM) | 100° C. | 18 min | 58 |
| 23 | Pd(PPh$_3$)$_4$ (15 mol %) | CuTc (2 equiv.) | dioxane (5 mM) | 100° C. | 20 min | 57 |

Example 20: Tetrazine Stability in PBS Buffer in Ambient Light at 25° C.

Solutions (3 mL) of tetrazine 5b, 5l and 6c (400 µM) were prepared in PBS buffer (pH 7.4) in vials and stored in ambient light at 25° C. Tetrazine concentrations were determined by recording the absorbance at 518 nm (6c) and 520 nm (5b and 5l) in cuvettes in day 0, 1, 3 and 5. A solution of 6a (50 µM) was prepared in PBS buffer (pH 7.4) in vials and stored in ambient light at room temperature. Tetrazine concentration was determined by recording the absorbance at 520 nm in cuvettes at day 0, 1, 3 and 5. Results show 5b, 5l, 6c and 6a have 1.8%, 1.7%, 3.9% and 0.8% decomposition per day respectively.

Example 21: Tetrazine Stability in Opti-MEM Media in Ambient Light at 25° C.

Solutions (10 mL) of tetrazine 5b and 6c (400 µM) were prepared in Opti-MEM media in vials and stored in ambient light at 25° C. 2 mL of solution was extracted by 2 mL of Et$_2$O in different time point. Tetrazine concentrations were determined by recording the absorbance of Et$_2$O at 545 nm. Results show 5b and 6c have 6.7% and 10.8% decomposition per day respectively.

Example 22: Stopped-Flow Kinetic Analysis of Tetrazines 5b, 6b, 6h, 6e and 4f with Eq-5-Hydroxy-Trans-Cyclooctene in PBS Buffer at 25° C.

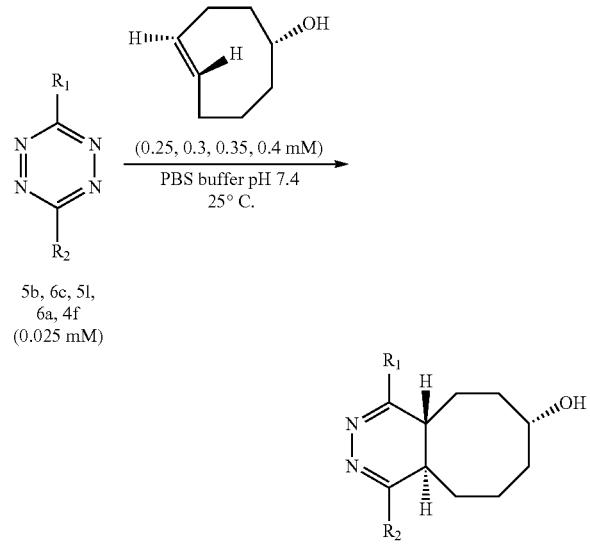

Solutions (5 mL) of tetrazines 5b, 6c, 5l, 6a and 4f (0.050 mM) were prepared in PBS buffer (pH 7.4). Solutions (10 mL) of eq-5-hydroxy-trans-cyclooctene (0.50, 0.60, 0.70, 0.80 mM) were prepared in PBS buffer (pH 7.4). The reactions between tetrazines and trans-cyclooctene were measured under pseudo-first order conditions using SX 18MV-R stopped-flow spectrophotometer (Applied Photophysics Ltd.). Each solution of tetrazine and trans-cyclooctene were injected in equal volumes via 3 mL syringes into the stopped-flow instrument at 25° C., resulting in final concentration of 0.025 mM of tetrazines and 0.25, 0.30, 0.35, 0.40 mM trans-cyclooctene. The reaction was monitored by the decay of absorbance associated with the tetrazines (5b at 263 nm, 6c at 268 nm, 5l at 274 nm, 6a at 296 nm, 4f at 266 nm). Reaction were repeated in triplicate. With Prism software, an observed rate constant, $k_{obs}$, was obtained by nonlinear regression. Second order rate constants, $k_2$, were calculated by linear regression between $k_{obs}$ and final concentration of trans-cyclooctene. The results are summarized below in Table 4.

TABLE 4

| | TCO (mM) | | | | | |
|---|---|---|---|---|---|---|
| | 0.25 | 0.30 | 0.35 | 0.40 | $k_2$ (M$^{-1}$s$^{-1}$) | $k_{rel}$ |
| 5b, $k_{obs}$ (s$^{-1}$) | 0.57 | 0.065 | 0.075 | 0.87 | 197.9 ± 13.36 | 1.0 |
| 6c, $k_{obs}$ (s$^{-1}$) | 0.20 | 0.24 | 0.28 | 0.33 | 833 ± 35.7 | 4.2 |
| 5l, $k_{obs}$ (s$^{-1}$) | 0.21 | 0.24 | 0.029 | 0.032 | 69.88 ± 4.824 | 0.35 |
| 6a, $k_{obs}$ (s$^{-1}$) | 0.52 | 0.62 | 0.70 | 0.83 | 2007 ± 101.3 | 10 |
| 4f, $k_{obs}$ (s$^{-1}$) | 0.53 | 0.61 | 0.68 | 0.77 | 1591 ± 25.74 | 8.0 |

Example 23: Synthesis of Methyl Thiocarbohydrazide Iodide Salt (2)

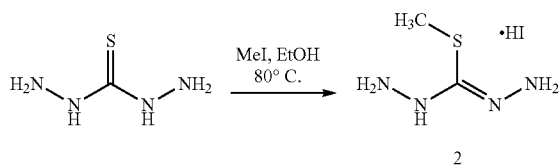

Compound 2 was prepared according to literature protocol. A dry round bottom flask was charged with thiocarbohydrazide (500 mg, 4.71 mmol, 1 equiv.), methyl iodide (323 µL, 5.18 mmol, 1.1 equiv.) and ethanol (15 mL, 0.3 M). After refluxing at 80° C. for 3 h, reaction mixture was cooled down and hexane was added. After cooling down in freezer (−20° C.) overnight, the reaction mixture was filtered, solid was washed with cold ethanol:hexane 1:1 and drying under vacuum, a white solid (700 mg, 2.82 mmol, 60%) was collected and used directly without further purification.

Example 24: General Protocol for the Synthesis of Oxetane Esters (15)

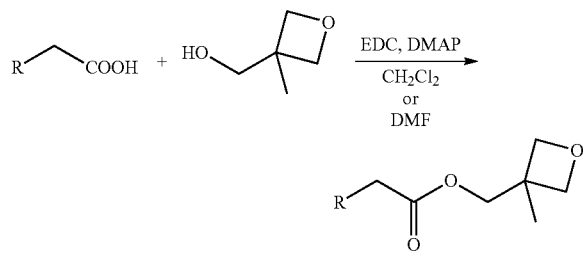

A dry round-bottom flask was charged with 3-methyl-3-oxetanemethanol (1.1 equiv.), 1-(3-dimethylaminopropyl)-3-ethylcarbodiimide hydrochloride (EDC.HCl, 1.2 equiv.) and DMAP (0.10 equiv.). The flask was outfitted with a septum-fitted gas inlet adapter and then evacuated and filled with nitrogen. Anhydrous CH$_2$Cl$_2$ or DMF was added to the flask via syringe. The flask was cooled by an ice bath (0° C.), and the carboxylic acid (1 equiv.) was added. After stirring under nitrogen at 0° C. for 15 min and at r.t overnight, the reaction mixture was diluted with CH$_2$Cl$_2$. The solution was washed with saturated sodium bicarbonate solution, water and brine, and the organics were dried over sodium sulfate and concentrated by rotary evaporation. The residue was purified by flash column chromatography on silica gel.

Example 24A: (3-methyloxetan-3-yl)methyl 2-(benzyloxy)acetate (15a)

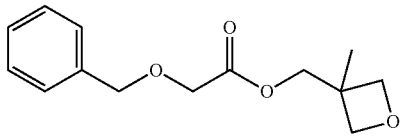 [SMILES: CC1(COC(=O)COCc2ccccc2)COC1]

The general protocol was followed with benzyloxyacetic acid (1196 mg, 11.83 mmol), 3-methyl-3-oxetanemethanol (1329 mg, 13.02 mmol), EDC (2721 mg, 14.20 mmol), DMAP (144.5 mg, 1.183 mmol) in CH$_2$Cl$_2$ (24 mL, 0.25 M). A colorless oil (2783 mg, 11.12 mmol, 94%) was obtained after column chromatography (Hexane:EA 100:0 to 75:25). $^1$H NMR (400 MHz, CDCl$_3$) δ 7.38-7.67 (m, 5H), 4.64 (s, 2H), 4.50 (d, J=6.0 Hz, 2H), 4.38 (d, J=6.0 Hz, 2H), 4.26 (s, 2H), 4.15 (s, 2H), 1.32 (s, 3H). $^{13}$C NMR (101 MHz, CDCl$_3$) δ 170.56 (C), 137.01 (C), 128.60 (CH), 128.15 (CH), 128.12 (CH), 79.50 (CH$_2$), 73.45 (CH$_2$), 68.99 (CH$_2$), 67.01 (CH$_2$), 39.12 (C), 21.18 (CH$_3$). IR (KBr), υ/cm$^{-1}$ 3064, 3031, 2962, 2872, 1750, 1455, 1257, 1197, 1127, 981, 740, 699. HRMS [M+H]$^+$ m/z calcd. for [C$_{14}$H$_{19}$O$_4$]$^+$ 251.1283, found 251.1278.

Example 24B: (3-methyloxetan-3-yl)methyl 4-((tert-butoxycarbonyl)amino)benzoate (15b)

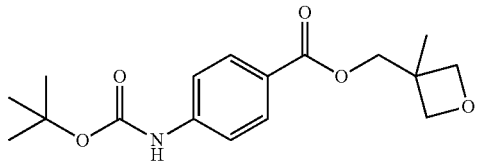 [SMILES: CC1(COC(=O)c2ccc(NC(=O)OC(C)(C)C)cc2)COC1]

The general protocol was followed with 4-(Boc-amino) benzoic acid (1899 mg, 8.01 mmol), 3-methyl-3-oxetanemethanol (900 mg, 8.81 mmol), EDC (1843 mg, 9.62 mmol), DMAP (97.8 mg, 0.801 mmol) in CH$_2$Cl$_2$ (16 mL, 0.5 M). A white solid (2468 mg, 7.68 mmol, 96%) was obtained after column chromatography (Hexane:EA 100:0 to 85:15). $^1$H NMR (400 MHz, CDCl$_3$) δ 7.98 (app d, J=8.8 Hz, 2H), 7.43 (app d, J=8.8 Hz, 2H), 6.74 (s, 1H), 4.64 (d, J=6.0 Hz, 2H), 4.45 (d, J=6.0 Hz, 2H), 4.37 (s, 2H), 1.53 (s, 9H), 1.42 (s, 3H). $^{13}$C NMR (101 MHz, CDCl$_3$) δ 166.29 (C), 152.26 (C), 143.09 (CH), 131.09 (CH), 124.12 (C), 117.52 (CH), 81.42 (C), 79.80 (CH$_2$), 68.95 (CH$_2$), 39.45 (C), 28.41 (CH$_3$), 21.46 (CH$_3$). IR (KBr), υ/cm$^{-1}$ 3375, 3100, 3060, 2971, 2886, 1724, 1678, 1600, 1543, 1411, 1324, 1240, 1159, 1115, 863, 767. HRMS [M+H]$^+$ m/z calcd. for [C$_{17}$H$_{24}$O$_5$N]$^+$ 322.1654, found 322.1646.

Example 24C: (3-methyloxetan-3-yl)methyl 4-(((tert-butoxycarbonyl)amino)methyl)benzoate (15c)

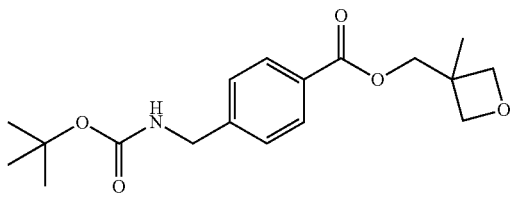 [SMILES: CC1(COC(=O)c2ccc(CNC(=O)OC(C)(C)C)cc2)COC1]

The general protocol was followed with Boc-(4-aminophenyl)acetic acid (2010 mg, 8.01 mmol), 3-methyl-3-oxetanemethanol (900 mg, 8.82 mmol), EDC (1834 mg, 9.62 mmol), DMAP (97.8 mg, 0.801 mmol) in CH$_2$Cl$_2$ (16 mL, 0.25 M). A white solid (2520 mg, 7.52 mmol, 94%) was obtained after column chromatography (Hexane:EA 100:0 to 75:25). $^1$H NMR (400 MHz, CDCl$_3$) δ 8.02 (app d, J=8.2 Hz, 2H), 7.36 (app d, J=8.2 Hz, 2H), 4.95 (s, 1H), 4.64 (d, J=6.0 Hz, 2H), 4.46 (d, J=6.0 Hz, 2H), 4.38 (s, 2H), 4.37 (s, 2H), 1.46 (s, 9H), 1.42 (s, 3H). $^{13}$C NMR (101 MHz, CDCl$_3$) δ 166.46 (C), 156.02 (C), 144.75 (C), 130.11 (CH), 128.97 (C), 127.36 (CH), 79.97 (C), 79.75 (CH$_2$), 69.12 (CH$_2$), 44.44 (CH$_2$), 39.42 (C), 28.52 (CH$_3$), 21.44 (CH$_3$). IR (KBr), υ/cm$^{-1}$ 3386, 3008, 2981, 2946, 2880, 1717, 1689, 1517, 1289, 1275, 1246, 1170, 1110, 983, 756. HRMS [M+H]$^+$ m/z calcd. for [C$_{18}$H$_{26}$O$_5$N]$^+$ 336.1811, found 336.1804.

Example 24D: (3-methyloxetan-3-yl)methyl 4-nitrobenzoate (15d)

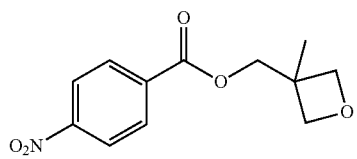 [SMILES: CC1(COC(=O)c2ccc([N+](=O)[O-])cc2)COC1]

The general protocol was followed with 4-nitro-benzoic acid (1191 mg, 7.12 mmol), 3-methyl-3-oxetanemethanol (800 mg, 7.84 mmol), EDC (1638 mg, 8.55 mmol), DMAP (86.9 mg, 0.712 mmol) in CH$_2$Cl$_2$ (35 mL, 0.2 M). A white solid (1520 mg, 6.05 mmol, 85%) was obtained after column chromatography (Hexane:Acetone 10:0 to 9:1). $^1$H NMR (400 MHz, CDCl$_3$) δ 8.28 (app d, J=9.0 Hz, 2H), 8.21 (app d, J=9.0 Hz, 2H), 4.61 (d, J=6.1 Hz, 2H), 4.47 (d, J=6.1 Hz, 2H), 4.44 (s, 2H), 1.42 (s, 3H). 13C NMR (101 MHz, CDCl$_3$) δ 164.70 (C), 150.68 (C), 135.26 (C), 130.82 (CH), 123.71 (CH), 79.49 (CH$_2$), 69.92 (CH$_2$), 39.32 (C), 21.24 (CH$_3$). IR (KBr), υ/cm$^{-1}$ 3010, 3000, 2961, 2874, 1715, 1708, 1607, 1525, 1344, 1280, 1263, 979, 847, 719. HRMS [M+H]$^+$ m/z calcd. for [C$_{12}$H$_{14}$O$_5$N]$^+$ 252.0872, found 252.0863.

Example 24E: (3-methyloxetan-3-yl)methyl 4-methoxybenzoate (15e)

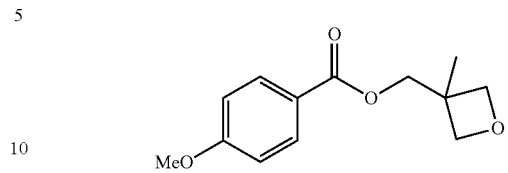

The general protocol was followed with 4-nitro-benzoic acid (608 mg, 3.56 mmol), 3-methyl-3-oxetanemethanol (400 mg, 3.92 mmol), EDC (819 mg, 4.27 mmol), DMAP (43.5 mg, 0.356 mmol) in CH$_2$Cl$_2$ (16 mL, 0.25 M). A colorless oil (576 mg, 2.40 mmol, 61%) was obtained after column chromatography (Hexane:Acetone 10:0 to 9:1). $^1$H NMR (400 MHz, CDCl$_3$) δ 8.01 (app d, J=8.9 Hz, 2H), 6.93 (app d, J=8.9 Hz, 2H), 4.64 (d, J=5.9 Hz, 2H), 4.45 (d, J=5.9 Hz, 2H), 4.36 (s, 2H), 3.86 (s, 3H), 1.42 (s, 3H). $^{13}$C NMR (101 MHz, CDCl$_3$) δ 166.41 (C), 163.63 (C), 131.79 (CH), 122.38 (C), 113.82 (CH), 79.78 (CH$_2$), 68.82 (CH$_2$), 55.59 (CH$_3$), 39.43 (C), 21.45 (CH$_3$). IR (KBr), υ/cm$^{-1}$ 3078, 2962, 2871, 1717, 1607, 1512, 1256, 1168, 1103, 982, 770. HRMS [M+H]$^+$ m/z calcd. for [C$_{13}$H$_{17}$O$_4$]$^+$ 237.1127, found 237.1120.

Example 24F: (3-methyloxetan-3-yl)methyl 4-bromobenzoate (15f)

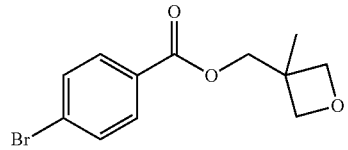 [SMILES: CC1(COC(=O)c2ccc(Br)cc2)COC1]

The general protocol was followed with 4-bromobenzoic acid (604 mg, 3.03 mmol), 3-methyl-3-oxetanemethanol (340 mg, 3.33 mmol), EDC (690 mg, 3.64 mmol), DMAP (37.0 mg, 0.303 mmol) in CH$_2$Cl$_2$ (15 mL, 0.20 M). A white solid (812 mg, 2.85 mmol, 95%) was obtained after column chromatography (Hexane:EA 10:0 to 95:5). $^1$H NMR (400 MHz, CDCl$_3$) δ 7.94 (app d, J=8.6 Hz, 2H), 7.62 (app d, J=8.6 Hz, 2H), 4.65 (d, J=6.0 Hz, 2H), 4.49 (d, J=6.0 Hz, 2H), 4.42 (s, 2H), 1.45 (s, 3H). 13C NMR (101 MHz, CDCl$_3$) δ 165.96 (C), 131.97 (CH), 131.28 (CH), 128.87 (C), 128.50 (C), 79.69 (CH$_2$), 69.37 (CH$_2$), 39.40 (C), 21.40 (CH$_3$). IR (KBr), υ/cm$^{-1}$ 3065, 2963, 2873, 1721, 1590, 1484, 1398, 1263, 1174, 1104, 1012, 982, 848, 756. HRMS [M+H]$^+$ m/z calcd. for [C$_{12}$H$_{14}$O$_3$Br]$^+$ 285.0126, found 285.0120.

Example 24G: methyl ((3-methyloxetan-3-yl)methyl) terephthalate (15g)

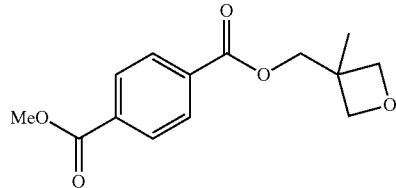 [SMILES: COC(=O)c1ccc(C(=O)OCC2(C)COC2)cc1]

The general protocol was followed with monomethyl terephthalate (1440 mg, 8.01 mmol), 3-methyl-3-oxetanemethanol (900 mg, 8.82 mmol), EDC (1840 mg, 9.62 mmol), DMAP (97.9 mg, 0.801 mmol) in CH$_2$Cl$_2$ (32 mL, 0.25 M). A white solid (1956 mg, 7.40 mmol, 93%) was obtained after column chromatography (Hexane:EA 10:0 to 8:2). $^1$H NMR (400 MHz, CDCl$_3$) δ 8.12 (app s, 4H), 4.65 (d, J=6.0 Hz, 2H), 4.48 (d, J=6.0 Hz, 2H), 4.43 (s, 2H), 3.96 (s, 3H), 1.44 (s, 3H). $^{13}$C NMR (101 MHz, CDCl$_3$) δ 166.36 (C), 165.90 (C), 134.27 (C), 133.74 (C), 129.79 (CH), 129.75 (CH), 79.71 (CH$_2$), 69.58 (CH$_2$), 52.67 (CH$_3$), 39.43 (C), 21.42 (CH$_3$). IR (KBr), υ/cm$^{-1}$ 3012, 2964, 2936, 2871, 1732, 1716, 1506, 1436, 1395, 1279, 1249, 1125, 1105, 1016, 979, 726. HRMS [M+H]$^+$ m/z calcd. for [C$_{14}$H$_{17}$O$_5$]$^+$ 265.1076, found 265.1067.

Example 24H: (3-methyloxetan-3-yl)methyl 4-cyanobenzoate (15h)

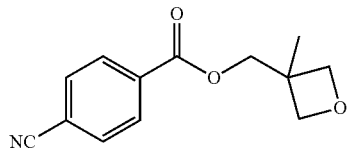 [SMILES: CC1(COC(=O)c2ccc(C#N)cc2)COC1]

The general protocol was followed with 4-cyanobenzoic acid (608 mg, 3.56 mmol), 3-methyl-3-oxetanemethanol (400 mg, 3.92 mmol), EDC (920 mg, 4.27 mmol), DMAP (43.5 mg, 0.356 mmol) in CH$_2$Cl$_2$ (16 mL, 0.25 M). A white solid (795 mg, 3.44 mmol, 86%) was obtained after column chromatography (Hexane:EA 10:0 to 9:1). $^1$H NMR (400 MHz, CDCl$_3$) δ 8.16 (app d, J=8.5 Hz, 2H), 7.77 (app d, J=8.5 Hz, 2H), 4.62 (d, J=6.0 Hz, 2H), 4.48 (d, J=6.0 Hz, 2H), 4.44 (s, 2H), 1.43 (s, 3H). 13C NMR (101 MHz, CDCl$_3$) δ 165.04 (C), 133.78 (C), 132.48 (CH), 130.28 (CH), 118.05 (C), 116.78 (C), 79.60 (CH$_2$), 69.86 (CH$_2$), 39.40 (C), 21.34 (CH$_3$). IR (KBr), υ/cm$^{-1}$ 3051, 2960, 2927, 2873, 2231, 1725, 1610, 1461, 1406, 1377, 1280, 1264, 1118, 1107, 981, 766. HRMS [M+H]$^+$ m/z calcd. for [C$_{13}$H$_{14}$O$_3$N]$^+$ 232.0974, found 232.0964

Example 24I: (3-methyloxetan-3-yl)methyl 6-methoxypicolinate (15i)

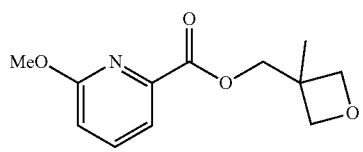 [SMILES: COc1cccc(C(=O)OCC2(C)COC2)n1]

The general protocol was followed with 6-methoxypyridine-2-carboxylic acid (640 mg, 4.18 mmol), 3-methyl-3-oxetanemethanol (472 mg, 4.62 mmol), EDC (962 mg, 5.02 mmol), DMAP (50.9 mg, 0.418 mmol) in CH$_2$Cl$_2$ (20 mL, 0.2 M). A colorless oil (833 mg, 3.50 mmol, 84%) was obtained after column chromatography (Hexane:EA 100:0 to 85:15). $^1$H NMR (400 MHz, CDCl$_3$) δ 7.72-7.63 (m, 2H), 6.93 (dd, J=7.2, 2.0 Hz, 1H), 4.64 (d, J=6.0 Hz, 2H), 4.44 (d, J=6.0 Hz, 2H), 4.42 (s, 2H), 4.00 (s, 3H), 1.43 (s, 3H). $^{13}$C NMR (101 MHz, CDCl$_3$) δ 165.17 (C), 164.01 (C), 145.21 (C), 139.10 (CH), 118.69 (CH), 115.59 (CH), 79.70 (CH$_2$), 69.51 (CH$_2$), 53.69 (CH$_3$), 39.44 (C), 21.35 (CH$_3$). IR (KBr), υ/cm$^{-1}$ 3078, 2957, 2872, 1740, 1721, 1595, 1574, 1470, 1415, 1329, 1274, 1140, 1028, 985, 825, 770. HRMS [M+H]$^+$ m/z calcd. for [C$_{12}$H$_{16}$O$_4$N]$^+$ 238.1079, found 238.1073.

Example 24J: (3-methyloxetan-3-yl)methyl isonicotinate (15j)

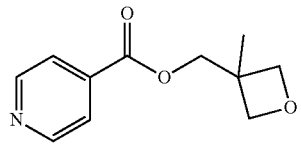

The general protocol was followed with 4-picolinic acid (985 mg, 8.01 mmol), 3-methyl-3-oxetanemethanol (900 mg, 8.82 mmol), EDC (1840 mg, 9.62 mmol), DMAP (97.9 mg, 0.801 mmol) in CH$_2$Cl$_2$ (16 mL, 0.5 M). A yellow oil (1410 mg, 6.80 mmol, 85%) was obtained after column chromatography (Hexane:EA 100:0 to 85:15). $^1$H NMR (400 MHz, CDCl$_3$) δ 8.78 (app d, J=6.0 Hz, 2H), 7.85 (app d, J=6.0 Hz, 2H), 4.61 (d, J=6.0 Hz, 2H), 4.46 (d, J=6.0 Hz, 2H), 4.43 (s, 2H), 1.41 (s, 3H). 13C NMR (101 MHz, CDCl$_3$) δ 165.50 (C), 151.16 (CH), 137.39 (C), 123.23 (CH), 79.86 (CH$_2$), 70.16 (CH$_2$), 39.66 (C), 21.59 (CH$_3$). IR (KBr), υ/cm$^{-1}$ 3034, 2935, 2873, 1730, 1678, 1562, 1408, 1387, 1287, 1124, 1092, 981, 759. HRMS [M+H]$^+$ m/z calcd. for [C$_{11}$H$_{14}$O$_3$N]$^+$ 208.0974, found 208.0969.

Example 24K: methyl ((3-methyloxetan-3-yl)methyl) succinate (15k)

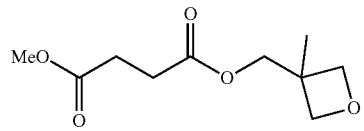

The general protocol was followed with monomethyl succinate (1159 mg, 9.821 mmol) was added into mixture of 3-Methyl-3-oxetanemethanol (1103 mg, 10.80 mmol), EDC (2254 mg, 11.79 mmol), DMAP (120.0 mg, 0.9821 mmol) in CH$_2$Cl$_2$ (20 mL, 0.5 M). A colorless oil (1992 mg, 9.167 mmol, 94%) was obtained after column chromatography (Hexane:EA 100:0 to 75:25). $^1$H NMR (600 MHz, CDCl$_3$) δ 4.50 (d, J=6.0 Hz, 2H), 4.37 (d, J=6.0 Hz, 2H), 4.18 (s, 2H), 3.69 (s, 3H), 2.70-2.66 (m, 2H), 2.65-2.62 (m, 2H), 1.32 (s, 3H). $^{13}$C NMR (101 MHz, CDCl$_3$) δ 172.79 (C), 172.44 (C), 79.62 (C), 69.01 (CH$_2$), 52.04 (CH$_3$), 39.16 (CH$_2$), 29.12 (CH$_2$), 28.94 (CH$_2$), 21.25 (CH$_3$). IR (KBr), υ/cm$^{-1}$ 2958, 2874, 1739, 1438, 1356, 1216, 1159, 981. HRMS [M+H]$^+$ m/z calcd. for [C$_{10}$H$_{17}$O$_5$]$^+$ 217.1076, found 217.1068.

Example 24L: tert-butyl ((3-methyloxetan-3-yl)methyl) succinate (15l)

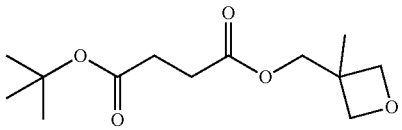 [SMILES: CC1(COC(=O)CCC(=O)OC(C)(C)C)COC1]

The general protocol was followed with mono-tert-butyl succinate (1861 mg, 10.68 mmol) was added into mixture of 3-Methyl-3-oxetanemethanol (1200 mg, 11.75 mmol), EDC (2457 mg, 12.82 mmol), DMAP (130.5 mg, 1.068 mmol) in CH$_2$Cl$_2$ (21 mL, 0.5 M). A colorless oil (2538 mg, 9.788 mmol, 92%) was obtained after column chromatography (Hexane:EA 100:0 to 75:25). $^1$H NMR (400 MHz, CDCl$_3$) δ 4.52 (d, J=6.0 Hz, 2H), 4.38 (d, J=6.0 Hz, 2H), 4.19 (s, 2H), 2.64-2.61 (m, 2H), 2.58-2.54 (m, 2H), 1.44 (s, 9H), 1.33 (s, 3H). $^{13}$C NMR (101 MHz, CDCl$_3$) δ 172.71 (C), 171.56 (C), 80.97 (C), 79.72 (CH$_2$), 68.97 (CH$_2$), 39.20 (C), 30.37 (CH$_2$), 28.20 (CH$_3$), 21.31 (CH$_3$). IR (KBr), υ/cm$^{-1}$ 2973, 2935, 2873, 1732, 1459, 1393, 1367, 1248, 1149, 983, 848. HRMS [M+H]$^+$ m/z calcd. for [C$_{13}$H$_{23}$O$_5$]$^+$ 259.1545, found 259.1539.

Example 24M: methyl ((3-methyloxetan-3-yl)methyl) malonate (15m)

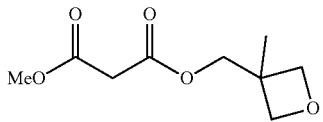

The general protocol was followed with monomethyl malonate (942 μL, 8.99 mmol) was added into mixture of 3-Methyl-3-oxetanemethanol (1010 mg, 9.89 mmol), EDC (2070 mg, 10.8 mmol), DMAP (110 mg, 0.899 mmol) in CH$_2$Cl$_2$ (18 mL, 0.5 M). A colorless oil (1237 mg, 6.11 mmol, 68%) was obtained after column chromatography (Hexane:EA 10:0 to 8:2). $^1$H NMR (400 MHz, CDCl$_3$) δ 4.50 (d, J=6.0 Hz, 2H), 4.37 (d, J=6.0 Hz, 2H), 4.23 (s, 2H), 3.74 (s, 3H), 3.43 (s, 2H), 1.33 (s, 3H). $^{13}$C NMR (101 MHz, CDCl$_3$) δ 166.93 (C), 166.65 (C), 79.47 (CH$_2$), 69.65 (CH$_2$), 52.70 (CH$_3$), 41.33 (CH$_2$), 39.16 (C), 21.15 (CH$_3$). IR (KBr), υ/cm$^{-1}$ 2959, 2875, 1737, 1438, 1338, 1277, 1202, 1151, 1024, 979. HRMS [M+H]$^+$ m/z calcd. for [C$_9$H$_{15}$O$_5$]$^+$ 203.0919, found 203.0913.

Example 24N: (3-methyloxetan-3-yl)methyl 2-((tert-butoxycarbonyl)amino)acetate (15n)

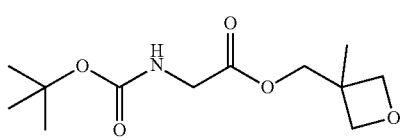 [SMILES: CC1(COC(=O)CNC(=O)OC(C)(C)C)COC1]

The general protocol was followed with Boc-glycine (1964 mg, 11.21 mmol) was added into mixture of 3-Methyl-3-oxetanemethanol (1259 mg, 12.33 mmol), EDC (2579 mg, 13.45 mmol), DMAP (137.0 mg, 1.121 mmol) in CH$_2$Cl$_2$ (22 mL, 0.5 M). A colorless oil (2613 mg, 10.07 mmol, 90%) was obtained after column chromatography (Hexane:EA 100:0 to 85:15). $^1$H NMR (400 MHz, CDCl$_3$) δ 5.06 (s, 1H), 4.49 (d, J=6.1 Hz, 2H), 4.37 (d, J=6.1 Hz, 2H), 4.24 (s, 2H), 3.93 (d, J=5.7 Hz, 2H), 1.44 (s, 9H), 1.32 (s, 3H). $^{13}$C NMR (101 MHz, CDCl$_3$) δ 170.67 (C), 155.82 (C), 80.21 (C), 79.55 (CH$_2$), 69.59 (CH$_2$), 42.43 (CH$_2$), 39.16 (C), 28.41 (CH$_3$), 21.17 (CH$_3$). IR (KBr), υ/cm$^{-1}$ 3355, 2972, 2935, 2875, 1755, 1717, 1523, 1457, 1366, 1284, 1252, 1166, 1055, 985. HRMS [M+H]$^+$ m/z calcd. for [C$_{12}$H$_{22}$O$_5$N]$^+$ 260.1498, found 260.1492.

Example 24O: (S)-1-tert-butyl 4-((3-methyloxetan-3-yl)methyl) 2-((tert-butoxycarbonyl)amino)succinate (15o)

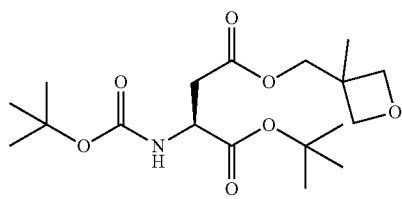 [SMILES: CC1(COC(=O)C[C@H](NC(=O)OC(C)(C)C)C(=O)OC(C)(C)C)COC1]

The general protocol was followed with N-Boc-L-aspartic acid 1-tert-butyl ester (1502 mg, 5.19 mmol) was added into mixture of 3-Methyl-3-oxetanemethanol (583 mg, 5.71 mmol), EDC (1194 mg, 6.23 mmol), DMAP (63.4 mg, 0.519 mmol) in CH$_2$Cl$_2$ CH2CL2(10 mL, 0.5 M). A colorless oil (1608 mg, 4.21 mmol, 81%) was obtained after column chromatography (Hexane:EA 100:0 to 80:20). $^1$H NMR (400 MHz, CDCl$_3$) δ 5.56 (d, J=8.4 Hz, 1H), 4.54-4.42 (m, 3H), 4.40 (d, J=6.1 Hz, 2H), 4.24 (d, J=11.1 Hz, 1H), 4.14 (d, J=11.1 Hz, 1H), 2.98 (dd, J=16.8, 4.7 Hz, 1H), 2.85 (dd, J=16.8, 4.8 Hz, 1H), 1.45 (s, 9H), 1.43 (s, 9H), 1.32 (s, 3H). $^{13}$C NMR (101 MHz, CDCl$_3$) δ 171.20 (C), 170.05 (C), 155.57 (C), 82.55 (C), 80.02 (C), 79.63 (C), 79.58 (CH$_2$), 69.17 (CH$_2$), 50.64 (CH), 39.19 (C), 37.11 (CH$_2$), 28.45 (CH$_3$), 28.04 (CH$_3$), 21.19 (CH$_3$). IR (KBr), υ/cm$^{-1}$ 3357, 2976, 2935, 2875, 1738, 1501, 1458, 1392, 1367, 1251, 1154, 984, 848. HRMS [M+H]$^+$ m/z calcd. for [C$_{18}$H$_{32}$O$_7$N]$^+$ 374.2179, found 374.2173.

Example 24P: (S)-1-tert-butyl 5-((3-methyloxetan-3-yl)methyl) 2-((tert-butoxycarbonyl)amino)pentanedioate (15p)

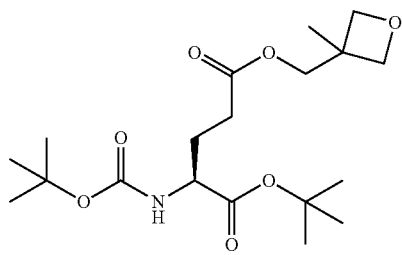 [SMILES: CC1(COC(=O)CC[C@H](NC(=O)OC(C)(C)C)C(=O)OC(C)(C)C)COC1]

The general protocol was followed with N-Boc-L-glutamic acid 1-tert-butyl ester (3023 mg, 9.972 mmol) was added into mixture of 3-Methyl-3-oxetanemethanol (1120 mg, 10.96 mmol), EDC (2291 mg, 11.97 mmol), DMAP (121.8 mg, 0.9972 mmol) in CH$_2$Cl$_2$ (18 mL, 0.25 M). A colorless oil (3287 mg, 8.476 mmol, 85%) was obtained after column chromatography (Hexane:EA 100:0 to 75:25). $^1$H NMR (400 MHz, CDCl$_3$) δ 5.10 (d, J=8.1 Hz, 1H), 4.49 (d, J=6.0 Hz, 2H), 4.37 (d, J=6.0 Hz, 2H), 4.22-4.13 (m, 3H), 2.51-2.35 (m, 2H), 2.21-2.12 (m, 1H), 1.94-1.84 (m, 1H), 1.45 (s, 9H), 1.42 (s, 9H), 1.32 (s, 3H), peak at 4.85, 4.04 ppm due to minor rotamer. $^{13}$C NMR (101 MHz, CDCl$_3$) δ 173.03 (C), 171.42 (C), 155.53 (C), 82.36 (C), 79.92 (C), 79.66 (CH$_2$), 68.98 (CH$_2$), 53.40 (CH), 39.13 (C), 30.27 (CH$_2$), 28.41 (CH$_3$), 28.19 (CH$_2$), 28.09 (CH$_3$), 21.28 (CH$_3$). IR (KBr), υ/cm$^{-1}$ 3361, 2976, 2935, 2874, 1739, 1716, 1517, 1455, 1392, 1367, 1251, 1156, 1050, 982. HRMS [M+H]$^+$ m/z calcd. for [C$_{19}$H$_{34}$O$_7$N]$^+$ 388.2335, found 388.2328.

Example 24Q: (3-methyloxetan-3-yl)methyl 5-((3aS,4S,6aR)-2-oxohexahydro-1H-thieno[3,4-d]imidazol-4-yl)pentanoate (1q)

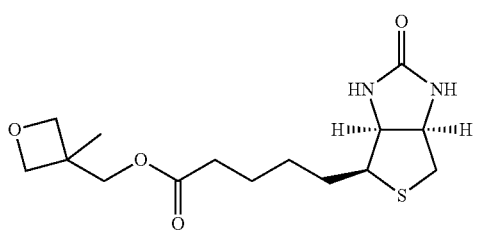 [SMILES: CC1(COC(=O)CCCC[C@@H]2SC[C@@H]3NC(=O)N[C@@H]32)COC1]

The general protocol was followed with biotin (219 mg, 0.896 mmol) was added into mixture of 3-Methyl-3-oxetanemethanol (100 mg, 0.986 mmol), EDC (220 mg, 1.08 mmol), DMAP (10.9 mg, 0.0896 mmol) in CH$_2$Cl$_2$ (9 mL, 0.1 M). A white solid (242 mg, 0.736 mmol, 82%) was obtained after column chromatography (CH$_2$Cl$_2$:Acetone 100:0 to 50:50). $^1$H NMR (400 MHz, CDCl$_3$) δ 6.10 (s, 1H), 5.54 (s, 1H), 4.61-4.42 (m, 3H), 4.37 (d, J=6.0 Hz, 2H), 4.29 (app dd, J=7.8, 4.6 Hz, 1H), 4.13 (s, 2H), 3.20-3.09 (m, 1H), 2.90 (dd, J=12.8, 5.0 Hz, 1H), 2.72 (d, J=12.8 Hz, 1H), 2.39 (t, J=7.5 Hz, 2H), 1.85-1.61 (m, 4H), 1.54-1.38 (m, 2H), 1.32 (s, 3H). $^{13}$C NMR (101 MHz, CDCl$_3$) δ 173.91 (C), 163.68 (C), 79.65 (CH$_2$), 68.53 (CH$_2$), 62.04 (CH), 60.20 (CH), 55.58 (CH), 40.70 (CH$_2$), 39.16 (C), 33.97 (CH$_2$), 28.52 (CH$_2$), 28.37 (CH$_2$), 24.97 (CH$_2$), 21.35 (CH$_3$). IR (KBr), υ/cm$^{-1}$ 3214, 2931, 2871, 1735, 1702, 1461, 1269, 1170, 981, 634. HRMS [M+H]$^+$ m/z calcd. for [C$_{15}$H$_{25}$O$_4$N$_2$S]$^+$ 329.1535, found 329.1528.

Example 24R: (R)-(3-methyloxetan-3-yl)methyl 4-((3R,5R,8R,9S,10S,13R,14S,17R)-3-hydroxy-10,13-dimethylhexadecahydro-1H-cyclopenta[a]phenanthren-17-yl)pentanoate (15r)

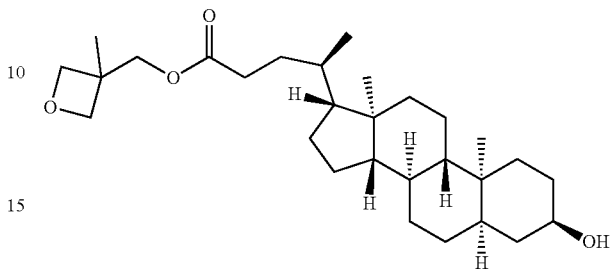

The general protocol was followed with lithocholic acid (203 mg, 0.537 mmol) was added into mixture of 3-Methyl-3-oxetanemethanol (220 mg, 2.15 mmol), EDC (124 mg, 0.65 mmol), DMAP (6.56 mg, 0.0537 mmol) in CH$_2$Cl$_2$ (4.3 mL, 0.12 M). A white solid (243 mg, 0.526 mmol, 98%) was obtained after column chromatography (Hexane:Et$_2$O 100:0 to 80:20). $^1$H NMR (400 MHz, CDCl$_3$) δ 4.52 (d, J=5.9 Hz, 2H), 4.38 (d, J=5.9 Hz, 2H), 4.15 (s, 2H), 3.69-3.56 (m, 1H), 2.40 (ddd, J=15.4, 10.0, 5.1 Hz, 1H), 2.27 (ddd, J=15.4, 9.4, 6.6 Hz, 1H), 2.00-1.92 (m, 1H), 1.90-0.95 (m, 29H), 0.98-0.88 (m, 6H), 0.63 (s, 3H). $^{13}$C NMR (101 MHz, CDCl$_3$) δ 174.55 (C), 79.76 (CH$_2$), 71.99 (CH), 68.64 (CH$_2$), 56.60 (CH), 56.03 (CH), 42.86 (CH$_2$), 42.19 (CH), 40.52 (CH), 40.28 (C), 39.19 (C), 36.55 (C), 35.95 (CH), 35.48 (CH), 35.45 (CH$_2$), 34.69 (CH$_2$), 31.28 (CH$_2$), 31.12 (CH$_2$), 30.66 (CH$_2$), 28.34 (CH$_2$), 27.31 (CH$_2$), 26.54 (CH$_2$), 24.33 (CH$_2$), 23.51 (CH$_3$), 21.38 (CH$_3$), 20.94 (CH$_2$), 18.37 (CH$_3$), 12.18 (CH$_3$). IR (KBr), υ/cm$^{-1}$ 3412, 2934, 2866, 1738, 1450, 1377, 1247, 1163, 1034, 982, 736. HRMS [M+H]$^+$ m/z calcd. for [C$_{29}$H$_{49}$O$_4$]$^+$ 461.1631, found 461.3625.

Example 24S: (3-methyloxetan-3-yl)methyl 6-(1-((5-(trifluoromethyl)pyridin-2-yl)oxy)cyclopropanoate (15s)

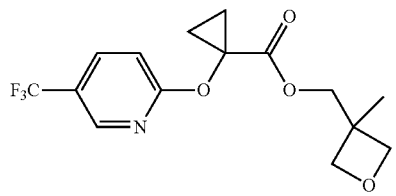 [SMILES: CC1(COC(=O)C2(Oc3ccc(C(F)(F)F)cn3)CC2)COC1]

The general protocol was followed with 6-(1-((5-(trifluoromethyl)pyridin-2-yl)oxy)cyclopropanoic acid (241 mg, 1.02 mmol) was added into mixture of 3-Methyl-3-oxetanemethanol (114 mg, 1.12 mmol), EDC (233 mg, 1.22 mmol), DMAP (12.4 mg, 0.102 mmol) in CH$_2$Cl$_2$ (5 mL, 0.2 M). A white solid (288 mg, 0.869 mmol, 89%) was obtained after column chromatography (CH$_2$Cl$_2$:MeOH 100:0 to 90:10). $^1$H NMR (600 MHz, CDCl$_3$) δ 8.45-8.41 (m, 1H), 7.81 (dd, J=8.7, 2.4 Hz, 1H), 6.88 (app d, J=8.7 Hz, 1H), 4.31 (d, J=6.0 Hz, 2H), 4.22 (d, J=6.0 Hz, 2H), 4.18 (s, 2H), 1.71-1.64 (m, 2H), 1.36-1.29 (m, 2H), 1.14 (s, 3H). $^{13}$C NMR (101 MHz, CDCl$_3$) δ 171.58 (C), 165.22 (C), 144.93

(q, $J_{C-F}$=43.7 Hz, CH), 136.17 (q, $J_{C-F}$=31.3 Hz, CH), 123.89 (q, $J_{C-F}$=269.7 Hz, C), 121.24 (q, $J_{C-F}$=33.0 Hz, C), 111.22 (CH), 79.33 (CH$_2$), 69.39 (CH$_2$), 57.97 (CH$_2$), 39.21 (C), 20.93 (CH$_3$), 16.77 (CH$_2$). IR (KBr), υ/cm$^{-1}$ 3021, 2965, 2875, 1738, 1613, 1580, 1493, 1396, 1330, 1289, 1159, 1127, 1079, 984, 837. HRMS [M+H]$^+$ m/z calcd. for [C$_{15}$H$_{17}$O$_4$NF$_3$]$^+$ 332.1110, found 332.1102.

Example 24T (S)-(3-methyloxetan-3-yl)methyl 2-((tert-butoxycarbonyl)amino)-3-(pyridin-4-yl)propanoate (15t)

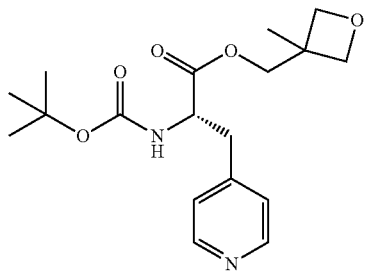 [SMILES: CC1(COC(=O)[C@H](Cc2ccncc2)NC(=O)OC(C)(C)C)COC1]

The general protocol was followed with (S)-2-((tert-butoxycarbonyl)amino)-3-(pyridin-4-yl)propanoic acid (236 mg, 0.899 mmol) was added into mixture of 3-Methyl-3-oxetanemethanol (101 mg, 0.989 mmol), EDC (207 mg, 1.08 mmol), DMAP (11.0 mg, 0.0899 mmol) in CH$_2$Cl$_2$ (6.5 mL, 0.2 M). A white solid (267 mg, 0.761 mmol, 86%) was obtained after column chromatography (CH$_2$Cl$_2$:MeOH 100:0 to 95:5). $^1$H NMR (400 MHz, CDCl$_3$) δ 8.55 (app d, J=6.1 Hz, 2H), 7.12 (app d, J=6.1 Hz, 2H), 5.11 (d, J=8.2 Hz, 1H), 4.74-4.50 (m, 1H), 4.42 (dd, J=6.1, 2.5 Hz, 2H), 4.38 (dd, J=6.1, 3.6 Hz, 2H), 4.26 (d, J=11.1 Hz, 1H), 4.18 (d, J=11.1 Hz, 1H), 3.16 (dd, J=13.9, 6.2 Hz, 1H), 3.06 (dd, J=13.9, 6.8 Hz, 1H), 1.43 (s, 9H), 1.28 (s, 3H). $^{13}$C NMR (101 MHz, CDCl$_3$) δ 171.70 (C), 155.06 (C), 150.04 (CH), 145.32 (C), 124.61 (CH), 80.49 (C), 79.44 (CH$_2$), 69.99 (CH$_2$), 53.84 (CH), 39.07 (CH$_2$), 38.02 (C), 28.36 (CH$_3$), 21.07 (CH$_3$). IR (KBr), υ/cm$^{-1}$ 3194, 2972, 2874, 1745, 1710, 1604, 1539, 1366, 1274, 1250, 1216, 1168, 980. HRMS [M+H]$^+$ m/z calcd. for [C$_{18}$H$_{27}$O$_5$N$_2$]$^+$ 351.1920, found 351.1912.

Example 24U: (3-methyloxetan-3-yl)methyl 2-(1-phenyl-5-(trifluoromethyl)-1H-pyrazol-4-yl)acetate (15u)

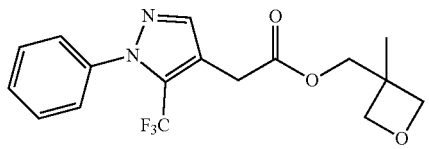 [SMILES: CC1(COC(=O)Cc2cnn(-c3ccccc3)c2C(F)(F)F)COC1]

The general protocol was followed with (1-phenyl-5-trifluoromethyl-1H-pyrazol-4-yl)-acetic acid (250 mg, 0.927 mmol) was added into mixture of 3-Methyl-3-oxetanemethanol (104 mg, 1.02 mmol), EDC (213 mg, 1.11 mmol), DMAP (11.3 mg, 0.0927 mmol) in CH$_2$Cl$_2$ (4.6 mL, 0.2 M). A colorless oil (285 mg, 0.805 mmol, 87%) was obtained after column chromatography (CH$_2$Cl$_2$:MeOH 100:0 to 90:10). $^1$H NMR (400 MHz, CDCl$_3$) δ 7.68 (s, 1H), 7.54-7.36 (m, 5H), 4.50 (d, J=6.0 Hz, 2H), 4.39 (d, J=6.0 Hz, 2H), 4.25 (s, 2H), 3.76 (s, 2H), 1.32 (s, 3H). $^{13}$C NMR (101 MHz, CDCl$_3$) δ 170.39 (C), 141.19 (CH), 139.48 (C), 129.95 (q, $J_{C-F}$=37.6 Hz, C), 129.37 (CH), 129.15 (CH), 126.08 (CH), 120.31 (q, $J_{C-F}$=268.2 Hz, C), 116.33 (C), 79.56 (CH$_2$), 69.58 (CH$_2$), 39.18 (C), 29.98 (CH$_2$), 21.18 (CH$_3$). IR (KBr), υ/cm$^{-1}$ 3066, 2965, 2876, 1743, 1598, 1504, 1473, 1399, 1311, 1247, 1183, 1092, 1058, 975, 769, 695. HRMS [M+H]$^+$ m/z calcd. for [C$_{17}$H$_{18}$O$_3$N$_2$F$_3$]$^+$ 355.1270, found 355.1265.

Example 24V: (2S,3S)-1-tert-butyl 2-((3-methyloxetan-3-yl)methyl) 3-(pyridin-4-ylmethyl)pyrrolidine-1,2-dicarboxylate (15v)

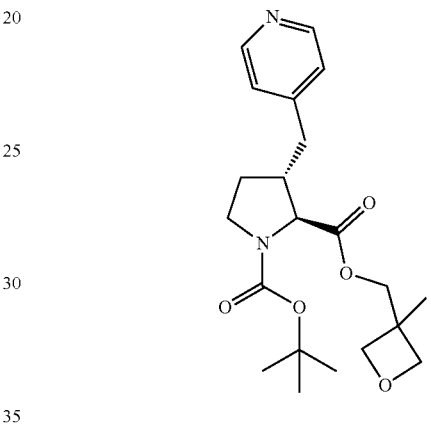

The general protocol was followed with (2S,3S)-1-[(2-methylpropan-2-yl)oxycarbonyl]-3-(pyridin-4-ylmethyl)pyrrolidine-2-carboxylic acid (248 mg, 0.81 mmol) was added into mixture of 3-Methyl-3-oxetanemethanol (91 mg, 0.89 mmol), EDC (186 mg, 0.97 mmol), DMAP (10 mg, 0.081 mmol) in CH$_2$Cl$_2$ (4 mL, 0.2 M). A colorless oil (276 mg, 0.70 mmol, 87%) was obtained after column chromatography (CH$_2$Cl$_2$:MeOH 100:0 to 95:5). Two rotamers: $^1$H NMR (400 MHz, CDCl$_3$) δ 8.54 (app dd, J=6.0, 1.5 Hz, 4H), 8.52 (app dd, J=6.0, 1.5 Hz, 4H), 7.13 (app dd, J=6.0, 1.5 Hz, 2H), 7.11 (app dd, J=6.0, 1.5 Hz, 2H), 4.54-4.44 (m, 4H), 4.40 (d, J=6.0 Hz, 2H), 4.37 (d, J=6.0 Hz, 2H), 4.26 (d, J=11.2 Hz, 1H), 4.21 (s, 1H), 4.21 (s, 1H), 4.15 (d, J=11.1 Hz, 1H), 4.08 (d, J=5.0 Hz, 1H), 3.98 (d, J=5.1 Hz, 1H), 3.68-3.41 (m, 4H), 2.98-2.92 (m, 2H), 2.69-2.55 (m, 4H), 2.02-1.93 (m, 2H), 1.68-1.58 (m, 2H), 1.45 (s, 9H), 1.41 (s, 9H), 1.32 (s, 3H), 1.31 (s, 3H). $^{13}$C NMR (101 MHz, CDCl$_3$) δ 172.69 (C), 172.47 (C), 154.41 (C), 153.79 (C), 150.14 (CH), 150.08 (CH), 148.08 (C), 148.01 (C), 124.42 (CH), 124.33 (CH), 80.49 (C), 80.30 (C), 79.53 (CH$_2$), 79.51 (CH$_2$), 79.43 (CH$_2$), 79.40 (CH$_2$), 69.22 (CH$_2$), 69.05 (CH$_2$), 64.15 (CH), 63.82 (CH), 45.66 (CH$_2$), 45.40 (CH$_2$), 45.19 (CH), 44.11 (CH), 39.34 (C), 39.31 (C), 38.60 (CH$_2$), 38.57 (CH$_2$), 29.91 (CH$_2$), 29.22 (CH$_2$), 28.54 (CH$_3$), 28.47 (CH$_3$), 21.27 (CH$_3$), 21.25 (CH$_3$). IR (KBr), υ/cm$^{-1}$ 3069, 2971, 2935, 2873, 1793, 1750, 1699, 1602, 1456, 1385, 1255, 1166, 1126, 982. HRMS [M+H]$^+$ m/z calcd. for [C$_{21}$H$_{31}$O$_5$N$_2$]$^+$ 391.2233, found 391.2224.

Example 24W: 5,5-difluoro-7,9-dimethyl-3-(3-((3-methyloxetan-3-yl)methoxy)-3-oxopropyl)-5H-dipyrrolo[1,2-c:2',1'-f][1,3,2]diazaborinin-4-ium-5-uide (15w)

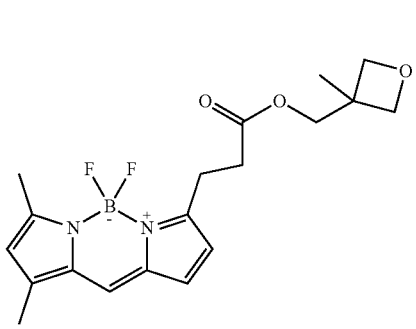

The general protocol was followed with BODIPY-FL propionic acid (69 mg, 0.24 mmol) was added into mixture of 3-Methyl-3-oxetanemethanol (29 mg, 0.28 mmol), EDC (55 mg, 0.28 mmol), DMAP (3.0 mg, 0.024 mmol) in CH$_2$Cl$_2$ (4.8 mL, 0.05 M). An orange solid (90 mg, 0.24 mmol, 100%) was obtained after column chromatography (CH$_2$Cl$_2$:MeOH 100:0 to 99:1). $^1$H NMR (600 MHz, CDCl$_3$) δ 7.08 (s, 1H), 6.88 (d, J=4.0 Hz, 1H), 6.27 (d, J=4.0 Hz, 1H), 6.12 (s, 1H), 4.48 (d, J=6.0 Hz, 2H), 4.35 (d, J=6.0 Hz, 2H), 4.20 (s, 2H), 3.31 (app t, J=7.5 Hz, 2H), 2.82 (app t, J=7.5 Hz, 2H), 2.56 (s, 3H), 2.25 (s, 3H), 1.31 (s, 3H). $^{13}$C NMR (101 MHz, CDCl$_3$) δ 172.69 (C), 160.70 (C), 156.78 (C), 144.11 (C), 135.36 (C), 133.33 (C), 128.06 (CH), 123.96 (CH), 120.61 (CH), 116.55 (CH), 79.72 (CH$_2$), 69.05 (CH$_2$), 39.12 (C), 33.34 (CH$_2$), 23.99 (CH$_2$), 21.24 (CH$_3$), 15.08 (CH$_3$), 11.43 (CH$_3$). IR (KBr), υ/cm$^{-1}$ 3107, 3063, 2962, 2934, 2873, 1734, 1607, 1529, 1489, 1251, 1173, 1135, 1085, 974, 668. HRMS [M+H]$^+$ m/z calcd. for [C$_{19}$H$_{24}$O$_3$N$_2$F$_2$B]$^+$ 377.1848, found 377.1831.

Example 24X: (3-methyloxetan-3-yl)methyl benzoate (15x)

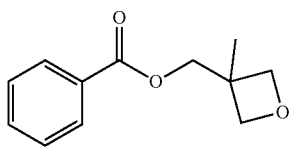

The general protocol was followed with benzoic acid (1730 mg, 14.17 mmol) was added into mixture of 3-Methyl-3-oxetanemethanol (1560 μL, 15.59 mmol), EDC (3281 mg, 17.11 mmol), DMAP (171.1 mg, 1.417 mmol) in CH$_2$Cl$_2$ (28 mL, 0.5 M). A colorless oil (2804 mg, 13.57 mmol, 96%) was obtained after column chromatography (Hexane:EA 10:0 to 8:2). $^1$H NMR (400 MHz, CDCl$_3$) δ 8.33-7.98 (m, 2H), 7.81-7.52 (m, 1H), 7.53-7.26 (m, 2H), 4.65 (d, J=6.0 Hz, 2H), 4.46 (d, J=6.0 Hz, 2H), 4.39 (s, 2H), 1.42 (s, 3H). $^{13}$C NMR (101 MHz, CDCl$_3$) δ 166.59 (C), 133.25 (CH), 129.93 (C), 129.69 (CH), 128.54 (CH), 79.68 (CH$_2$), 69.06 (CH$_2$), 39.35 (C), 21.36 (CH$_3$). IR (KBr), υ/cm$^{-1}$ 3064, 3035, 2963, 2872, 1718, 1602, 1452, 1315, 1282, 1113, 983, 712. HRMS [M+H]$^+$ m/z calcd. for [C$_{11}$H1403N]$^+$ 207.1021, found 207.1014.

Example 24Y: (3-methyloxetan-3-yl)methyl 2-fluoro benzoate (15y)

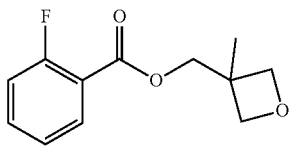 [SMILES: CC1(COC(=O)c2ccccc2F)COC1]

The general protocol was followed with 2-fluorobenzoic acid (1242 mg, 8.87 mmol) was added into mixture of 3-Methyl-3-oxetanemethanol (823 mg, 8.06 mmol), EDC (1854 mg, 9.67 mmol), DMAP (105 mg, 0.806 mmol) in CH$_2$Cl$_2$ (17 mL, 0.5 M). A colorless oil (1889 mg, 8.43 mmol, 95%) was obtained after column chromatography (Hexane:EA 10:0 to 9:1). $^1$H NMR (400 MHz, CDCl$_3$) δ 7.95 (td, J=7.5, 1.9 Hz, 1H), 7.52 (m, 1H), 7.21 (td, J=7.6, 1.1 Hz, 1H), 7.13 (m, 1H), 4.61 (d, J=6.0 Hz, 2H), 4.44 (d, J=6.0 Hz, 2H), 4.41 (s, 2H), 1.42 (s, 3H). $^{13}$C NMR (101 MHz, CDCl$_3$) δ 164.60 (d, J$_{C-F}$=3.9 Hz, C), 162.10 (d, J$_{C-F}$=258.7 Hz, C), 134.82 (d, J$_{C-F}$=9.0 Hz, CH), 132.24 (CH), 124.14 (d, J$_{C-F}$=3.9 Hz, CH), 118.50 (d, J$_{C-F}$=10.2 Hz, C), 117.16 (d, J$_{C-F}$=22.2 Hz, CH), 79.67 (CH$_2$), 69.58 (CH$_2$), 39.30 (C), 21.32 (CH$_3$). HRMS [M+H]$^+$ m/z calcd. for [C$_{12}$H$_{14}$O$_3$F]$^+$ 225.0927, found 225.0918.

Example 25A: General protocol A for the one-pot synthesis of tetrazine thioethers (R=alkyl)

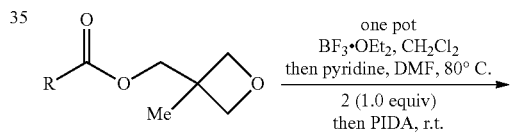

A dry round-bottom flask was charged with the oxetane ester 15 (1.0 equiv.) and a magnetic stirbar. The flask was outfitted with a septum-fitted gas inlet adapter, evacuated and refilled with nitrogen. Anhydrous CH$_2$Cl$_2$ (to 1.0 M in oxetane ester) was added via syringe and the resulting solution was cooled by an ice/brine bath (−12° C.) and boron trifluoride etherate (0.50-1.5 equiv.) was added via syringe. The resulting mixture was allowed to stir under nitrogen with continued cooling by the cold bath (maintained between −12° C. to −4° C.) for 3-6 h. The reactions were monitored by TLC of aliquots that were quenched with trimethylamine before spotting the TLC plate. When the oxetane was completely consumed, the reaction mixture was quenched with pyridine (2.0-3.0 equiv.), and then 2 (0.70-0.80 equiv.) and DMF (to 1.0 M in 2) were added. The mixture was stirred vigorously and vacuum was carefully applied to remove CH$_2$Cl$_2$. The resulting mixture was then heated by an oil bath at 80° C. and the mixture was allowed to stir under nitrogen at 80° C. for 20-30 min. After cooling to r.t., PIDA (0.70-0.80 equiv.) was added to the flask and the mixture allowed to stir at r.t. for 30 min. The mixture was diluted with CH$_2$Cl$_2$ and sequentially washed with saturated sodium bicarbonate, water and brine, dried over sodium sulfate and concentrated by rotary evaporation. The residue was purified by flash column chromatography on silica gel.

Example 25B: General protocol B for the one-pot synthesis of tetrazine thioethers (R=aryl)

A dry round-bottom flask was charged with the oxetane ester 15 (1.0 equiv.) and a magnetic stirbar. The flask was outfitted with a septum-fitted gas inlet adapter, evacuated and refilled with nitrogen. Anhydrous CH$_2$Cl$_2$ (to 1.0 M in oxetane ester) was added via syringe and the resulting solution was cooled by an ice/brine bath (−5° C.) and boron trifluoride etherate (0.50-1.5 equiv.) was added via syringe. The resulting mixture was allowed to stir under nitrogen with continued cooling by the cold bath (maintained between −5° C. to −0° C.) for 3-6 h. The reactions were monitored by TLC of aliquots that were quenched with trimethylamine before spotting the TLC plate. When the oxetane was completely consumed, the reaction mixture was quenched with pyridine (2.0-3.0 equiv.), and then 2 (0.70 equiv.) and DMF (to 1.0 M in 2) were added. The mixture was stirred vigorously and vacuum was carefully applied to remove CH$_2$Cl$_2$. The resulting mixture was then heated by an oil bath at 80° C. and the mixture was allowed to stir under nitrogen at 80° C. for 1-2 h. After cooling to r.t., PIDA (0.70 equiv.) was added to the flask and the mixture allowed to stir at r.t. for 1 h. The mixture was diluted with CH$_2$Cl$_2$ and sequentially washed with saturated sodium bicarbonate, water and brine, dried over sodium sulfate and concentrated by rotary evaporation. The residue was purified by flash column chromatography on silica gel.

Example 25C: General Protocol C for the One-Pot Synthesis of Tetrazine Thioethers (R=4-pyridyl or 3-methoxypyrid-2-yl)

A dry round-bottom flask was charged with the oxetane ester 15 (1.0 equiv.) and a magnetic stirbar. The flask was outfitted with a septum-fitted gas inlet adapter, evacuated and refilled with nitrogen. Anhydrous CH$_2$Cl$_2$ (to 1.0 M in oxetane ester) was added via syringe and the resulting solution was cooled by an ice/brine bath (−0° C.) and boron trifluoride etherate (1.2 equiv.) was added via syringe. The resulting mixture was allowed to stir under nitrogen with continued cooling by the cold bath for 2 h, followed by stirring for 12 h at r.t. The reactions were monitored by TLC of aliquots that were quenched with trimethylamine before spotting the TLC plate. When the oxetane was completely consumed, the reaction mixture was quenched with pyridine (3.0 equiv.), and then 2 (0.70 equiv.) and DMF (to 1.0 M in 2) were added. The mixture was stirred vigorously and vacuum was carefully applied to remove CH$_2$Cl$_2$. The resulting mixture was then heated by an oil bath at 80° C. and the mixture was allowed to stir for 2 h. After cooling to r.t., PIDA (0.70 equiv.) was added to the flask and the mixture allowed to stir at r.t. for 2 h. The mixture was diluted with CH$_2$Cl$_2$ and sequentially washed with saturated sodium bicarbonate, water and brine, dried over sodium sulfate and concentrated by rotary evaporation. The residue was purified by flash column chromatography on silica gel.

Example 25AA: 3-((benzyloxy)methyl)-6-(methylthio)-1,2,4,5-tetrazine (3a)

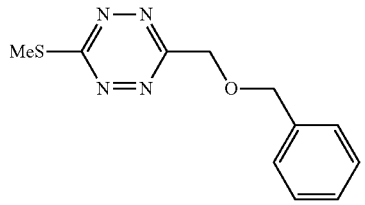 [SMILES: CSc1nnc(COCc2ccccc2)nn1]

General protocol A was followed using BF$_3$.OEt$_2$ (222 μL, 1.81 mmol), 15a (905 mg, 3.62 mmol), CH$_2$Cl$_2$ (3.6 mL) for 4 h at −12° C. to −4° C.; Pyridine (580 μL, 7.24 mmol), 2 (714 mg, 2.90 mmol) and DMF (2.9 mL) for 20 min at 80° C.; and PIDA (930 mg, 2.91 mmol) at r.t. for 30 min. A red oil (336 mg, 1.35 mmol, 70%) was obtained after chromatography (hexane:acetone 100:0 to 98:2). $^1$H NMR (400 MHz, CDCl$_3$) δ 7.47-7.27 (m, 5H), 5.05 (s, 2H), 4.77 (s, 2H), 2.74 (s, 3H). $^{13}$C NMR (101 MHz, CDCl$_3$) δ 176.87 (C), 164.33 (C), 137.15 (C), 128.69 (CH), 128.23 (CH), 128.21 (CH), 73.78 (CH$_2$), 69.63 (CH$_2$), 13.54 (CH$_3$). IR (KBr), υ/cm$^{-1}$ 3063, 3030, 2930, 2863, 1454, 1327, 1305, 1163, 1098, 893, 740, 699. HRMS [M+H]$^+$ m/z calcd. for [C$_{11}$H$_{13}$ON$_4$S]$^+$ 249.0810, found 249.0802.

Example 25BB: tert-butyl (4-(6-(methylthio)-1,2,4,5-tetrazin-3-yl)phenyl)carbamate (3b)

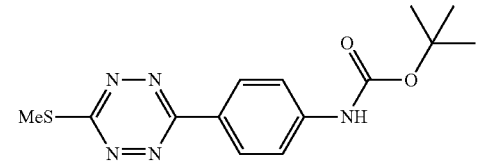 [SMILES: CSc1nnc(-c2ccc(NC(=O)OC(C)(C)C)cc2)nn1]

General protocol B was followed using BF$_3$.OEt$_2$ (85.2 μL, 0.692 mmol), 15b (442 mg, 1.38 mmol), CH$_2$Cl$_2$ (1.38 mL) for 4 h at −2° C. to −0° C.; Pyridine (222 μL, 2.77 mmol), 2 (240 mg, 0.969 mmol) and DMF (0.82 mL) for 2 h at 80° C.; and PIDA (267 mg, 0.969 mmol) at r.t. for 1 h. A red solid (245 mg, 0.767 mmol, 56%) was obtained after purified by chromatography (Hexane:Et$_2$O 100:0 to 85:15). $^1$H NMR (400 MHz, CDCl$_3$) δ 8.47 (app d, J=8.8 Hz, 2H), 7.58 (app d, J=8.6 Hz, 2H), 6.71 (s, 1H), 2.78 (s, 3H), 1.55 (s, 9H). $^{13}$C NMR (101 MHz, CDCl$_3$) δ 174.73 (C), 162.02 (C), 152.34 (C), 142.41 (C), 128.74 (CH), 125.92 (C), 118.51 (CH), 81.45 (C), 28.43 (CH$_3$), 13.59 (CH$_3$). IR (KBr), υ/cm$^{-1}$ 3368, 3100, 3007, 2980, 2964, 2928, 1708, 1592, 1526, 1510, 1361, 1312, 1244, 1171, 1053, 853. HRMS [M+H]$^+$ m/z calcd. for [C$_{14}$H$_{18}$O$_2$N$_5$S]$^+$ 320.1181, found 320.1167.

Example 25BC: tert-butyl 4-(6-(methylthio)-1,2,4,5-tetrazin-3-yl)benzylcarbamate (3c)

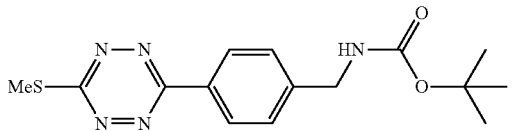 [SMILES: CSc1nnc(-c2ccc(CNC(=O)OC(C)(C)C)cc2)nn1]

General protocol B was followed using BF$_3$.OEt$_2$ (165 µL, 1.33 mmol), 15c (892 mg, 2.66 mmol), CH$_2$Cl$_2$ (2.7 mL) for 4 h at −5° C. to −0° C.; Pyridine (430 µL, 5.32 mmol), 2 (462 mg, 1.86 mmol) and DMF (2.2 mL) for 1.5 h at 80° C.; and PIDA (599 mg, 1.86 mmol) at r.t. for 1 h. A red solid (403 mg, 1.21 mmol, 65%) was obtained after purified by chromatography (CH$_2$Cl$_2$:acetone 100:0 to 97:3). $^1$H NMR (600 MHz, CDCl$_3$) δ 8.49 (app d, J=8.4 Hz, 2H), 7.49 (app d, J=8.4 Hz, 2H), 4.95 (s, 1H), 4.43 (d, J=6.1 Hz, 2H), 2.79 (s, 3H), 1.48 (s, 9H). $^{13}$C NMR (101 MHz, CDCl$_3$) δ 175.36 (C), 162.23 (C), 156.05 (C), 143.78 (C), 130.72 (C), 128.22 (CH), 127.89 (CH), 79.97 (C), 44.52 (CH$_2$), 28.54 (CH$_3$), 13.59 (CH$_3$). IR (KBr), υ/cm$^{-1}$ 3352, 3021, 2974, 2930, 1684, 1512, 1355, 1249, 1195, 1166, 1051, 894. HRMS [M+H]$^+$ m/z calcd. for [C$_{15}$H$_{20}$O$_2$N$_5$S]$^+$ 334.1338, found 334.1323.

Example 25BD: 3-(methylthio)-6-(4-nitrophenyl)-1,2,4,5-tetrazine (3d)

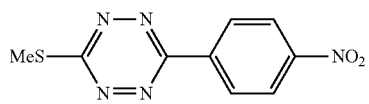

General protocol B was followed using BF$_3$.OEt$_2$ (54 µL, 0.54 mmol), 15d (271 mg, 1.1 mmol), CH$_2$Cl$_2$ (1.1 mL) for 6 h at 0° C.; Pyridine (174 µL, 1.1 mmol), 2 (187 mg, 0.76 mmol) and DMF (0.76 mL) for 2 h at 80° C.; and PIDA (254 mg, 0.76 mmol) at r.t. for 1 h. A red solid (126 mg, 0.51 mmol, 67%) was obtained after purified by chromatography (Hexane:CH$_2$Cl$_2$ 7:3 to 1:1). $^1$H NMR (400 MHz, CDCl$_3$) δ 8.73 (app d, J=9.0 Hz, 2H), 8.43 (app d, J=9.0 Hz, 2H), 2.83 (s, 3H). $^{13}$C NMR (101 MHz, CDCl$_3$) δ 176.67 (C), 160.99 (C), 150.26 (C), 137.52 (C), 128.44 (CH), 124.54 (CH), 13.71 (CH$_3$). IR (KBr), υ/cm$^{-1}$ 3079, 2926, 1604, 1516, 1342, 1193, 871. HRMS [M+H]$^+$ m/z calcd. for [C$_9$H$_8$O$_2$N$_5$S]$^+$ 250.0399, found 250.0389.

Example 25BE: 3-(4-methoxyphenyl)-6-(methylthio)-1,2,4,5-tetrazine (3e)

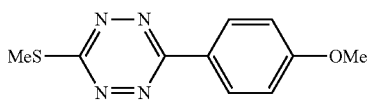 [SMILES: COc1ccc(-c2nnc(SC)nn2)cc1]

General protocol B was followed using BF$_3$.OEt$_2$ (79 µL, 0.64 mmol), 15e (302 mg, 1.3 mmol), CH$_2$Cl$_2$ (1.3 mL) for 4 h at −5° C. to −0° C.; Pyridine (207 µL, 2.6 mmol), 2 (222 mg, 0.89 mmol) and DMF (0.9 mL) for 2 h at 80° C.; and PIDA (289 mg, 0.89 mmol) at r.t. for 1 h. A red solid (143 mg, 0.62 mmol, 69%) was obtained after purified by chromatography (Hexane:EA 10:0 to 9:1). $^1$H NMR (400 MHz, CDCl$_3$) δ 8.48 (app d, J=9.0 Hz, 2H), 7.07 (app d, J=9.0 Hz, 2H), 3.91 (s, 3H), 2.78 (s, 3H). $^{13}$C NMR (101 MHz, CDCl$_3$) δ 174.50 (C), 163.20 (C), 162.19 (C), 129.42 (CH), 124.08 (C), 114.83 (CH), 55.65 (CH$_3$), 13.57 (CH$_3$). IR (KBr), υ/cm$^{-1}$ 3003, 2936, 2838, 1603, 1513, 1424, 1353, 1252, 1192, 1037, 846. HRMS [M+H]$^+$ m/z calcd. for [C$_{10}$H$_{11}$ON$_4$S]$^+$ 235.0654, found 230.0645.

Example 25BF: 3-(4-bromophenyl)-6-(methylthio)-1,2,4,5-tetrazine (3f)

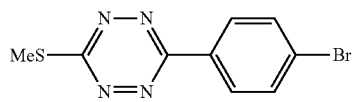 [SMILES: CSc1nnc(-c2ccc(Br)cc2)nn1]

General protocol B was followed using BF$_3$.OEt$_2$ (67 µL, 0.54 mmol), 15f (305 mg, 1.1 mmol), CH$_2$Cl$_2$ (1.1 mL) for 4 h at −2° C. to −0° C.; Pyridine (173 µL, 1.1 mmol), 2 (186 mg, 0.75 mmol) and DMF (0.75 mL) for 2 h at 80° C.; and PIDA (242 mg, 0.75 mmol) at r.t. for 1 h. A red solid (115 mg, 0.41 mmol, 54%) was obtained after purified by chromatography (Hexane:EA 100:0 to 95:5). $^1$H NMR (400 MHz, CDCl$_3$) δ 8.40 (app d, J=8.6 Hz, 2H), 7.72 (app d, J=8.6 Hz, 2H), 2.80 (s, 3H). $^{13}$C NMR (101 MHz, CDCl$_3$) δ 175.72 (C), 161.87 (C), 132.73 (CH), 130.67 (C), 129.01 (CH), 127.51 (C), 13.63 (CH$_3$). IR (KBr), υ/cm$^{-1}$ 3093, 2924, 1585, 1355, 1194, 1004, 800. HRMS [M+H]$^+$ m/z calcd. for [C$_9$H$_8$N$_4$SBr]$^+$ 282.9653, found 282.9643.

Example 25BG: methyl 4-(6-(methylthio)-1,2,4,5-tetrazin-3-yl)benzoate (3g)

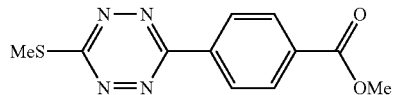 [SMILES: COC(=O)c1ccc(-c2nnc(SC)nn2)cc1]

General protocol B was followed using BF$_3$.OEt$_2$ (116 µL, 0.938 mmol), 15g (248 mg, 0.938 mmol), CH$_2$Cl$_2$ (0.94 mL) for 4 h at 0° C.; Pyridine (190 µL, 2.36 mmol), 2 (165 mg, 0.657 mmol) and DMF (0.66 mL) for 2 h at 80° C.; and PIDA (213 mg, 0.657 mmol) at r.t. for 1 h. A red solid (135 mg, 0.514 mmol, 79%) was obtained after purified by chromatography (Hexane: CH$_2$Cl$_2$ 1:1 to 3:7). $^1$H NMR (600 MHz, CDCl$_3$) δ 8.61 (app d, J=8.5 Hz, 2H), 8.24 (app d, J=8.5 Hz, 2H), 3.98 (s, 3H), 2.81 (s, 3H). $^{13}$C NMR (101 MHz, CDCl$_3$) δ 176.04 (C), 166.52 (C), 161.82 (C), 135.72 (C), 133.43 (C), 130.51 (CH), 127.50 (CH), 52.63 (CH$_3$), 13.65 (CH$_3$). IR (KBr), υ/cm$^{-1}$ 3060, 2994, 2945, 1713, 1355, 1276, 1190, 1111, 768. HRMS [M+H]$^+$ m/z calcd. for [C$_{11}$H11O$_2$N$_4$S]$^+$ 263.0603, found 263.0593.

Example 25BH: 4-(6-(methylthio)-1,2,4,5-tetrazin-3-yl)benzonitrile (3h)

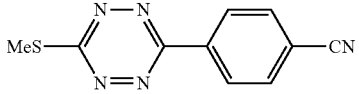 [SMILES: CSc1nnc(-c2ccc(C#N)cc2)nn1]

General protocol B was followed using BF$_3$.OEt$_2$ (162 µL, 1.31 mmol), 15h (300 mg, 1.31 mmol), CH$_2$Cl$_2$ (1.3 mL) for 6 h at 0° C.; Pyridine (212 µL, 2.63 mmol), 2 (227 mg, 0.917 mmol) and DMF (0.9 mL) for 2 h at 80° C.; and PIDA (296 mg, 0.917 mmol) at r.t. for 1 h. A red solid (140 mg, 0.611 mmol, 67%) was obtained after purified by chromatography (Hexane:EA 9:1 to 8:2). $^1$H NMR (600 MHz, CDCl$_3$) δ 8.61 (app d, J=8.5 Hz, 2H), 8.24 (app d, J=8.5 Hz, 2H), 3.98 (s, 3H), 2.81 (s, 3H). $^{13}$C NMR (101 MHz, CDCl$_3$) δ 176.53 (C), 161.17 (C), 135.87 (C), 133.12 (CH), 127.94 (CH), 118.32 (C), 115.78 (C), 13.69 (CH$_3$). IR (KBr), υ/cm$^{-1}$ 3096, 2923, 2852, 2227, 1653, 1394, 853. HRMS [M+H]$^+$ m/z calcd. for [C$_{10}$H$_8$N$_5$S]$^+$ 230.0500, found 230.0493

Example 25BI: 3-(6-methoxypyridin-2-yl)-6-(methylthio)-1,2,4,5-tetrazine (3i)

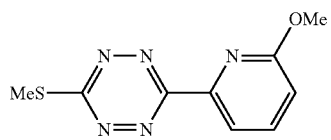 [SMILES: COc1cccc(-c2nnc(SC)nn2)n1]

General protocol B was followed using BF$_3$.OEt$_2$ (190 µL, 1.54 mmol), 15i (305 mg, 1.29 mmol), CH$_2$Cl$_2$ (1.3 mL) for 2 h at 0° C. followed by 12 h at r.t.; Pyridine (310 µL, 3.84 mmol), 2 (223 mg, 0.903 mmol) and DMF (0.9 mL) for 2 h at 80° C.; and PIDA (290 mg, 0.903 mmol) at r.t. for 2 h. A red solid (128 mg, 61%) was obtained after purified by chromatography (Hexane:CH$_2$Cl$_2$ 1:1 to 3:7). $^1$H NMR (400 MHz, CDCl$_3$) δ 8.16 (dd, J=7.4, 0.8 Hz, 1H), 7.80 (dd, J=8.3, 7.4 Hz, 1H), 6.98 (dd, J=8.3, 0.8 Hz, 1H), 4.10 (s, 3H), 2.81 (s, 3H). $^{13}$C NMR (101 MHz, CDCl$_3$) δ 176.05 (C), 164.74 (C), 162.04 (C), 147.69 (C), 139.58 (CH), 117.10 (CH), 114.52 (CH), 53.94 (CH$_3$), 13.63 (CH$_3$). IR (KBr), υ/cm$^{-1}$ 3016, 2922, 2852, 1632, 1473, 1352, 1295, 1212, 1189. HRMS [M+H]$^+$ m/z calcd. for [C$_9$H$_{10}$ON$_5$S]$^+$ 236.0606, found 236.0597

Example 25BJ: 3-(methylthio)-6-(pyridin-4-yl)-1,2,4,5-tetrazine (3j)

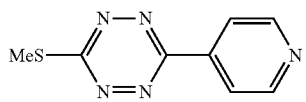

General protocol B was followed using BF$_3$.OEt$_2$ (100 µL, 0.810 mmol), 15j (140 mg, 0.675 mmol), CH$_2$Cl$_2$ (0.68 mL) for 2 h at 0° C. followed by 12 h at r.t.; Pyridine (164 µL, 2.03 mmol), 2 (118 mg, 0.473 mmol) and DMF (0.47 mL) for 2 h at 80° C.; and PIDA (152 mg, 0.473 mmol) at r.t. for 2 h. A red solid (50.5 mg, 0.246 mmol, 51%) was obtained after purified by chromatography (Hexane:Acetone 100:0 to 9:1). $^1$H NMR (400 MHz, CDCl$_3$) δ 8.88 (app d, J=6.2 Hz, 2H), 8.37 (app d, J=6.2 Hz, 2H), 2.82 (s, 3H). $^{13}$C NMR (101 MHz, CDCl$_3$) δ 177.10 (C), 161.09 (C), 151.13 (CH), 139.26 (C), 120.92 (CH), 13.69 (CH$_3$). IR (KBr), υ/cm$^{-1}$ 3085, 2923, 1594, 1560, 1355, 1194, 905. HRMS [M+H]$^+$ m/z calcd. for [C$_8$H$_8$N$_5$S]$^+$ 206.0500, found 206.0492.

Example 25BK: methyl 3-(6-(methylthio)-1,2,4,5-tetrazin-3-yl)propanoate (3k)

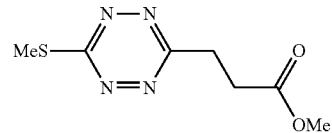 [SMILES: COC(=O)CCc1nnc(SC)nn1]

General protocol A was followed using BF$_3$.OEt$_2$ (147 µL, 1.19 mmol), 15k (515 mg, 2.38 mmol), CH$_2$Cl$_2$ (1.4 mL) for 4 h at −12° C. to −4° C.; Pyridine (384 µL, 4.76 mmol), 2 (473 mg, 1.90 mmol) and DMF (1.9 mL) for 20 min at 80° C.; and PIDA (611 mg, 1.90 mmol) at r.t. for 30 min. A red solid (277 mg, 1.29 mmol, 68%) was obtained after purified by chromatography (Hexane:EA 100:0 to 85:15). $^1$H NMR (600 MHz, CDCl$_3$) δ 3.70 (s, 3H), 3.59 (app t, J=7.1 Hz, 2H), 3.03 (app t, J=7.1 Hz, 2H), 2.73 (s, 3H). $^{13}$C NMR (101 MHz, CDCl$_3$) δ 175.85 (C), 172.58 (C), 166.37 (C), 52.15 (CH$_3$), 30.77 (CH$_2$), 29.39, (CH$_2$) 13.51 (CH$_3$). IR (KBr), υ/cm$^{-1}$ 2953, 2932, 2849, 1737, 1437, 1338, 1292, 1199, 1163. HRMS [M+H]$^+$ m/z calcd. for [C$_7$H$_{11}$O$_2$N$_4$S]$^+$ 215.0603, found 215.0596.

Example 25AL: tert-butyl 3-(6-(methylthio)-1,2,4,5-tetrazin-3-yl)propanoate (3I)

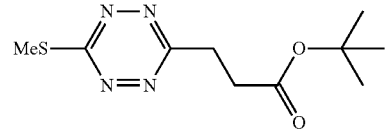 [SMILES: CSc1nnc(CCC(=O)OC(C)(C)C)nn1]

General protocol A was followed using BF$_3$.OEt$_2$ (466 µL, 3.78 mmol), 15l (1950 mg, 7.55 mmol), CH$_2$Cl$_2$ (7.6 mL) for 6 h at −12° C. to −4° C.; Pyridine (1.22 mL, 15.1 mmol), 2 (1.50 g, 6.04 mmol) and DMF (6.0 mL) for 20 min at 80° C.; and PIDA (1.95 mg, 6.04 mmol) at r.t. for 30 min. A red solid (896 mg, 3.50 mmol, 60%) was obtained after purified by chromatography (Hexane:EA 10:0 to 9:1). $^1$H NMR (400 MHz, CDCl$_3$) δ 3.53 (app t, J=7.1 Hz, 2H), 2.93 (app t, J=7.1 Hz, 2H), 2.73 (s, 3H), 1.42 (s, 9H). $^{13}$C NMR (101 MHz, CDCl$_3$) δ 175.69 (C), 171.31 (C), 166.76 (C), 81.22 (C), 32.39 (CH$_2$), 29.68 (CH$_2$), 28.17 (CH$_3$), 13.51 (CH$_3$). IR (KBr), υ/cm$^{-1}$ 2953, 2931, 1734, 1636, 1436, 1198, 1160. HRMS [M+H]$^+$ m/z calcd. for [C$_{10}$H$_{17}$O$_2$N$_4$S]$^+$ 257.1072, found 257.1061.

Example 25AM: methyl 2-(6-(methylthio)-1,2,4,5-tetrazin-3-yl)acetate (3m)

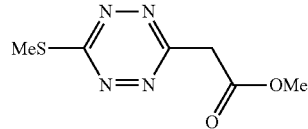 [SMILES: COC(=O)Cc1nnc(SC)nn1]

General protocol A was followed using BF$_3$.OEt$_2$ (670 µL, 5.44 mmol), 15m (2200 mg, 10.9 mmol), CH$_2$Cl$_2$ (10 mL) for 4 h at −12° C. to −4° C.; Pyridine (1760 µL, 21.8 mmol), 2 (2159 mg, 8.71 mmol) and DMF (8.7 mL) for 20 min at 80° C.; and PIDA (2800 mg, 8.71 mmol) at r.t. for 30 min. A red oil (1041 mg, 5.20 mmol, 60%) was obtained after purified by chromatography (Hexane:CH$_2$Cl$_2$ 8:2 to 6:4). $^1$H NMR (400 MHz, CDCl$_3$) δ 4.32 (s, 2H), 3.77 (s, 3H), 2.75 (s, 3H). $^{13}$C NMR (101 MHz, CDCl$_3$) δ 176.43 (C), 168.68 (C), 162.36 (C), 52.95 (CH$_3$), 40.38 (CH$_2$), 13.55 (CH$_3$). IR (KBr), υ/cm$^{-1}$ 2954, 2847, 1743, 1436, 1358, 1257, 1206, 1069. HRMS [M+H]$^+$ m/z calcd. for [C$_6$H$_9$O$_2$N$_4$S]$^+$ 201.0446, found 201.0440.

Example 25AN: tert-butyl ((6-(methylthio)-1,2,4,5-tetrazin-3-yl)methyl)carbamate (3n)

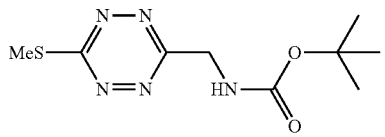 [SMILES: CSc1nnc(CNC(=O)OC(C)(C)C)nn1]

General protocol A was followed using BF$_3$.OEt$_2$ (264 µL, 2.14 mmol), 15n (1100 mg, 4.28 mmol), CH$_2$Cl$_2$ (4.3 mL) for 4 h at −12° C. to −4° C.; Pyridine (690 µL, 8.56 mmol), 2 (850 mg, 3.42 mmol) and DMF (3.4 mL) for 20 min at 80° C.; and PIDA (1101 mg, 3.42 mmol) at r.t. for 30 min. A red solid (602 mg, 2.34 mmol, 69%) was obtained after purified by chromatography (Hexane:EA 100:0 to 85:15). $^1$H NMR (400 MHz, CDCl$_3$) δ 5.56 (s, 1H), 4.88 (d, J=6.0 Hz, 2H), 2.72 (s, 3H), 1.43 (s, 9H). $^{13}$C NMR (101 MHz, CDCl$_3$) δ 176.67 (C), 164.44 (C), 155.86 (C), 80.43 (C), 43.18 (CH$_2$), 28.40 (CH$_3$), 13.50 (CH$_3$). IR (KBr), υ/cm$^{-1}$ 3356, 2978, 2833, 1704, 1517, 1367, 1280, 1170.HRMS [M+H]$^+$ m/z calcd. for [C$_9$H$_{15}$O$_2$N$_5$S]$^+$ 258.1025, found 258.1013.

Example 25AO: (S)-tert-butyl 2-((tert-butoxycarbonyl)amino)-3-(6-(methylthio)-1,2,4,5-tetrazin-3-yl)propanoate (3o)

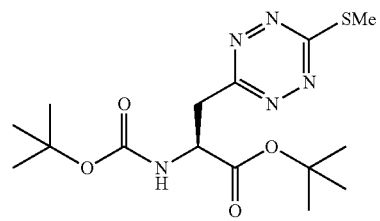 [SMILES: CSc1nnc(C[C@H](NC(=O)OC(C)(C)C)C(=O)OC(C)(C)C)nn1]

General protocol A was followed using BF$_3$.OEt$_2$ (86 µL, 0.68 mmol), 15o (510 mg, 1.4 mmol), CH$_2$Cl$_2$ (1.4 mL) for 4 h at −12° C. to −4° C.; Pyridine (220 µL, 2.74 mmol), 2 (238 mg, 0.96 mmol) and DMF (0.9 mL) for 20 min at 80° C.; and PIDA (307 mg, 0.96 mmol) at r.t. for 30 min. A red oil (475 mg, 1.3 mmol, 64%) was obtained after purified by chromatography (Hexane:Et$_2$O 100:0 to 85:15). $^1$H NMR (400 MHz, CDCl$_3$) δ 5.42 (d, J=7.9 Hz, 1H), 4.72-4.67 (m, 1H), 3.74 (dd, J=14.6, 5.2 Hz, 1H), 3.62 (dd, J=14.6, 7.0 Hz, 1H), 2.71 (s, 3H), 1.41 (s, 9H), 1.37 (s, 9H), peak at 5.09, 4.60 ppm due to minor rotamer. $^{13}$C NMR (101 MHz, CDCl$_3$) δ 175.92 (C), 169.79 (C), 164.70 (C), 155.17 (C), 83.06 (C), 80.16 (C), 52.85 (CH), 37.75 (CH$_2$), 28.34 (CH$_3$), 28.00 (CH$_3$), 13.45 (CH$_3$). IR (KBr) υ/cm$^{-1}$ 3344, 2979, 2933, 1737, 1713, 1502, 1367, 1154. HRMS [M+H]$^+$ m/z calcd. for [C$_{15}$H$_{26}$O$_4$N$_5$S]$^+$ 372.1706, found 372.1691.

Example 25AP: (S)-tert-butyl 2-((tert-butoxycarbonyl)amino)-4-(6-(methylthio)-1,2,4,5-tetrazin-3-yl)butanoate (3p)

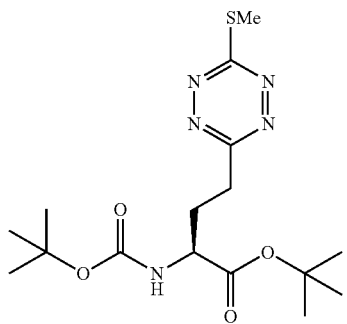 [SMILES: CSc1nnc(CC[C@H](NC(=O)OC(C)(C)C)C(=O)OC(C)(C)C)nn1]

General protocol A was followed using BF$_3$.OEt$_2$ (118 µL, 0.955 mmol), 15p (524 mg, 1.91 mmol), CH$_2$Cl$_2$ (1.9 mL) for 4 h at −12° C. to −4° C.; Pyridine (309 µL, 3.83 mmol), 2 (322 mg, 1.34 mmol) and DMF (1.3 mL) for 20 min at 80° C.; and PIDA (431 mg, 1.34 mmol) at r.t. for 30 min. A red solid (720 mg, 1.87 mmol, 70%) was obtained after purified by chromatography (Hexane:Et$_2$O 100:0 to 85:15). $^1$H NMR (400 MHz, CDCl$_3$) δ 5.14 (d, J=8.2 Hz, 1H), 4.35 (app dt, J=8.2, 4.8 Hz, 1H), 3.39-3.24 (m, 2H), 2.72 (s, 3H), 2.51-2.43 (m, 1H), 2.24-2.15 (m, 1H), 1.47 (s, 9H), 1.43 (s, 9H), peak at 4.90, 4.18 ppm due to minor rotamer. $^{13}$C NMR (101 MHz, CDCl$_3$) δ 175.67 (C), 171.30 (C), 167.23 (C), 155.42 (C), 82.61 (C), 80.05 (C), 53.52 (CH), 31.25 (CH$_2$), 30.66 (CH$_2$), 28.42 (CH$_3$), 28.12 (CH$_3$), 13.49 (CH$_3$). IR (KBr), υ/cm$^{-1}$ 3369, 2977, 2917, 2849, 1722, 1636, 1367, 1164, 738. HRMS [M+H]$^+$ m/z calcd. for [C$_{16}$H$_{28}$O$_4$N$_5$S]$^+$ 386.1862, found 386.1847.

Example 25AQ: (3S,4S,6R)-4-(4-(6-(methylthio)-1,2,4,5-tetrazin-3-yl)butyl)tetrahydro-1H-thieno[3,4-d]imidazol-2(3H)-one (3q)

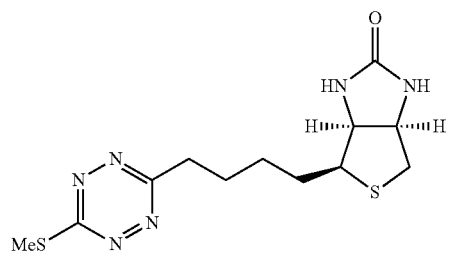 [SMILES: CSc1nnc(CCCC[C@@H]2SC[C@@H]3NC(=O)N[C@@H]32)nn1]

General protocol A was followed using BF$_3$.OEt$_2$ (121 µL, 0.982 mmol), 15q (215 mg, 0.654 mmol), CH$_2$Cl$_2$ (0.65 mL) for 4 h at −12° C. to −4° C.; Pyridine (159 µL, 1.96 mmol), 2 (112 mg, 0.452 mmol) and DMF (0.45 mL) for 20 min at 80° C.; and PIDA (140 mg, 0.452 mmol) at r.t. for 30 min. A red solid (95.9 mg, 0.294 mmol, 66%) was obtained after purified by chromatography (CH$_2$Cl$_2$:MeOH 100:0 to 95:5). $^1$H NMR (600 MHz, CDCl$_3$) δ 6.17 (s, 1H), 5.35 (s, 1H), 4.51 (app dd, J=7.6, 5.0 Hz, 1H), 4.32 (app dd, J=7.6, 5.0 Hz, 1H), 3.27 (t, J=7.7 Hz, 2H), 3.18-3.14 (m, 1H), 2.90 (dd, J=12.8, 5.0 Hz, 1H), 2.76-2.69 (m, 4H), 2.03-1.90 (m, 2H), 1.86-1.70 (m, 2H), 1.62-1.50 (m, 2H). $^{13}$C NMR (101 MHz, CDCl$_3$) δ 175.54 (C), 167.90 (C), 163.84 (C), 62.00 (CH), 60.23 (CH), 55.63 (CH), 40.69 (CH$_2$), 34.01 (CH$_2$), 28.40 (CH$_2$), 28.37 (CH$_2$), 28.36 (CH$_2$), 13.51 (CH$_3$). IR (KBr), υ/cm$^{-1}$ 3422, 2931, 2859, 1702, 1460, 1265, 1159, 739. HRMS [M+H]$^+$ m/z calcd. for [C$_{12}$H$_{19}$ON$_6$S$_2$]$^+$ 327.1062, found 327.1049.

Example 25AR: (3R,5R,8R,9S,10S,13R,14S,17R)-10,13-dimethyl-17-((R)-4-(6-(methylthio)-1,2,4,5-tetrazin-3-yl)butan-2-yl)hexadecahydro-1H-cyclopenta[a]phenanthren-3-ol (3r)

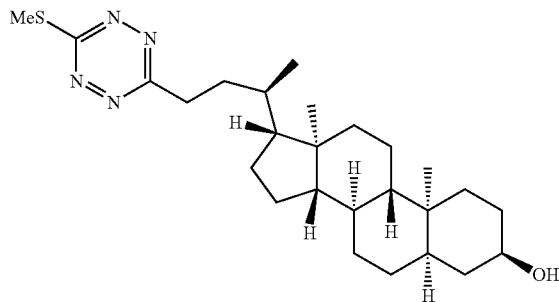

General protocol A was followed using BF$_3$.OEt$_2$ (227 µL, 1.79 mmol), 15r (550 mg, 1.19 mmol), CH$_2$Cl$_2$ (1.20 mL) for 4 h at −12° C. to −4° C.; Pyridine (290 µL, 3.58 mmol), 2 (206 mg, 0.831 mmol) and DMF (0.83 mL) for 20 min at 80° C.; and PIDA (267 mg, 0.831 mmol) at r.t. for 30 min. A red solid (365 mg, 0.798 mmol, 67%) was obtained after purified by chromatography (CH$_2$Cl$_2$:Et$_2$O 100:0 to 85:15). $^1$H NMR (600 MHz, CDCl$_3$) δ 3.65-3.58 (m, 1H), 3.28 (ddd, J=14.0, 10.7, 4.9 Hz, 1H), 3.12 (ddd, J=14, 10.7, 6.2 Hz, 1H), 2.72 (s, 3H), 2.09-1.94 (m, 2H), 1.92-1.71 (m, 4H), 1.69-1.45 (m, 7H), 1.45-0.84 (m, 20H), 0.65 (s, 3H). $^{13}$C NMR (151 MHz, CDCl$_3$) δ 175.36, 168.79, 67.24, 56.66, 56.13, 42.97, 42.27, 40.62, 40.36, 36.65, 36.03, 35.77, 35.52, 34.94, 34.74, 31.48, 30.74, 28.39, 27.35, 26.57, 24.35, 23.52, 21.00, 18.64, 13.45, 12.24. IR (KBr), υ/cm$^{-1}$ 3362, 2932, 2863, 1449, 1360, 1313, 1162, 1068, 737. HRMS [M+H]$^+$ m/z calcd. for [C$_{26}$H$_{43}$ON$_4$S]$^+$ 459.3158, found 459.3142

Example 25AS: 3-(methylthio)-6-(1-((5-(trifluoromethyl)pyridin-2-yl)oxy)cyclopropyl)-1,2,4,5-tetrazine (3s)

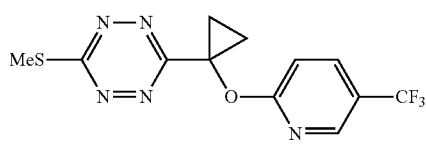 [SMILES: CSc1nnc(C2(Oc3ccc(C(F)(F)F)cn3)CC2)nn1]

General protocol A was followed using BF$_3$.OEt$_2$ (53.1 µL, 0.432 mmol), 15s (95.4 mg, 0.288 mmol), CH$_2$Cl$_2$ (0.29 mL) for 4 h at −12° C. to −4° C.; Pyridine (69.7 L, 0.864 mmol), 2 (50.1 mg, 0.202 mmol) and DMF (0.20 mL) for 20 min at 80° C.; and PIDA (65.0 mg, 0.202 mmol) at r.t. for 30 min. A red oil (43.2 mg, 0.131 mmol, 65%) was obtained after purified by chromatography (Hexane: Et$_2$O 10:0 to 9:1). $^1$H NMR (400 MHz, CDCl$_3$) δ 8.27 (s, 1H), 7.83 (dd, J=8.7, 2.5 Hz, 1H), 7.00 (d, J=8.7 Hz, 1H), 2.70 (s, 3H), 2.10-1.89 (m, 2H), 1.82-1.64 (m, 2H). $^{13}$C NMR (101 MHz, CDCl$_3$) δ 175.22 (C), 167.13 (C), 164.93 (C), 144.83 (CH, q, J$_{C-F}$=4.1 Hz), 136.31 (CH, q, J$_{C-F}$=1.5 Hz), 123.89 (C, q, J$_{C-F}$=269.7 Hz), 121.27 (C, q, J$_{C-F}$=32.9 Hz), 111.69 (CH), 59.04 (C), 19.45 (CH$_2$), 13.49 (CH$_3$). IR (KBr), υ/cm$^{-1}$ 3016, 2931, 2853, 1614, 1582, 1492, 1289, 1208, 1125. HRMS [M+H]$^+$ m/z calcd. for [C$_{12}$H$_{11}$ON$_5$SF$_3$]$^+$ 330.0636, found 330.0624.

Example 25AT: (S)-tert-butyl (1-(6-(methylthio)-1,2,4,5-tetrazin-3-yl)-2-(pyridin-4-yl)ethyl)carbamate (3t)

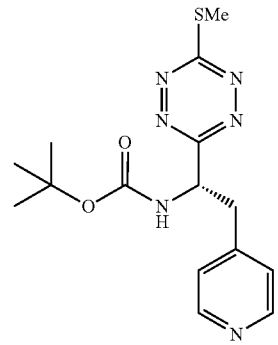 [SMILES: CSc1nnc([C@H](Cc2ccncc2)NC(=O)OC(C)(C)C)nn1]

General protocol A was followed using BF$_3$.OEt$_2$ (51 µL, 0.42 mmol), 15t (97 mg, 0.28 mmol), CH$_2$Cl$_2$ (0.28 mL) for 4 h at −12° C. to −4° C.; Pyridine (67 µL, 0.83 mmol), 2 (50 mg, 0.20 mmol) and DMF (0.2 mL) for 20 min at 80° C.; and PIDA (60 mg, 0.20 mmol) at r.t. for 30 min. A red oil (39 mg, 0.11 mmol, 55%) was obtained after purified by chromatography (CH$_2$Cl$_2$:MeOH 100:0 to 97:3). $^1$H NMR (400 MHz, CDCl$_3$) δ 8.51 (m, 2H), 7.08-7.07 (m, 2H), 5.65-5.62 (m, 1H), 5.53-5.51 (m, 1H), 3.44-3.39 (m, 1H), 3.30-3.24 (m, 1H), 2.74 (s, 3H), 1.39 (s, 9H). $^{13}$C NMR (101 MHz, CDCl$_3$) δ 176.94 (C), 166.05 (C), 155.00 (C), 149.96 (CH), 145.18 (C), 124.99 (CH), 80.73 (C), 53.78 (CH$_2$), 40.82 (CH$_2$), 28.35 (CH$_3$), 13.57 (CH$_3$). IR (KBr), υ/cm$^{-1}$ 3006, 2925, 2852, 1710, 1604, 1519, 1366, 1249, 1165. HRMS [M+H]$^+$ m/z calcd. for [C$_{15}$H$_{21}$O$_2$N$_6$S]$^+$ 349.1447, found 349.1443.

Example 25AU: 3-(methylthio)-6-((1-phenyl-5-(trifluoromethyl)-1H-pyrazol-4-yl)methyl)-1,2,4,5-tetrazine (3u)

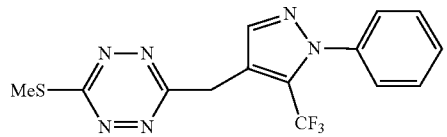

General protocol A was followed using BF₃.OEt₂ (88 μL, 0.72 mmol), 15u (102 mg, 0.29 mmol), CH₂Cl₂ (0.29 mL) for 4 h at −12° C. to −4° C.; Pyridine (117 μL, 1.4 mmol), 2 (50 mg, 0.20 mmol) and DMF (0.20 mL) for 20 min at 80° C.; and PIDA (65 mg, 0.20 mmol) at r.t. for 30 min. A red solid (48 mg, 0.14 mmol, 68%) was obtained after purified by chromatography (Hexane:CH₂Cl₂ 3:7 to 0:10). ¹H NMR (400 MHz, CDCl₃) δ 7.72 (s, 1H), 7.56-7.40 (m, 5H), 4.66 (d, J=1.4 Hz, 2H), 2.75 (s, 3H). ¹³C NMR (101 MHz, CDCl₃) δ 176.19 (C), 165.89 (C), 141.21 (CH), 139.51 (C), 129.98 (q, $J_{C-F}$=37.6 Hz, C), 129.62 (CH), 129.19 (CH), 126.12 (CH), 120.45 (q, $J_{C-F}$=268.5 Hz, C), 118.02 (C), 29.65 (CH₂), 13.56 (CH₃). IR (KBr), υ/cm⁻¹ 3056, 2974 2933, 2825, 1653, 1528, 1266, 740, 702. HRMS [M+H]⁺ m/z calcd. for [C₁₄H₁₂N₆F₃S]⁺ 353.0796, found 353.0784.

Example 25AV: (2S,3S)-tert-butyl 2-(6-(methylthio)-1,2,4,5-tetrazin-3-yl)-3-(pyridin-4-ylmethyl)pyrrolidine-1-carboxylate (3v)

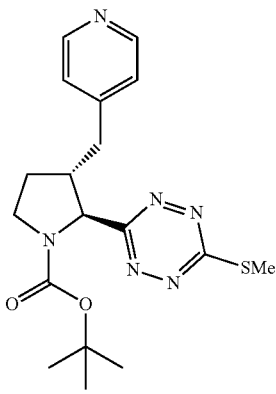 [SMILES: CSc1nnc([C@@H]2[C@@H](Cc3ccncc3)CCN2C(=O)OC(C)(C)C)nn1]

General protocol A was followed using BF₃.OEt₂ (42 μL, 0.34 mmol), 15v (90 mg, 0.23 mmol), CH₂Cl₂ (0.23 mL) for 4 h at −12° C. to −4° C.; Pyridine (56 μL, 0.68 mmol), 2 (40 mg, 0.16 mmol) and DMF (0.16 mL) for 20 min at 80° C.; and PIDA (51 mg, 0.16 mmol) at r.t. for 30 min. A red solid (41 mg, 0.11 mmol, 64%) was obtained after purified by chromatography (CH₂Cl₂:Acetone 10:0 to 85:15). Two rotamers: ¹H NMR (400 MHz, CDCl₃) δ 8.48-8.46 (m, 4H), 7.09 (d, J=5.0 Hz, 2H), 7.04 (d, J=5.0 Hz, 2H), 5.00 (d, J=5.6 Hz, 1H), 4.86 (d, J=6.2 Hz, 1H), 3.83 (ddd, J=11.3, 7.9, 3.7 Hz, 1H), 3.76-3.57 (m, 3H), 3.07-2.64 (m, 12H), 2.33-2.04 (m, 2H), 1.83-1.68 (m, 2H), 1.40 (s, 9H), 1.13 (s, 9H). ¹³C NMR (101 MHz, CDCl₃) δ 176.25 (C), 176.15 (C), 168.47 (C), 168.08 (C), 154.40 (C), 153.35 (C), 150.09 (CH, both rotamers), 147.78 (C), 147.67 (C), 124.41 (CH), 124.29 (CH), 80.48 (C, both rotamers), 65.12 (CH), 64.88 (CH), 48.33 (CH), 47.20 (CH), 46.38 (CH₂), 46.26 (CH₂), 37.79 (CH₂, both rotamers), 29.77 (CH₂), 29.71 (CH₂), 28.48 (CH₃), 28.25 (CH₃), 13.53 (CH₃, both rotamers). IR (KBr), υ/cm⁻¹ 3057, 2962, 2917, 2850, 1726, 1640, 1529, 1266, 741. HRMS [M+H]⁺ m/z calcd. for [C₁₈H₂₅O₂N₆S]⁺ 389.1760, found 389.1745

Example 25AW: 5,5-difluoro-7,9-dimethyl-3-(2-(6-(methylthio)-1,2,4,5-tetrazin-3-yl)ethyl)-5H-dipyrrolo[1,2-c:2',1'-f][1,3,2]diazaborinin-4-ium-5-uide (3w)

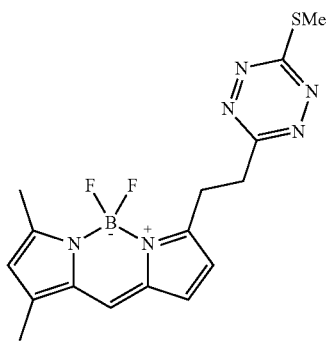

General protocol A was followed using BF₃.OEt₂ (20 μL, 0.16 mmol), 15w (40 mg, 0.11 mmol), CH₂Cl₂ (0.16 mL) for 4 h at −12° C. to −4° C.; Pyridine (27 μL, 0.33 mmol), 2 (19 mg, 0.077 mmol) and DMF (77 μL) for 20 min at 80° C.; and PIDA (24 mg, 0.077 mmol) at r.t. for 30 min. An orange solid (16 mg, 0.043 mmol, 57%) was obtained after purified by chromatography (Hexane: CH₂Cl₂ 1:1 to 1:9). ¹H NMR (400 MHz, CDCl₃) δ 7.09 (s, 1H), 6.86 (d, J=4.0 Hz, 1H), 6.25 (d, J=4.0 Hz, 1H), 6.12 (s, 1H), 3.71 (app t, J=7.5, 1.3 Hz, 2H), 3.60 (app t, J=7.5 Hz, 2H), 2.73 (s, 3H), 2.56 (s, 3H), 2.25 (s, 3H). ¹³C NMR (101 MHz, CDCl₃) δ 175.69 (C), 166.95 (C), 161.16 (C), 155.99 (C), 144.33 (C), 135.58 (C), 133.37 (C), 127.97 (CH), 124.04 (CH), 120.80 (CH), 116.72 (CH), 33.60 (CH₂), 26.84 (CH₂), 15.16 (CH₃), 13.51 (CH₃), 11.49 (CH₃). IR (KBr), υ/cm⁻¹ 3062, 3030, 2930, 2864, 1454, 1327, 1306, 1163, 1098, 893, 741, 699. HRMS [M+H]⁺ m/z calcd. for [C₁₆H₁₈N₆F₂BS]⁺ 375.1375, found 375.1369

Example 25BX: 3-(methylthio)-6-phenyl-1,2,4,5-tetrazine (3x)

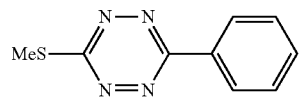

General protocol B was followed using BF₃.OEt₂ (362 μL, 2.94 mmol), 15x (1200 mg, 5.87 mmol), CH₂Cl₂ (0.59 mL) for 4 h at −5° C. to −0° C.; Pyridine (948 μL, 11.7 mmol), 2 (1019 mg, 4.11 mmol) and DMF (4.1 mL) for 1 h at 80° C.; and PIDA (1323 mg, 4.11 mmol) at r.t. for 30 min. A red solid (587 mg, 2.87 mmol, 72%) was obtained after purified by chromatography (CH₂Cl₂: ether 100:0 to 95:5). ¹H NMR (400 MHz, CDCl₃) δ 8.65-8.20 (m, 2H), 8.09-7.46 (m, 3H), 2.80 (s, 3H). ¹³C NMR (101 MHz, CDCl₃) δ 175.43 (C), 162.44 (C), 132.45 (CH), 131.71 (C), 129.38 (CH), 127.62 (CH), 13.60 (CH₃). IR (KBr), υ/cm⁻¹ 3074, 3014, 2936, 1356, 1196, 897, 760. HRMS [M+H]⁺ m/z calcd. for [C₉H₉N₄S]⁺ 205.0548, found 205.0540.

Example 25BY: 3-(methylthio)-2-fluoro-6-phenyl-1,2,4,5-tetrazine (3y)

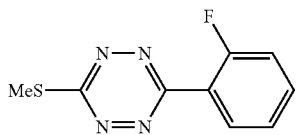 [SMILES: CSc1nnc(-c2ccccc2F)nn1]

General protocol B was followed using $BF_3 \cdot OEt_2$ (98.5 μL, 0.798 mmol), 15y (358 mg, 1.60 mmol), $CH_2Cl_2$ (1.6 mL) for 6 h at −2° C. to −0° C.; Pyridine (258 μL, 3.19 mmol), 2 (277 mg, 1.12 mmol) and DMF (1.1 mL) for 1 h at 80° C.; and PIDA (361 mg, 1.12 mmol) at r.t. for 1 h. A red solid (177 mg, 0.797 mmol, 50%) was obtained after purified by chromatography (Hexane: EA 100:0 to 95:5). $^1$H NMR (400 MHz, CDCl$_3$) δ 8.21 (td, J=7.6, 1.8 Hz, 1H), 7.59 (m, 1H), 7.37 (td, J=7.6, 1.2 Hz, 1H), 7.30 (m, 1H), 2.80 (s, 3H). $^{13}$C NMR (101 MHz, CDCl$_3$) δ 175.21 (C), 162.06 (d, $J_{C-F}$=5.5 Hz, C), 161.33 (d, $J_{C-F}$=257.0 Hz, C), 133.76 (d, $J_{C-F}$=8.5 Hz, CH), 131.07 (d, $J_{C-F}$=1.4 Hz, CH), 124.88 (d, $J_{C-F}$=3.9 Hz, CH), 120.57 (d, $J_{C-F}$=9.9 Hz, C), 117.43 (d, $J_{C-F}$=21.5 Hz, CH), 13.58 (CH$_3$). HRMS [M+H]$^+$ m/z calcd. for [C$_9$H$_8$N$_4$FS]$^+$ 223.0454, found 223.0447.

Example 26: General Procedure for the Synthesis of 3-Monosubstituted Tetrazines

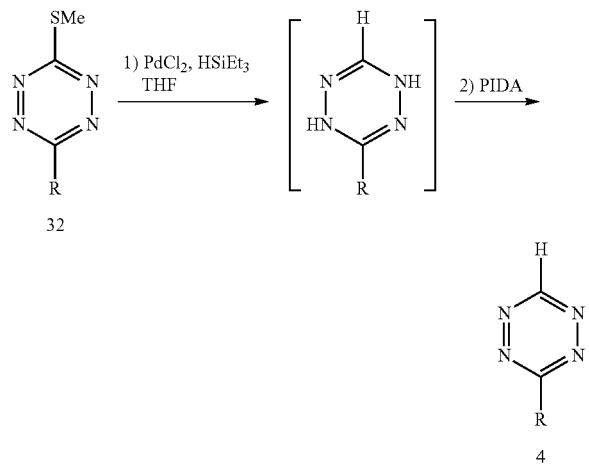

To a dry round-bottom flask was added tetrazine thioether 32 (1 equiv.) and PdCl$_2$ (10 mol %). The flask was outfitted with a septum-fitted gas inlet adapter, and was twice evacuated and backfilled with nitrogen. Triethylsilane (3 equiv.) and anhydrous THF (to 0.1 M in 3) were added via syringe, and the flask was heated by an oil bath at 45° C. The mixture was allowed to stir at 45° C. for 24 h. PIDA (1.2 equiv) was added as a solid at r.t. After stirring at room temperature for 1 h, the reaction mixture was diluted with $CH_2Cl_2$, transferred to a separatory funnel and was sequentially washed with saturated sodium bicarbonate, water, brine, dried over sodium sulfate and concentrated by rotary evaporation. The residue was purified by flash column chromatography on silica gel.

Example 26A: tert-butyl (4-(1,2,4,5-tetrazin-3-yl)phenyl)carbamate (4a)

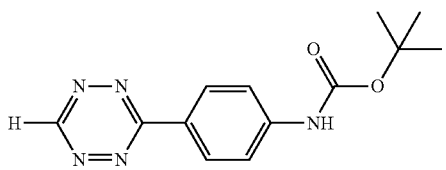 [SMILES: CC(C)(C)OC(=O)Nc1ccc(-c2nncnn2)cc1]

The general protocol for thioether reduction was followed using 3b (67 mg, 0.21 mmol), PdCl$_2$ (3.7 mg, 0.021 mmol), HSiEt$_3$ (0.10 mL, 0.63 mmol), THF (2.1 mL) and PIDA (80 mg, 0.25 mmol). A pink solid (47 mg, 0.17 mmol, 82%) was obtained after column chromatography (CH$_2$Cl$_2$:Et$_2$O 100:0 to 97:3). $^1$H NMR (400 MHz, CDCl$_3$) δ 10.15 (s, 1H), 8.57 (app d, J=8.9 Hz, 2H), 7.61 (d, J=8.9 Hz, 2H), 6.75 (s, 1H), 1.55 (s, 9H). $^{13}$C NMR (101 MHz, CDCl$_3$) δ 166.12, 157.58, 152.28, 143.24, 129.65, 125.82, 118.51, 81.60, 28.43. IR (KBr), υ/cm$^{-1}$ 3055, 2932, 2862, 1653, 1528, 1266, 741. HRMS [M+H]$^+$ m/z calcd. for [C$_{13}$H$_{16}$O$_2$N$_5$]$^+$274.1304, found 274.1293.

Example 26B: tert-butyl 4-(1,2,4,5-tetrazin-3-yl)benzylcarbamate (4b)

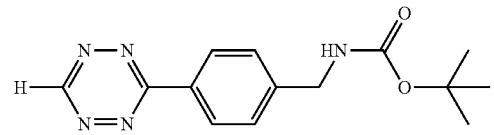 [SMILES: CC(C)(C)OC(=O)NCc1ccc(-c2nncnn2)cc1]

The general protocol for thioether reduction was followed using 3c (150 mg, 0.45 mmol), PdCl$_2$ (8.0 mg, 0.045 mmol), HSiEt$_3$ (0.22 mL, 1.4 mmol), THF (4.5 mL) and PIDA (174 mg, 0.54 mmol). A pink solid (106 mg, 0.37 mmol, 82%) was obtained after column chromatography (Hexane:Et$_2$O 100:0 to 85:15). $^1$H NMR (400 MHz, CDCl$_3$) δ 10.21 (s, 1H), 8.59 (app d, J=8.1 Hz, 2H), 7.52 (app d, J=8.1 Hz, 2H), 4.98 (s, 1H), 4.45 (d, J=6.2 Hz, 2H), 1.48 (s, 9H). $^{13}$C NMR (101 MHz, CDCl$_3$) δ 166.35, 157.87, 156.06, 144.79, 130.60, 128.65, 128.21, 79.96, 44.43, 28.51. IR (KBr), υ/cm$^{-1}$ 3352, 3087, 2980, 2930, 2884, 1702, 1684, 1610, 1510, 1435, 1349, 1247, 1168. HRMS [M+H]$^+$ m/z calcd. for [C$_{14}$H$_{18}$O$_2$N$_5$]$^+$288.1460, found 288.1449.

Example 26C: 3-(4-methoxyphenyl)-1,2,4,5-tetrazine (4c)

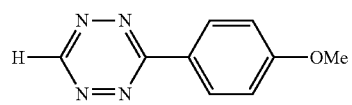

The general protocol for thioether reduction was followed using 3e (50 mg, 0.21 mmol), PdCl$_2$ (3.8 mg, 0.021 mmol), HSiEt$_3$ (0.10 mL, 0.64 mmol), THF (2.1 mL) and PIDA (82 mg, 0.26 mmol). A pink solid (34 mg, 0.18 mmol, 85%) was obtained after column chromatography (Hexane:Et$_2$O 100:0 to 94:6). $^1$H NMR (400 MHz, CDCl$_3$) δ 10.13 (s, 1H), 8.58

(app d, J=8.9 Hz, 2H), 7.09 (app d, J=8.9 Hz, 2H), 3.93 (s, 3H). $^{13}$C NMR (101 MHz, CDCl$_3$) δ 166.21, 163.86, 157.44, 130.28, 124.00, 114.92, 55.67. IR (KBr), υ/cm$^{-1}$ 3058, 2963, 2932, 2871, 1640, 1529, 1267, 740. HRMS [M+H]$^+$ m/z calcd. for [C$_9$H$_9$ON$_4$]$^+$ 189.0776, found 189.0769.

Example 26D: methyl 4-(1,2,4,5-tetrazin-3-yl)benzoate (4d)

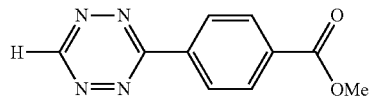

The general protocol for thioether reduction was followed using 3g (50 mg, 0.19 mmol), PdCl$_2$ (3.3 mg, 0.019 mmol), HSiEt$_3$ (0.091 mL, 0.57 mmol), THF (1.9 mL) and PIDA (73 mg, 0.23 mmol). A pink solid (30 mg, 0.14 mmol, 73%) was obtained after column chromatography (Hexane:EA 100:0 to 92:8). $^1$H NMR (400 MHz, CDCl$_3$) δ 10.28 (s, 1H), 8.72 (app d, J=8.7 Hz, 2H), 8.27 (app d, J=8.7 Hz, 2H), 3.99 (s, 3H). $^{13}$C NMR (151 MHz, CDCl$_3$) δ 166.37, 166.12, 158.11, 135.61, 134.28, 130.58, 128.39, 52.67. IR (KBr), υ/cm$^{-1}$ 3060, 2994, 2946, 1714, 1432, 1355, 1275, 1190, 1111, 767. HRMS [M+H]$^+$ m/z calcd. for [C$_{10}$H$_9$O$_2$N$_4$]$^+$ 217.0726, found 217.0720.

Example 26E: 4-(1,2,4,5-tetrazin-3-yl)benzonitrile (4e)

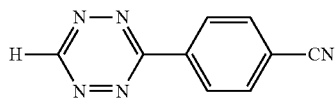

The general protocol for thioether reduction was followed using 3h (50 mg, 0.22 mmol), PdCl$_2$ (3.9 mg, 0.022 mmol), HSiEt$_3$ (0.10 mL, 0.65 mmol), THF (2.2 mL) and PIDA (84 mg, 0.26 mmol). A pink solid (27 mg, 0.15 mmol, 68%) was obtained after column chromatography (Hexane:Et$_2$O 100:0 to 9:1). $^1$H NMR (400 MHz, CDCl$_3$) δ 10.33 (s, 1H), 8.78 (app d, J=8.5 Hz, 2H), 7.93 (app d, J=8.5 Hz, 2H). $^{13}$C NMR (101 MHz, CDCl$_3$) δ 165.49, 158.28, 135.68, 133.20, 128.83, 118.10, 116.74. IR (KBr), υ/cm$^{-1}$ 3095, 3053, 2931, 2225, 1445, 1354, 1200, 903, 855.

Example 26F: methyl 3-(1,2,4,5-tetrazin-3-yl)propanoate (4f)

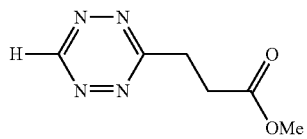 [SMILES: COC(=O)CCc1nncnn1]

The general protocol for thioether reduction was followed using 3k (225 mg, 1.05 mmol), PdCl$_2$ (18.6 mg, 0.105 mmol), HSiEt$_3$ (0.510 mL, 3.15 mmol), THF (10.5 mL) and PIDA (405 mg, 1.26 mmol). A pink solid (133 mg, 0.790 mmol, 75%) was obtained after column chromatography (Hexane:EA 100:0 to 85:15). $^1$H NMR (400 MHz, CDCl$_3$) δ 10.21 (s, 1H), 3.86-3.50 (m, 5H), 3.09 (app t, J=7.0 Hz, 2H). $^{13}$C NMR (101 MHz, CDCl$_3$) δ 172.48, 171.59, 158.22, 52.19, 30.53, 30.29. IR (KBr), υ/cm$^{-1}$ 2962, 2918, 2838, 1726, 1653, 1529, 1266, 740. HRMS [M+H]$^+$ m/z calcd. for [C$_6$H$_9$O$_2$N$_4$]$^+$ 169.0726, found 169.0720.

Example 26G: tert-butyl ((1,2,4,5-tetrazin-3-yl)methyl)carbamate (4g)

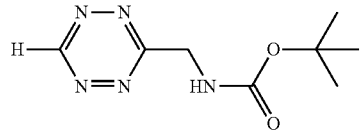

The general protocol for thioether reduction was followed using 3n (200 mg, 0.777 mmol), PdCl$_2$ (13.7 mg, 0.0777 mmol), HSiEt$_3$ (371 μL, 2.33 mmol), THF (7.8 mL) and PIDA (300 mg, 0.932 mmol). A pink solid (129 mg, 0.611 mmol, 79%) was obtained after column chromatography (Hexane:EA 100:0 to 82:18). $^1$H NMR (400 MHz, CDCl$_3$) δ 10.27 (s, 1H), 5.60 (s, 1H), 5.01 (d, J=6.0 Hz, 2H), 1.45 (s, 9H). $^{13}$C NMR (101 MHz, CDCl$_3$) δ 169.53, 158.82, 155.90, 80.66, 43.89, 28.41. IR (KBr), υ/cm$^1$ 3350, 2979, 2934, 1709, 1517, 1251, 1168. HRMS [M+H]$^+$ m/z calcd. for [C$_8$H$_{14}$O$_2$N$_5$]$^+$ 212.1147, found 212.1140.

Example 26H: (S)-tert-butyl 2-((tert-butoxycarbonyl)amino)-3-(1,2,4,5-tetrazin-3-yl)propanoate (4h)

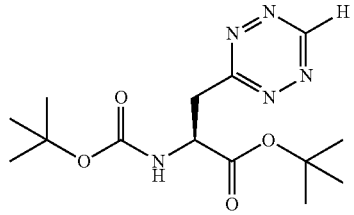 [SMILES: CC(C)(C)OC(=O)N[C@@H](Cc1nncnn1)C(=O)OC(C)(C)C]

The general protocol for thioether reduction was followed using 3o (165 mg, 0.444 mmol), PdCl$_2$ (7.86 mg, 0.0444 mmol), HSiEt$_3$ (213 μL, 1.33 mmol), THF (4.4 mL) and PIDA (170 mg, 0.533 mmol). A pink solid (95.2 mg, 0.293 mmol, 66%) was obtained after column chromatography (Hexane:Et$_2$O 100:0 to 75:25). $^1$H NMR (400 MHz, CDCl$_3$) δ 10.22 (s, 1H), 5.47 (d, J=7.8 Hz, 1H), 4.80-4.76 (m, 1H), 3.87 (dd, J=14.7, 5.2 Hz, 1H), 3.75 (dd, J=14.7, 7.3 Hz, 1H), 1.41 (s, 9H), 1.37 (s, 9H), peak at 5.13, 4.71 ppm due to minor rotamer. $^{13}$C NMR (101 MHz, CDCl$_3$) δ 170.01, 169.64, 158.19, 155.18, 83.21, 80.29, 52.83, 38.75, 28.35, 27.98. IR (KBr), υ/cm$^{-1}$ 3371, 2979, 2833, 1715, 1502, 1368, 1251, 155, 1058, 892, 845. HRMS [M+H]$^+$ m/z calcd. for [C$_{14}$H$_{24}$O$_4$N$_5$]$^+$ 326.1828, found 326.1817.

Example 26I: (S)-tert-butyl 2-((tert-butoxycarbonyl)amino)-4-(1,2,4,5-tetrazin-3-yl)butanoate (4i)

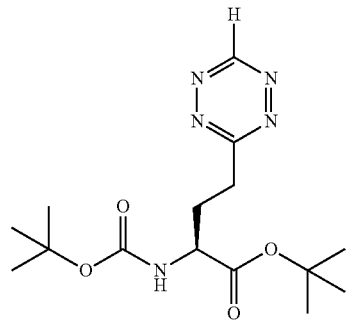 [SMILES: CC(C)(C)OC(=O)N[C@@H](CCc1nncnn1)C(=O)OC(C)(C)C]

The general protocol for thioether reduction was followed using 3p (291 mg, 0.755 mmol), PdCl$_2$ (13.4 mg, 0.0755 mmol), HSiEt$_3$ (360 µL, 2.26 mmol), THF (7.6 mL) and PIDA (293 mg, 0.906 mmol). A pink solid (200 mg, 0.589 mmol, 78%) was obtained after column chromatography (Hexane:EA 100:0 to 85:15). $^1$H NMR (400 MHz, CDCl$_3$) δ 10.20 (s, 1H), 5.17 (d, J=8.2 Hz, 1H), 4.36 (app td, J=8.2, 4.8 Hz, 1H), 3.50-3.35 (m, 2H), 2.58-2.49 (m, 1H), 2.29-2.20 (m, 1H), 1.47 (s, 9H), 1.42 (s, 9H), peak at 4.93, 4.19 ppm due to minor rotamer. $^{13}$C NMR (151 MHz, CDCl$_3$) δ 172.43, 171.22, 158.12, 155.44, 82.67, 80.09, 53.50, 31.60, 31.05, 28.43, 28.14. IR (KBr), υ/cm$^{-1}$ 3372, 2980, 2936, 1730, 1700, 1505, 1366, 1153, 1050, 893. HRMS [M+H]$^+$ m/z calcd. for [C$_{15}$H$_{26}$O$_4$N$_5$]$^+$ 340.1985, found 340.1973.

Example 26J: 3-(1-((5-(trifluoromethyl)pyridin-2-yl)oxy)cyclopropyl)-1,2,4,5-tetrazine (4j)

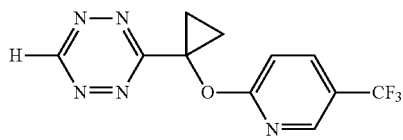 [SMILES: FC(F)(F)c1ccc(OC2(c3nncnn3)CC2)nc1]

The general protocol for thioether reduction was followed using 3s (40 mg, 0.12 mmol), PdCl$_2$ (2.1 mg, 0.012 mmol), HSiEt$_3$ (58 µL, 0.36 mmol), THF (1.2 mL) and PIDA (46 mg, 0.14 mmol). A pink solid (24 mg, 0.097 mmol, 71%) was obtained after column chromatography (Hexane:CH$_2$Cl$_2$ 8:2 to 6:4). $^1$H NMR (400 MHz, CDCl$_3$) δ 10.15 (s, 1H), 8.23-8.22 (m, 1H), 7.85 (dd, J=8.7, 2.4 Hz, 1H), 7.03 (d, J=8.7 Hz, 1H), 2.07 (app dd, J=8.8, 5.9 Hz, 2H), 1.78 (app dd, J=8.7, 5.8 Hz, 2H). $^{13}$C NMR (101 MHz, CDCl$_3$) δ 172.18 (C), 164.80 (C), 157.72 (CH), 144.74 (CH, q, J$_{C-F}$=4.4 Hz), 136.41 (CH, q, J$_{C-F}$=3.3 Hz), 123.86 (C, q, J$_{C-F}$=269.7 Hz), 121.24 (C, q, J$_{C-F}$=33.0 Hz) 111.78 (CH), 59.35 (C), 20.50 (CH$_2$). IR (KBr), υ/cm$^{-1}$ 3088, 2923, 2851, 1615, 1581, 1492, 1453, 1329, 1288, 1189, 1127, 1078. HRMS [M+H]$^+$ m/z calcd. for [C$_{11}$H$_{19}$ON$_5$F$_3$]$^+$ 284.0759, found 284.0749.

Example 26K: 3-((1-phenyl-5-(trifluoromethyl)-1H-pyrazol-4-yl)methyl)-1,2,4,5-tetrazine (4k)

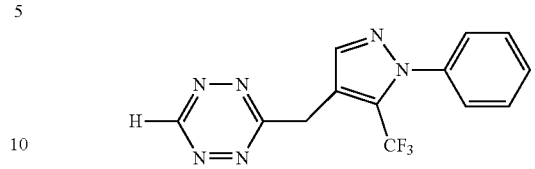

The general protocol for thioether reduction was followed using 3u (53 mg, 0.15 mmol), PdCl$_2$ (2.7 mg, 0.015 mmol), HSiEt$_3$ (72 µL, 0.45 mmol), THF (1.5 mL) and PIDA (57 mg, 0.18 mmol). A pink solid (35 mg, 0.11 mmol, 75%) was obtained after column chromatography (CH$_2$Cl$_2$:Et$_2$O 100:0 to 95:5). $^1$H NMR (400 MHz, CDCl$_3$) δ 10.27 (s, 1H), 7.74 (s, 1H), 7.50-7.44 (m, 5H), 4.78 (s, 2H). $^{13}$C NMR (101 MHz, CDCl$_3$) δ 170.99, 158.30, 141.26, 139.43, 130.11 (q, J$_{C-F}$=37.7 Hz), 129.67, 129.20, 126.11 (q, J$_{C-F}$=1.0 Hz), 120.38 (q, J$_{C-F}$=268.4 Hz) 117.47 (q, J$_{C-F}$=1.8 Hz), 30.62. IR (KBr), υ/cm$^{-1}$ 3077, 1924, 2853, 1598, 1503, 1472, 1309, 1183, 1132, 1091, 975. HRMS [M+H]$^+$ m/z calcd. for [C$_{13}$H$_{10}$N$_6$F$_3$]$^+$ 307.0919, found 307.0908.

Example 26L: (3R,5R,8R,9S,10S,13R,14S,17R)-17-((R)-4-(1,2,4,5-tetrazin-3-yl)butan-2-yl)-10,13-dimethylhexadecahydro-1H-cyclopenta[a]phenanthren-3-ol (4l)

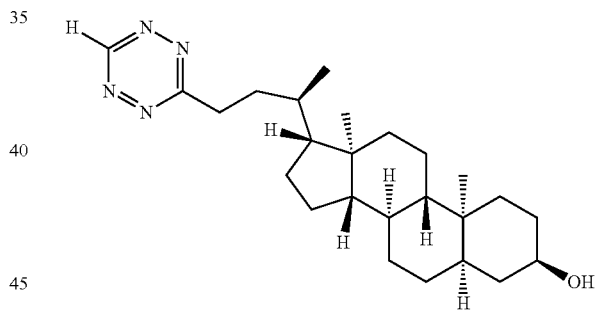

The general protocol for thioether reduction was followed using 3r (180 mg, 0.39 mmol), PdCl$_2$ (7.0 mg, 0.039 mmol), HSiEt$_3$ (0.19 mL, 1.2 mmol), THF (3.9 mL) and PIDA (170 mg, 0.533 mmol). After aqueous work up and rotary evaporation, THF (1.0 ml), TFA (0.2 mL) and water (0.2 mL) was added into crude and stirred for 2 h at r.t. The resulting residue was concentrated. A pink solid (112 mg, 0.27 mmol, 70%) was obtained after column chromatography (CH$_2$Cl$_2$:Et$_2$O 100:0 to 98:2). $^1$H NMR (400 MHz, CDCl$_3$) δ 10.19 (s, 1H), 3.63 (tt, J=10.8, 5.3 Hz, 1H), 3.40 (ddd, J=14.0, 10.8, 5.0 Hz, 1H), 3.24 (ddd, J=14.0, 10.5, 6.1 Hz, 1H), 2.15-2.03 (m, 1H), 2.02-0.77 (m, 32H), 0.65 (s, 3H). $^{13}$C NMR (101 MHz, CDCl$_3$) δ 174.02, 158.05, 72.01, 56.61, 55.99, 42.94, 42.20, 40.54, 40.30, 36.58, 35.97, 35.83, 35.47, 35.00, 34.71, 32.46, 30.68, 29.86, 28.40, 27.31, 26.54, 24.33, 23.52, 20.96, 18.63, 12.21. IR (KBr), υ/cm$^{-1}$ 3366, 2959, 2934, 2830, 1653, 1527, 1267, 741. HRMS [M+H]$^+$ m/z calcd. for [C$_{25}$H$_{41}$ON$_4$]$^+$ 413.3280, found 413.3254.

Example 26M: 3-(2-(1,2,4,5-tetrazin-3-yl)ethyl)-5,5-difluoro-7,9-dimethyl-5H-dipyrrolo[1,2-c:2',1'-f][1,3,2]diazaborinin-4-ium-5-uide (4m)

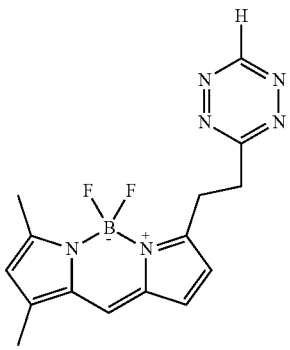

The general protocol for thioether reduction was followed using 3w (16 mg, 0.043 mmol), PdCl$_2$ (0.76 mg, 0.0043 mmol), HSiEt$_3$ (21 uL, 0.13 mmol), THF (0.43 mL) and PIDA (17 mg, 0.051 mmol). An orange solid (8.5 mg, 0.026 mmol, 61%) was obtained after column chromatography (CH$_2$Cl$_2$:Et$_2$O 100:0 to 98:2). $^1$H NMR (400 MHz, CDCl$_3$) δ 10.20 (s, 1H), 7.09 (s, 1H), 6.86 (d, J=4.0 Hz, 1H), 6.24 (d, J=4.0 Hz, 1H), 6.12 (s, 1H), 3.82 (app t, J=7.6 Hz, 2H), 3.65 (app t, J=7.6 Hz, 2H), 2.55 (s, 3H), 2.25 (s, 3H). $^{13}$C NMR (101 MHz, CDCl$_3$) δ 172.11, 161.38, 158.19, 155.49, 144.50, 135.67, 133.33, 127.89, 124.09, 120.89, 116.70, 34.68, 26.74, 15.17, 11.49. HRMS [M+H]$^+$ m/z calcd. for [C$_{15}$H$_{16}$N$_6$BF$_2$]$^+$ 329.1498, found 329.1483.

Example 27: Synthesis of Unsymmetrical Tetrazines Via Ag-Mediated Liebeskind Coupling with Boronic Acids

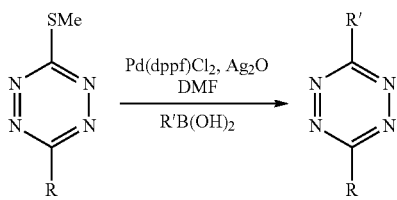

Example 27A: tert-butyl ((6-(4-methoxyphenyl)-1,2,4,5-tetrazin-3-yl)methyl)carbamate (5a)

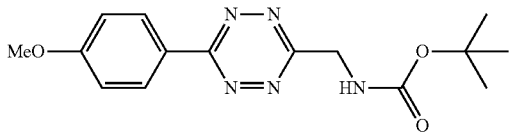 [SMILES: COc1ccc(-c2nnc(CNC(=O)OC(C)(C)C)nn2)cc1]

To a dry round bottomed flask was sequentially charged with 3n (54 mg, 0.21 mmol), Pd(dppf)Cl$_2$ (23 mg, 0.031 mmol, 15 mol %), 4-methoxyphenylboronic acid (61 mg, 0.40 mmol) and Ag$_2$O (122 mg, 0.52 mmol). The flask was outfitted with a septum-fitted gas inlet adapter, evacuated and filled with nitrogen. DMF (2.1 mL) was added to the flask via syringe. After heating under nitrogen at 60° C. for 20 h, the DMF was removed by rotary evaporation under high vacuum. The residue was purified by column chromatography (hexane:EA 10:0 to 8:2) to give the title compound as a pink solid (50 mg, 78%). $^1$H NMR (400 MHz, CDCl$_3$) δ 8.56 (app d, J=9.0 Hz, 2H), 7.09 (app d, J=9.0 Hz, 2H), 5.57 (s, 1H), 4.99 (d, J=5.7 Hz, 2H), 3.92 (s, 3H), 1.47 (s, 9H). $^{13}$C NMR (101 MHz, CDCl$_3$) δ 165.83 (C), 164.82 (C), 163.68 (C), 155.91 (C), 130.15 (CH), 123.96 (C), 114.91 (CH), 80.47 (C), 55.69 (CH$_3$), 43.53 (CH$_2$), 28.47 (CH$_3$). IR (KBr), υ/cm$^{-1}$ 3360, 3056, 2973, 2928, 1712, 1678, 1605, 1525, 1396, 1260, 1158. HRMS [M+H]$^+$ m/z calcd. for [C$_{15}$H$_{20}$O$_3$N$_5$]$^+$318.1566, found 318.1553.

Example 27B: methyl 3-(6-phenyl-1,2,4,5-tetrazin-3-yl)propanoate (5b)

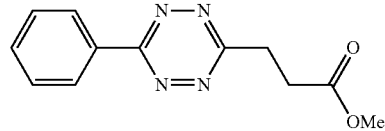 [SMILES: COC(=O)CCc1nnc(-c2ccccc2)nn1]

To a microwave reaction tube was sequentially charged with 3k (54 mg, 0.25 mmol), Pd(dppf)Cl$_2$ (28 mg, 0.038 mmol, 15 mol %), phenylboronic acid (92 mg, 0.76 mmol), Ag$_2$O (146 mg, 0.63 mmol) and DMF (2.5 mL) in glove box. After heating under nitrogen at 100° C. for 3 h, the DMF was removed by rotary evaporation under high vacuum. The residue was purified by column chromatography (hexane: EA 100:0 to 85:15) to give the title compound as pink solid (52 mg, 84%). $^1$H NMR (400 MHz, CDCl$_3$) δ 8.82-8.38 (m, 2H), 7.78-7.43 (m, 3H), 4.17-3.34 (m, 5H), 3.12 (app t, J=7.1 Hz, 2H). $^{13}$C NMR (101 MHz, CDCl$_3$) δ 172.63 (C), 168.57 (C), 164.51 (C), 132.82 (CH), 131.80 (C), 129.40 (CH), 128.14 (CH), 52.19 (CH$_3$), 30.77 (CH$_2$), 29.83 (CH$_2$). IR (KBr), υ/cm$^{-1}$ 3063, 3001, 2950, 2926, 1736, 1375, 1301, 1234, 1175, 758, 696. HRMS [M+H]$^+$ m/z calcd. for [C$_{12}$H$_{13}$O$_2$N$_4$]$^+$ 245.1039, found 245.1031.

Example 27C: methyl 4-(6-(4-(hydroxymethyl)phenyl)-1,2,4,5-tetrazin-3-yl)benzoate (5c)

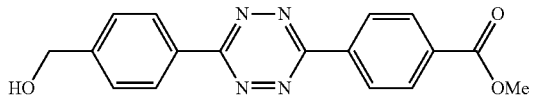 [SMILES: COC(=O)c1ccc(-c2nnc(-c3ccc(CO)cc3)nn2)cc1]

To a dry round bottomed flask was sequentially charged with 3g (48 mg, 0.18 mmol), Pd(dppf)Cl$_2$ (20 mg, 0.028 mmol, 15 mol %), p-hydroxymethylphenylboronic acid (54 mg, 0.35 mmol) and Ag$_2$O (107 mg, 0.46 mmol). The flask was outfitted with a septum-fitted gas inlet adapter, evacuated and filled with nitrogen. DMF (1.8 mL) was added to the flask via syringe. After heating under nitrogen at 60° C. for 20 h, the DMF was removed by rotary evaporation under high vacuum. The residue was purified by column chromatography (CH$_2$Cl$_2$:Et$_2$O 100:0 to 93:7) to give the title compound as pink solid (35 mg, 59%). $^1$H NMR (400 MHz, DMSO-d$_6$) δ 8.67 (app d, J=8.5 Hz, 2H), 8.53 (app d, J=8.3

Hz, 2H), 8.26 (app d, J=8.5 Hz, 2H), 7.64 (app d, J=8.3 Hz, 2H), 5.47 (t, J=5.5 Hz, 1H), 4.66 (d, J=5.5 Hz, 2H), 3.93 (s, 3H). $^{13}$C NMR (101 MHz, DMSO-d$_6$) δ 165.73 (C), 163.37 (C), 162.79 (C), 147.98 (C), 136.19 (C), 132.75 (C), 130.19 (CH), 130.04 (C), 127.85 (CH), 127.67 (CH), 127.22 (CH), 62.49 (CH$_2$), 52.60 (CH$_3$). IR (KBr), υ/cm$^{-1}$ 3345, 3058, 3012, 2957, 2919, 1720, 1607, 1509, 1394, 1280, 1112, 1010, 697. HRMS [M+H]$^+$ m/z calcd. for [C$_{17}$H$_{15}$O$_3$N$_4$]$^+$ 323.1144, found 323.1132.

Example 27D: methyl 4-(6-(4-(((tert-butoxycarbonyl)amino)methyl)phenyl)-1,2,4,5-tetrazin-3-yl)benzoate (5d)

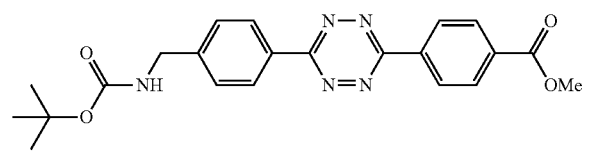 [SMILES: COC(=O)c1ccc(-c2nnc(-c3ccc(CNC(=O)OC(C)(C)C)cc3)nn2)cc1]

To a dry round bottomed flask was sequentially charged with 3g (47 mg, 0.18 mmol), Pd(dppf)Cl$_2$ (20 mg, 0.027 mmol, 15 mol %), 4-(tert-Butoxycarbonylaminomethyl)phenylboronic acid (85 mg, 0.34 mmol) and Ag$_2$O (103 mg, 0.45 mmol). The flask was outfitted with a septum-fitted gas inlet adapter, evacuated and filled with nitrogen. DMF (1.8 mL) was added to the flask via syringe. After heating under nitrogen at 60° C. for 20 h, the DMF was removed by rotary evaporation under high vacuum. The residue was purified by column chromatography (CH$_2$Cl$_2$:Et$_2$O 100:0 to 97:3) to give the title compound as a pink solid (61 mg, 81%). $^1$H NMR (400 MHz, DMSO-d) δ 8.67 (app d, J=8.4 Hz, 2H), 8.52 (app d, J=8.1 Hz, 2H), 8.26 (app d, J=8.4 Hz, 2H), 7.56 (m, 3H), 4.28 (d, J=6.0 Hz, 2H), 3.93 (s, 3H), 1.42 (s, 9H). $^{13}$C NMR (101 MHz, DMSO) δ 165.72 (C), 163.32 (C), 162.80 (C), 145.51 (C), 136.17 (C), 132.76 (C), 130.18 (CH), 130.15 (C), 127.93 (CH), 127.85 (CH), 127.76 (C), 78.06 (C), 52.59 (CH$_3$), 43.30 (CH$_2$), 28.28 (CH$_3$). IR (KBr), υ/cm$^{-1}$ 3348, 3081, 3008, 2984, 2947, 1722, 1683, 1606, 1512, 1394, 1277, 1250, 1168, 1111. HRMS [M+H]$^+$ m/z calcd. for [C$_{22}$H$_{24}$O$_4$N$_5$]$^+$ 422.1828, found 422.1815.

Example 27E: tert-butyl 3-(6-(4-chlorophenyl)-1,2,4,5-tetrazin-3-yl)propanoate (5e)

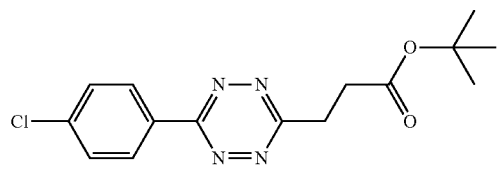 [SMILES: CC(C)(C)OC(=O)CCc1nnc(-c2ccc(Cl)cc2)nn1]

To a dry round bottomed flask was sequentially charged with 3l (70 mg, 0.27 mmol), Pd(dppf)Cl$_2$ (30 mg, 0.040 mmol, 15 mol %), 4-chlorophenylboronic acid (80 mg, 0.51 mmol) and Ag$_2$O (156 mg, 0.67 mmol). The flask was outfitted with a septum-fitted gas inlet adapter, evacuated and filled with nitrogen. DMF (2.7 mL) was added to the flask via syringe. After heating under nitrogen at 60° C. for 20 h, the DMF was removed by rotary evaporation under high vacuum. The residue was purified by column chromatography (hexane:EA 10:0 to 9:1) to give the title compound as pink solid (67 mg, 78%). $^1$H NMR (400 MHz, CDCl$_3$): δ 8.55 (m, 2H), 7.57 (m, 2H), 3.65 (app t, J=7.1 Hz, 2H), 3.01 (app t, J=7.1 Hz, 2H), 1.42 (s, 9H). $^{13}$C NMR (101 MHz, CDCl$_3$): δ 171.31 (C), 169.09 (C), 163.77 (C), 139.30 (C), 130.38 (C), 129.76 (CH), 129.37 (CH), 81.30 (C), 32.33 (CH$_2$), 30.15 (CH$_2$), 28.18 (CH$_3$). IR (KBr), υ/cm$^{-1}$ 3055, 2980, 2932, 1730, 1598, 1398, 1366, 1265, 1153, 1095, 848, 738. HRMS (ESI+) [M+H]$^+$ Calculated for [C$_{15}$H$_{18}$O$_2$N$_4$Cl]$^+$ 321.1118; found 321.1114.

Example 27F: tert-butyl 3-(6-(4-(2H-1,2,3-triazol-2-yl)phenyl)-1,2,4,5-tetrazin-3-yl)propanoate (5f)

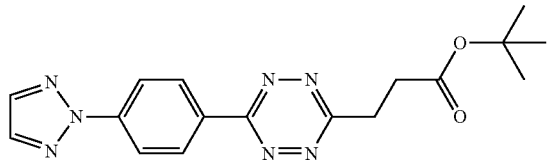 [SMILES: CC(C)(C)OC(=O)CCc1nnc(-c2ccc(-n3nccn3)cc2)nn1]

To a dry round bottomed flask was sequentially charged with 3l (80 mg, 0.31 mmol), Pd(dppf)Cl$_2$ (34 mg, 0.047 mmol, 15 mol %), 4-(triazol-2-yl)phenylboronic acid (112 mg, 0.59 mmol) and Ag$_2$O (181 mg, 0.67 mmol). The flask was outfitted with a septum-fitted gas inlet adapter, evacuated and filled with nitrogen. DMF (3.1 mL) was added to the flask via syringe. After heating under nitrogen at 60° C. for 20 h, the DMF was removed by rotary evaporation under high vacuum. The residue was purified by column chromatography (Hexane:EA 10:0 to 90:1) to give the title compound as pink solid (66 mg, 60%). $^1$H NMR (400 MHz, CDCl$_3$): δ 8.75 (m, 2H), 8.33 (m, 2H), 7.89 (s, 2H), 3.66 (app t, J=7.1 Hz, 2H), 3.03 (app t, J=7.1 Hz, 2H), 1.43 (s, 9H). $^{13}$C NMR (101 MHz, CDCl$_3$): δ 171.33 (C), 169.02 (C), 163.76 (C), 142.82 (C), 136.48 (CH), 130.82 (C), 129.37 (CH), 119.56 (CH), 81.30 (C), 32.38 (CH$_2$), 30.17 (CH$_2$), 28.20 (CH$_3$). IR (KBr), υ/cm$^{-1}$ 3089, 3005, 2977, 2915, 2848, 1720, 1605, 1403, 1365, 1263, 945. HRMS (ESI+) [M+H]$^+$ Calculated for [C$_{17}$H$_{20}$O$_2$N$_7$]$^+$ 354.1678; found 354.1674.

Example 27G: tert-butyl 3-(6-(4-((5-(trifluoromethyl)pyridin-2-yl)oxy)phenyl)-1,2,4,5-tetrazin-3-yl)propanoate (5g)

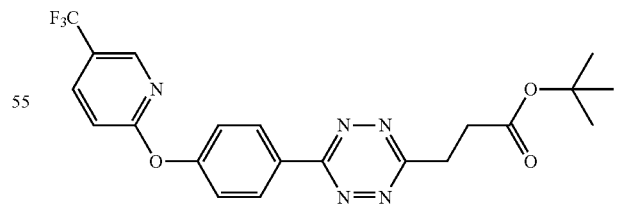

To a dry round bottomed flask was sequentially charged with 3l (60 mg, 0.23 mmol), Pd(dppf)Cl$_2$ (26 mg, 0.035 mmol, 15 mol %), 3-([5-(trifluoromethyl)pyridin-2-yl]oxy)phenylboronic acid (198 mg, 0.70 mmol) and Ag$_2$O (135 mg, 0.59 mmol). The flask was outfitted with a septum-fitted gas inlet adapter, evacuated and filled with nitrogen. DMF (2.3 mL) was added to the flask via syringe. After heating under nitrogen at 60° C. for 20 h, the DMF was removed by rotary evaporation under high vacuum. The residue was purified by column chromatography (Hexane:EA 10:0 to 90:1) to give the title compound as pink solid (68 mg, 65%). $^1$H NMR (400 MHz, CDCl$_3$) δ 8.55-8.50 (m, 1H), 8.46-8.43 (m, 1H), 8.42-8.39 (m, 1H), 7.99-7.93 (m, 1H), 7.67 (t, J=8.0 Hz, 1H), 7.46-7.40 (m, 1H), 7.16-7.08 (m, 1H), 3.65 (app, t, J=7.1 Hz, 2H), 3.01 (app, t, J=7.1 Hz, 2H), 1.41 (s, 9H). $^{13}$C NMR (101 MHz, CDCl$_3$): δ 171.28 (C), 169.17 (C), 165.47 (C, q, $J_{C-F}$=1.1 Hz), 163.75 (C), 154.03 (C), 145.50 (q, $J_{C-F}$=4.4 Hz, CH), 137.06 (q, $J_{C-F}$=3.1 Hz, CH), 133.68 (C), 130.81 (CH), 125.88 (CH), 125.02 (CH), 123.71 (q, $J_{C-F}$=272.5 Hz, C), 122.01 (q, $J_{C-F}$=33.5 Hz, C), 121.1 (CH), 111.9 (CH), 81.26 (C), 32.36 (CH$_2$), 30.10 (CH$_2$), 28.12 (CH$_3$). IR (KBr), υ/cm$^{-1}$ 3005, 2932, 1724, 1614, 1589, 1489, 1394, 1328, 1262, 1130, 1078, 757, 689. HRMS (ESI+) [M+H]$^+$ Calculated for [C$_{21}$H$_{21}$O$_3$N$_5$F$_3$]$^+$ 448.1596 found 448.1599.

Example 27H: methyl 4-(6-(((tert-butoxycarbonyl)amino)methyl)-1,2,4,5-tetrazin-3-yl)benzoate (5h)

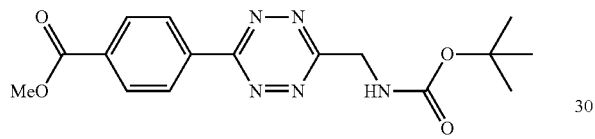

To a microwave reaction tube was sequentially charged with 3n (57 mg, 0.22 mmol), Pd(dppf)Cl$_2$ (24 mg, 0.033 mmol, 15 mol %), 4-methoxycarbonylphenylboronic acid (120 mg, 0.66 mmol), Ag$_2$O (128 mg, 0.55 mmol) and DMF (2.2 mL) in glove box. After heating under nitrogen at 100° C. for 3 h, the DMF was removed by rotary evaporation under high vacuum. The residue was purified by column chromatography (CH$_2$Cl$_2$:Et$_2$O 100:0 to 95:5) to give the title compound as pink solid (53 mg, 69%). $^1$H NMR (400 MHz, CDCl$_3$) δ 8.67 (app d, J=8.3 Hz, 2H), 8.24 (app d, J=8.3 Hz, 2H), 5.62 (s, 1H), 5.05 (d, J=5.8 Hz, 2H), 3.98 (s, 3H), 1.47 (s, 9H). $^{13}$C NMR (101 MHz, CDCl$_3$) δ 166.95 (C), 166.42 (C), 164.59 (C), 155.95 (C), 135.52 (C), 133.95 (C), 130.52 (CH), 128.20 (CH), 80.63 (C), 52.67 (CH$_2$), 43.67 (CH$_3$), 28.45 (CH$_3$). IR (KBr), υ/cm$^{-1}$ 3070, 2979, 2930, 1723, 1697, 1515, 1367, 1281, 1251, 1171, 1110. HRMS [M+H]$^+$ m/z calcd. for [C$_{16}$H$_{20}$O$_4$N$_5$]$^+$ 346.1515, found 346.1503.

Example 27I: methyl 3-(6-(3-cyanophenyl)-1,2,4,5-tetrazin-3-yl)propanoate (5i)

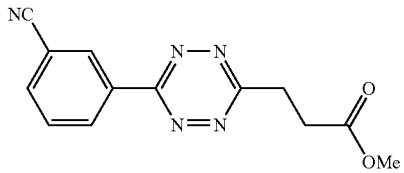 [SMILES: COC(=O)CCc1nnc(-c2cccc(C#N)c2)nn1]

To a microwave reaction tube was sequentially charged with 3k (55 mg, 0.26 mmol), Pd(dppf)Cl$_2$ (28 mg, 0.038 mmol, 15 mol %), 3-cyanophenylboronic acid (112 mg, 0.76 mmol), Ag$_2$O (147 mg, 0.64 mmol) and DMF (2.5 mL) in glove box. After heating under nitrogen at 100° C. for 3 h, the DMF was removed by rotary evaporation under high vacuum. The residue was purified by column chromatography (Hexane:EA 100:0 to 75:25) to give the title compound as pink solid (42 mg, 61%). $^1$H NMR (600 MHz, CDCl$_3$) δ 8.92 (app t, J=1.7 Hz, 1H), 8.84 (ddd, J=7.9, 1.7, 1.2 Hz, 1H), 7.91 (app dt, J=7.9, 1.2 Hz, 1H), 7.74 (td, J=7.9, 0.6 Hz, 1H), 3.74 (app t, J=7.0 Hz, 2H), 3.71 (s, 3H), 3.13 (app t, J=7.0 Hz, 2H). $^{13}$C NMR (101 MHz, CDCl$_3$) δ 172.51 (C), 169.41 (C), 162.96 (C), 135.74 (CH), 133.20 (C), 131.91 (CH), 131.54 (CH), 130.34 (CH), 118.05 (C), 113.90 (C), 52.20 (CH$_3$), 30.58 (CH$_2$), 29.89 (CH$_2$). IR (KBr), υ/cm$^{-1}$ 3079, 2954, 2924, 2232, 1737, 1603, 1437, 1396, 1369, 1198, 1176, 905, 687. HRMS [M+H]$^+$ m/z calcd. for [C$_{13}$H$_{12}$O$_2$N$_5$]$^+$ 270.0991, found 270.0981.

Example 27J: (S)-tert-butyl 2-((tert-butoxycarbonyl)amino)-4-(6-(4-(trifluoromethyl)phenyl)-1,2,4,5-tetrazin-3-yl)butanoate (5j)

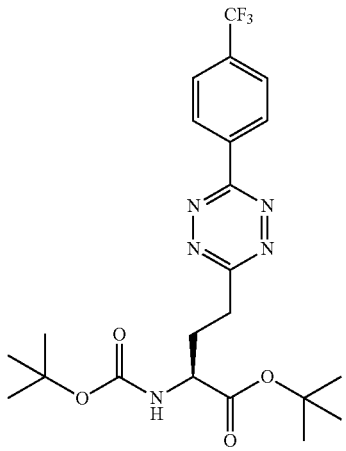 [SMILES: CC(C)(C)OC(=O)N[C@@H](CCc1nnc(-c2ccc(C(F)(F)F)cc2)nn1)C(=O)OC(C)(C)C]

To a microwave reaction tube was sequentially charged with 3p (72 mg, 0.19 mmol), Pd(dppf)Cl$_2$ (21 mg, 0.028 mmol, 15 mol %), 4-trifluoromethylboronic acid (107 mg, 0.56 mmol), Ag$_2$O (108 mg, 0.47 mmol) and DMF (1.9 mL) in glove box. After heating under nitrogen at 100° C. for 3 h, the DMF was removed by rotary evaporation under high vacuum. The residue was purified by column chromatography (CH$_2$Cl$_2$:Et$_2$O 100:0 to 97:3) to give the title compound as pink solid (37 mg, 56%). $^1$H NMR (400 MHz, CDCl$_3$) δ 8.73 (app d, J=8.2 Hz, 2H), 7.86 (app d, J=8.2 Hz, 2H), 5.17 (d, J=8.0 Hz, 1H), 4.40 (app dt, J=8.0, 4.9 Hz, 1H), 3.72-3.32 (m, 2H), 2.65-2.49 (m, 1H), 2.38-2.20 (m, 1H), 1.49 (s, 9H), 1.41 (s, 9H), peak at 4.92, 4.24 ppm due to minor rotamer. $^{13}$C NMR (101 MHz, CDCl$_3$) δ 171.26 (C), 170.03 (C), 163.46 (C), 155.45 (C), 135.17 (C), 134.26 (q, $J_{C-F}$=32.7 Hz, C), 128.39 (CH), 126.30 (q, $J_{C-F}$=1.9 Hz, CH), 123.83 (q, $J_{C-F}$=271.0 Hz, C), 82.72 (C), 80.11 (C), 53.50 (CH), 31.18 (CH$_2$), 28.40 (CH$_3$), 28.14 (CH$_3$). IR (KBr), υ/cm$^{-1}$ 3378, 3063, 2980, 2932, 1713, 1502, 1395, 1368, 1325, 1168, 1138, 1069, 859, 606. HRMS [M+H]$^+$ m/z calcd. for [C$_{22}$H$_{29}$O$_4$N$_5$F$_3$]$^+$ 484.2172, found 484.2160.

Example 27-2: Synthesis of Furyl-Substituted Tetrazines Via Ag-Mediated Liebeskind Coupling with 3-Furanboronic Acid

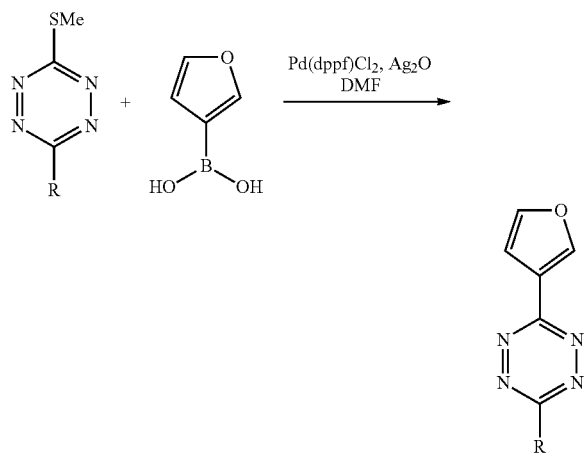

To a microwave reaction tube was sequentially charged with tetrazine thioether 3 (1 equiv.) Pd(dppf)Cl₂ (30 mol %), 3-furanboronic acid (6 equiv.), Ag₂O (5 equiv.) and DMF (0.05 M) in glove box. After heating under nitrogen at 100° C. for 3 h, the DMF was removed by rotary evaporation under high vacuum. Mixture of product and unreacted starting material was collect by flash column chromatography on silica gel and concentrated by rotary evaporation. Purification method A: oxidizing unreacted starting material. To a dry round bottom flask was charged with the mixture and CH₂Cl₂ (0.1 M). mCPBA (0.3 equiv.) was added at 0° C. After stirring at 0° C. for 2 h, 5% sodium bisulfite aqueous solution was added to quench excessive mCPBA. Aqueous and organic layers were separated. Aqueous layer was extracted by CH₂Cl₂ twice. All organic layers were combined, sequentially washed with saturate sodium bicarbonate solution, water, brine, dried over sodium sulfate and concentrated by rotary evaporation. The residue was purified by flash column chromatography on silica gel. Purification method B: reverse phase chromatography. Two 14 g YAMAZEN C18 columns were stacked. Tetrazine mixture was dissolved in minimum amount of methanol, diluted by water and loaded on column. H₂O:MeOH 10:0 to 0:10 was used as the eluent, flow rate 15 mL/min.

Example 27K: (2S,3S)-tert-butyl 2-(6-(furan-3-yl)-1,2,4,5-tetrazin-3-yl)-3-(pyridin-4-ylmethyl)pyrrolidine-1-carboxylate (5k)

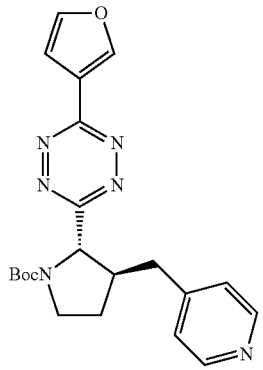 [SMILES: CC(C)(C)OC(=O)N1CC[C@H](Cc2ccncc2)[C@H]1c1nnc(-c2ccoc2)nn1]

The general protocol was followed with 3v (21 mg, 0.054 mmol), Pd(dppf)Cl₂ (12 mg, 0.016 mmol), 3-furanboronic acid (36 mg, 0.32 mmol), Ag₂O (63 mg, 0.27 mmol) and DMF (1.1 ml). A pink solid (13 mg, 0.033 mmol, 60%) was obtained following purification method B. Two rotamers: ¹H NMR (400 MHz, CDCl₃) δ 8.57-8.43 (m, 6H), 7.63 (s, 1H), 7.61 (s, 1H), 7.23 (s, 1H), 7.21 (s, 1H), 7.10 (app d, J=4.5 Hz, 2H), 7.06 (app d, J=4.5 Hz, 2H), 5.08 (d, J=4.8 Hz, 1H), 4.94 (d, J=5.9 Hz, 1H), 3.92-3.66 (m, 4H), 3.09-2.72 (m, 6H), 2.08-2.03 (m, 2H), 1.87-1.69 (m, 2H), 1.40 (s, 9H), 1.11 (s, 9H). ¹³C NMR (101 MHz, CDCl₃) δ 170.35 (C), 169.89 (C), 162.37 (C), 162.28 (C), 154.45 (C), 153.37 (C), 150.08 (CH, both rotamers), 147.80 (C), 147.70 (C), 146.24 (CH), 146.12 (CH), 145.18 (CH), 145.01 (CH), 124.45 (CH), 124.33 (CH), 121.13 (C), 120.88 (C), 108.78 (CH, both rotamers), 80.50 (C, both rotamers), 65.42 (CH), 65.16 (CH), 48.41 (CH), 47.23 (CH), 46.40 (CH₂), 46.30 (CH₂), 37.83 (CH₂, both rotamers), 29.79 (CH₂), 29.70 (CH₂), 28.49 (CH₃), 28.24 (CH₃). IR (KBr), υ/cm⁻¹ 3128, 3027, 2976, 2930, 1696, 1600, 1515, 1389, 1367, 1161, 1126, 1081, 935, 878, 736. HRMS [M+H]⁺ m/z calcd. for [C₂₁H₂₅O₃N₆]⁺ 409.1988, found 409.1976.

Example 27I: methyl 3-(6-(furan-3-yl)-1,2,4,5-tetrazin-3-yl)propanoate (5l)

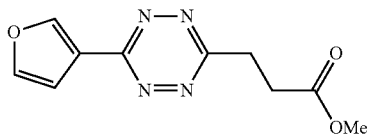 [SMILES: COC(=O)CCc1nnc(-c2ccoc2)nn1]

The general protocol was followed with 3k (42 mg, 0.20 mmol), Pd(dppf)Cl₂ (43 mg, 0.059 mmol), 3-furanboronic acid (132 mg, 1.2 mmol), Ag₂O (227 mg, 0.98 mmol) and DMF (3.9 ml). A pink solid (28 mg, 0.12 mmol, 61%) was obtained following purification method A after column chromatography (Hexane:EA 100:0 to 85:15). ¹H NMR (400 MHz, CDCl₃) δ 8.51-8.50 (m, 1H), 7.61 (app t, J=1.7 Hz, 1H), 7.22 (dd, J=1.8, 0.8 Hz, 1H), 3.70 (s, 3H), 3.66 (app t, J=7.1 Hz, 2H), 3.08 (app t, J=7.1 Hz, 2H). ¹³C NMR (101 MHz, CDCl₃) δ 172.62 (C), 168.22 (C), 162.07 (C), 145.99 (CH), 145.03 (CH), 121.10 (C), 108.76 (CH), 52.18 (CH₃), 30.76 (CH₂), 29.89 (CH₂). IR (KBr), υ/cm⁻¹ 3145, 2931, 1730, 1591, 1258, 1194, 1168, 1084. HRMS [M+H]⁺ m/z calcd. for [C₁₀H₁₁O₃N₄]⁺ 235.0831, found 235.0823.

Example 27M: (S)-tert-butyl 2-((tert-butoxycarbonyl)amino)-4-(6-(furan-3-yl)-1,2,4,5-tetrazin-3-yl)butanoate (5m)

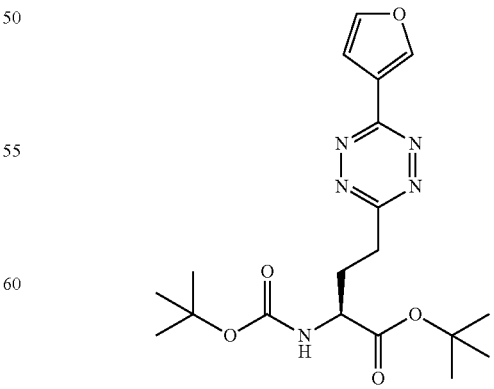

The general protocol was followed with 3p (75 mg, 0.19 mmol), Pd(dppf)Cl₂ (43 mg, 0.058 mmol), 3-furanboronic acid (131 mg, 1.2 mmol), Ag$_2$O (225 mg, 0.97 mmol) and DMF (3.9 ml). A pink solid (43 mg, 0.11 mmol, 56%) was obtained following purification method A after column chromatography (Hexane:EA 100:0 to 85:15). $^1$H NMR (400 MHz, CDCl$_3$) δ 8.53 (dd, J=1.8, 0.8 Hz, 1H), 7.64 (app t, J=1.7 Hz, 1H), 7.25 (dd, J=1.8, 0.8 Hz, 1H), 5.18 (d, J=8.2 Hz, 1H), 4.41 (app td, J=7.9, 4.8 Hz, 1H), 3.51-3.35 (m, 2H), 2.71-2.46 (m, 1H), 2.32-2.23 (m, 1H), 1.51 (s, 9H), 1.45 (s, 9H), peak at 4.94, 4.24 ppm due to minor rotamer. $^{13}$C NMR (101 MHz, CDCl$_3$) δ 171.33 (C), 169.12 (C), 161.95 (C), 155.44 (C), 145.93 (CH), 145.02 (CH), 121.13 (C), 108.76 (CH), 82.65 (C), 80.08 (C), 53.57 (CH), 31.26 (CH$_2$), 31.19 (CH$_2$), 28.43 (CH$_3$), 28.15 (CH$_3$). IR (KBr), υ/cm$^{-1}$ 3366, 3131, 2979, 2933, 1715, 1589, 1515, 1368, 1250, 1159, 873. HRMS [M+H]$^+$ m/z calcd. for [C$_{19}$H$_{28}$O$_5$N$_5$]$^+$406.2090, found 406.2079.

Example 27N: tert-butyl ((6-(furan-3-yl)-1,2,4,5-tetrazin-3-yl)methyl)carbamate (5n)

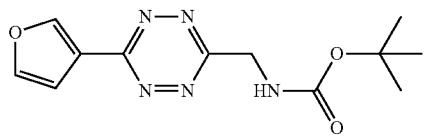 [SMILES: CC(C)(C)OC(=O)NCc1nnc(-c2ccoc2)nn1]

The general protocol was followed with 3n (50 mg, 0.19 mmol), Pd(dppf)Cl$_2$ (43 mg, 0.058 mmol), 3-furanboronic acid (130 mg, 1.2 mmol), Ag$_2$O (225 mg, 0.97 mmol) and DMF (3.9 ml). A pink solid (34 mg, 0.12 mmol, 62%) was obtained following purification method A after column chromatography (Hexane:EA 10:0 to 8:2). $^1$H NMR (400 MHz, CDCl$_3$) δ 8.52-8.52 (m, 1H), 7.61 (app t, J=1.8 Hz, 1H), 7.21 (app d, J=1.8 Hz, 1H), 5.60 (s, 1H), 4.96 (d, J=6.0 Hz, 2H), 1.45 (s, 9H). $^{13}$C NMR (101 MHz, CDCl$_3$) δ 166.20 (C), 162.65 (C), 155.92 (C), 146.23 (CH), 145.07 (CH), 120.94 (C), 108.72 (CH), 80.45 (C), 43.61 (CH$_2$), 28.42 (CH$_3$). IR (KBr), υ/cm$^{-1}$ 3360, 3138, 2979, 2931, 1711, 1588, 1368, 1250, 1161. HRMS [M+H]$^+$ m/z calcd. for [C$_{12}$H$_{16}$O$_3$N$_5$]$^+$ 278.1253, found 278.1242.

Example 27O: (S)-tert-butyl (1-(6-(furan-3-yl)-1,2,4,5-tetrazin-3-yl)-2-(pyridin-4-yl)ethyl)carbamate (5o)

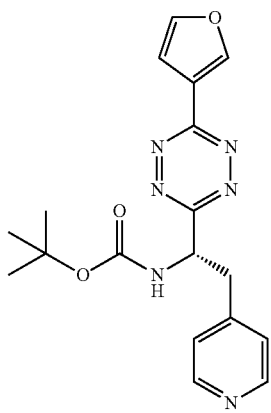 [SMILES: CC(C)(C)OC(=O)N[C@@H](Cc1ccncc1)c1nnc(-c2ccoc2)nn1]

The general protocol was followed with 3t (18 mg, 0.052 mmol), Pd(dppf)Cl$_2$ (11 mg, 0.016 mmol), 3-furanboronic acid (35 mg, 0.31 mmol), Ag$_2$O (60 mg, 0.26 mmol) and DMF (1.0 ml). A pink solid (9.0 mg, 0.024 mmol, 47%) was obtained following purification method B. $^1$H NMR (400 MHz, CDCl$_3$) δ 8.53-8.49 (m, 3H), 8.50 (app d, J=5.0 Hz, 2H), 7.63 (app t, J=1.8 Hz, 1H), 7.22 (app d, J=1.8 Hz, 1H), 7.08 (app d, J=5.0 Hz, 2H), 5.73-5.51 (m, 1H), 5.58 (d, J=8.8 Hz, 1H), 3.46 (dd, J=14.0, 5.9 Hz, 1H), 3.30 (dd, J=14.0, 7.6 Hz, 1H), 1.40 (s, 9H). $^{13}$C NMR (101 MHz, CDCl$_3$) δ 167.81 (C), 162.69 (C), 155.05 (C), 150.14 (CH), 146.56 (CH), 145.24 (CH), 144.96 (C), 124.79 (CH), 120.85 (C), 108.76 (CH), 80.74 (C), 54.13 (CH), 40.85 (CH$_2$), 28.36 (CH$_3$). IR (KBr), υ/cm$^{-1}$ 3337, 3153, 3028, 2978, 2930, 1708, 1609, 1589, 1515, 1367, 1250, 1161. HRMS [M+H]$^+$ m/z calcd. for [C$_{18}$H$_{21}$O$_3$N$_6$]$^+$ 369.1675, found 369.1662.

Example 27P: (3aS,4S,6aR)-4-(4-(6-(furan-3-yl)-1,2,4,5-tetrazin-3-yl)butyl)tetrahydro-1H-thieno[3,4-d]imidazol-2(3H)-one (5p)

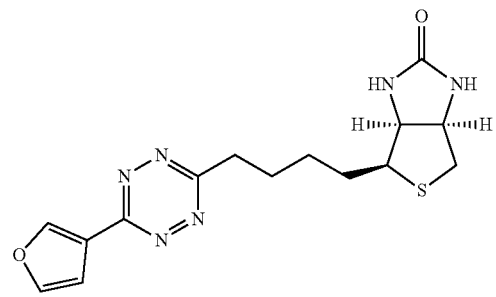 [SMILES: O=C1N[C@H]2[C@H](CS[C@H]2CCCCc2nnc(-c3ccoc3)nn2)N1]

The general protocol was followed with 3q (40 mg, 0.12 mmol), Pd(dppf)Cl$_2$ (27 mg, 0.037 mmol), 3-furanboronic acid (81 mg, 0.72 mmol), Ag$_2$O (141 mg, 0.61 mmol) and DMF (2.4 ml). A pink solid (20 mg, 0.058 mmol, 48%) was obtained following purification method B. $^1$H NMR (400 MHz, CDCl$_3$) δ 8.49-8.48 (m, 1H), 7.61 (app t, J=1.6 Hz, 1H), 7.21 (app d, J=1.6 Hz, 1H), 6.12 (s, 1H), 5.32 (s, 1H), 4.53 (app dd, J=7.4, 4.9 Hz, 1H), 4.33 (app dd, J=7.4, 5.0 Hz, 1H), 3.34 (app t, J=7.7 Hz, 2H), 3.20-3.15 (m, 1H), 2.91 (dd, J=12.8, 5.0 Hz, 1H), 2.74 (d, J=12.8 Hz, 1H), 2.09-1.93 (m, 2H), 1.91-1.69 (m, 2H), 1.70-1.48 (m, 2H). $^{13}$C NMR (101 MHz, CDCl$_3$) δ 169.71 (C), 163.60 (C), 161.95 (C), 145.86 (CH), 145.00 (CH), 121.13 (C), 108.75 (CH), 62.01 (CH), 60.23 (CH), 55.56 (CH), 40.70 (CH$_2$), 34.49 (CH$_2$), 28.40 (CH$_2$), 28.36 (CH$_2$), 28.33 (CH$_2$). IR (KBr), υ/cm$^{-1}$ 3223, 3134, 2932, 2858, 1703, 1589, 1515, 1462, 1267, 1159, 872. HRMS [M+H]$^+$ m/z calcd. for [C$_{15}$H$_{19}$O$_2$N$_6$S]$^+$ 347.1290, found 347.1279.

Example 28: Synthesis of Vinylether-Substituted Tetrazine (61) Via Cu-Mediated Liebeskind Coupling with tributyl(1-ethoxyvinyl)tin

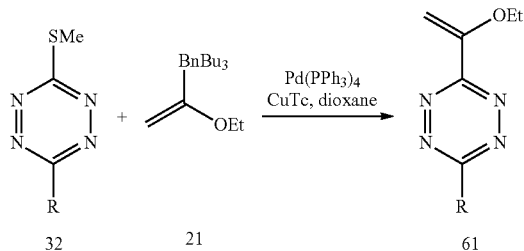

To a dry round-bottom flask was added tetrazine thioether 32 (1 equiv.), Pd(PPh$_3$)$_4$ (15 mol %) and CuTc (2 equiv.) The flask was outfitted with a septum-fitted gas inlet adapter, and was twice evacuated and backfilled with nitrogen. Tributyl (1-ethoxyvinyl)tin 21 (2 equiv.) and anhydrous dioxane (5 mM in 3) were added via syringe, and the flask was heated by an oil bath at 100° C. for 16-30 min. After cooling down, the reaction mixture was diluted with hexane and filtered through short pad of 10% K2CO$_3$ modified silica gel. Et$_2$O was used to washed off all red fractions. The residue was concentrated by rotary evaporation and purified by flash column chromatography on 10% K2CO$_3$ modified silica gel.

Vinylether tetrazines with alkyl substituents 6h-k was stored as 1-5 mM solution in CH$_2$Cl$_2$ in −20° C. to prevent self-condensation.

Example 28A: 3-(1-ethoxyvinyl)-6-phenyl-1,2,4,5-tetrazine (6a)

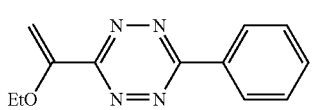

The general protocol was followed with 3x (50 mg, 0.24 mmol), Pd(PPh$_3$)$_4$ (43 mg, 0.037 mmol), CuTc (94 mg, 0.49 mmol), tributyl(1-ethoxyvinyl)tin (0.17 mL, 0.49 mmol) and 1,4-dioxane (49 mL) at 100° C. for 30 min. A pink solid (41 mg, 0.18 mmol, 74%) was obtained after column chromatography (CH$_2$Cl$_2$:Et$_2$O 100:0 to 96:4). $^1$H NMR (400 MHz, CDCl$_3$) δ 8.63 (dd, J=8.2, 1.6 Hz, 2H), 7.72-7.46 (m, 3H), 6.02 (d, J=2.9 Hz, 1H), 4.93 (d, J=2.9 Hz, 1H), 4.15 (q, J=7.0 Hz, 2H), 1.55 (t, J=7.0 Hz, 3H). $^{13}$C NMR (101 MHz, CDCl$_3$) δ 164.15 (C), 161.78 (C), 153.73 (C), 133.00 (CH), 131.74 (C), 129.44 (CH), 128.30 (CH), 93.16 (CH$_2$), 64.67 (CH$_2$), 14.51 (CH$_3$). IR (KBr), υ/cm$^{-1}$ 3072, 2978, 2929, 1614, 1599, 1421, 1314, 1182, 1056. HRMS [M+H]$^+$ m/z calcd. for [C$_{12}$H$_{13}$ON$_4$]$^+$ 229.1089, found 229.1082.

Example 28B: (3R,5R,8R,9S,10S,13R,14S,17R)-17-((R)-4-(6-(1-ethoxyvinyl)-1,2,4,5-tetrazin-3-yl)butan-2-yl)-10,13-dimethylhexadecahydro-1H-cyclopenta[a]phenanthren-3-ol (6b)

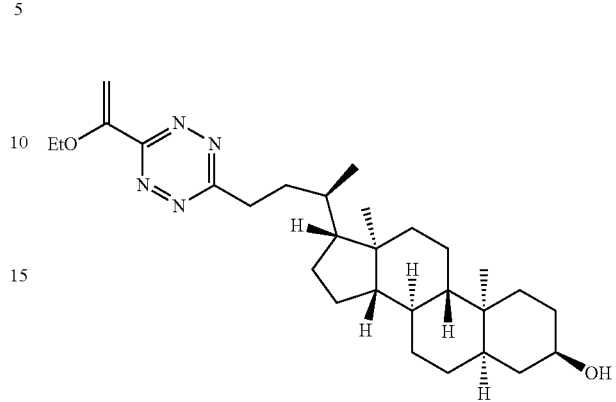

The general protocol was followed with 3r (62 mg, 0.14 mmol), Pd(PPh$_3$)$_4$ (23 mg, 0.020 mmol), CuTc (52 mg, 0.27 mmol), tributyl(1-ethoxyvinyl)tin (0.092 mL, 0.27 mmol) and 1,4-dioxane (27 mL) at 100° C. for 16 min. A pink oil (41 mg, 0.082 mmol, 61%) was obtained after column chromatography (CH$_2$Cl$_2$:Et$_2$O 100:0 to 85:15). $^1$H NMR (400 MHz, CDCl$_3$) δ 5.94 (d, J=2.9 Hz, 1H), 4.88 (d, J=2.9 Hz, 1H), 4.11 (q, J=7.0 Hz, 2H), 3.67-3.57 (m, 1H), 3.38 (ddd, J=14.1, 10.5, 5.0 Hz, 1H), 3.23 (ddd, J=14.1, 10.1, 6.4 Hz, 1H), 2.06 (dddd, J=13.2, 10.1, 6.4, 2.7 Hz, 1H), 2.11-1.95 (m, 2H), 1.91-0.93 (m, 30H), 0.92 (s, 3H), 0.64 (s, 3H). $^{13}$C NMR (101 MHz, CDCl$_3$) δ 171.26, 161.93, 153.72, 92.82, 72.01, 64.62, 56.59, 56.07, 42.93, 42.20, 40.54, 40.30, 36.57, 35.96, 35.76, 35.47, 34.86, 34.70, 31.93, 30.68, 28.37, 27.31, 26.53, 24.33, 23.51, 20.95, 18.58, 14.46, 12.22. IR (KBr), υ/cm$^{-1}$ 3390, 2934, 2836, 1670, 1618, 1447, 1379, 1269, 1160, 1057, 736. HRMS [M+H]$^+$ m/z calcd. for [C$_{29}$H$_{47}$O$_2$N$_4$]$^+$ 483.3699, found 483.3685.

Example 28C: methyl 3-(6-(1-ethoxyvinyl)-1,2,4,5-tetrazin-3-yl)propanoate (6c)

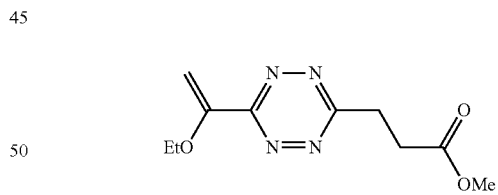

The general protocol was followed with 3k (50 mg, 0.23 mmol), Pd(PPh$_3$)$_4$ (40 mg, 0.035 mmol), CuTc (90 mg, 0.47 mmol), tributyl(1-ethoxyvinyl)tin (0.16 mL, 0.47 mmol) and 1,4-dioxane (47 mL) at 100° C. for 30 min. A pink oil (29 mg, 0.12 mmol, 52%) was obtained after column chromatography (CH$_2$Cl$_2$:Et$_2$O 100:0 to 97:3). $^1$H NMR (400 MHz, CDCl$_3$) δ 5.97 (d, J=2.9 Hz, 1H), 4.90 (d, J=2.9 Hz, 1H), 4.12 (q, J=7.0 Hz, 2H), 3.82-3.59 (m, 5H), 3.07 (app t, J=7.1 Hz, 2H), 1.52 (t, J=7.0 Hz, 3H). $^{13}$C NMR (101 MHz, CDCl$_3$) 172.52 (C), 168.84 (C), 162.13 (C), 153.57 (C), 93.19 (C), 64.65 (CH$_2$), 52.15 (CH$_3$), 30.66 (CH$_2$), 29.84 (CH$_2$), 14.45 (CH$_3$). IR (KBr), υ/cm$^{-1}$ 2923, 2851, 1737, 1620, 1437, 1378, 1271, 1160, 1056, 847. HRMS [M+H]$^+$ m/z calcd. for [C$_{10}$H$_{15}$O$_3$N$_4$]$^+$ 239.1144, found 239.1123.

Example 28D: 3-(1-ethoxyvinyl)-6-((1-phenyl-5-(trifluoromethyl)-1H-pyrazol-4-yl)methyl)-1,2,4,5-tetrazine (6d)

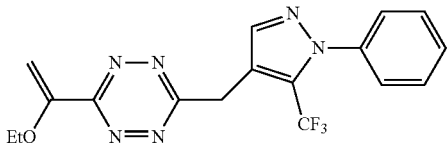 [SMILES: C=C(OCC)c1nnc(Cc2cnn(-c3ccccc3)c2C(F)(F)F)nn1]

The general protocol was followed with 3u (27 mg, 0.075 mmol), Pd(PPh₃)₄ (13 mg, 0.011 mmol), CuTc (29 mg, 0.15 mmol), tributyl(1-ethoxyvinyl)tin (0.051 mL, 0.15 mmol) and 1,4-dioxane (15 mL) at 100° C. for 16 min. A pink oil (16 mg, 0.042 mmol, 57%) was obtained after column chromatography (CH₂Cl₂:Et₂O 100:0 to 97:3). ¹H NMR (400 MHz, CDCl₃) δ 7.73 (s, 1H), 7.60-7.38 (m, 5H), 6.01 (d, J=2.9 Hz, 1H), 4.93 (d, J=2.9 Hz, 1H), 4.76 (s, 2H), 4.12 (q, J=7.0 Hz, 2H), 1.52 (t, J=7.0 Hz, 3H). ¹³C NMR (101 MHz, CDCl₃) δ 168.28 (C), 162.13 (C), 153.44 (C), 141.24 (CH), 139.49 (C), 130.63 (q, $J_{C-F}$=37.8 Hz, C), 129.61 (CH), 129.17 (CH), 126.13 (q, $J_{C-F}$=0.8 Hz, CH), 120.30 (q, $J_{C-F}$=268.7 Hz, C), 117.74 (q, $J_{C-F}$=1.5 Hz, C), 93.64 (C), 64.71 (CH₂), 30.12 (CH₂), 30.10 (CH₂), 14.45 (CH₃). IR (KBr), υ/cm⁻¹ 3064, 2983, 2930, 1618, 1598, 1502, 1398, 1310, 1184, 1159, 1132, 1091, 1053, 975, 768, 695. HRMS [M+H]⁺ m/z calcd. for [C₁₇H₁₆ON₆F₃]⁺ 377.1338, found 377.1317

Example 28E: 3-(2-(6-(1-ethoxyvinyl)-1,2,4,5-tetrazin-3-yl)ethyl)-5,5-difluoro-7,9-dimethyl-5H-dipyrrolo[1,2-c:2',1'-f][1,3,2]diazaborinin-4-ium-5-uide (6e)

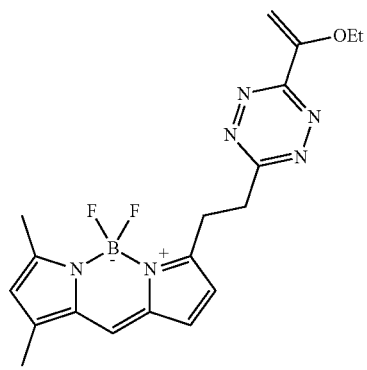

The general protocol was followed with 3w (20 mg, 0.053 mmol), Pd(PPh₃)₄ (9.3 mg, 0.0080 mmol), CuTc (21 mg, 0.11 mmol), tributyl(1-ethoxyvinyl)tin (0.038 mL, 0.11 mmol) and 1,4-dioxane (11 mL) at 100° C. for 16 min. An orange solid (10 mg, 0.026 mmol, 47%) was obtained after column chromatography (CH₂Cl₂:Et₂O 100:0 to 99:1). ¹H NMR (600 MHz, CDCl₃) δ 7.08 (s, 1H), 6.85 (d, J=4.0 Hz, 1H), 6.24 (d, J=4.0 Hz, 1H), 6.11 (s, 1H), 5.95 (d, J=2.9 Hz, 1H), 4.89 (d, J=2.9 Hz, 1H), 4.12 (q, J=7.0 Hz, 2H), 3.81 (app t, J=7.6 Hz, 2H), 3.66 (app t, J=7.6 Hz, 2H), 2.56 (s, 3H), 2.25 (s, 3H), 1.52 (t, J=7.0 Hz, 3H). ¹³C NMR (101 MHz, CDCl₃) δ 169.44 (C), 162.05 (C), 161.14 (C), 155.94 (C), 153.69 (C) 144.31 (C), 133.59 (C), 127.95 (CH), 124.05 (CH), 120.78 (CH), 116.79 (CH), 93.13 (C), 64.63 (CH₂), 34.03 (CH₂), 26.67 (CH₂), 15.15 (CH₃), 14.47 (CH₃), 11.49 (CH₃). HRMS [M+H]⁺ m/z calcd. for [C₁₉H₂₂ON₆F₂B]⁺ 399.1916, found 399.1898.

Example 29: Synthesis of New MAGL Probes

Example 29A: 1,1,1,3,3,3-hexafluoropropan-2-yl 4-(((4-(methoxycarbonyl)phenyl)sulfonamido)methyl)piperidine-1-carboxylate

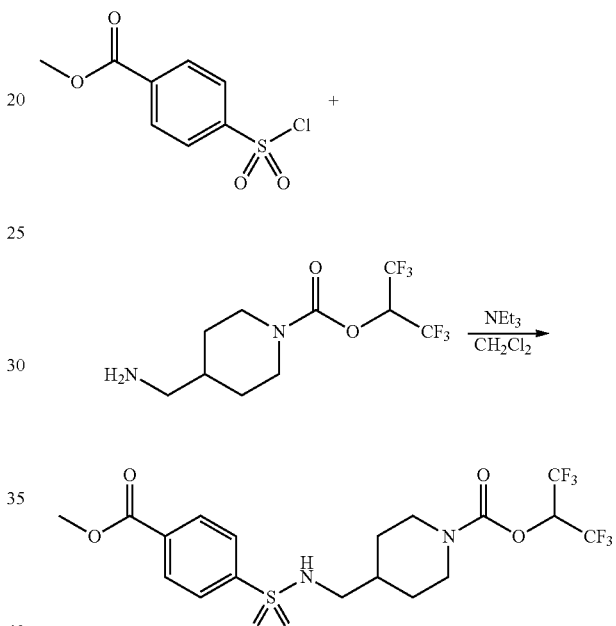

A round bottom flask was charged with 1,1,1,3,3,3-hexafluoropropan-2-yl 4-(aminomethyl)piperidine-1-carboxylate hydrochloride(1.30 g, 3.8 mmol) and methyl 4-(chlorosulfonyl)benzoate(1.77 g, 7.54 mmol). The flask was outfitted with a septum-fitted gas inlet adapter and then evacuated and filled with nitrogen. Anhydrous CH₂C₂ (50 mL) was added to the flask via syringe. The flask was cooled by an ice bath (0° C.), and triethylamine (763 mg, 7.54 mmol) was added. After stirring under nitrogen at 20° C. for 1 h, the reaction was diluted with CH₂Cl₂ (50 mL), then the organic phase was washed with water (50 mL×2) and brine (50 mL), dried over sodium sulfate, filtered and concentrated by rotary evaporation. An off-white solid (1.20 g, 2.37 mmol, 63%) was obtained after column chromatography (petroleum ether:EA 100:0 to 55:45). ¹H NMR (400 MHz, CDCl₃) 8.19 (app d, J=8.6 Hz, 2H), 7.92 (app d, J=8.5 Hz, 2H), 5.73 (hept, J=6.2 Hz, 1H), 4.55 (t, J=6.6 Hz, 1H), 4.31-4.04 (m, 2H), 3.97 (s, 3H), 2.99-2.72 (m, 4H), 1.83-1.67 (m, 3H), 1.20-1.03 (m, 2H). ¹³C NMR (101 MHz, DMSO) δ 165.65, 151.02, 145.18, 133.25, 130.48, 127.30, 121.34 (q, $J_{C-F}$=282.0 Hz), 67.68 (hept, $J_{C-F}$=33.0 Hz), 52.97, 47.91, 44.19, 43.70, 35.76, 29.47, 29.10. HRMS [M+H]⁺ m/z calcd. for [C₁₈H₂₀O₆N₂F₆SNa]⁺ 529.0844, found 529.0844.

Example 29B: 4-(N-((1-(((1,1,1,3,3,3-hexafluoropropan-2-yl)oxy)carbonyl)piperidin-4-yl)methyl)sulfamoyl)benzoic acid

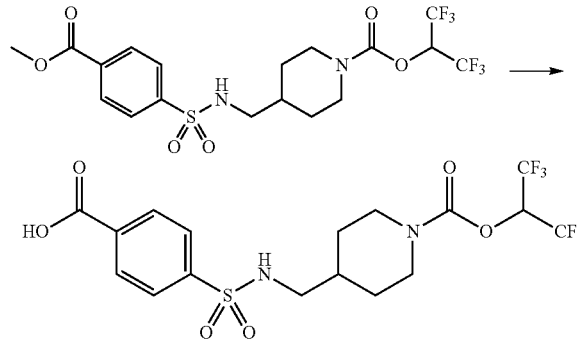

A round bottom flask was charged with 1,1,1,3,3,3-hexafluoropropan-2-yl 4-(((4-(methoxycarbonyl)phenyl)sulfonamido)methyl) piperidine-1-carboxylate (880 mg, 1.74 mmol), LiOH·H$_2$O (182 mg, 4.34 mmol) in THF (20 mL) and H$_2$O (20 mL). After stirring at 20° C. for 2 h, the mixture was acidized by 2 N HCl to pH 3~4 and extracted by EA (50 mL×2). The organic phase was washed with water (30 mL) and brine (30 mL×2), dried over Na2SO4, filtered and concentrated by rotary evaporation. An off-white solid (735 mg, 1.53 mmol, 86%) was obtained after triturating from CH$_2$Cl$_2$/Hexane (3 mL/15 mL). $^1$H NMR (400 MHz, DMSO) δ 13.40 (s, 1H), 8.12 (app d, J=8.5 Hz, 2H), 8.05-7.60 (m, 3H), 6.52 (hept, J=6.4 Hz, 1H), 3.91 (t, J=14.2 Hz, 2H), 3.05-2.74 (m, 2H), 2.67 (t, J=6.3 Hz, 2H), 1.80-1.37 (m, 3H), 1.37-0.68 (m, 2H). $^{13}$C NMR (101 MHz, DMSO) δ 166.24, 150.56, 144.30, 134.07, 130.14, 126.71, 120.90 (q, J$_{C-F}$=281.0 Hz), 67.20 (hept, J$_{C-F}$=33.2 Hz), 47.45, 44.21, 43.76, 35.31, 29.03, 28.65. LCMS [M+H]-m/z calcd. for [C$_{17}$H$_{16}$O$_6$N$_2$F$_6$SNa]$^+$ 515.0687, found 515.0685.

Example 29C: 1,1,1,3,3,3-hexafluoropropan-2-yl 4-((4-(((3-methyloxetan-3 yl)methoxy)carbonyl)phenylsulfonamido) methyl)piperidine-1-carboxylate (11)

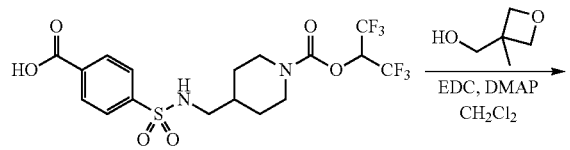

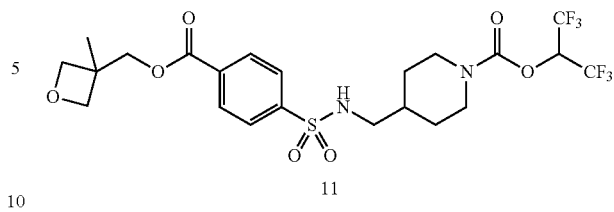

A dry round-bottom flask was charged with 3-methyl-3-oxetanemethanol (57.0 mg, 0.559 mmol), 1-(3-dimethylaminopropyl)-3-ethylcarbodiimide hydrochloride (117 mg, 0.609 mmol) and DMAP (6.20 mg, 0.0508 mmol). The flask was outfitted with a septum-fitted gas inlet adapter and then evacuated and filled with nitrogen. Anhydrous CH$_2$Cl$_2$ (5 mL, 0.1 M) was added to the flask via syringe. The flask was cooled by an ice bath (0° C.), and 4-(N-((1-(((1,1,1,3,3,3-hexafluoropropan-2-yl)oxy)carbonyl)piperidin-4-yl)methyl)sulfamoyl)benzoic acid (250 mg, 0.508 mmol) was added. After stirring under nitrogen at 0° C. for 15 min and at r.t overnight, the reaction mixture was diluted with CH$_2$Cl$_2$. The solution was washed with saturated sodium bicarbonate solution, water and brine, and the organics were dried over sodium sulfate and concentrated by rotary evaporation. A white solid (280 mg, 0.486 mmol, 96%) was obtained after column chromatography (CH$_2$Cl$_2$:EA 100:0 to 95:5). $^1$H NMR (400 MHz, CDCl$_3$) δ 8.21 (app d, J=8.4 Hz, 2H), 7.94 (app d, J=8.4 Hz, 2H), 5.73 (hept, J=6.3 Hz, 1H), 4.64-4.61 (m, 3H), 4.49 (d, J=6.0 Hz, 2H), 4.44 (s, 2H), 4.27-4.06 (m, 2H), 2.99-2.76 (m, 4H), 1.89-1.65 (m, 3H), 1.44 (s, 3H), 1.23-1.05 (m, 2H). $^{13}$C NMR (101 MHz, CDCl$_3$) δ 176.52 (C), 161.22 (C), 151.45 (C), 143.20 (C), 135.91 (C), 128.27 (CH), 127.91 (CH), 120.80 (q, J$_{C-F}$=281.6 Hz, C), 68.16 (hept, J$_{C-F}$=34.2 Hz, CH), 48.51 (CH$_2$), 44.79 (CH$_2$), 44.19 (CH$_2$), 36.47 (CH), 29.56 (CH$_2$), 29.20 (CH$_2$), 13.68 (CH$_3$). HRMS [M+H]$^+$ m/z calcd. for [C$_{22}$H$_{27}$O$_7$N$_2$F$_6$S]$^+$ 577.1443, found 577.1421.

Example 29D: 1,1,1,3,3,3-hexafluoropropan-2-yl 4-((4-(6-(methylthio)-1,2,4,5-tetrazin-3-yl)phenylsulfonamido)methyl)piperidine-1-carboxylate (31)

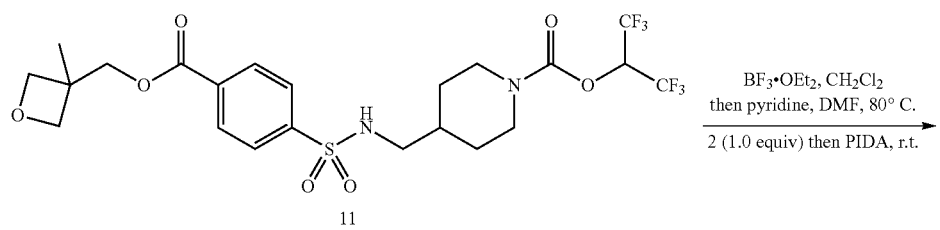

-continued

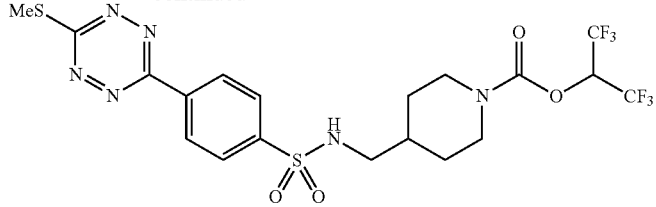

31

A dry round-bottom flask was charged with 11 (93 mg, 0.16 mmol) and a magnetic stirbar. The flask was outfitted with a septum-fitted gas inlet adapter, evacuated and refilled with nitrogen. Anhydrous $CH_2Cl_2$ (0.16 mL) was added via syringe and the resulting solution was cooled by an ice/brine bath (−5° C.) and $BF_3 \cdot OEt_2$ (10 µL, 0.081 mmol) was added via syringe. The resulting mixture was allowed to stir under nitrogen with continued cooling by the cold bath (maintained between −5° C. to −0° C.) for 4 h. Reaction mixture was quenched with pyridine (39 µL, 0.48 mmol), and then 2 (28 mg, 0.11 mmol) and DMF (0.11 mL) were added. The mixture was stirred vigorously and vacuum was carefully applied to remove $CH_2Cl_2$. The resulting mixture was then heated by an oil bath at 80° C. and the mixture was allowed to stir under nitrogen at 80° C. for 2 h. After cooling to r.t., PIDA (36 mg, 0.11 mmol) was added to the flask and the mixture allowed to stir at r.t. for 1 h. The mixture was diluted with $CH_2Cl_2$ and sequentially washed with saturated sodium bicarbonate, water and brine, dried over sodium sulfate and concentrated by rotary evaporation. A red solid (47 mg, 0.082 mmol, 72%) was obtained after purified by chromatography ($CH_2Cl_2$:$Et_2O$ 100:0 to 95:5). $^1$H NMR (600 MHz, $CDCl_3$) δ 8.69 (app d, J=8.5 Hz, 2H), 8.05 (app d, J=8.5 Hz, 2H), 5.72 (hept, J=6.3 Hz, 1H), 4.80 (t, J=6.6 Hz, 1H), 4.19-4.13 (m, 2H), 2.93 (t, J=6.5 Hz, 2H), 2.92-2.82 (m, 2H), 2.82 (s, 3H), 1.81-1.71 (m, 3H), 1.22-1.10 (m, 2H). $^{13}$C NMR (101 MHz, $CDCl_3$) δ 176.52 (C), 161.22 (C), 151.45 (C), 143.20 (C), 135.91 (C), 128.27 (CH), 127.91 (CH), 120.80 (q, $J_{C-F}$=281.6 Hz, C), 68.16 (hept, $J_{C-F}$=34.2 Hz, CH), 48.51 ($CH_2$), 44.79 ($CH_2$), 44.19 ($CH_2$), 36.47 (CH), 29.56 ($CH_2$), 29.20 ($CH_2$), 13.68 ($CH_3$). IR (KBr), υ/cm$^{-1}$ 3060, 2932, 2834, 1734, 1653, 1527, 1267, 1183, 740. HRMS [M+H]$^+$ m/z calcd. for $[C_{19}H_{21}O_4N_6F_6S_2]^+$ 575.0970, found 575.0956.

Example 30A: 1,1,1,3,3,3-hexafluoropropan-2-yl 4-((4-(6-(furan-3-yl)-1,2,4,5-tetrazin-3-yl)phenylsulfonamido)methyl)piperidine-1-carboxylate (100a)

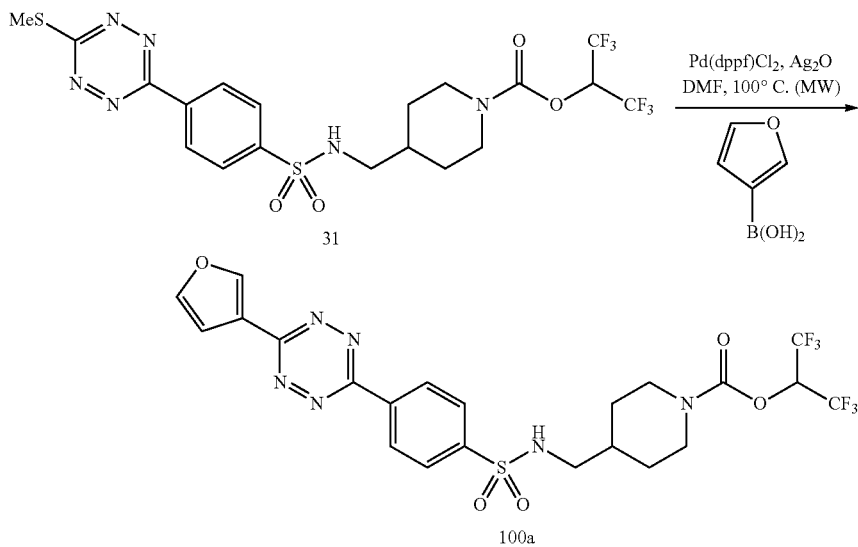

To a microwave reaction tube was sequentially charged with 31 (28 mg, 0.049 mmol), Pd(dppf)$Cl_2$ (11 mg, 0.015 mmol), 3-furanboronic acid (33 mg, 0.29 mmol), $Ag_2O$ (57 mg, 0.24 mmol) and DMF (1.0 ml) in glove box. After heating under nitrogen at 100° C. for 3 h, the DMF was removed by rotary evaporation under high vacuum. A pink solid (21 mg, 0.036 mmol, 74%) was obtained after reverse phase chromatography with two stacked 14 g YAMAZEN C18 columns ($H_2O$:MeOH 10:0 to 0:10). $^1$H NMR (400 MHz, $CDCl_3$) δ 8.78 (d, J=8.4 Hz, 2H), 8.60 (s, 1H), 8.08 (d, J=8.3 Hz, 2H), 7.67 (t, J=1.7 Hz, 1H), 7.29 (d, J=1.7 Hz, 1H), 5.73 (hept, J=6.1 Hz, 1H), 4.61 (t, J=6.6 Hz, 1H), 4.18 (t, J=14.3 Hz, 1H), 2.95 (t, J=6.6 Hz, 1H), 2.91-2.73 (m, 1H), 1.92-1.68 (m, 2H), 1.16 (t, J=13.2 Hz, 1H). $^{13}$C NMR (101 MHz, $CDCl_3$) δ 162.70 (C), 162.10 (C), 151.46 (C), 146.70 (CH), 145.36 (CH), 143.45 (C), 136.07 (C), 128.60 (CH), 127.95 (CH), 122.81 (q, $J_{C-F}$=279.9 Hz, C), 121.02 (C), 108.77 (CH), 68.16 (hept, $J_{C-F}$=34.2 Hz, CH), 48.54 ($CH_2$), 44.80 ($CH_2$), 44.20 ($CH_2$), 36.50 (CH), 29.57 ($CH_2$), 29.21 ($CH_2$). HRMS [M+H]$^+$ m/z calcd. for $[C_{22}H_{21}O_5N_6F_6S]^+$ 595.1198, found 595.1180.

Example 30B: 1,1,1,3,3,3-hexafluoropropan-2-yl 4-((4-(6-(1-ethoxyvinyl)-1,2,4,5-tetrazin-3-yl)phenylsulfonamido) methyl)piperidine-1-carboxylate (100b)

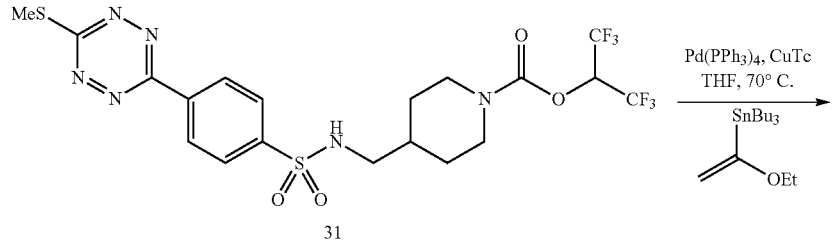

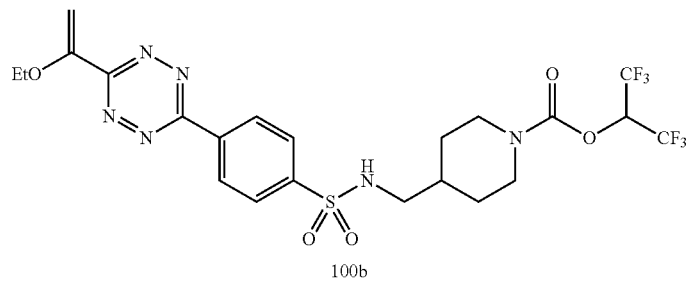

To a dry round-bottom flask was added 31 (15 mg, 0.026 mmol), Pd(PPh$_3$)$_4$ (4.5 mg, 0.039 mmol), CuTc (10 mg, 0.052 mmol). The flask was outfitted with a septum-fitted gas inlet adapter, and was twice evacuated and backfilled with nitrogen. Tributyl(1-ethoxyvinyl)tin (0.017 mL, 0.052 mmol) and anhydrous dioxane (5.2 mL) were added via syringe, and the flask was heated by an oil bath at 100° C. for 30 min. After cooling down, the reaction mixture was diluted with hexane and filtered through short pad of 10% K2CO$_3$ modified silica gel. Et$_2$O was used to washed off all red fractions. A pink oil (11 mg, 0.018 mmol, 67%) was obtained after column chromatography with 10% K2CO$_3$ modified silica gel (CH$_2$Cl$_2$:Et$_2$O 100:0 to 85:15). $^1$H NMR (400 MHz, CDCl$_3$) δ 8.79 (app d, J=8.5 Hz, 2H), 8.07 (app d, J=8.5 Hz, 2H), 6.09 (d, J=3.0 Hz, 1H), 5.72 (hept, J=6.3 Hz, 1H), 5.01 (d, J=3.0 Hz, 1H), 4.65 (t, J=6.6 Hz, 1H), 4.21-4.14 (m, 4H), 2.94 (app t, J=6.5 Hz, 2H), 2.90-2.80 (m, 2H), 1.90-1.70 (m, 3H), 1.56 (t, J=7.0 Hz, 3H), 1.20-1.13 (m, 2H). $^{13}$C NMR (101 MHz, CDCl$_3$) δ 163.05 (C), 162.04 (C), 153.42 (C), 151.46 (C), 143.72 (C), 135.77 (C), 128.95 (CH), 127.94 (CH), 120.81 (q, J$_{C-F}$=281.0 Hz, C), 94.37 (C), 68.16 (hept, J$_{C-F}$=34.2 Hz, C), 64.84 (CH$_2$), 48.55 (C), 44.79 (CH$_2$), 44.19 (CH$_2$), 36.50 (CH), 29.56 (CH$_2$), 29.21 (CH$_2$), 14.49 (CH$_3$). HRMS [M+H]$^+$ m/z calcd. for [C$_{22}$H$_{25}$O$_5$N$_6$F$_6$S]$^+$ 599.1511, found 599.1496.

Example 30C: 1,1,1,3,3,3-hexafluoropropan-2-yl 4-((4-(1,2,4,5-tetrazin-3-yl)phenylsulfonamido) methyl)piperidine-1-carboxylate (100c)

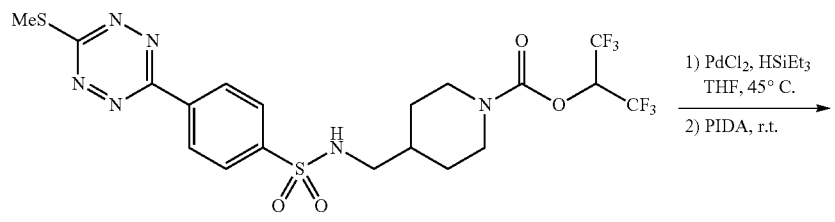

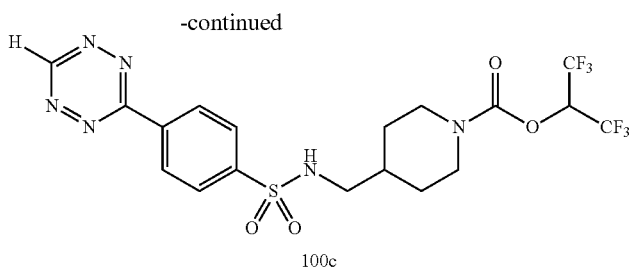

100c

To a dry round-bottom flask was added 31 (20 mg, 0.035 mmol), PdCl$_2$ (0.62 mg, 0.0035 mmol). The flask was outfitted with a septum-fitted gas inlet adapter, and was twice evacuated and backfilled with nitrogen. Triethylsilane (17 μL, 0.10 mmol) and anhydrous THF (0.35 mL) were added via syringe, and the flask was heated by an oil bath at 45° C. The mixture was allowed to stir at 45° C. for 24 h. PIDA (12 mg, 0.042 mmol) was added as a solid at r.t. After stirring at room temperature for 1 h, the reaction mixture was diluted with CH$_2$Cl$_2$, transferred to a separatory funnel and was sequentially washed with saturated sodium bicarbonate, water, brine, dried over sodium sulfate and concentrated by rotary evaporation. A pink solid (10 mg, 0.019 mmol, 54%) was obtained after column chromatography (CH$_2$Cl$_2$:Et$_2$O 100:0 to 95:5). $^1$H NMR (400 MHz, CDCl$_3$) δ 10.32 (s, 1H), 8.81 (app d, J=8.6 Hz, 2H), 8.10 (app d, J=8.6 Hz, 2H), 5.73 (hept, J=5.9 Hz, 1H), 4.65 (t, J=6.6 Hz, 1H), 4.19 (app d, J=13.6 Hz, 1H), 4.15 (app d, J=13.6 Hz, 1H), 2.95 (app t, J=6.6 Hz, 2H), 2.90 (app td, J=13.0, 2.1 Hz, 1H), 2.84 (app td, J=13.0, 2.1 Hz, 1H), 1.18-1.69 (m, 3H), 1.20-1.12 (m, 2H). $^{13}$C NMR (101 MHz, CDCl$_3$) δ 165.53, 158.32, 151.45, 144.14, 135.72, 129.20, 127.99, 120.80 (q, J$_{C-F}$=281.0 Hz), 69.16 (hept, J$_{C-F}$=34.2 Hz), 48.54, 44.78, 44.19, 36.50, 29.55, 29.20. HRMS [M+H]$^+$ m/z calcd. for [C$_{18}$H$_{19}$O$_4$N$_6$F$_6$S]$^+$ 529.1093, found 529.0932.

Example 31: Stopped-flow kinetic analysis of MAGL tetrazines 10aa, 100b, 100c and 12 with eq-5-hydroxy-trans-cyclooctene in MeOH at 25° C.

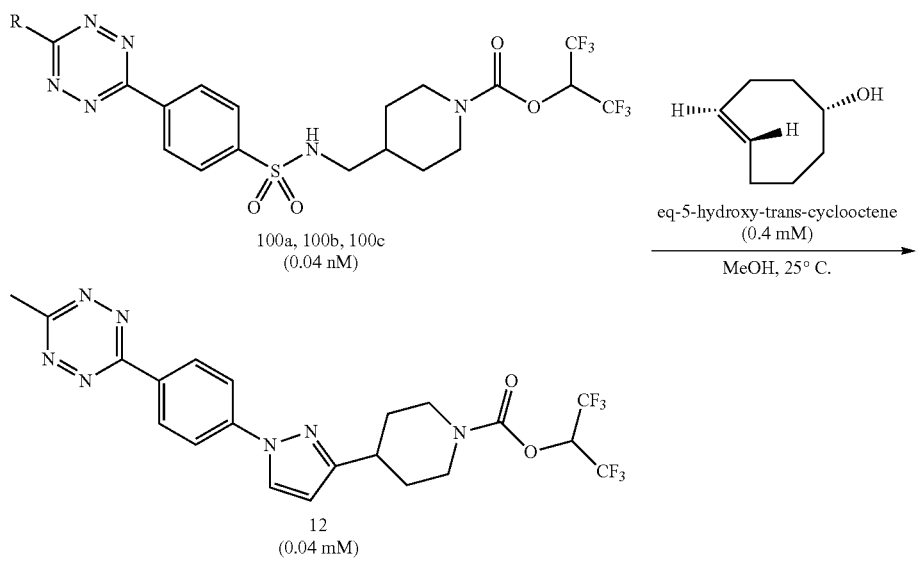

-continued

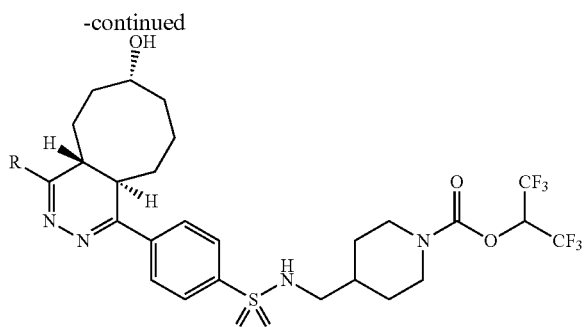

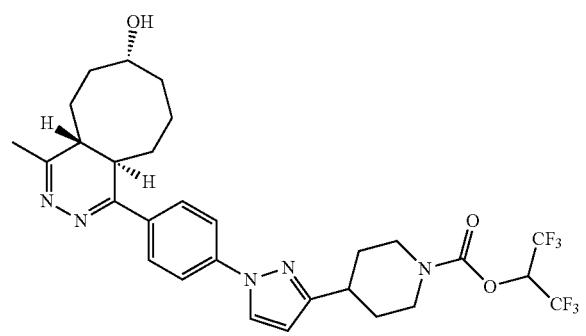

Solutions (3 mL) of tetrazines 100a, 100b, 100c and 12 (0.080 mM) was prepared in MeOH. Solutions (3 mL) of eq-5-hydroxy-trans-cyclooctene (0.80 mM) were prepared in MeOH. The reactions between tetrazines and trans-cyclooctene were measured under pseudo-first order conditions using SX 18MV-R stopped-flow spectrophotometer (Applied Photophysics Ltd.). Each solution of tetrazine and trans-cyclooctene were injected in equal volumes via 3 mL syringes into the stopped-flow instrument at 25° C., resulting in final concentration of 0.04 mM of tetrazines and 0.40 mM trans-cyclooctene. The reaction was monitored by the decay of absorbance associated with the tetrazines (10a and 10b at 300 nm, 10c at 280 nm). Reaction were repeated in triplicate. With Prism software, an observed rate constant, $k_{obs}$, was obtained by nonlinear regression. The results are summarized in the Table 5 below.

TABLE 5

| Compounds | $k_{obs}$ (s$^{-1}$) | $k_{rel}$ |
|---|---|---|
| 100a | 0.003623 | 3 |
| 100b | 0.031 | 25 |
| 100c | 0.2011 | 162 |
| 12 | 0.001244 | 1 |

Example 32: MAGL Probe Experiment

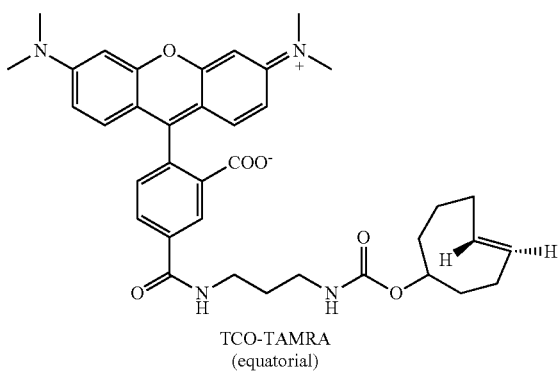

TCO-TAMRA
(equatorial)

-continued

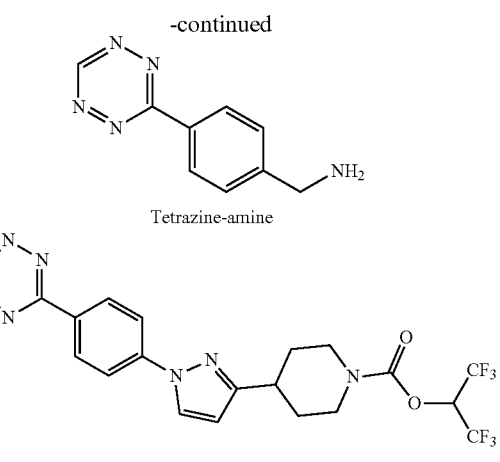

MAGL probe with 6-methyltetrazen-3-yl substituent
12

Materials. Tetrazine amine was purchased from Click Chemistry Tools. TCO-TAMRA were synthesized according to literature protocol. Human brain vascular pericytes and pericyte growth supplement were purchased from ScienCell Research Laboratories. Phosphate-based saline (PBS) was purchased from Mediatech, Inc. Media and other supplements for cell culture were purchased from Thermo Fisher Scientific unless otherwise noted. For cell experiments, all reagents were prepared as 1000× stock solutions in DMSO and stored at −80° C.

MAGL in vitro activity assay. The MAGL in vitro activity assay was performed based on a reported protocol. Briefly, human MAGL enzyme was pre-treated with compounds at room temperature for 30 min, and subsequently incubated with 7-hydroxycoumarinyl arachidonate (7-HCA) as a substrate at room temperature for 1 h. The fluorescence signals were measured on an Envision plate reader (excitation 355 nm, emission 460 nm).

Cell culture and probe treatment. Human brain vascular pericytes were cultured in Dulbecco's Modified Eagle Medium/Nutrient Mixture F-12 (DMEM/F-12) GlutaMAX media supplemented with 5% heat-inactivated fetal bovine serum (HI FBS), 1× pericyte growth supplement (PGS), and 1× penicillin-streptomycin at 37° C. with 5% $C_{O2}$ in a humidified environment. Cells were plated in 6-well plates and cultured overnight in growth media.

To assess cellular potency of probe 100c, live cells were treated with 100c (0.32 nM-10 μM) at 37° C. for 1 h, after which the cells were washed with fresh media. The media were then placed with fresh media containing 2 μM of TCO-TAMRA, and the cells were incubated at 37° C. for 30 min. The reaction was quenched by replacing the media with PBS containing 100 μM tetrazine amine, and the cells were washed with cold PBS and harvested with a scrapper.

To measure the cellular labeling kinetics of TCO-TAMRA with 100c and 12, live cells were treated with 100c (1 μM) or 12 (32 nM) at 37° C. for 1 h. At these concentrations, both probes achieved full labeling of MAGL. Subsequently, the cells were washed with fresh growth media, which were placed with fresh media containing 50 nM, 200 nM, or 2 μM of TCO-TAMRA, and the cells were incubated at 37° C. for 2, 5, 10, 15, 20, 30, and 60 min. To quench the reaction, the media were replaced with PBS containing 100 μM tetrazine amine, and the cells were washed with cold PBS and harvested with a scrapper.

The suspensions were centrifuged at 10,000×g for 1 min at 37° C., and the cell pellets were lysed in PBS containing 0.25% sodium dodecyl sulfate (SDS) with sonication. The protein concentration was measured with a bicinchoninic acid (BCA) assay kit (Thermo Scientific) and normalized.

In-gel fluorescence and data analysis. Same procedure as described in Example 17 was used.

Example 33: Early Catalyst Screening Using a Copper Mediator

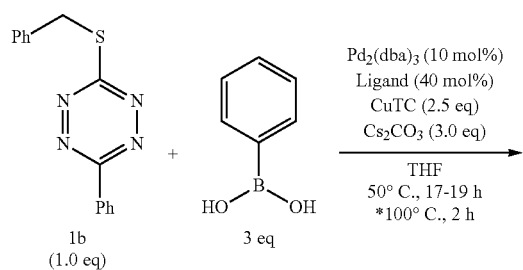

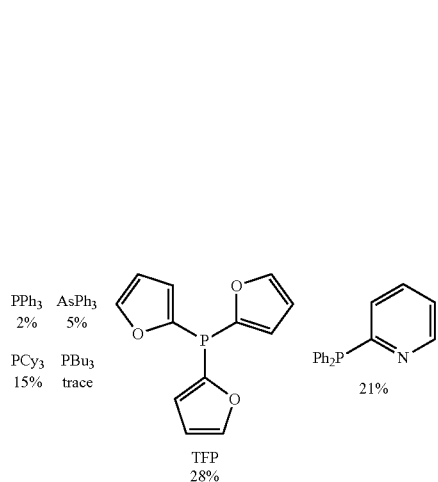

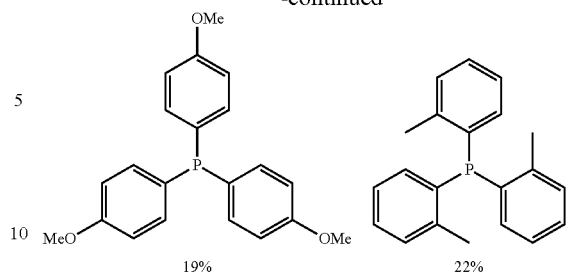

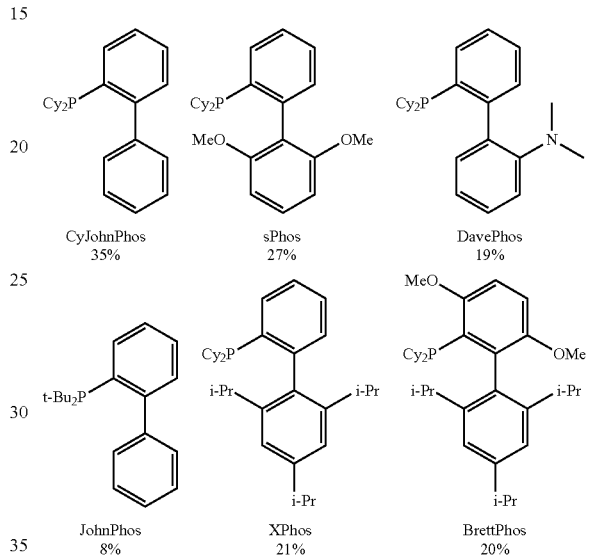

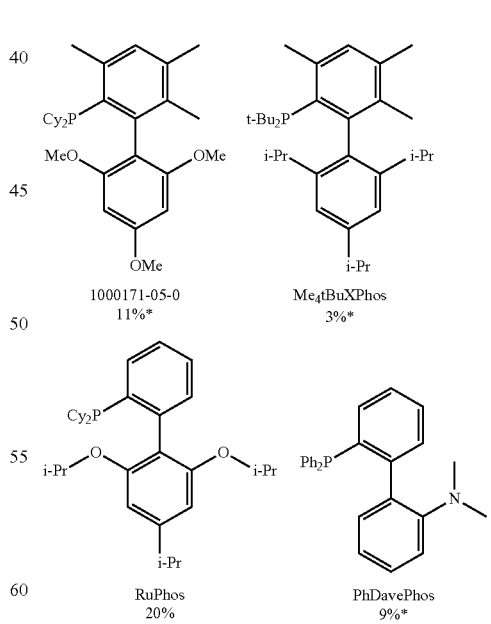

A variety of phosphine ligands, in combination with a Pd catalyst in the presence of CuTc and $CS_2CO_3$, were shown to be capable of catalyzing the coupling of tetrazine thioether 1b with phenylboronic acid.

Example 34: Optimization of the Copper Mediated Conditions

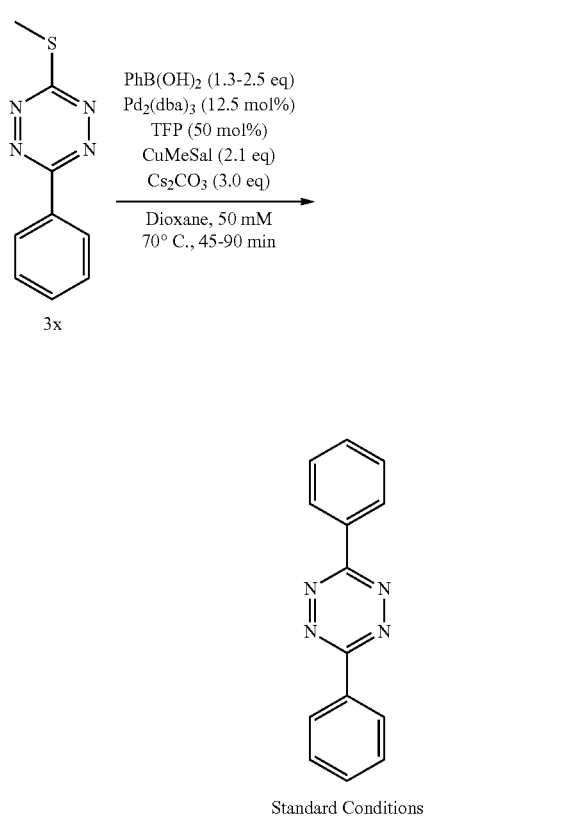

Standard Conditions
Pd₂(dba)₃ increased to 12.5 mol% to drive reaction completion
CuMeSal loading reduced to 2.1 eq with no loss in yield Portion Addition of CuMeSal
Standard conditions (without portionwise addition) 74%
CuMeSal dissolved in DMSO, added over 25 min. 59%
CuMeSal/Dioxane slurry, 5x100 µL (8 min intervals) 74%
CuMeSal/Dioxane slurry, 5x100 µL (4 min intervals) 80%

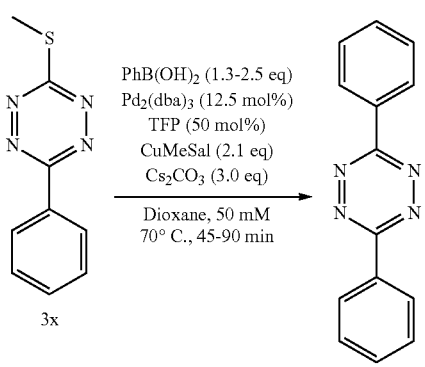

| PhB(OH)₂: | 1.3 eq | 1.9 eq | 2.5 eq |
|---|---|---|---|
| Yield based on Tz | 68% | 80% | 86% |
| Yield based on B(OH)₂ | 52% | 42% | 34% |

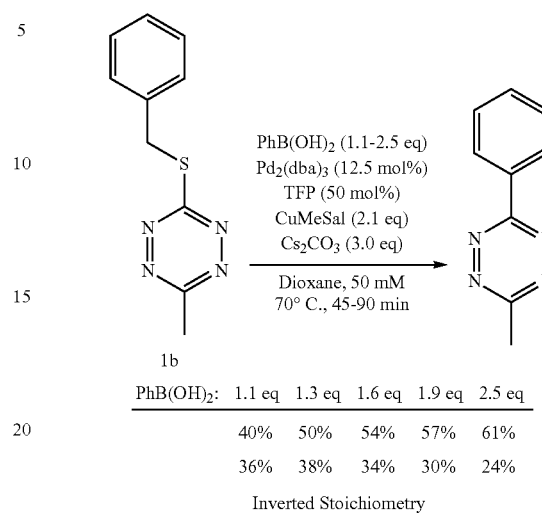

| PhB(OH)₂: | 1.1 eq | 1.3 eq | 1.6 eq | 1.9 eq | 2.5 eq |
|---|---|---|---|---|---|
| | 40% | 50% | 54% | 57% | 61% |
| | 36% | 38% | 34% | 30% | 24% |

Inverted Stoichiometry
(1.0 eq PhB(OH)₂)

| 1b: | 1.9 eq | 2.5 eq |
|---|---|---|
| Yield based on B(OH)₂ | 35% | 27% |

Under optimized copper-mediated conditions tetrazine 1b performed better than b-Tz 1a

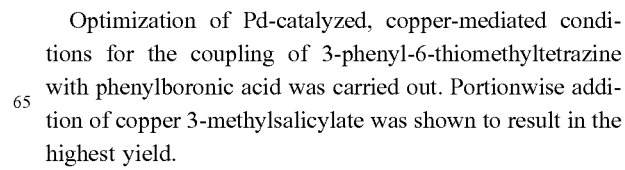

Optimization of Pd-catalyzed, copper-mediated conditions for the coupling of 3-phenyl-6-thiomethyltetrazine with phenylboronic acid was carried out. Portionwise addition of copper 3-methylsalicylate was shown to result in the highest yield.

Example 35: Initial Hit With a Silver Mediator

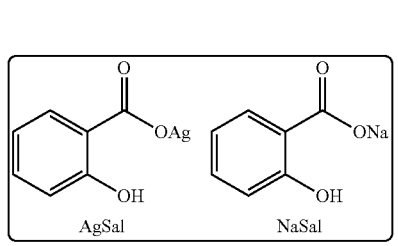

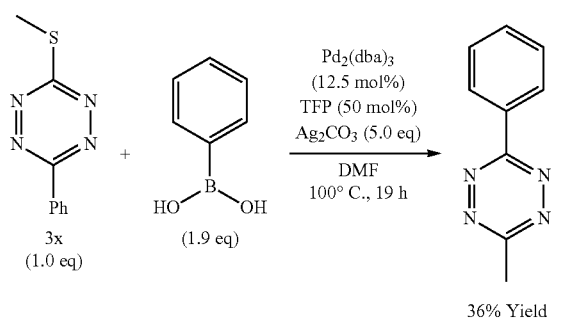

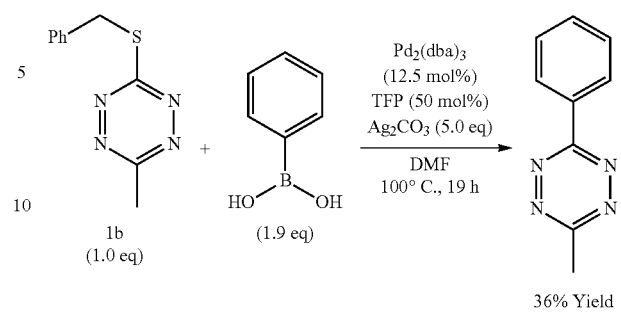

Initial efforts to identify Ag-based additives as alternatives to traditional Cu-based additives were successful. Ag-salicylate and $Ag_2CO_3$ were shown to be effective reagents for mediating the Liebeskind-Srogl cross coupling of phenylboronic acid with tetrazine thioether reagents.

Example 36A: Screening Buchwald Ligands for Silver Mediated Reaction

| Buchwald Ligands |
|---|
| Optimized conditions with tetrazine 1b |

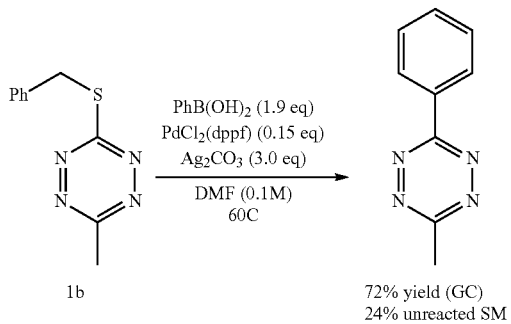

72% yield (GC)
24% unreacted SM

| Entry | Modification from Optimized Conditions | Silver | (° C.) | Time(h) | GC yield (%) | 1b (%) |
|---|---|---|---|---|---|---|
| 1 | Pd$_2$(dba)$_3$ (0.125 eq)/PhDavePhos (0.5 eq) | Ag$_2$CO$_2$ (5 eq) | 85 | 17 | 13 | 29 |
| 2 | Pd$_2$(dba)$_3$ (0.125 eq)/DavePhos (0.5 eq) | Ag$_2$CO$_2$ (5 eq) | 85 | 17 | 13 | 41 |
| 3 | Pd$_2$(dba)$_3$ (0.125 eq)/RuPhos (0.5 eq) | Ag$_2$CO$_2$ (5 eq) | 85 | 17 | 12 | 39 |
| 4 | Pd$_2$(dba)$_3$ (0.125 eq)/APhos (0.5 eq) | Ag$_2$CO$_2$ (5 eq) | 85 | 17 | 8 | 21 |
| 5 | Pd$_2$(dba)$_3$ (0.125 eq)/SPhos (0.5 eq) | Ag$_2$CO$_2$ (5 eq) | 85 | 17 | 26 | 15 |
| 6 | Pd$_2$(dba)$_3$ (0.125 eq)/MePhos (0.5 eq) | Ag$_2$CO$_2$ (5 eq) | 85 | 17 | 20 | 16 |
| 7 | Pd$_2$(dba)$_3$ (0.125 eq)/XPhos (0.5 eq) | Ag$_2$CO$_2$ (5 eq) | 85 | 17 | 25 | 16 |
| 8 | Pd$_2$(dba)$_3$ (0.125 eq)/TrixiePhos (0.5 eq) | Ag$_2$CO$_2$ (5 eq) | 85 | 17 | 11 | 31 |
| 9 | Pd$_2$(dba)$_3$ (0.125 eq)/CyJohnPhos (0.5 eq) | Ag$_2$CO$_2$ (5 eq) | 85 | 19 | 32 | 3 |
| 10 | Pd$_2$(dba)$_3$ (0.125 eq)/BrettPhos (0.5 eq) | Ag$_2$CO$_2$ (5 eq) | 85 | 19 | 6 | 65 |
| 11 | Pd$_2$(dba)$_3$ (0.125 eq)/Me4tBuXPhos (0.5 eq) | Ag$_2$CO$_2$ (5 eq) | 85 | 19 | 14 | 44 |
| 12 | Pd$_2$(dba)$_3$ (0.125 eq)/1000171-05-0 (0.5 eq) | Ag$_2$CO$_2$ (5 eq) | 85 | 19 | 30 | 17 |

Under Pd-catalyzed, Ag-mediated conditions the Buchwald family of phosphines were shown to be effective supporting ligands for the coupling of tetrazine thioether 1b with phenylboronic acid.

Example 36B: Screening Bidentate Ligands for Silver Mediated Reaction

Bidentate Ligands
Optimized conditions with tetrazine 1b

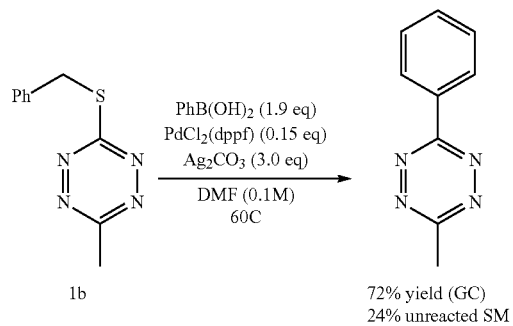

1b

72% yield (GC)
24% unreacted SM

| Entry | Modification from Optimized Conditions | Silver | (° C.) | Time(h) | GC yield (%) | 1b (%) |
| --- | --- | --- | --- | --- | --- | --- |
| 1 | Pd$_2$(dba)$_3$ (0.125 eq)/XantPhos (0.5 eq) | Ag$_2$CO$_2$ (5 eq) | 70 | 18 | 25 | 60 |
| 2 | Pd$_2$(dba)$_3$ (0.125 eq)/N-XantPhos (0.5 eq) | Ag$_2$CO$_2$ (5 eq) | 70 | 18 | 54 | 28 |
| 3 | Pd$_2$(dba)$_3$ (0.125 eq)/dppe 0.5 eq) | Ag$_2$CO$_2$ (5 eq) | 70 | 18 | 0 | 55 |
| 4 | Pd$_2$(dba)$_3$ (0.125 eq)/dppp (0.5 eq) | Ag$_2$CO$_2$ (5 eq) | 70 | 18 | 8 | 51 |
| 5 | Pd$_2$(dba)$_3$ (0.125 eq)/dppb (0.5 eq) | Ag$_2$CO$_2$ (5 eq) | 70 | 18 | 32 | 40 |
| 6 | Pd$_2$(dba)$_3$ (0.125 eq)/dpppe (0.5 eq) | Ag$_2$CO$_2$ (5 eq) | 70 | 18 | trace | 45 |
| 7 | Pd$_2$(dba)$_3$ (0.125 eq)/dppf (0.5 eq) | Ag$_2$CO$_2$ (5 eq) | 70 | 22 | 7 | 12 |
| 8 | Pd$_2$(dba)$_3$ (0.125 eq)/BINAP (0.5 eq) | Ag$_2$CO$_2$ (5 eq) | 70 | 18 | 0 | 80 |
| 9 | Pd$_2$(dba)$_3$ (0.125 eq)/Tol-BINAP (0.5 eq) | Ag$_2$CO$_2$ (5 eq) | 70 | 18 | 0 | 75 |
| 10 | Pd$_2$(dba)3 (0.125 eq)/DPEPhos (0.5 eq) | Ag$_2$CO$_2$ (5 eq) | 70 | 18 | 34 | 37 |
| 11 | Pd$_2$(dba)$_3$ (0.125 eq(/ (+30)-DIOP (0.5 eq) | Ag$_2$CO$_2$ (5 eq) | 70 | 18 | 44 | 13 |
| 12 | Pd$_2$(dba)$_3$ (0.125 eq)/1,4-bis(dicycohexylphosphino)butane (0.5 eq) | Ag$_2$CO$_2$ (5 eq) | 70 | 18 | trace | 26 |
| 13 | Pd$_2$(dba)$_3$ (0.125 eq)/1,2-bis(di-tert-butylphospinomethyl)Benzene (0.5 eq) | Ag$_2$CO$_2$ (5 eq) | 70 | 18 | 0 | 93 |

Under Pd-catalyzed, Ag-mediated conditions, bidentate phosphines were shown to be effective supporting ligands for the coupling of tetrazine thioether 1b with phenylboronic acid.

Example 36C: Screening N-XantPhos and Precatalysts for Silver Mediated Reaction

N-XantPhos and Precatalysts
Optimized conditions with tetrazine 1b

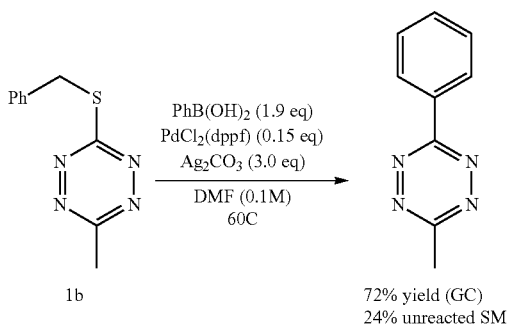

1b

72% yield (GC)
24% unreacted SM

| Entry | Modification from Optimized Conditions | Silver | (° C.) | Time(h) | GC yield (%) | 1b (%) |
| --- | --- | --- | --- | --- | --- | --- |
| 1 | Pd(OAc)$_2$ (0.15 eq)/N-XantPhos (0.15 eq) | Ag$_2$CO$_2$ (3 eq) | 60 | 18 | 21 | 77 |
| 2 | Pd(COD)(CH$_2$TMS)$_2$(0.15 eq)/N-XantPhos (0.15 eq) | Ag$_2$CO$_2$ (3 eq) | 60 | 66 | 16 | 53 |

-continued

| | | | | | | |
|---|---|---|---|---|---|---|
| 3 | Pd(COD)(CH$_2$TMS)$_2$(0.15 eq)/dppf (0.15 eq) | Ag$_2$CO$_2$ (3 eq) | 60 | 66 | 39 | 19 |
| 4 | PdCl2(N-XantPhos) (0.10 eq) | Ag$_2$CO$_2$ (3 eq) | 60 | 22 | 31 | 69 |
| 5 | PdCl2(N-XantPhos) (0.10 eq) | Ag$_2$O (3 eq) | 60 | 22 | 45 | 33 |
| 6 | Pd(N-XantPhos)$_2$ (0.15 eq) | Ag$_2$CO$_2$ (3 eq) | 60 | 21 | 24 | 76 |
| 7 | PdCl$_2$(PPh$_3$)$_2$ (0.25 eq) | Ag$_2$CO$_2$ (5 eq) | 70 | 18 | 33 | 34 |
| 8 | Pd(PPh$_3$)$_4$ (0.25 eq) | Ag$_2$CO$_2$ (5 eq) | 70 | 18 | 0 | 71 |
| 9 | Pd-PEPPSI-IPr (0.25 eq) | Ag$_2$CO$_2$ (5 eq) | 70 | 18 | 34 | 37 |
| 10 | Pd-PEPPSI-SIPr (0.25 eq) | Ag$_2$CO$_2$ (5 eq) | 70 | 18 | 33 | 41 |
| 11 | CyJohnPhos Pd G4 (0.25 eq) | Ag$_2$CO$_2$ (5 eq) | 70 | 18 | 49 | 24 |

Under Pd-catalyzed, Ag-mediated conditions, N-XantPhos was shown to be effective supporting ligands for the coupling of tetrazine thioether 1b with phenylboronic acid.

Example 37: Screening Tz-Thioethers

Under optimized silver-mediated conditions b-Tz 1a performed better than tetrazines 1b-1g (GC yields)

Optimized conditions with tetrazine 1b

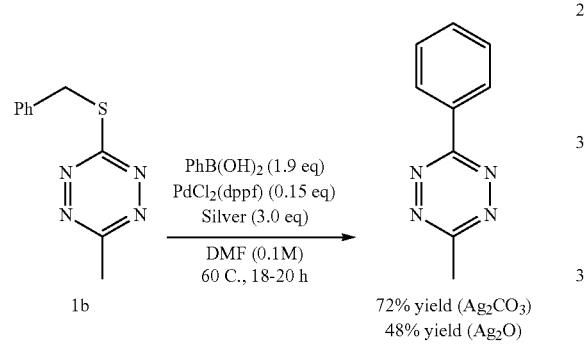

Optimized conditions with tetrazine 1a

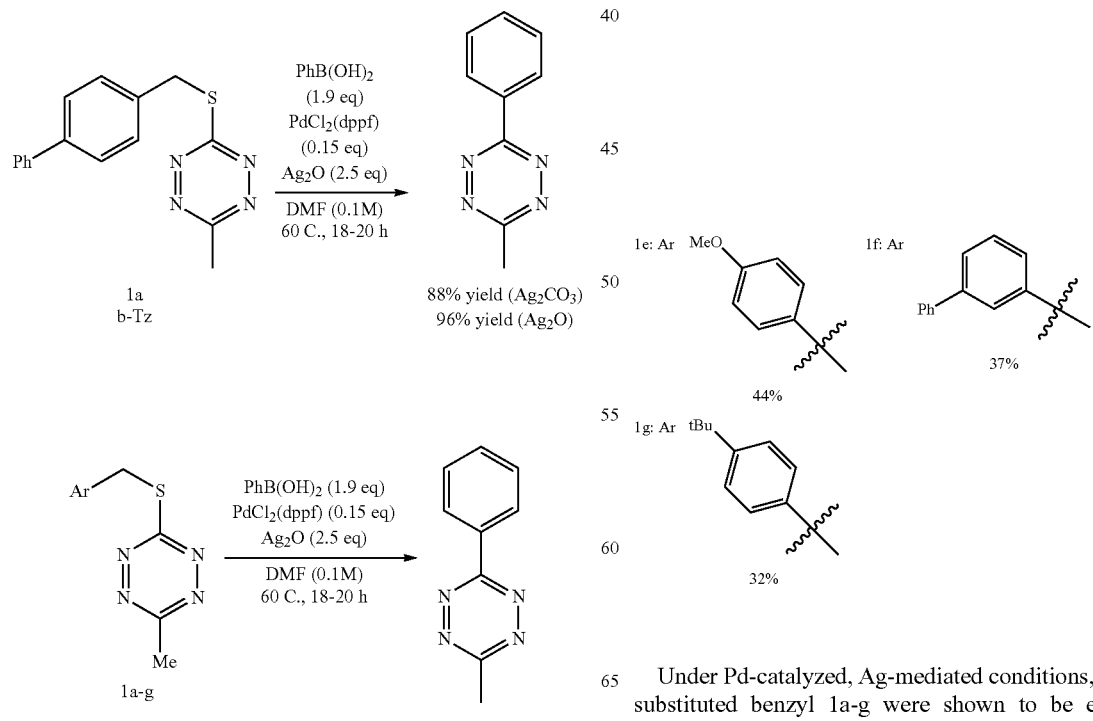

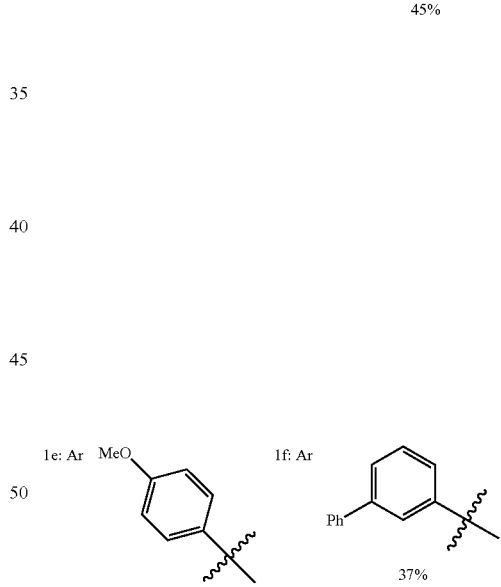

Under Pd-catalyzed, Ag-mediated conditions, a variety of substituted benzyl 1a-g were shown to be effective for coupling reactions with phenylboronic acid.

Example 38: Screening Silver Mediators

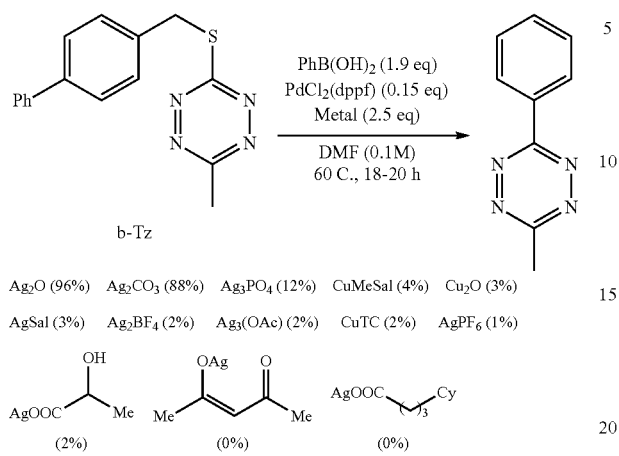

Ag$_2$O (96%)  Ag$_2$CO$_3$ (88%)  Ag$_3$PO$_4$ (12%)  CuMeSal (4%)  Cu$_2$O (3%)

AgSal (3%)  Ag$_2$BF$_4$ (2%)  Ag$_3$(OAc) (2%)  CuTC (2%)  AgPF$_6$ (1%)

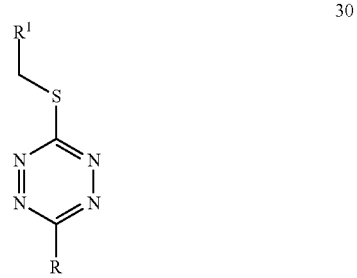

Under Pd-catalyzed conditions, a variety of Ag-salts were shown to be effective for coupling reactions of b-Tz with phenylboronic acid.

Example 39: Deviation from Standard Silver Mediated Conditions

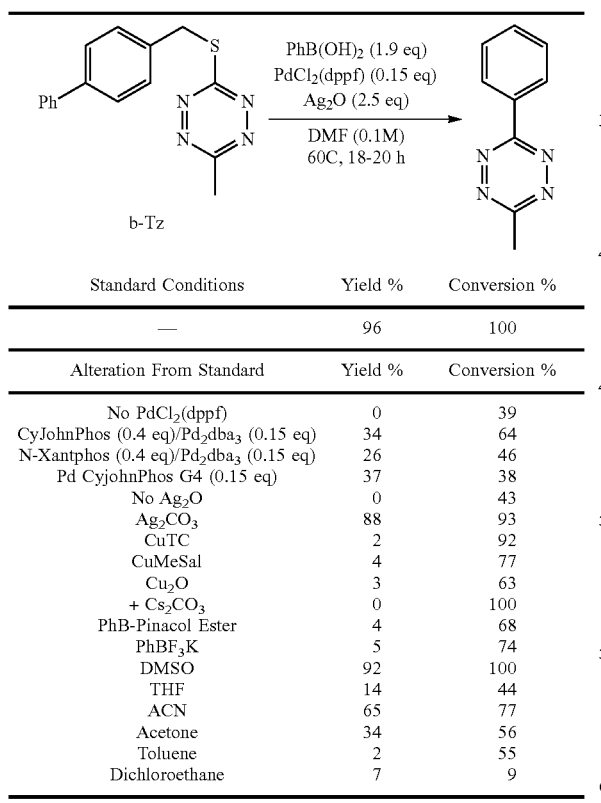

| Standard Conditions | Yield % | Conversion % |
|---|---|---|
| — | 96 | 100 |
| Alteration From Standard | Yield % | Conversion % |
| No PdCl$_2$(dppf) | 0 | 39 |
| CyJohnPhos (0.4 eq)/Pd$_2$dba$_3$ (0.15 eq) | 34 | 64 |
| N-Xantphos (0.4 eq)/Pd$_2$dba$_3$ (0.15 eq) | 26 | 46 |
| Pd CyjohnPhos G4 (0.15 eq) | 37 | 38 |
| No Ag$_2$O | 0 | 43 |
| Ag$_2$CO$_3$ | 88 | 93 |
| CuTC | 2 | 92 |
| CuMeSal | 4 | 77 |
| Cu$_2$O | 3 | 63 |
| + Cs$_2$CO$_3$ | 0 | 100 |
| PhB-Pinacol Ester | 4 | 68 |
| PhBF$_3$K | 5 | 74 |
| DMSO | 92 | 100 |
| THF | 14 | 44 |
| ACN | 65 | 77 |
| Acetone | 34 | 56 |
| Toluene | 2 | 55 |
| Dichloroethane | 7 | 9 |

A variety of phosphines and solvents were shown to be effective for Pd-catalyzed, Ag-mediated coupling reactions of b-Tz with phenylboronic acid.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A compound according to the following structure:

30

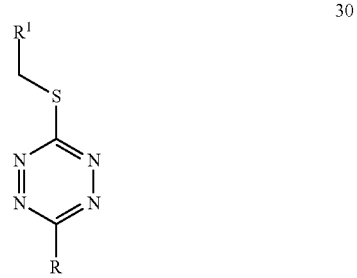

wherein R is hydrogen, an alkyl group, a substituted alkyl group, an aryl group, a substituted aryl group, a heteroaryl group or a substituted heteroaryl group;

wherein R$^1$ is an aryl group, a substituted aryl group, a heteroaryl group, or a substituted heteroaryl group;

wherein a substituent for the substituted alkyl group, the substituted aryl group, and the substituted heteroaryl group is selected from the group consisting of an alkyl group, a halogen, a cycloalkyl group, a heterocyclic group, an aryl group, and a heteroaryl group;

wherein the alkyl group has 1-20 carbon atoms, the cycloalkyl group has 3-20 carbon atoms, the aryl group has 6-40 carbon atoms, the heteroaryl group has 2-30 carbon atoms;

wherein the heteroaryl group is pyridyl group, a (uranyl group, a thiophenyl group, a quinolinyl group, an isoquinolinyl group, a pyrazinyl group, a pyrimidyl group, a pyridazinyl group, a pyrrolyl group, an imidazolyl group, an oxazolyl group, an isoxazolyl group, a thiazolyl group, an isothiazolyl group, an indazolyl group, a benzofuranyl group, a benzothiophenyl or a triazinyl group; and wherein the heterocyclic group is a piperazine ring, a pyrrolidine ring, a pyrrolidone ring, an azetidine ring, a morpholine ring, a dioxane ring, a tetrahydrofuran ring, an oxirane ring, a pyran ring, a piperidine ring, or a cyclic amide.

2. The compound according to claim 1, wherein R$^1$ is selected from

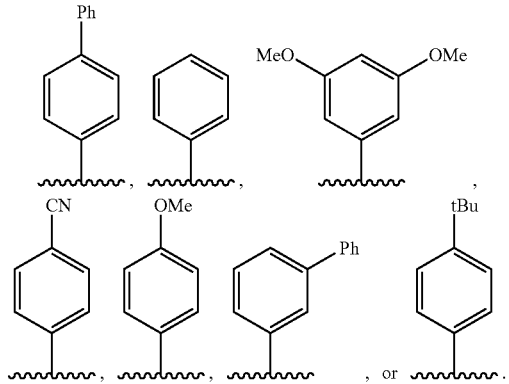

3. The compound according to claim 2, wherein the compound has one of the following structures:

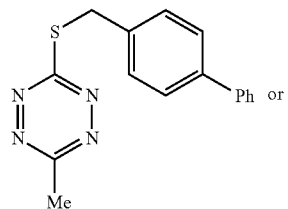

32

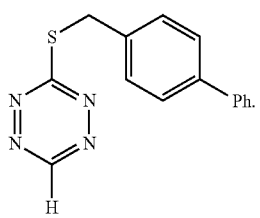

34

4. A compound according to the following structure:

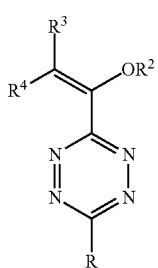

60 wherein R is hydrogen, an alkyl group, a substituted alkyl group, an aryl group, a substituted aryl group, a heteroaryl group, or a substituted heteroaryl group;
wherein $R^2$ is hydrogen, an alkyl group, a substituted alkyl group, an aryl group, a substituted aryl group, a cycloalkyl group, a substituted cycloalkyl group, a heterocyclic group, or a substituted heterocyclic group;
wherein $R^3$ and $R^4$ are independently H, an alkyl group, a cycloalkyl group, or a heterocyclic group;
wherein a substituent for the substituted alkyl group and the substituted aryl group comprises an alkyl group, a halogen, a cycloalkyl group, a heterocyclic group, an aryl group, and/or a heteroaryl group;
wherein the alkyl group has 1-20 carbon atoms, the cycloalkyl group has 3-20 carbon atoms, the aryl group has 6-40 carbon atoms, the aryl group has 6-40 carbon atoms;
wherein the heteroaryl group is pyridyl group, a furanyl group, a thiophenyl group, a quinolinyl group, an isoquinolinyl group, a pyrazinyl group, a pyrimidyl group, a pyridazinyl group, a pyrrolyl group, an imidazolyl group, an oxazolyl group, an isoxazolyl group, a thiazolyl group, an isothiazolyl group, an indazolyl group, a benzofuranyl group, a benzothiophenyl or a triazinyl group; and
wherein the heterocyclic group is a piperazine ring, a pyrrolidine ring, a pyrrolidone ring, an azetidine ring, a morpholine ring, a dioxane ring, a tetrahydrofuran ring, an oxirane ring, a pyran ring, a piperidine ring, or a cyclic amide.

5. A compound according to the following structure:

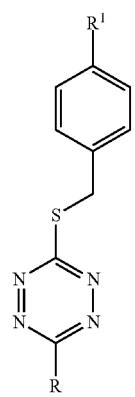

70 wherein $R^1$ is an aryl group, a substituted aryl group, a heteroaryl group, or a substituted heteroaryl group;
wherein R is hydrogen, an alkyl group, a substituted alkyl group, an aryl group, a substituted aryl group, a heteroaryl group, or a substituted heteroaryl group;
wherein a substituent for the substituted alkyl group and the substituted aryl group comprises an alkyl group, a halogen, a cycloalkyl group, a heterocyclic group, an aryl group, and/or a heteroaryl group;
wherein the alkyl group has 1-20 carbon atoms, the cycloalkyl group has 3-20 carbon atoms, the aryl group has 6-40 carbon atoms, the aryl group has 6-40 carbon atoms;
wherein the heteroaryl group is pyridyl group, a furanyl group, a thiophenyl group, a quinolinyl group, an isoquinolinyl group, a pyrazinyl group, a pyrimidyl group, a pyridazinyl group, a pyrrolyl group, an imidazolyl group, an oxazolyl group, an isoxazolyl group, a thiazolyl group, an isothiazolyl group, an indazolyl group, a benzofuranyl group, a benzothiophenyl or a triazinyl group; and
wherein the heterocyclic group is a piperazine ring, a pyrrolidine ring, a pyrrolidone ring, an azetidine ring, a morpholine ring, a dioxane ring, a tetrahydrofuran ring, an oxirane ring, a pyran ring, a piperidine ring, or a cyclic amide.

6. A method for converting an oxetanyl ester 15 to a thio-substituted tetrazine 30,
the method comprising:
contacting the oxetanyl ester 15 with a Lewis base and a 5-isothiocarbonohydrazidium salt 20 to form a thio-substituted tetrazine 30, as shown below in reaction scheme (3):

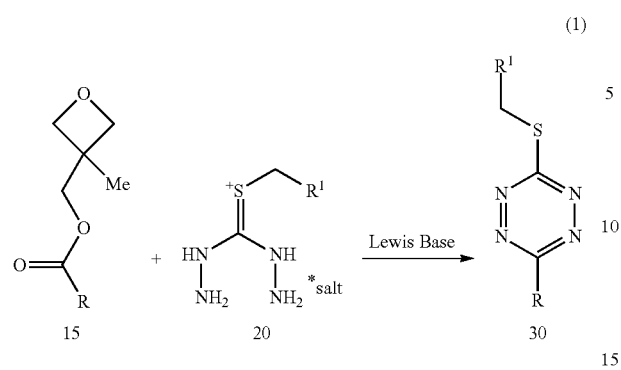

(1)

wherein R is hydrogen, an alkyl group, a substituted alkyl group, an aryl group, a substituted aryl group, a heteroaryl group or a substituted heteroaryl group;

wherein $R^1$ is an aryl group, a substituted aryl group, a heteroaryl group, or a substituted heteroaryl group;

wherein a substituent for the substituted alkyl group and the substituted aryl group comprises an alkyl group, a halogen, a cycloalkyl group, a heterocyclic group, an aryl group, and/or a heteroaryl group, wherein the alkyl group has 1-20 carbon atoms, the cycloalkyl group has 3-20 carbon atoms, the aryl group has 6-40 carbon atoms, the aryl group has 6-40 carbon atoms, wherein the heteroaryl group is pyridyl group, a furanyl group, a thiophenyl group, a quinolinyl group, an isoquinolinyl group, a pyrazinyl group, a pyrimidyl group, a pyridazinyl group, a pyrrolyl group, an imidazolyl group, an oxazolyl group, an isoxazolyl group, a thiazolyl group, an isothiazolyl group, an indazolyl group, a benzofuranyl group, a benzothiophenyl or a triazinyl group, and wherein the heterocyclic group is a piperazine ring, a pyrrolidine ring, a pyrrolidone ring, an azetidine ring, a morpholine ring, a dioxane ring, a tetrahydrofuran ring, an oxirane ring, a pyran ring, a piperidine ring, or a cyclic amide.

7. The method of claim 6, wherein the Lewis base is pyridine, triethylamine, potassium carbonate, cesium carbonate, or potassium tert-butoxide.

8. The method of claim 6, wherein when the R group is not hydrogen, the R group is substituted with a functional group selected from an alkoxycarbonylalkylene, alkoxycarbonylarylene butyloxycarbonyl (Boc) amino group, nitro, alkoxy, halo, nitrite, alkyoxyarylene, alkoxyalkylene, hetrocycle, optionally substituted pyridine or phenyl, protected amino acid, biotin, or fluoro-borondipyrromethene (BODIPY-FL).

9. The method of claim 6, wherein the R group of the thio-substituted tetrazine 3 is one of the formulae 3a to 3w:

3a

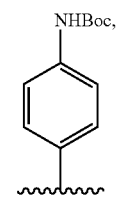

3b

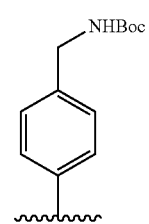

3c

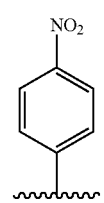

3d

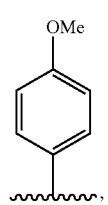

3e

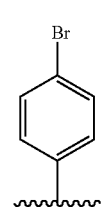

3f

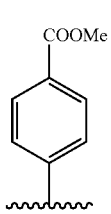

3g

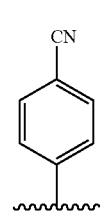

3h

3i

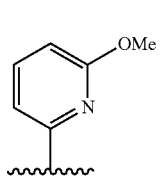

10. The method of claim 6 further comprising converting the thio substituted tetrazine 30 to a mono-substituted tetrazine 4, the method comprising reducing the thio-substituted tetrazine 30 in the presence of a catalyst and a reductant, followed by treatment with an oxidant to form the mono-substituted tetrazine 4, as shown below in reaction scheme (2):

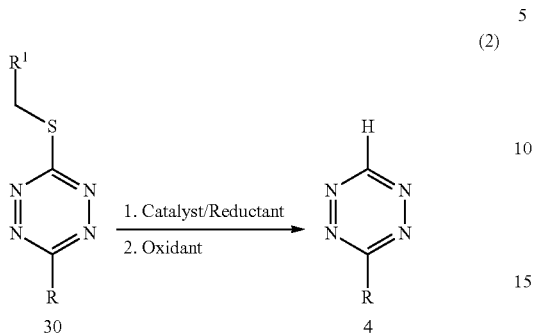

wherein the catalyst is a Pd-containing catalyst, a Pt-containing catalyst or a Ni-containing catalyst.

11. The method of claim 10, wherein the catalyst is $PdCl_2$, Pd/CPd(OAc)$_2$, Pd$_2$(dba)$_3$, PtCl$_2$ or Pt/C, or Ra-Ni; and
wherein the reductant is a silane, formic acid, formate salts, or hydrogen gas.

12. The method of claim 10, wherein the oxidant is phenyliodonium diacetate (PISA), NaNO$_2$, isoamyl nitrite, quinones, FeCl$_3$, or a Cu(OAc)$_2$ in air, or air alone.

13. The method of claim 10, wherein the compound 4 has one of the following structures 4a to 4m:

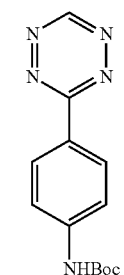

4a

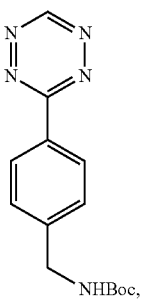

4b

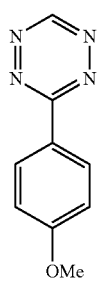

4c

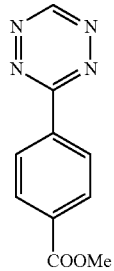

4d

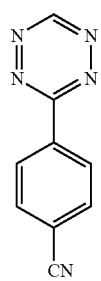

4e

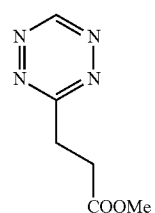

4f

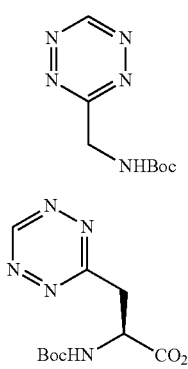

4g

4h

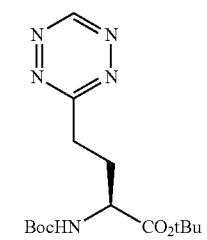

4i

-continued

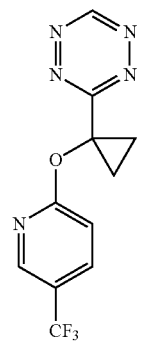
4j

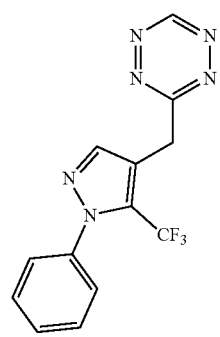
4k

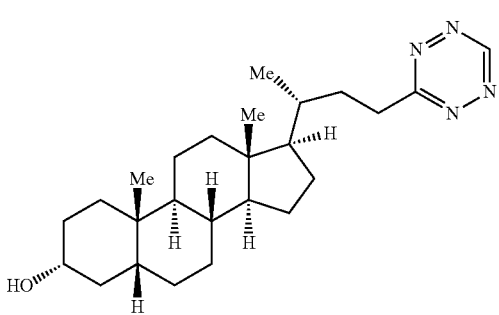
4l

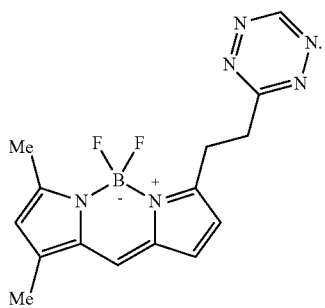
4m 15-fold fluorescence
turn-on with TCO

14. The method of claim 6 further comprising catalytically converting the thio-substituted tetrazine 30 to a di-substituted tetrazine 50, the method comprising reacting substituted tetrazine thio-substituted 30 in a silver-mediated, catalyzed coupling with a substituted boronic acid to form the di-substituted tetrazine 50, as shown below in reaction scheme (3):

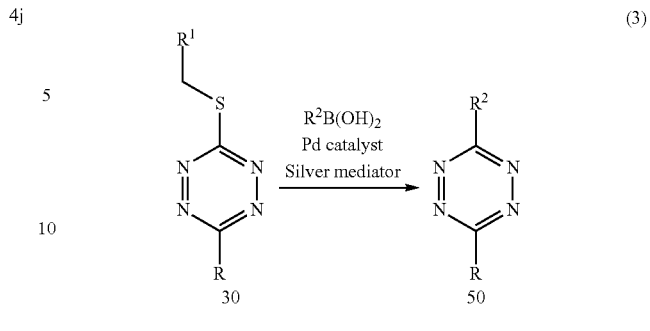
(3)

wherein $R^1$ is selected from an aryl group, a substituted aryl group, a heteroaryl group, or a substituted heteroaryl group, wherein $R^2$ is selected from hydrogen, an alkyl group, a substituted alkyl group, an aryl group, a substituted aryl group, a cycloalkyl group, a substituted cycloalkyl group, a heterocyclic group, or a substituted heterocyclic group, and wherein the catalyst is a Pd-containing catalyst.

15. The method of claim 14, wherein the silver compound is $Ag_2O$, $Ag_2CO_3$, $Ag_3PO_4$, Ag(salicylate), $AgBF_4$, Ag(acetate), $AgPF_6$, or Ag(trifluoromethanesulfonate).

16. The method of claim 14, wherein the Pd-containing catalyst is at least one of:

(i) Pd ligand combination of 1,1'-bis(diphenylphosphino)ferrocene]dichloropalladium(II) (Pd(dppf)Cl$_2$), Pd(dppf)Cl$_2$ and PdI$_2$ with 1,1'-Bis(diisopropylphosphino)ferrocene (DiPPF);

(ii) Pd(OAc)$_2$, Pd$_2$(DBA)$_3$, Pd(COD)(CH$_2$TMS)$_2$, CyJohnPhos/Pd$_2$(DBA)$_3$, PdCl$_2$(XantPhos), PdCl$_2$(N-XantPhos), Pd(XantPhos)$_2$, Pd(N-XantPhos)$_2$, PdCl$_2$(PPh$_3$), Pd(PPh$_3$)$_4$, Pd-PEPPSI-IPr, Pd-PEPPSI-SiPr, CyJohnphos Pd G4, or (iii) Pd$_2$DBA$_3$ in combination with PPh$_3$, AsPh$_3$, tri-furylphosphine, diphenyl-(2 pyridyl)phosphine, tri-(p-methoxyphenyl)phosphine, tri-otolylphosphine, Cy-JohnPhos, SPhos, DavePhos, JohnPhos, XPhos, BrettPhoss, MetBuXPhos, RuPhos, APhos, MePhos, TrixiePhos, or Ph-DavePhos, and (iv) PdI$_2$, PdCl$_2$ or PdBr$_2$ in combination with the following ligands:

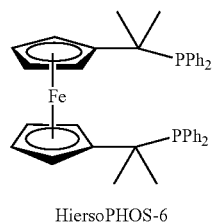
(A)

HiersoPHOS-6

-continued
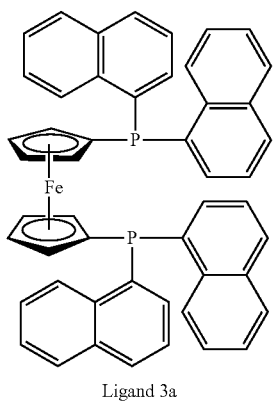
Ligand 3a
(B)
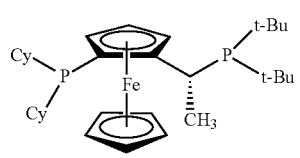
Josiphos SL-J009-1
(C)
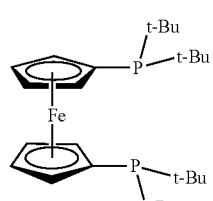
Mandyphos SL-M004-1
(D)
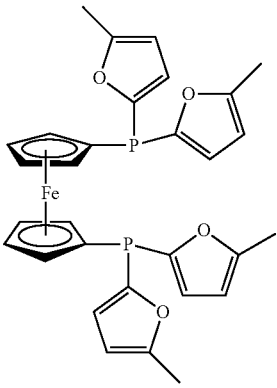
dtbpf
(E)
-continued
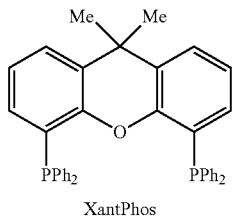
CAS 756824-22-3
(F)
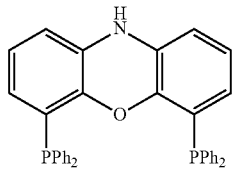
XantPhos
(G)
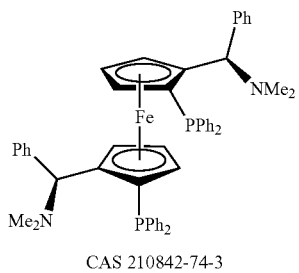
N-XantPhos
(H)
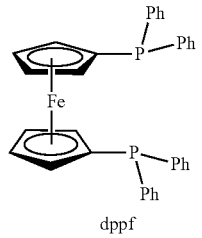
CAS 210842-74-3
(I)
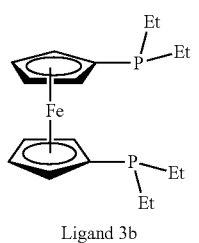
dppf
(J)
Ligand 3b
(K)

137
-continued
(L)
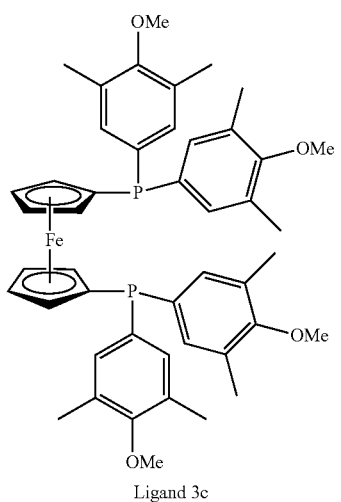
Ligand 3c
(M)
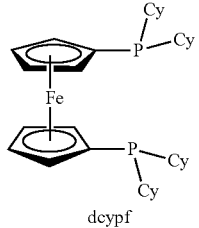
dcypf
(N)
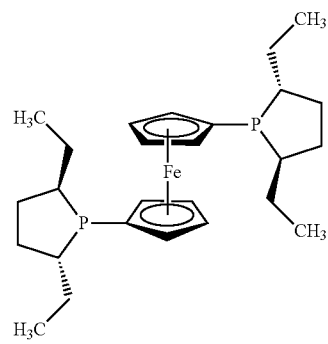
R,R-Et-Ferrocelane™
(O)
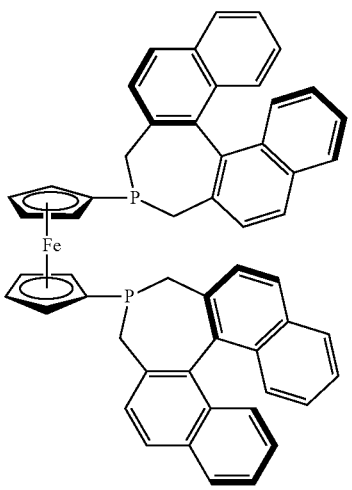
(S,S)-f-BINAPHANE
138
-continued
(P)
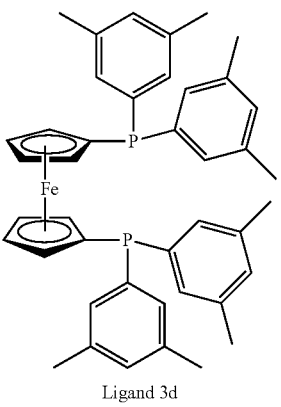
Ligand 3d
(Q)
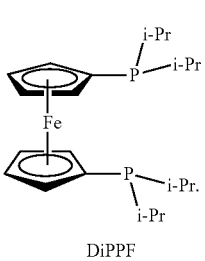
DiPPF
17. The method of m 14, wherein the compound 50 has one of the following structures 5a to 5p:
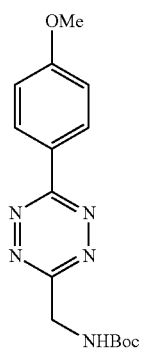
5a
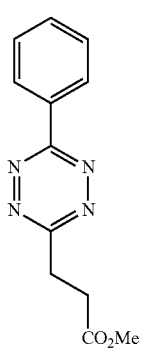
5b

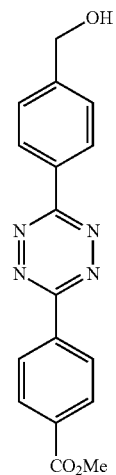
5c
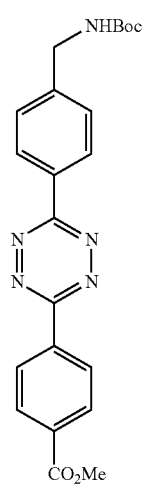
5d
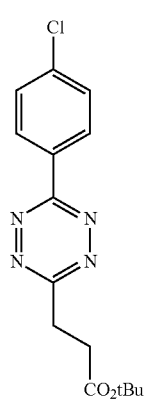
5e
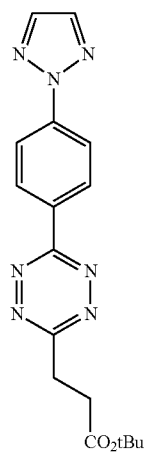
5f
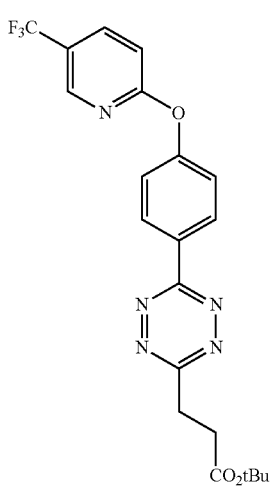
5g
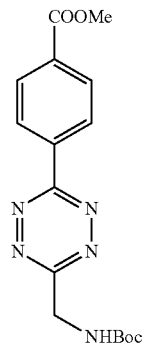
5h
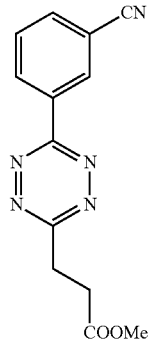
5i 141
-continued 5j
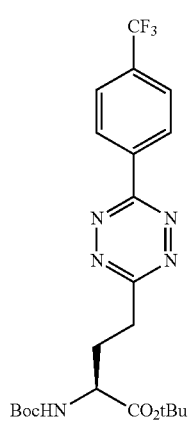

5k
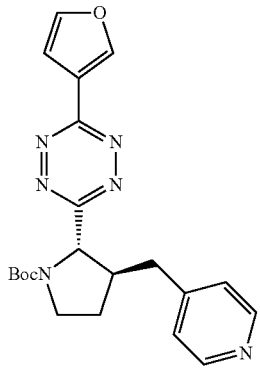

5l
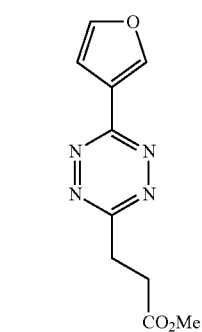

5m
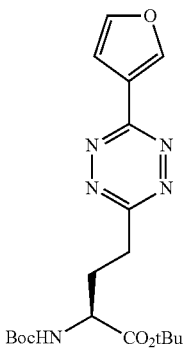

142
-continued

5n
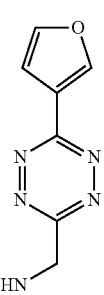

5o
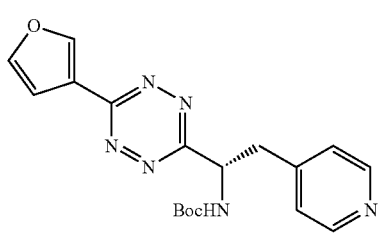

5p
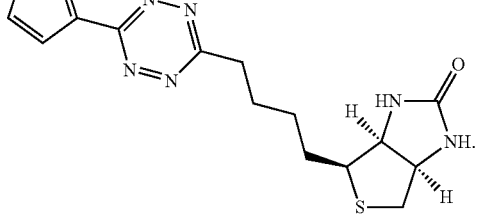

18. The method of claim 6, further comprising catalytically converting the thio-substituted tetrazine 30 to a vinylether disubstituted tetrazine 60,
the method comprising cross coupling the thio-substituted tetrazine 30 in the presence of a Pd containing catalyst with a vinyl stannate under Cu-promoted or Ag-promoted conditions to form the vinylether di-substituted tetrazine 60, as shown below in reaction scheme (4):

(4)
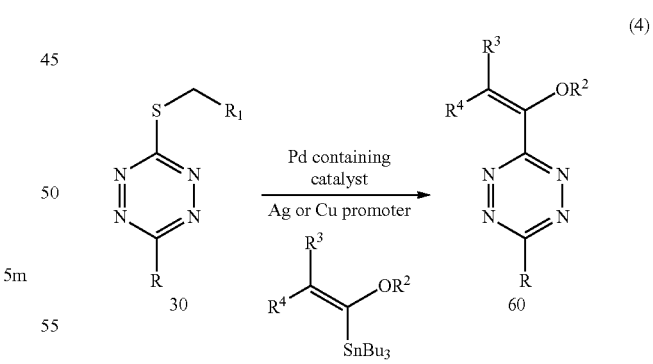

wherein $R^2$ is hydrogen, an alkyl group, a substituted alkyl group, an aryl group, a substituted aryl group, a cycloalkyl group, a substituted cycloalkyl group, a heterocyclic group, or a substituted heterocyclic group; and
wherein $R^3$ and $R^4$ are independently H, an alkyl group, a cycloalkyl group, or a heterocyclic group.

19. The method of claim 18, wherein the Cu-promoted conditions have a Cu-promoter comprising CuMeSal (Cu(I) 3-methylsalicylate) or $Cu_2O$, and wherein Ag-promoted conditions have a silver promoter comprising Ag$_2$O, Ag$_2$CO$_3$, Ag$_3$PO$_4$, Ag(salicylate), AgBF$_4$, Ag(OAc), AgPF$_6$, or Ag(OTf).

20. The method of claim 18, wherein the Pd-containing catalyst is at least one of:
(i) Pd ligand combination of 1,1'-bis(diphenylphosphino)ferrocene]dichloropalladium(II) (Pd(dppf)Cl$_2$), Pd(dppf)Cl$_2$ and PdI$_2$ with 1,1'-Bis(diisopropylphosphino)ferrocene (DiPPF);
(ii) Pd(OAc)$_2$, Pd$_2$(DBA)$_3$, Pd(COD)(CH$_2$TMS)$_2$, CyJohnPhos/Pd$_2$(DBA)$_3$, PdCl$_2$(XantPhos), PdCl$_2$(N-XantPhos), Pd(XantPhos)$_2$, Pd(N-XantPhos)$_2$, PdCl$_2$(PPh$_3$), Pd(PPh$_3$)$_4$, Pd-PEPPSI-IPr, Pd-PEPPSI-SiPr, CyJohnphos Pd G4, or
(iii) Pd$_2$(DBA)$_3$ in combination with PPh$_3$, AsPh$_3$, tri-furylphosphine, diphenyl-(2-pyridyl)phosphine, tri(p-methoxyphenyl)phosphine, tri-otolylphosphine, Cy-JohnPhos, SPhos, DavePhos, JohnPhos, XPhos, BrettPhoss, MetBuXPhos, RuPhos, APhos, MePhos, TrixiePhos, or Ph-DavePhos, and
(iv) PdI$_2$, PdCl$_2$ or PdBr$_2$ in combination with the following ligands:

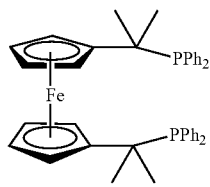

HiersoPHOS-6

(A)

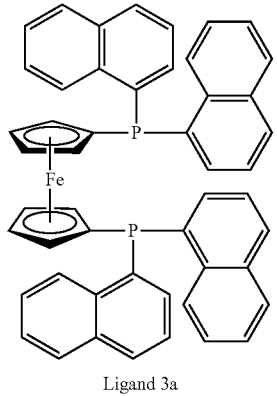

Ligand 3a (B)

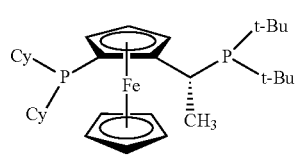

Josiphos SL-J009-1

(C)

-continued

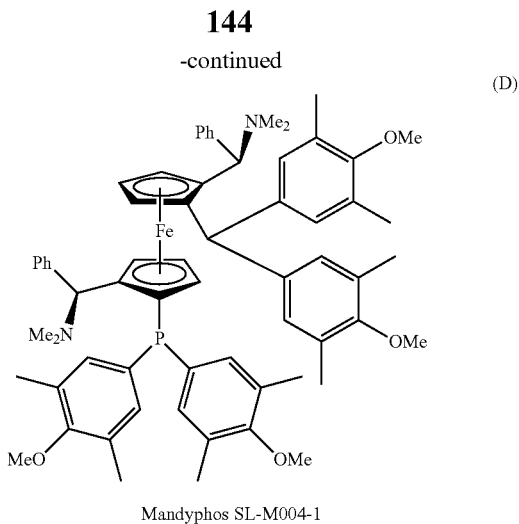

Mandyphos SL-M004-1

(D)

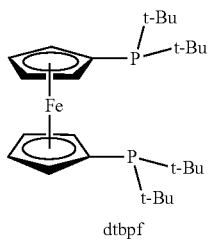

dtbpf (E)

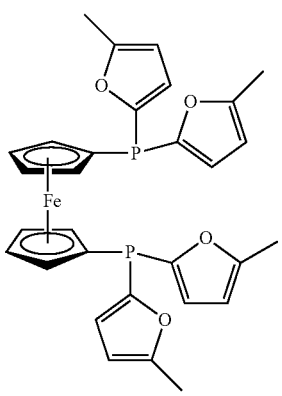

CAS 756824-22-3

(F)

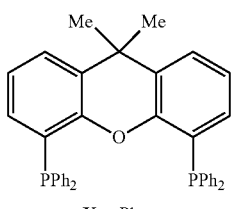

XantPhos (G)

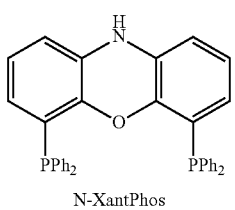

N-XantPhos (H)

-continued
(I)
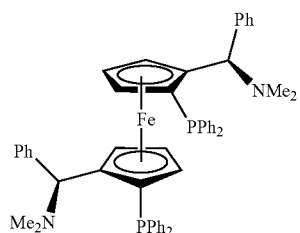
CAS 210842-74-3
(J)
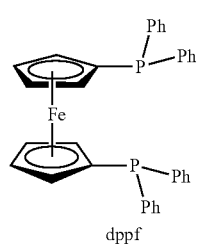
dppf
(K)
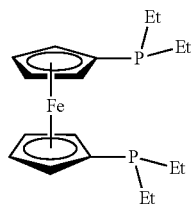
Ligand 3b
(L)
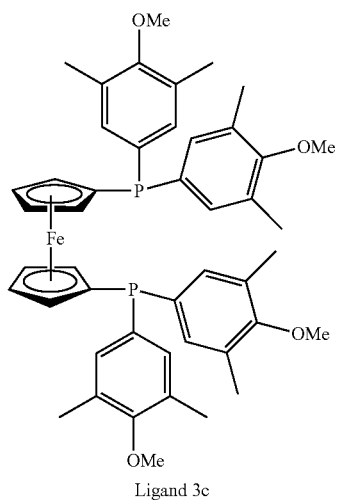
Ligand 3c
(M)
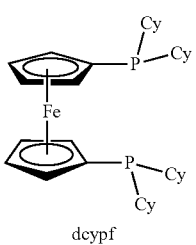
dcypf
-continued
(N)
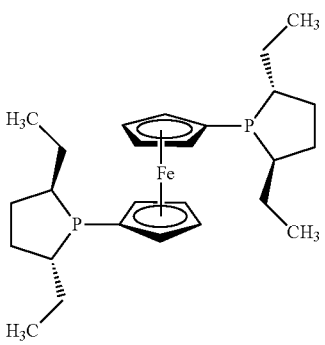
R,R-Et-Ferrocelane™
(O)
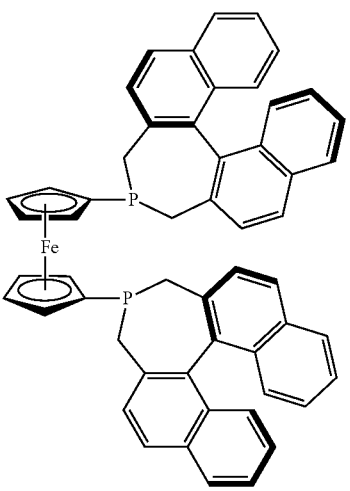
(S,S)-f-BINAPHANE
(P)
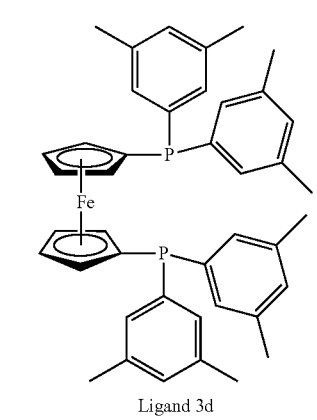
Ligand 3d
(Q)
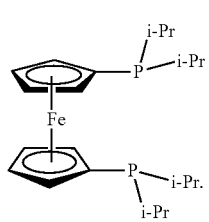
DiPPF 21. The method of claim 18, wherein the compound 60 has one of the following structures 6a to 6e:
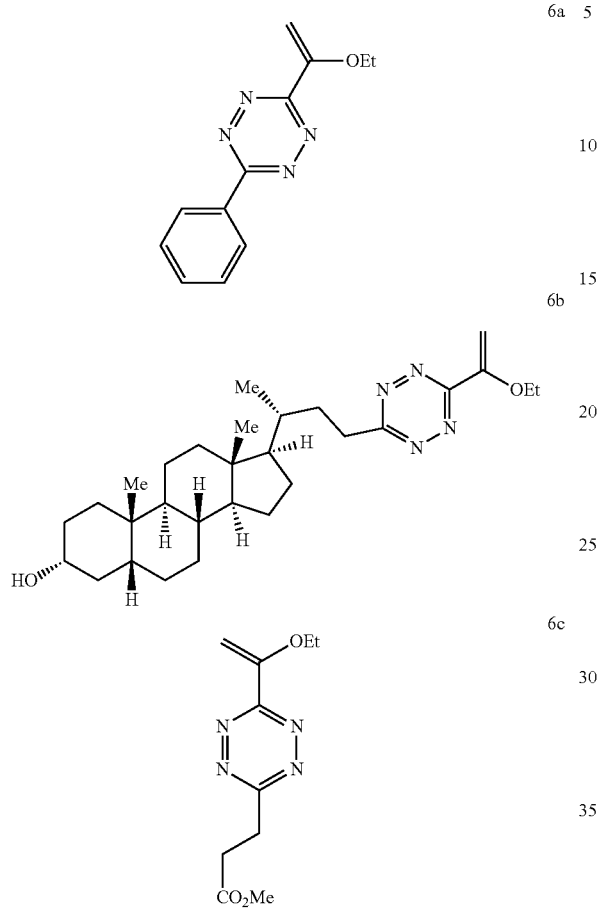
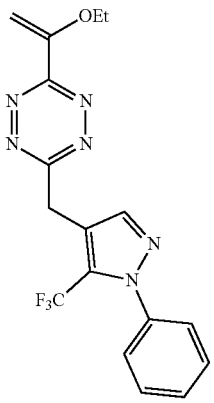
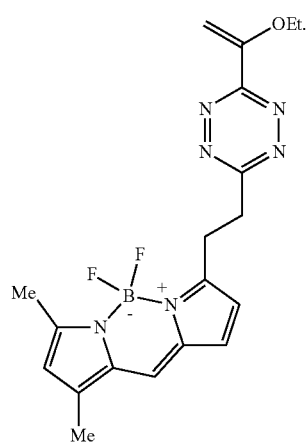
* * * * *

UNITED STATES PATENT AND TRADEMARK OFFICE
CERTIFICATE OF CORRECTION

| | | |
|---|---|---|
| PATENT NO. | : 11,767,302 B2 | Page 1 of 1 |
| APPLICATION NO. | : 17/492016 | |
| DATED | : September 26, 2023 | |
| INVENTOR(S) | : Joseph M. Fox et al. | |

It is certified that error appears in the above-identified patent and that said Letters Patent is hereby corrected as shown below:

In the Claims

In Claim 1, Column 124, Line 35, "a (uranyl" should read -- a furanyl --

In Claim 1, Column 124, Line 33, "has 6-40 carbon atoms, the heteroaryl group has 2-30" should read -- has 6-40 carbon atoms, and the heteroaryl group has 2-30 --

In Claim 4, Column 125, Line 62, "has 6-40 carbon atoms, the heteroaryl group has 2- 30" should read -- has 6-40 carbon atoms, and the heteroaryl group has 2-30 --

In Claim 5, Column 126, Line 43, "has 6-40 carbon atoms, the heteroaryl group has 2- 30" should read -- has 6-40 carbon atoms, and the heteroaryl group has 2-30 --

In Claim 6, Column 126, Line 65, "5-isothiocarbonohydrazidium" should read -- *S*-isothiocarbonohydrazidium --

In Claim 6, Column 127, Line 29, "has 6-40 carbon atoms, the heteroaryl group has 2- 30" should read -- has 6-40 carbon atoms, and the heteroaryl group has 2-30 --

In Claim 12, Column 131, Line 27, "diacetate (PISA)" should read -- diacetate (PIDA) --

Signed and Sealed this
Nineteenth Day of December, 2023

Katherine Kelly Vidal
*Director of the United States Patent and Trademark Office*